United States Patent
Okumura et al.

(10) Patent No.: US 9,657,230 B2
(45) Date of Patent: May 23, 2017

(54) ALKENYL DIOXANE COMPOUND, LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Kazuo Okumura, Chiba (JP); Kenji Hirata, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

(21) Appl. No.: 15/071,257

(22) Filed: Mar. 16, 2016

(65) Prior Publication Data
US 2016/0280996 A1 Sep. 29, 2016

(30) Foreign Application Priority Data
Mar. 27, 2015 (JP) ................................. 2015-065990

(51) Int. Cl.
| | |
|---|---|
| G02F 1/1333 | (2006.01) |
| C09K 19/34 | (2006.01) |
| C07D 319/06 | (2006.01) |
| C09K 19/32 | (2006.01) |
| C09K 19/04 | (2006.01) |

(52) U.S. Cl.
CPC ........ C09K 19/3458 (2013.01); C07D 319/06 (2013.01); C09K 19/32 (2013.01); C09K 19/322 (2013.01); C09K 19/3402 (2013.01); C09K 2019/0466 (2013.01); C09K 2019/3422 (2013.01); C09K 2019/3425 (2013.01)

(58) Field of Classification Search
CPC C09K 19/3458; C09K 19/3402; C09K 19/32; C09K 19/322; C09K 2019/3422; C09K 2019/0466; C09K 2019/3425; C07D 319/06; G02F 1/1333
USPC .............. 252/299.01, 299.6, 299.61; 428/1.1
See application file for complete search history.

(56) References Cited

U.S. PATENT DOCUMENTS

| | | | | |
|---|---|---|---|---|
| 5,728,319 | A | 3/1998 | Matsui et al. | |
| 5,792,386 | A * | 8/1998 | Matsui .................. | C07C 43/225 252/299.01 |
| 5,858,270 | A * | 1/1999 | Matsui .................. | C07C 43/225 252/299.01 |
| 7,767,277 | B2 * | 8/2010 | Lietzau ................. | C09K 19/20 252/299.61 |

FOREIGN PATENT DOCUMENTS

WO 96/11897 4/1996

* cited by examiner

*Primary Examiner* — Geraldina Visconti
(74) *Attorney, Agent, or Firm* — Wenderoth, Lind & Ponack, L.L.P.

(57) ABSTRACT

A problem is to provide a liquid crystal compound satisfying at least one physical property such as high stability to heat and light, high clearing point, low minimum temperature of liquid crystal phase, small viscosity, suitable optical anisotropy, large dielectric anisotropy, suitable elastic constant and excellent compatibility with other liquid crystal compounds, a liquid crystal composition containing the compound, and a liquid crystal display device including the composition. The compound is represented by formula (1).

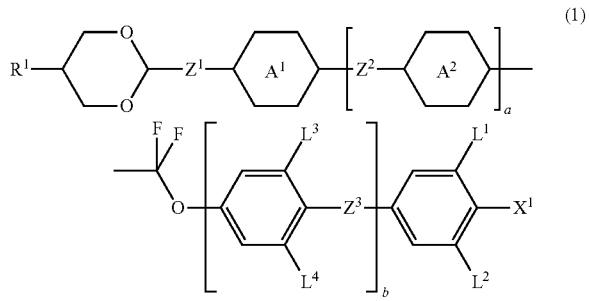

In formula (1), for example, $R^1$ is alkenyl; ring $A^1$ and ring $A^2$ are 1,4-cyclohexylene or 1,4-phenylene; $Z^1$, $Z^2$, $Z^3$ are a single bond or —COO—; $X^1$ is hydrogen or fluorine; $L^1$, $L^2$, $L^3$ and $L^4$ are hydrogen or fluorine; and a and b are each independently 0 or 1, a sum of a and b is 1, and when a is 1, at least one of ring $A^1$ and ring $A^2$ is 1,4-cyclohexylene.

13 Claims, No Drawings

ALKENYL DIOXANE COMPOUND, LIQUID CRYSTAL COMPOSITION AND LIQUID CRYSTAL DISPLAY DEVICE

TECHNICAL FIELD

The invention relates to a liquid crystal compound, a liquid crystal composition and a liquid crystal display device. More specifically, the invention relates to an alkenyldioxane compound, a liquid crystal composition that contains the compound and has a nematic phase, and a liquid crystal display device including the composition.

A liquid crystal display device is widely used for a display of a personal computer, a television and so forth. The device utilizes physical properties such as optical anisotropy and dielectric anisotropy of a liquid crystal compound. As an operating mode of the liquid crystal display device, a variety of modes are known, such as a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a vertical alignment (VA) mode, a fringe field switching (FFS) mode and a polymer sustained alignment (PSA) mode.

In such a liquid crystal display device, a liquid crystal composition having suitable physical properties is used. In order to further improve characteristics of the device, a liquid crystal compound contained in the composition preferably has physical properties (1) to (8). (1) A high stability to heat and light, (2) a high clearing point (or a high maximum temperature of the nematic phase), (3) a low minimum temperature of a liquid crystal phase, (4) a small viscosity ($\eta$), (5) a suitable optical anisotropy ($\Delta n$), (6) a large dielectric anisotropy ($\Delta\varepsilon$), (7) a suitable elastic constant (K), and (8) an excellent compatibility with other liquid crystal compounds.

An effect of physical properties of the liquid crystal compound on the characteristics of the device is as described below. A compound having the high stability to heat and light as described in (1) increases a voltage holding ratio of the device. Thus, a service life of the device becomes longer. A compound having the high clearing point as described in (2) extends a temperature range in which the device can be used. A compound having the low minimum temperature of the liquid crystal phase such as the nematic phase and a smectic phase, as described in (3), in particular, a compound having the low minimum temperature of the nematic phase, also extends the temperature range in which the device can be used. A compound having the small viscosity as described in (4) decreases a response time in the device.

Accordance to a design of the device, a compound having the suitable optical anisotropy, more specifically a large optical anisotropy or a small optical anisotropy, is required. When the response time is shortened by decreasing a cell gap of the device, a compound having the large optical anisotropy is suitable. A compound having the large dielectric anisotropy as described in (6) decreases a threshold voltage of the device. Thus, an electric power consumption of the device is reduced. On the other hand, a compound having the small dielectric anisotropy has an effect of shortening the response time by decreasing viscosity of the composition, or an effect of extending the temperature range in which the device can be used by increasing the maximum temperature of the nematic phase.

With regard to (7), a compound having a large elastic constant shortens the response time of the device. A compound having a small elastic constant reduces the threshold voltage of the device. Therefore, the suitable elastic constant is required according to the characteristics that are desirably improved. A compound having the excellent compatibility with other liquid crystal compounds as described in (8) is preferred. The reason is that the physical properties of the composition are adjusted by mixing the liquid crystal compound having different physical properties.

A variety of liquid crystal compounds having the large dielectric anisotropy have so far been prepared, and various liquid crystal compounds having the large optical anisotropy have also been prepared, because a new compound is expected to have excellent physical properties not found in conventional compounds. The new compound is expected to have a suitable balance regarding at least two physical properties in the liquid crystal composition by adding the new compound to the composition. In view of such a situation, desire has been expressed for a compound having the excellent physical properties and the suitable balance regarding the physical properties (1) to (8) as described above.

CITATION LIST

Patent Literature

Patent literature No. 1: WO 1996/011897 A.

SUMMARY OF INVENTION

Technical Problem

A first object is to provide a liquid crystal compound satisfying at least one of physical properties such as a high stability to heat and light, a high clearing point (or a high maximum temperature of a nematic phase), a low minimum temperature of a liquid crystal phase, a small viscosity, a suitable optical anisotropy, a large dielectric anisotropy, a suitable elastic constant and an excellent compatibility with other liquid crystal compounds. The object is to provide a compound having a smaller viscosity and a larger dielectric anisotropy in comparison with a similar compound. A second object is to provide a liquid crystal composition that contains the compound and satisfies at least one of physical properties such as a high stability to heat and light, a high maximum temperature of a nematic phase, a low minimum temperature of the nematic phase, a small viscosity, a suitable optical anisotropy, a large dielectric anisotropy, a large specific resistance and a suitable elastic constant. The object is to provide a liquid crystal composition having a suitable balance regarding at least two of the physical properties. A third object is to provide a liquid crystal display device that includes the composition and has a wide temperature range in which the device can be used, a short response time, a large voltage holding ratio, a low threshold voltage, a large contrast ratio and a long service life.

Solution to Problem

The invention concerns a compound represented by formula (1), a liquid crystal composition containing the compound, and a liquid crystal display device including the composition.

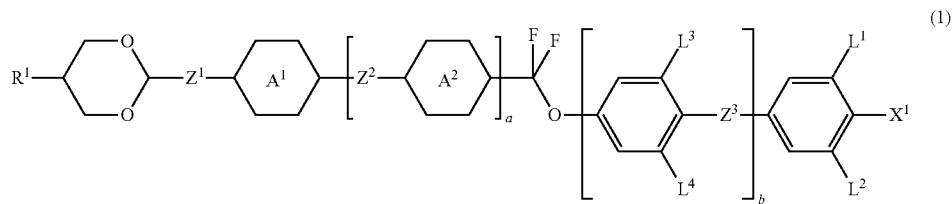

(1)

In formula (1), $R^1$ is alkenyl having 2 to 10 carbons, and in the alkenyl, at least one piece of hydrogen may be replaced by fluorine; ring $A^1$ and ring $A^2$ are each independently 1,4-cyclohexylene, 1,4-phenylene, or 1,4-phenylene in which at least one piece of hydrogen is replaced by fluorine; $Z^1$, $Z^2$, and $Z^3$ are each independently a single bond, —COO—, —OCH$_2$—, —CF$_2$O—, —CH$_2$CH$_2$—, —CF$_2$CF$_2$—, —CF=CF—, —C≡C—, —(CH$_2$)$_4$— or —CH$_2$CH=CHCH$_2$—; $X^1$ is hydrogen, fluorine, —CF$_3$ or —OCF$_3$; $L^1$, $L^2$, $L^3$ and $L^4$ are each independently hydrogen or fluorine; and a and b are each independently 0 or 1, a sum of a and b is 1, and when a is 1, at least one of ring $A^1$ and ring $A^2$ is 1,4-cyclohexylene.

Advantageous Effects of Invention

A first advantage is to provide a liquid crystal compound satisfying at least one of physical properties such as a high stability to heat and light, a high clearing point (or a high maximum temperature of a nematic phase), a low minimum temperature of a liquid crystal phase, a small viscosity, a suitable optical anisotropy, a large dielectric anisotropy, a suitable elastic constant and an excellent compatibility with other liquid crystal compounds. The advantage is to provide a compound having a smaller viscosity and a larger dielectric anisotropy in comparison with a similar compound (see Comparative Examples 1 and 2). A second advantage is to provide a liquid crystal composition that contains the compound and satisfies at least one of physical properties such as a high stability to heat and light, a high maximum temperature of a nematic phase, a low minimum temperature of the nematic phase, a small viscosity, a suitable optical anisotropy, a large dielectric anisotropy, a large specific resistance and a suitable elastic constant. The advantage is to provide a liquid crystal composition having a suitable balance regarding at least two of the physical properties. A third advantage is to provide a liquid crystal display device that includes the composition and has a wide temperature range in which the device can be used, a short response time, a large voltage holding ratio, a low threshold voltage, a large contrast ratio and a long service life.

DESCRIPTION OF EMBODIMENTS

Usage of terms herein is as described below. Terms "liquid crystal compound," "liquid crystal composition" and "liquid crystal display device" may be occasionally abbreviated as "compound," "composition" and "device," respectively. "Liquid crystal compound" is a generic term for a compound having a liquid crystal phase such as a nematic phase or a smectic phase, and also a compound having no liquid crystal phase but being added for the purpose of adjusting physical properties of the liquid crystal composition such as a maximum temperature, a minimum temperature, viscosity and dielectric anisotropy. The compound has a six-membered ring such as 1,4-cyclohexylene or 1,4-phenylene, and has a rod-like molecular structure. "Liquid crystal display device" is a generic term for a liquid crystal display panel and a liquid crystal display module. "Polymerizable compound" is a compound added for the purpose of generating a polymer in the composition.

The liquid crystal composition is prepared by mixing two or more liquid crystal compounds. A proportion (content) of the liquid crystal compound is expressed in terms of weight percent (% by weight) based on the weight of the liquid crystal composition. An additive such as a polymerizable compound, a polymerization initiator, a polymerization inhibitor, an optically active compound, an antioxidant, an ultraviolet light absorber, a light stabilizer, a heat stabilizer, a dye, and a defoaming agent are added to the composition if needed. A proportion (amount of addition) of the additive is expressed in terms of weight percent (% by weight) based on the weight of the liquid crystal composition in a manner similar to the proportion of the liquid crystal compound. Weight per million (ppm) is occasionally used. A proportion of the polymerization initiator or the polymerization inhibitor is exceptionally expressed based on the weight of the polymerizable compound.

"Clearing point" is a transition temperature between the liquid crystal phase and an isotropic phase in the liquid crystal compound. "Minimum temperature of the liquid crystal phase" is a transition temperature between a solid and the liquid crystal phase (the smectic phase, the nematic phase or the like) in the liquid crystal compound. "Maximum temperature of the nematic phase" is a transition temperature between the nematic phase and the isotropic phase in a mixture of the liquid crystal compound and a base liquid crystal or in the liquid crystal composition, and may be occasionally abbreviated as "maximum temperature." "Minimum temperature of the nematic phase" may be occasionally abbreviated as "minimum temperature." An expression "increasing dielectric anisotropy" means that a value thereof positively increases when the composition has a positive dielectric anisotropy, and means that the value negatively increases when the composition has a negative dielectric anisotropy.

The compound represented by formula (1) may be occasionally abbreviated as "compound (1)." At least one compound selected from the group of compounds represented by formula (1) may be occasionally abbreviated as "compound (1)." "Compound (1)" means one compound, a mixture of two compounds or a mixture of three or more compounds represented by formula (1). Same rules apply to any other compound represented by any other formula. In formula (1) to formula (15), a symbol $A^1$, $B^1$, $C^1$ or the like surrounded by a hexagonal shape corresponds to ring $A^1$, ring $B^1$, ring $C^1$ or the like, respectively. The hexagonal shape represents a 6-membered ring such as cyclohexane or benzene. The hexagonal shape may occasionally represent a condensed ring such as naphthalene, and a bridged ring such as adamantane.

A symbol of terminal group $R^1$ is used in a plurality of compounds in chemical formulas of component compounds. In the compounds, two groups represented by two pieces of arbitrary $R^1$ may be identical or different. In one case, for example, $R^1$ of compound (1-1) is ethyl and $R^1$ of compound (1-2) is ethyl. In another case, $R^1$ of compound (1-1) is ethyl and $R^1$ of compound (1-2) is propyl. A same rule also applies to a symbol such as $R^{11}$ and $Z^{11}$. When i is 2, two rings $D^1$ exist in compound (8). In the compounds, two groups represented by two rings $D^1$ may be identical or different. When i is larger than 2, a same rule also applies to two arbitrary rings $D^1$. A same rule is also applied to any other symbol.

An expression "at least one piece of 'A'" means that the number of 'A' is arbitrary. An expression "at least one piece of 'A' may be replaced by 'B'" means that a position of 'A' is arbitrary when the number of 'A' is 1, and the positions can be selected without limitation also when the number of 'A' is 2 or more. A same rule also applies to an expression "at least one piece of 'A' was replaced by 'B'." An expression "at least one piece of 'A' may be replaced by 'B', 'C' or 'D'" means inclusion of a case where arbitrary 'A' is replaced by 'B', a case where arbitrary 'A' is replaced by 'C', a case where arbitrary 'A' is replaced by 'D', and further a case where a plurality of pieces of 'A' are replaced by at least two pieces of 'B', 'C' and/or 'D'. For example, an expression "alkyl in which at least one piece of —$CH_2$— may be replaced by —O— or —CH═CH—" includes alkyl, alkoxy, alkoxyalkyl, alkenyl, alkoxyalkenyl and alkenyloxyalkyl. In addition, such a case where replacement of two successive pieces of —$CH_2$— by —O— results in forming —O—O— is not preferred. In alkyl or the like, a case where replacement of —$CH_2$— of a methyl part (—$CH_2$—H) by —O— results informing —O—H is not preferred, either.

Halogen means fluorine, chlorine, bromine and iodine. Preferred halogen is fluorine and chlorine. Further preferred halogen is fluorine. Alkyl in the liquid crystal compound has a straight chain or a branched chain, and does not include cyclic alkyl. Straight-chain alkyl is generally further preferred to branched-chain alkyl. A same rule also applies to a terminal group such as alkoxy and alkenyl. With regard to a configuration of 1,4-cyclohexylene, trans is preferred to cis for increasing the maximum temperature. Then, 2-fluoro-1, 4-phenylene means two divalent groups described below. In a chemical formula, fluorine may be leftward (L) or rightward (R). A same rule also applies to an asymmetrical divalent group such as tetrahydropyran-2,5-diyl formed by removing two pieces of hydrogen from a ring.

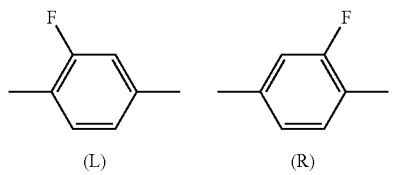

(L)　　　(R)

The invention includes the items described below.

Item 1. A compound represented by formula (1):

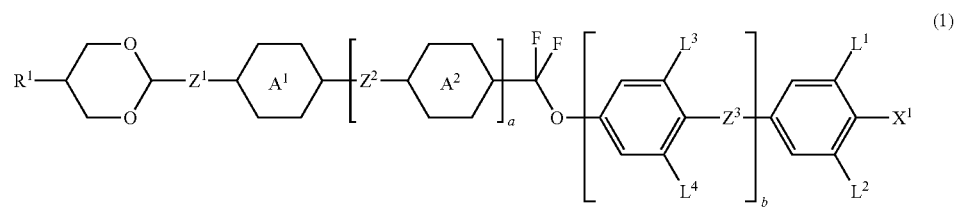

(1)

wherein, in formula (1), $R^1$ is alkenyl having 2 to 10 carbons, and in the alkenyl, at least one piece of hydrogen may be replaced by fluorine; ring and ring $A^2$ are each independently 1,4-cyclohexylene, 1,4-phenylene, or 1,4-phenylene in which at least one piece of hydrogen is replaced by fluorine; $Z^1$, $Z^2$ and $Z^3$ are each independently a single bond, —COO—, —$OCH_2$—, —$CF_2O$—, —$CH_2CH_2$—, —$CF_2CF_2$—, —CF═CF—, —C≡C—, —$(CH_2)_4$— or —$CH_2CH$═$CHCH_2$—; $X^1$ is hydrogen, fluorine, —$CF_3$ or —$OCF_3$; $L^1$, $L^2$, $L^3$ and $L^4$ are each independently hydrogen or fluorine; and a and b are each independently 0 or 1, a sum of a and b is 1, and when a is 1, at least one of ring $A^1$ and ring $A^2$ is 1,4-cyclohexylene.

Item 2. The compound according to item 1, represented by any one of formula (1-1), formula (1-2) and formula (1-3)

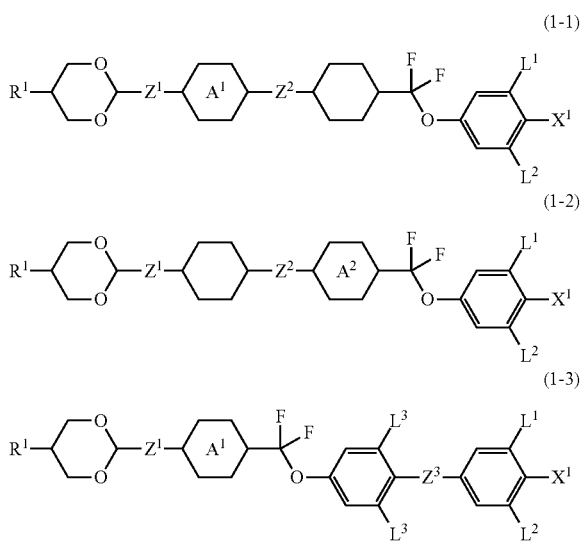

wherein, in formula (1-1) to formula (1-3), $R^1$ is alkenyl having 2 to 10 carbons; ring $A^1$ and ring $A^2$ are each independently 1,4-cyclohexylene, 1,4-phenylene, or 1,4-phenylene in which arbitrary hydrogen is replaced by fluorine; $Z^1$, $Z^2$ and $Z^3$ are each independently a single bond, —COO—, —$CF_2O$—, —$OCH_2$— or —$CH_2CH_2$; $X^1$ is hydrogen, fluorine, —CF$_3$ or —OCF$_3$; and L$^1$, L$^2$, L$^3$ and L$^4$ are each independently hydrogen or fluorine.

Item 3. The compound according to item 2, wherein, in formula (1-1), formula (1-2) or formula (1-3) described in item 2, R$^1$ is alkenyl having 2 to 5 carbons; ring A$^1$ and ring A$^2$ are each independently 1,4-cyclohexylene, 1,4-phenylene, or 1,4-phenylene in which arbitrary hydrogen is replaced by fluorine; Z$^1$, Z$^2$ and Z$^3$ are each independently a single bond, —COO— or —CF$_2$O—; X$^1$ is hydrogen, fluorine, —CF$_3$ or —OCF$_3$; and L$^1$, L$^2$, L$^3$ and L$^4$ are each independently hydrogen or fluorine.

Item 4. The compound according to any one of items 1 to 3, represented by any one of formula (1-a) to formula (1-s):

(1-a)
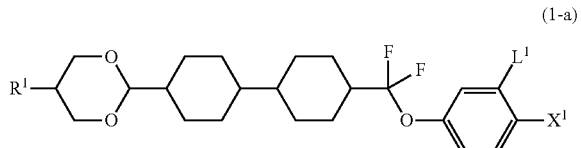

(1-b)
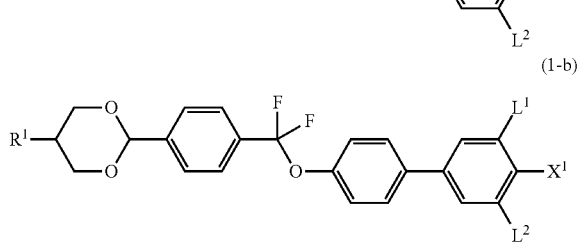

(1-c)
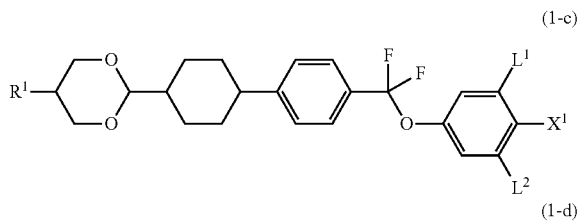

(1-d)
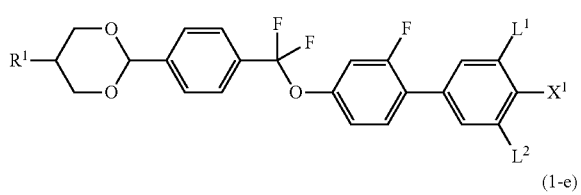

(1-e)
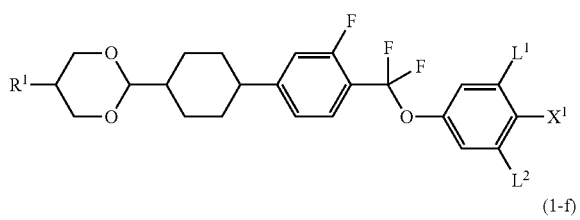

(1-f)
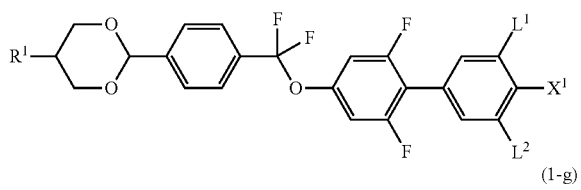

(1-g)
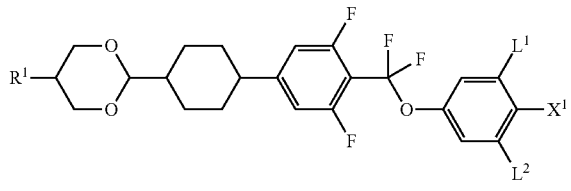

-continued (1-h)
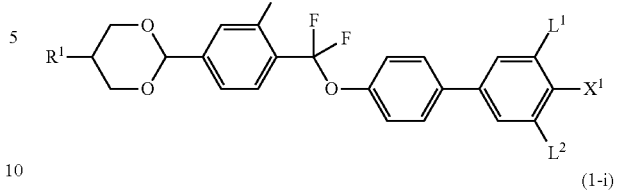

(1-i)
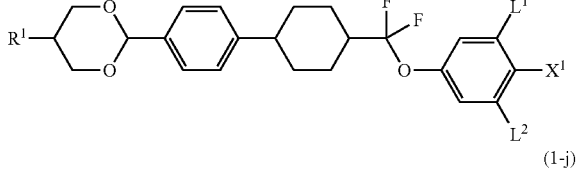

(1-j)
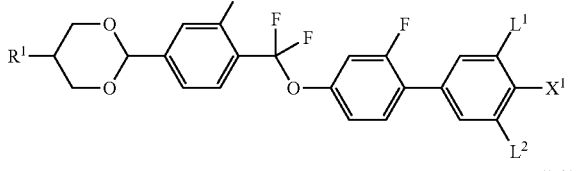

(1-k)
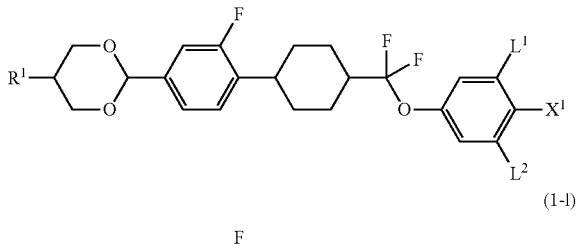

(1-l)
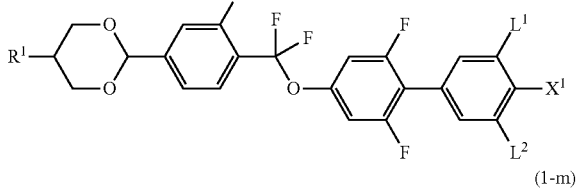

(1-m)
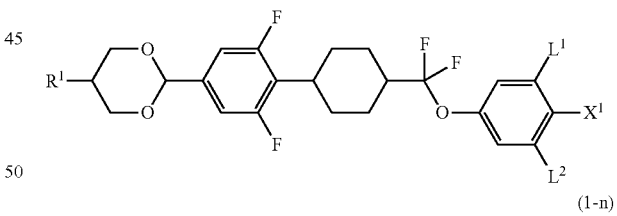

(1-n)
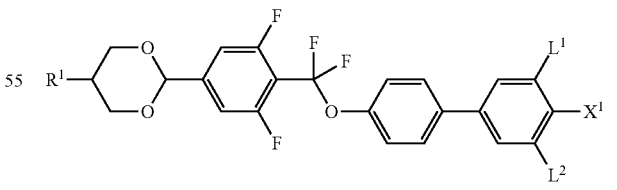

(1-o)
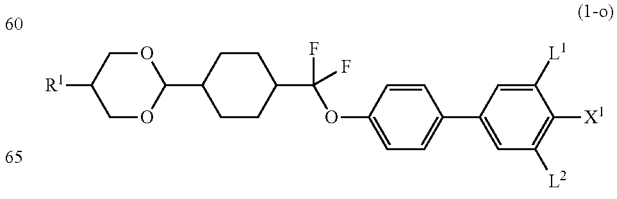

(1-p)
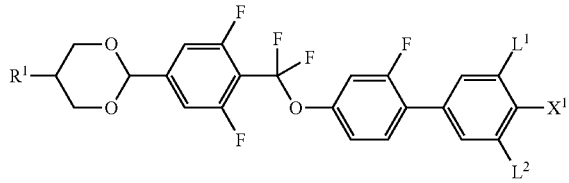

(1-q)
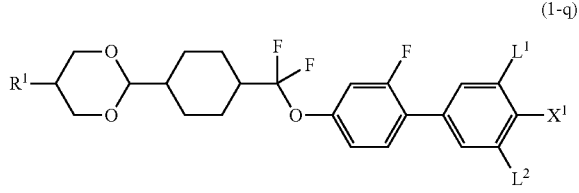

(1-r)
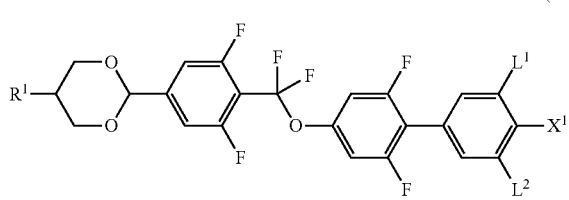

(1-s)
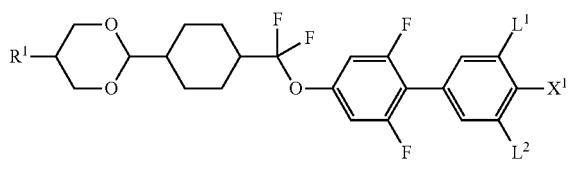

wherein, in formula (1-a) to formula (1-s), $R^1$ is alkenyl having 2 to 5 carbons; $X^1$ is hydrogen, fluorine, —$CF_3$ or —$OCF_3$; and $L^1$ and $L^2$ are each independently hydrogen or fluorine.

Item 5. The compound according to item 4, wherein, in formula (1-a) to formula (1-s) described in item 4, $R^1$ is vinyl, 1-propenyl, 3-butenyl or 3-pentenyl.

Item 6. The compound according to item 4, wherein, in formula (1-a) to formula (1-s) described in item 4, $R^1$ is vinyl, 1-propenyl, 3-butenyl or 3-pentenyl; $X^1$ is fluorine; and $L^1$ and $L^2$ are hydrogen or fluorine.

Item 7. The compound according to item 4, wherein, in formula (1-a) to formula (1-s) described in item 4, $R^1$ is vinyl, 1-propenyl, 3-butenyl, or 3-pentenyl; $X^1$ is —$OCF_3$; $L^1$ and $L^2$ are each independently hydrogen or fluorine.

Item 8. A liquid crystal composition containing at least one compound according to any one of items 1 to 7.

Item 9. The liquid crystal composition according to item 8, further containing at least one compound selected from the group of compounds represented by formula (2) to formula (4):

(2)
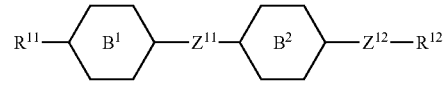

(3)
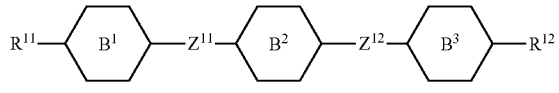

(4)
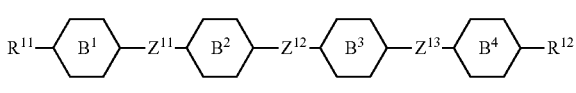

wherein, in formula (2) to formula (4), $R^{11}$ and $R^{12}$ are each independently alkyl having 1 to 10 carbons or alkenyl having 2 to 10 carbons, and in the alkyl and the alkenyl, at least one piece of —$CH_2$— may be replaced by —O—, and at least one piece of hydrogen may be replaced by fluorine;

ring $B^1$, ring $B^2$, ring $B^3$ and ring $B^4$ are each independently 1,4-cyclohexylene, 1,4-phenylene, 2-fluoro-1,4-phenylene, 2,5-difluoro-1,4-phenylene or pyrimidine-2,5-diyl; and $Z^{11}$, $Z^{12}$ and $Z^{13}$ are each independently a single bond, —$CH_2CH_2$—, —CH=CH—, —C≡C— or —COO—.

Item 10. The liquid crystal composition according to item 8 or 9, further containing at least one compound selected from the group of compounds represented by formula (5) to formula (7):

(5)
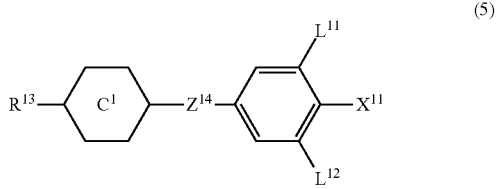

(6)
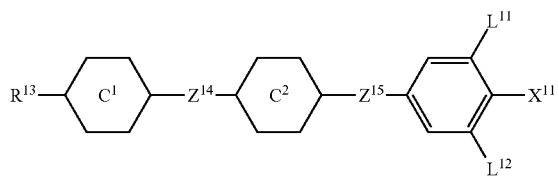

(7)
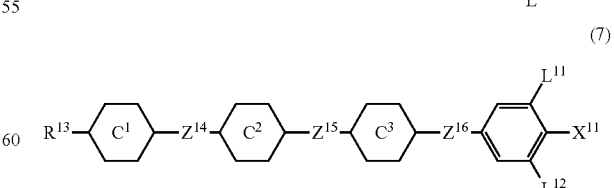

wherein, in formula (5) to formula (7), $R^{13}$ is alkyl having 1 to 10 carbons or alkenyl having 2 to 10 carbons, and in the alkyl and the alkenyl, at least one piece of —CH$_2$— may be replaced by —O— and at least one piece of hydrogen may be replaced by fluorine;

X$^{11}$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$;

ring C$^1$, ring C$^2$ and ring C$^3$ are each independently 1,4-cyclohexylene, 1,4-phenylene in which at least one piece of hydrogen may be replaced by fluorine, tetrahydropyran-2,5-diyl, 1,3-dioxane-2,5-diyl or pyrimidine-2,5-diyl;

Z$^{14}$, Z$^{15}$ and Z$^{16}$ are each independently a single bond, —CH$_2$CH$_2$—, —CH═CH—, —C≡C—, —COO—, —CF$_2$O—, —OCF$_2$—, —CH$_2$O— or —(CH$_2$)$_4$—; and L$^{11}$ and L$^{12}$ are each independently hydrogen or fluorine.

Item 11. The liquid crystal composition according to any one of items 8 to 10, further containing at least one compound selected from the group of compounds represented by formula (8):

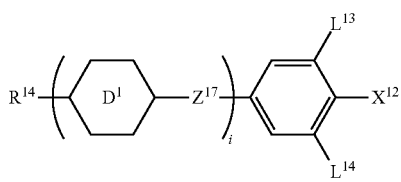
(8)

wherein, in formula (8),

R$^{14}$ is alkyl having 1 to 10 carbons or alkenyl having 2 to 10 carbons, and in the alkyl and the alkenyl, at least one piece of —CH$_2$— may be replaced by —O— and at least one piece of hydrogen may be replaced by fluorine;

X$^{12}$ is —C≡N or —C≡C—C≡N;

ring D$^1$ is each independently 1,4-cyclohexylene, 1,4-phenylene in which at least one piece of hydrogen may be replaced by fluorine, tetrahydropyran-2,5-diyl, 1,3-dioxane-2,5-diyl or pyrimidine-2,5-diyl;

Z$^{17}$ is each independently a single bond, —CH$_2$CH$_2$—, —C≡C—, —COO—, —CF$_2$O—, —OCF$_2$—, or —CH$_2$O—;

L$^{13}$ and L$^{14}$ are each independently hydrogen or fluorine; and i is 1, 2, 3 or 4.

Item 12. The liquid crystal composition according to any one of items 8 to 11, further containing at least one compound selected from the group of compounds represented by formula (9) to formula (15):

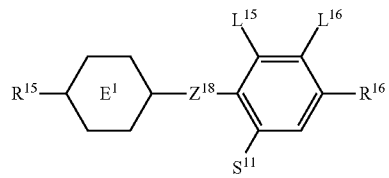
(9)

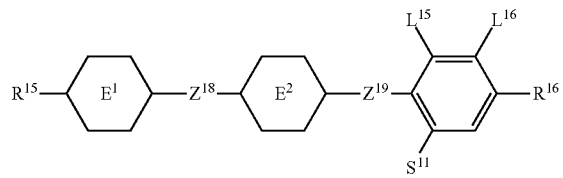
(10)

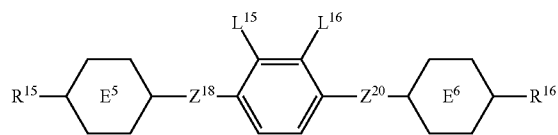
(11)

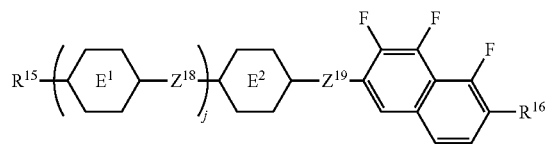
(12)

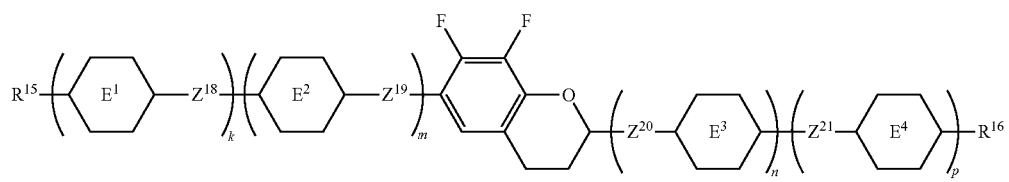
(13)

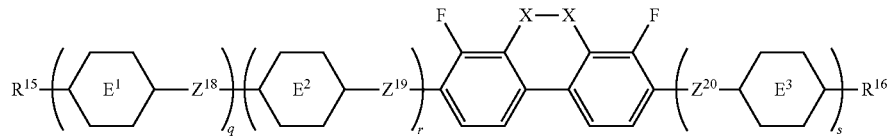
(14)

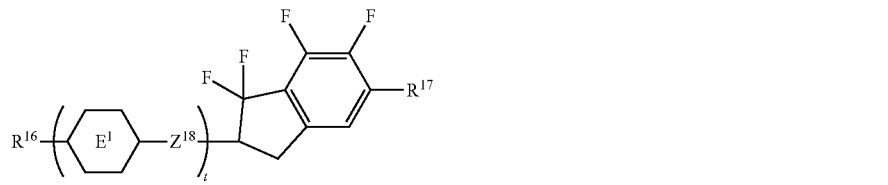
(15)

wherein, in formula (9) to formula (15), $R^{15}$ and $R^{16}$ are each independently alkyl having 1 to 10 carbons or alkenyl having 2 to 10 carbons, and in the alkyl and the alkenyl, at least one piece of —CH$_2$— may be replaced by —O—, and at least one piece of hydrogen may be replaced by fluorine;

$R^{17}$ is hydrogen, fluorine, alkyl having 1 to 10 carbons or alkenyl having 2 to 10 carbons, and in the alkyl and the alkenyl, at least one piece of —CH$_2$— may be replaced by —O—, and at least one piece of hydrogen may be replaced by fluorine;

ring $E^1$, ring $E^2$, ring $E^3$ and ring $E^4$ are each independently 1,4-cyclohexylene, 1,4-cyclohexenylene, 1,4-phenylene in which at least one piece of hydrogen may be replaced by fluorine, tetrahydropyran-2,5-diyl or decahydronaphthalene-2,6-diyl;

ring $E^5$ and ring $E^6$ are each independently 1,4-cyclohexylene, 1,4-cyclohexenylene, 1,4-phenylene, tetrahydropyran-2,5-diyl or decahydronaphthalene-2,6-diyl;

$Z^{18}$, $Z^{19}$, $Z^{20}$ and $Z^{21}$ are each independently a single bond, —CH$_2$CH$_2$—, —COO—, —CH$_2$O—, —OCF$_2$— or —OCF$_2$CH$_2$CH$_2$;

$L^{15}$ and $L^{16}$ are each independently fluorine or chlorine;

$S^{11}$ is hydrogen or methyl;

X is —CHF— or —CF$_2$—; and j, k, m, n, p, q, r and s are each independently 0 or 1, a sum of k, m, n and p is 1 or 2, a sum of q, r and s is 0, 1, 2 or 3, and t is 1, 2 or 3.

Item 13. A liquid crystal display device including the liquid crystal composition according to any one of items 8 to 12.

The invention further includes the following items: (a) the composition, further containing one, two or at least three additives selected from the group of a polymerizable compound, a polymerization initiator, a polymerization inhibitor, an optically active compound, an antioxidant, an ultraviolet light absorber, a light stabilizer, a heat stabilizer, a dye and a defoaming agent, (b) the liquid crystal composition, having a maximum temperature of a nematic phase of 70° C. or higher, an optical anisotropy (measured at 25° C.) at a wavelength of 589 nm of 0.07 or more, and a dielectric anisotropy (measured at 25° C.) at a frequency of 1 kHz of 2 or more, and (c) the liquid crystal display device, wherein an operating mode in the liquid crystal display device is a TN mode, an ECB mode, an OCB mode, an IPS mode or an FPA mode, and a driving mode in the liquid crystal display device is an active matrix (AM) mode.

An aspect of compound (1), a method for preparing compound (1), the liquid crystal composition and the liquid crystal display device are described in the order.

1. Aspect of Compound (1)

Compound (1) of the invention has features of having an alkenyl terminal group and a CF$_2$O bonding group. The compound has a smaller viscosity and a larger dielectric anisotropy in comparison with a similar compound (see Comparative Examples 1 and 2). A preferred example of compound (1) is described. Preferred examples of terminal groups $R^1$ and $X^1$, rings $A^1$ and $A^2$, bonding groups $Z^1$, $Z^2$ and $Z^3$, and substituents $L^1$ and $L^2$ in compound (1) are also applied to subordinate formulas of compound (1). In compound (1), physical properties can be arbitrarily adjusted by suitably combining kinds of groups. Incidentally, compound (1) may contain an isotope such as $^2$H (deuterium) and $^{13}$C in an amount larger than an amount of natural abundance because no significant difference exists in physical properties of the compound. In addition, definitions of symbols of compound (1) are as described in item 1.

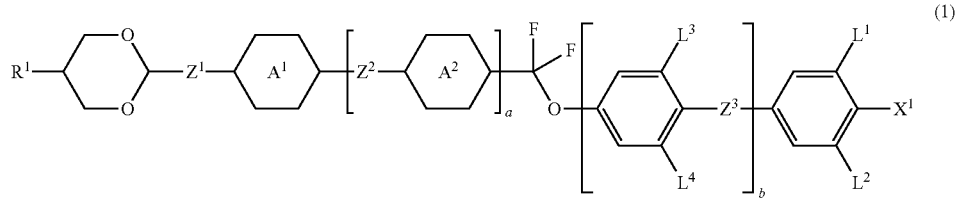

(1)

Examples of preferred compound (1) include compound (1-1) to compound (1-3) described in item 2. Further preferred examples include compound (1-a) to compound (1-s) described in item 4. Most preferred examples include compounds described in items 5 to 7. In compound (1-a) to compound (1-s), preferred examples include compounds (1-a) to (1-g), compound (1-j), compound (1-l), and compounds (1-n) to (1-s). Further preferred examples include compound (1-d) to (1-h), compound (1-j), compound (1-l), compound (1-n), and compounds (1-p) to (1-s). Particularly preferred examples include compound (1-d), compound (1-e), compound (1-g), compound (1-i), compound (1-l), compound (1-p), and compound (1-f).

In formula (1), $R^1$ is alkenyl having 2 to 10 carbons, and in the alkenyl, at least one piece of hydrogen may be replaced by fluorine.

Preferred alkenyl is vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl or 5-hexenyl. Further preferred alkenyl is vinyl, 1-propenyl, 3-butenyl or 3-pentenyl for decreasing the viscosity. A preferred configuration of —CH═CH— in the alkenyl depends on a position of a double bond. Trans is preferred in the alkenyl such as 1-propenyl, 1-butenyl, 1-pentenyl, 1-hexenyl, 3-pentenyl and 3-hexenyl for decreasing the viscosity, for instance. Cis is preferred in the alkenyl such as 2-butenyl, 2-pentenyl and 2-hexenyl.

Preferred examples of alkenyl in which at least one piece of hydrogen is replaced by fluorine include 2,2-difluorovinyl, 3,3-difluoro-2-propenyl, 4,4-difluoro-3-butenyl, 5,5-difluoro-4-pentenyl or 6,6-difluoro-5-hexenyl. For decreasing the viscosity, further preferred examples include 2,2-difluorovinyl or 4,4-difluoro-3-butenyl.

When $R^1$ has a straight chain, a temperature range of the liquid crystal phase is wide and the viscosity is small. When $R^1$ has a branched chain, compatibility with other liquid crystal compounds is good. A compound in which $R^1$ is optically active is useful as a chiral dopant. A reverse twisted domain that is generated in the liquid crystal display device can be prevented by adding the compound to the composition. A compound in which $R^1$ is not optically active is useful as a component of the composition. When $R^1$ is alkenyl, the preferred configuration depends on the position of the double bond. The alkenyl compound having the preferred configuration has a small viscosity, a high maximum temperature or a wide temperature range of the liquid crystal phase.

Preferred $R^1$ includes vinyl, 1-propenyl, 3-butenyl, 3-pentenyl, 2,2-difluorovinyl or 4,4-difluoro-3-butenyl. Further preferred $R^1$ includes vinyl, 1-propenyl, 3-butenyl or 3-pentenyl. Further preferred $R^1$ includes 2,2-difluorovinyl or 4,4-difluoro-3-butenyl. Particularly preferred $R^1$ is 1-propenyl.

In formula (1), ring $A^1$ and ring $A^2$ are each independently 1,4-cyclohexylene, 1,4-phenylene, or 1,4-phenylene in which at least one piece of hydrogen is replaced by fluorine.

Preferred ring $A^1$ or ring $A^2$ are 1,4-cyclohexylene, 1,4-phenylene, 2-fluoro-1,4-phenylene, 2,3-difluoro-1,4-phenylene or 2,6-difluoro-1,4-phenylene. Further preferred ring $A^1$ or ring $A^2$ is 1,4-cyclohexylene, 1,4-phenylene, 2-fluoro-1,4-phenylene or 2,6-difluoro-1,4-phenylene. Particularly preferred ring $A^1$ or ring $A^2$ is 1,4-cyclohexylene, 1,4-phenylene, 2-fluoro-1,4-phenylene or 2,6-difluoro-1,4-phenylene.

In formula (1), $Z^1$, $Z^2$ and $Z^3$ are each independently a single bond, —COO—, —OCH$_2$—, —CF$_2$O—, —CH$_2$CH$_2$—, —CF$_2$CF$_2$—, —CF=CF—, —C≡C—, —CH$_2$CH=CHCH$_2$—, or —(CH$_2$)$_4$—.

Preferred $Z^1$, $Z^2$ or $Z^3$ includes a single bond, —COO—, —OCH$_2$—, —CF$_2$O—, —CH$_2$CH$_2$—, or —C≡C—. Further preferred $Z^1$, $Z^2$ or $Z^3$ includes a single bond, —COO—, —OCH$_2$—, —CF$_2$O—, —CH$_2$CH$_2$—, or —C≡C—. Particularly preferred $Z^1$, $Z^2$ or $Z^3$ includes a single bond, —COO— or —OCH$_2$—. Most preferred $Z^1$ $Z^2$ or $Z^3$ includes a single bond.

In formula (1), $X^1$ is hydrogen, fluorine, —CF$_3$ or —OCF$_3$. Preferred $X^1$ includes fluorine, —CF$_3$ or —OCF$_3$. Further preferred $X^1$ includes fluorine. Further preferred $X^1$ includes —OCF$_3$.

In formula (1), $L^1$, $L^2$, $L^3$ and $L^4$ are each independently hydrogen or fluorine. Preferred $L^1$ and $L^2$ are a combination of hydrogen and fluorine. Preferred $L^3$ and $L^4$ are a combination of hydrogen and fluorine.

In formula (1), a and b are each independently 0 or 1, and a sum of a and b is 1. Furthermore, when a is 1, at least one of ring $A^1$ and ring $A^2$ is 1,4-cyclohexylene.

2. Synthesis of Compound (1)

A method for preparing compound (1) is described. Compound (1) can be prepared by suitably combining techniques of synthetic organic chemistry. A method for introducing an objective terminal group, ring and bonding group into a starting material is described in books such as Organic Syntheses (John Wiley & Sons, Inc.), Organic Reactions (John Wiley & Sons, Inc.), Comprehensive Organic Synthesis (Pergamon Press) and New Experimental Chemistry Course (Shin Jikken Kagaku Koza, in Japanese) (Maruzen Co., Ltd.).

2-1. Formation of Bonding Group Z

With regard to methods for forming bonding groups $Z^1$ to $Z^3$, a scheme is first shown. Next, reactions described in the scheme are described in methods (1) to (11). In the scheme, MSG$^1$ (or MSG$^2$) is a monovalent organic group having at least one ring. The monovalent organic groups represented by two or more MSG$^1$ (or MSG$^2$) used in the scheme may be identical or different. Compounds (1A) to (1J) correspond to compound (1)

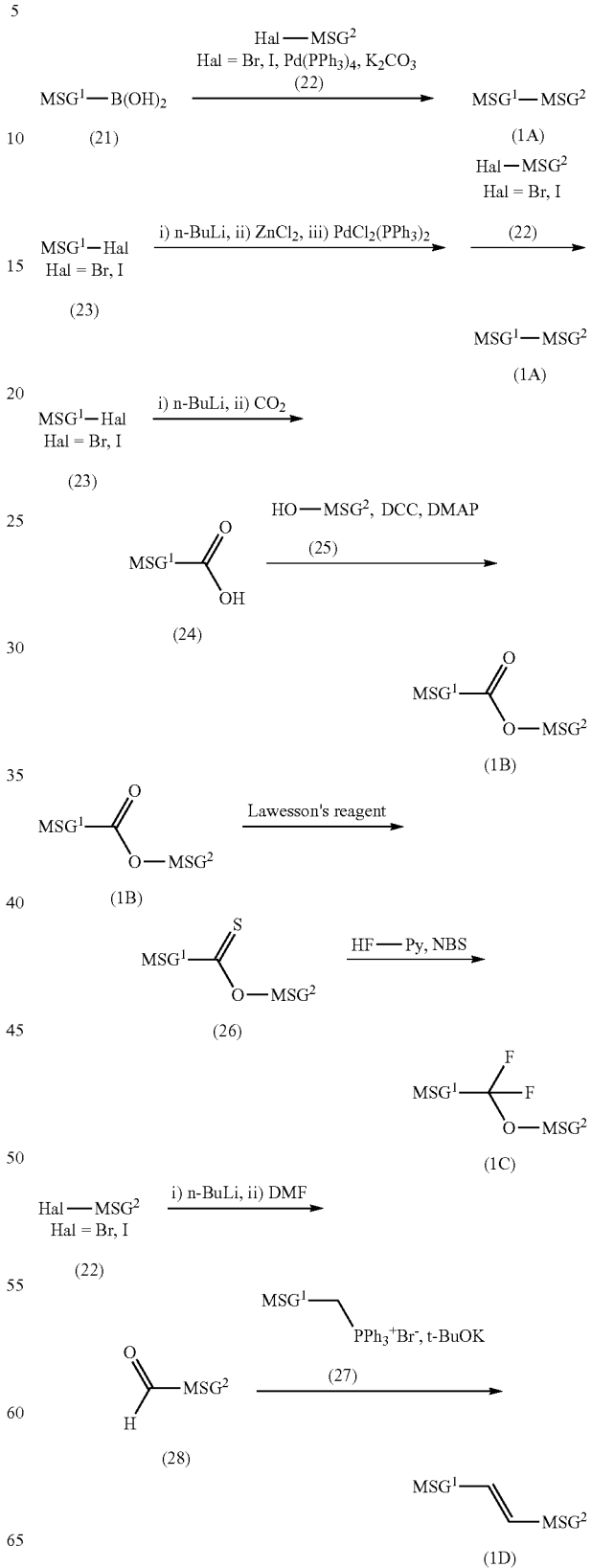

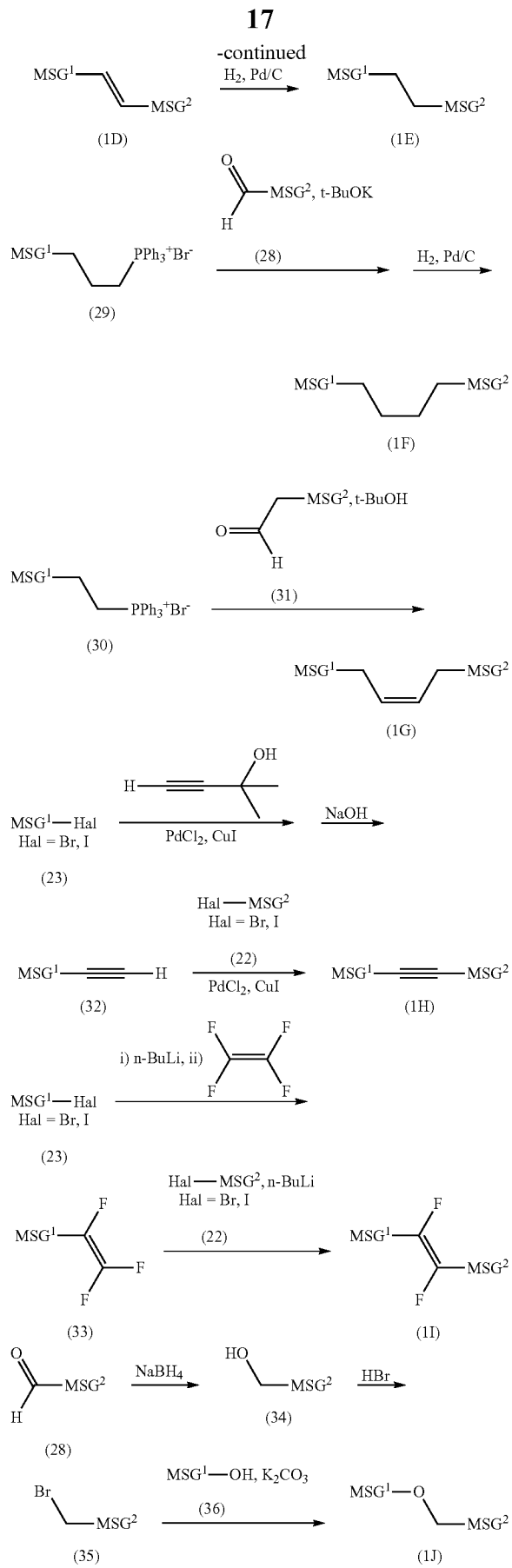

(1) Formation of Single Bond

Compound (1A) is prepared by allowing aryl boric acid (21) prepared by a publicly known method to react with halide (22) in the presence of catalysts such as carbonate and tetrakis(triphenylphosphine)palladium. Compound (1A) is also prepared by allowing halide (23) prepared according to a known method to react with n-butyllithium and subsequently with zinc chloride, and further with halide (22) in the presence of a catalyst such as dichlorobis(triphenylphosphine)palladium.

(2) Formation of —COO—

Carboxylic acid (24) is obtained by allowing halide (23) to react with n-butyllithium and then with carbon dioxide. Compound (1B) is prepared by dehydrating compound (25) and carboxylic acid prepared according to a known method in the presence of 1,3-dicyclohexylcarbodiimide (DCC) and 4-dimethylaminopyridine (DMAP).

(3) Formation of —CF$_2$O—

Thionoester (26) is obtained by treating compound (18) with a thiation agent such as Lawesson's reagent. Compound (1C) is prepared by fluorinating thionoester (26) with a hydrogen fluoride pyridine complex and N-bromosuccinimide (NES). Refer to M. Kuroboshi et al., Chem. Lett., 1992, 827. Compound (1C) is also prepared by fluorinating thionoester (26) with (diethylamino) sulfur trifluoride (DAST). Refer to W. H. Bunnelle et al., J. Org. Chem. 1990, 55, 768. The bonding group can also be formed according to the method described in Peer Kirsch et al., Angew. Chem. Int. Ed. 2001, 40, 1480.

(4) Formation of —CH=CH—

Aldehyde (28) is obtained by treating halide (22) with n-butyllithium and then allowing the resulting compound to react with formamide such as N,N-dimethylformamide (DMF). Phosphorus ylide is generated by treating phosphonium salt (27) prepared by a publicly known method with a base such as potassium t-butoxide. Compound (1D) is prepared by allowing the phosphorus ylide (28) to react with aldehyde (28). Because a cis isomer is formed depending on reaction conditions, the cis isomer is isomerized into a trans isomer according to a known method, when necessary.

(5) Formation of —CH$_2$CH$_2$—

Compound (1E) is prepared by hydrogenating compound (1D) in the presence of a catalyst such as palladium on carbon.

(6) Formation of —(CH$_2$)$_4$—

A compound having —(CH$_2$)$_2$—CH=CH— is obtained according to method (4) by using a phosphonium salt (29) in place of phosphonium salt (27). Compound (1F) is prepared by performing catalytic hydrogenation of the compound obtained.

(7) Formation of —CH$_2$CH=CHCH$_2$—

Compound (1G) is prepared according to method (4) by using a phosphonium salt (30) in place of phosphonium salt (27) and aldehyde (31) in place of aldehyde (28). Because a trans isomer is formed depending on reaction conditions, the trans isomer is isomerized into a cis isomer according to a known method, when necessary.

(8) Formation of —C≡C—

Compound (32) is obtained by allowing compound (23) to react with 2-methyl-3-butyn-2-ol in the presence of catalysts including dichloropalladium and copper halide, and then performing deprotection under basic conditions. Compound (1H) is prepared by allowing compound (32) to react with halide (22) in the presence of catalysts including dichloropalladium and copper halide.

(9) Formation of —CF=CF—

Compound (33) is obtained by treating halide (23) with n-butyllithium and then allowing the treated compound to react with tetrafluoroethylene. Compound (11) is prepared by treating halide (22) with n-butyllithium and then allowing the treated compound to react with compound (33).

(10) Formation of —OCH$_2$—

Compound (34) is obtained by reducing aldehyde (28) with a reducing agent such as sodium boron hydride. Bromide (35) is obtained by brominating compound (34) with hydrobromic acid or the like. Compound (1J) is prepared by allowing bromide (35) to react with compound (36) in the presence of a base such as potassium carbonate.

(11) Formation of —CF$_2$CF$_2$—

A compound having —(CF$_2$)$_2$— is obtained by fluorinating a diketone (—COCO—) with sulfur tetrafluoride in the presence of a hydrogen fluoride catalyst according to the method described in J. Am. Chem. Soc., 2001, 123, 5414.

2-2. Formation of Ring A$^1$ and Ring A$^2$

With regard to a ring such as 1,4-cyclohexylene, 1,4-phenylene, 2-fluoro-1,4-phenylene, 2,6-difluoro-1,4-phenylene, tetrahydropyran-2,5-diyl, 1,3-dioxane-2,5-diyl, pyrimidine-2,5-diyl or pyridine-2,5-diyl, a starting material is commercially available or a synthesis method is well known.

2-3. Synthesis Example

An example of a method for preparing compound (1) is as described below. Then, 1,3-diol and aldehyde prepared by a publicly known method are heated and stirred under acidic conditions, and can be led to compound (1). In the compounds, definitions of symbols such as R$^1$ and ring A$^1$ are identical with the definitions in item 1 described above.

of approximately 1% by weight to approximately 99% by weight in order to develop excellent physical properties. In a composition having a positive dielectric anisotropy, a preferred content of compound (1) is in the range of approximately 5% by weight to approximately 60% by weight. In a composition having a negative dielectric anisotropy, a preferred content of compound (1) is approximately 30% or less by weight. The composition may also contain compound (1) and a liquid crystal compound that is not described herein.

The composition contains compound (1) as component A, and further preferably contains a liquid crystal compound selected from components B, C, D and E shown below. Component B includes compounds (2) to (4). Component C includes compounds (5) to (7). Component D includes compound (8). Component E includes compounds (9) to (15). The composition may also contain any other liquid crystal compound different from compounds (2) to (15). When the composition is prepared, components B, C, D and E are preferably selected in taking into account positive or negative dielectric anisotropy and magnitude thereof. A composition having suitably selected components has a high stability to heat and light, a high maximum temperature, a low minimum temperature, a small viscosity, a suitable optical anisotropy (namely, a large optical anisotropy or a small optical anisotropy), a large dielectric anisotropy, a large specific resistance and a suitable elastic constant (that is, a large elastic constant or a small elastic constant).

Component B is a compound in which two terminal groups are alkyl or the like. Preferred examples of component B include compounds (2-1) to (2-11), compounds (3-1) to (3-19), and compounds (4-1) to (4-7). In the compounds, R$^{11}$ and R$^{12}$ are each independently alkyl having 1 to 10 carbons or alkenyl having 2 to 10 carbons, and in the alkyl and the alkenyl, at least one piece of —CH$_2$— may be replaced by —O—, and at least one piece of hydrogen may be replaced by fluorine.

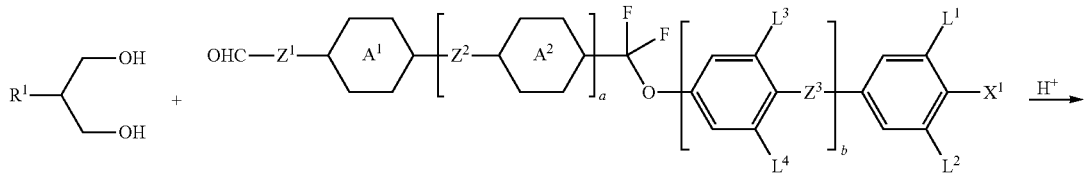

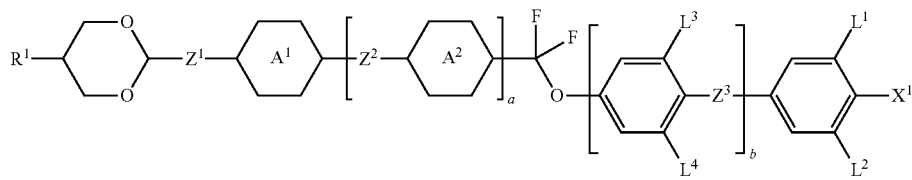

(1)

3. Liquid Crystal Composition 3-1. Component Compound

The liquid crystal composition of the invention will be described below. The composition contains at least one compound (1) as component A. The composition may contain two or more compounds (1). A component in the composition may be compound (1) only. The composition preferably contains at least one compound (1) in the range

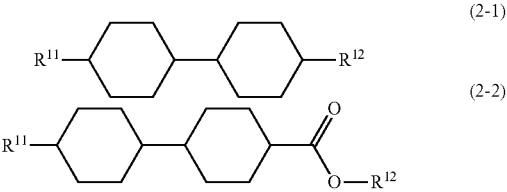

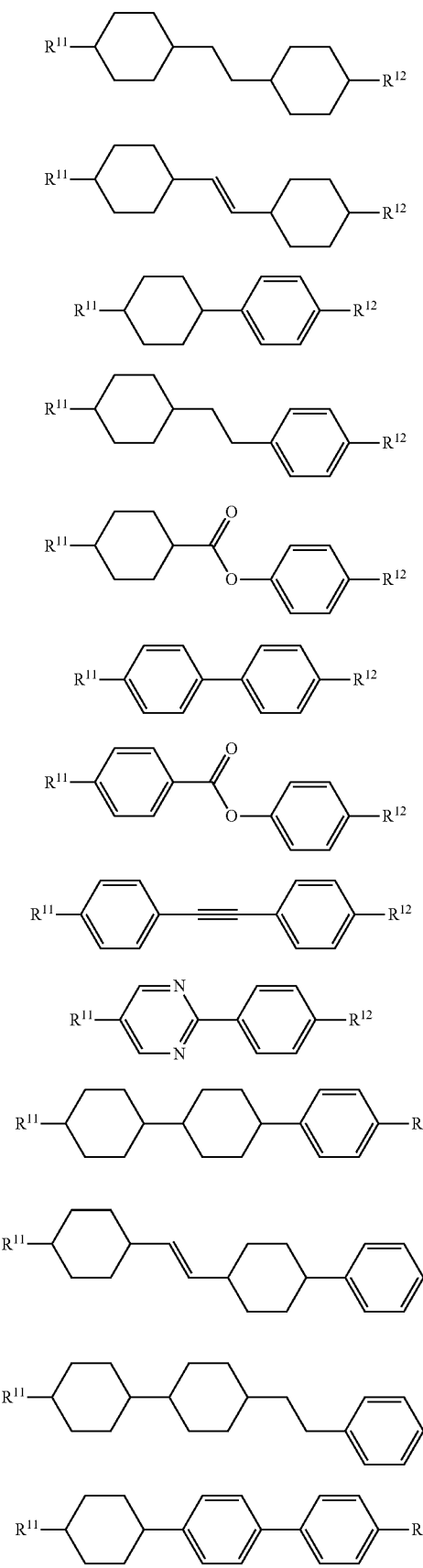
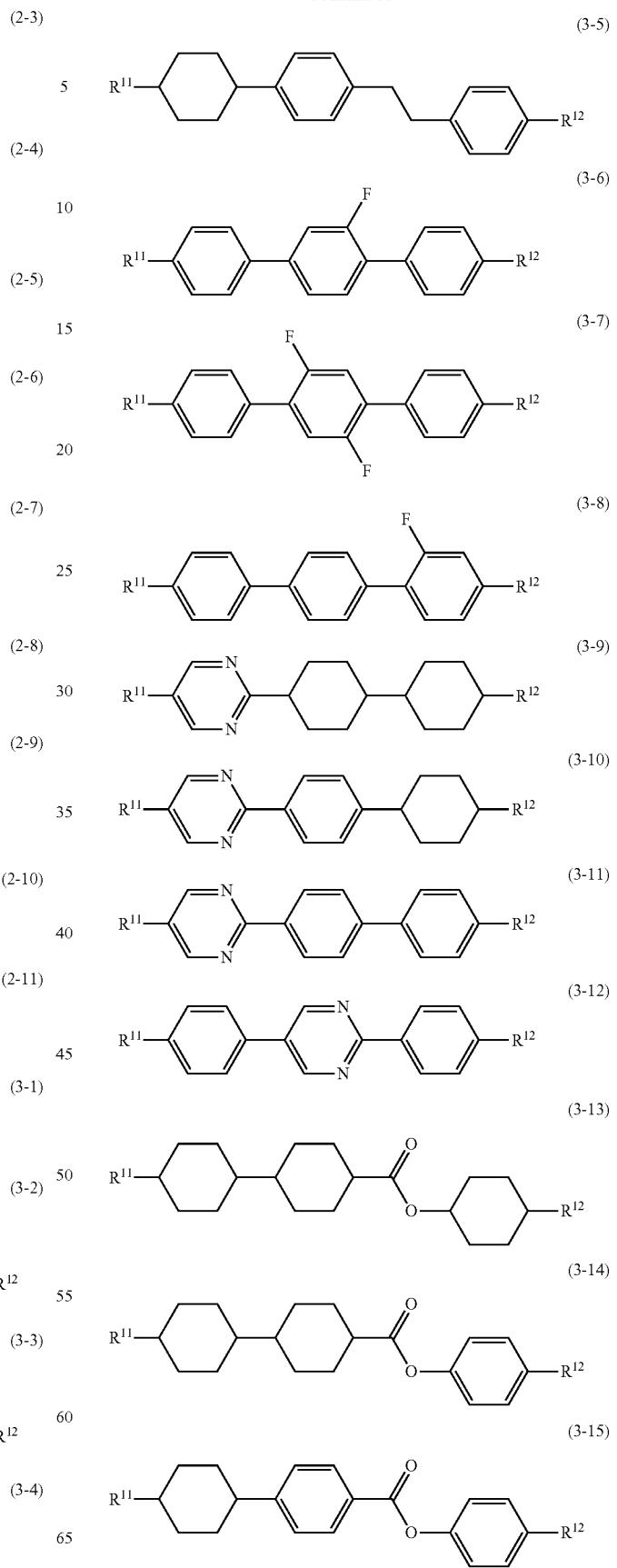

-continued (3-16)
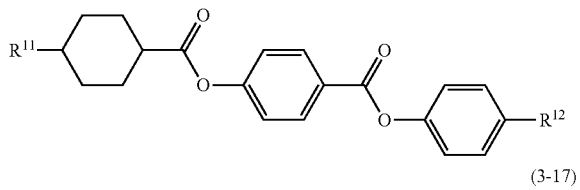

(3-17)
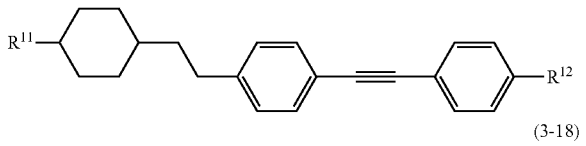

(3-18)
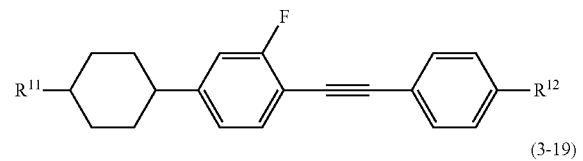

(3-19)
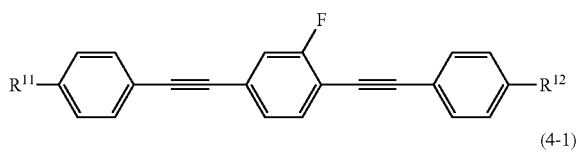

(4-1)
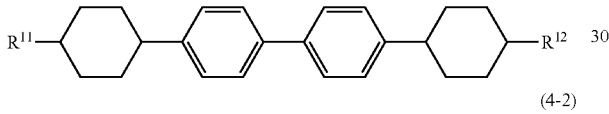

(4-2)

(4-3)
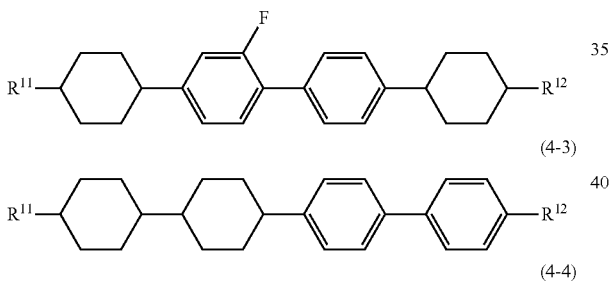

(4-4)

(4-5)

(4-6)
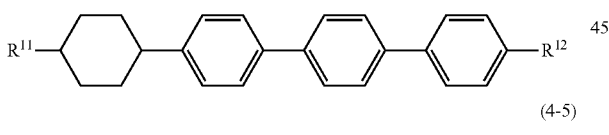

(4-7)
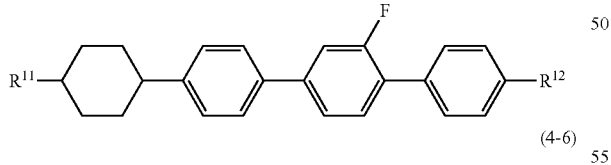

Component B has a small dielectric anisotropy. Component B is close to neutrality. Compound (2) is effective in decreasing the viscosity or adjusting the optical anisotropy. Compounds (3) and (4) are effective in extending the temperature range of the nematic phase by increasing the maximum temperature or adjusting the optical anisotropy.

When the content of component B is increased, the viscosity of the composition decreases, but the dielectric anisotropy also decreases. Thus, as long as a desired value of threshold voltage of the device is satisfied, the content is preferably as large as possible. When a composition for the IPS mode, the VA mode or the like is prepared, the content of component B is preferably approximately 30% by weight or more, and further preferably, approximately 40% by weight or more, based on the weight of the liquid crystal composition.

Component C is a compound having halogen or a fluorine-containing group at a right terminal. Preferred examples of component C include compounds (5-1) to (5-16), compounds (6-1) to (6-113), and compounds (7-1) to (7-57). In the compounds, $R^{13}$ is alkyl having 1 to 10 carbons or alkenyl having 2 to 10 carbons, and in the alkyl and the alkenyl, at least one piece of —$CH_2$— may be replaced by —O—, and at least one piece of hydrogen may be replaced by fluorine; and $X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$.

(5-1)
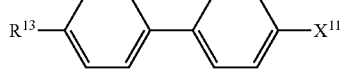

(5-2)
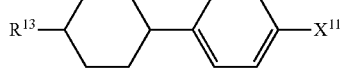

(5-3)
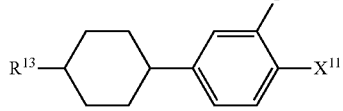

(5-4)
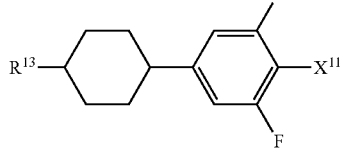

(5-5)
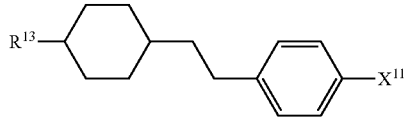

(5-6)
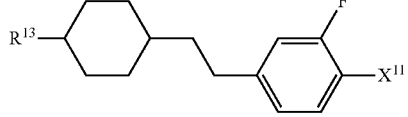

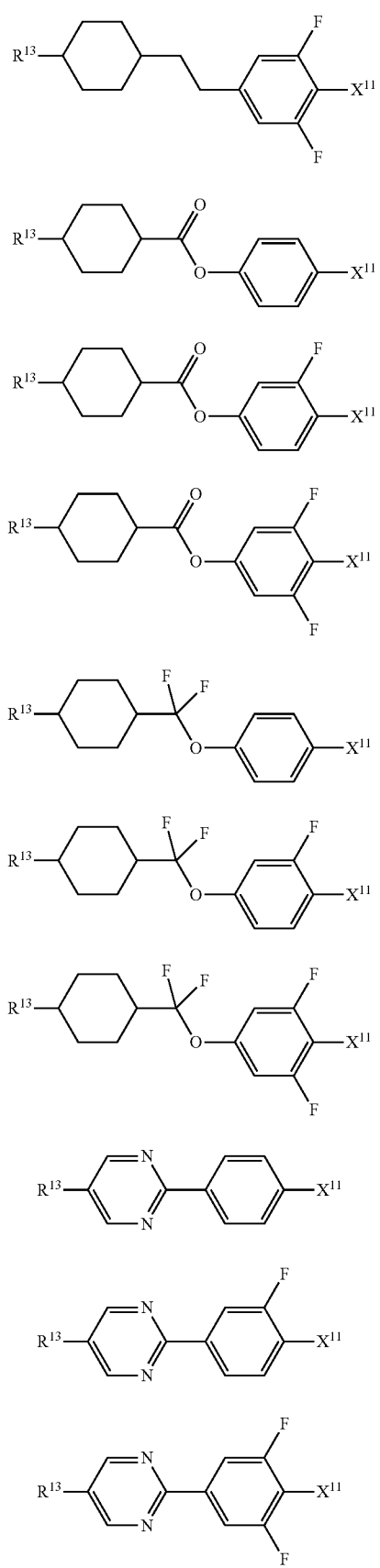
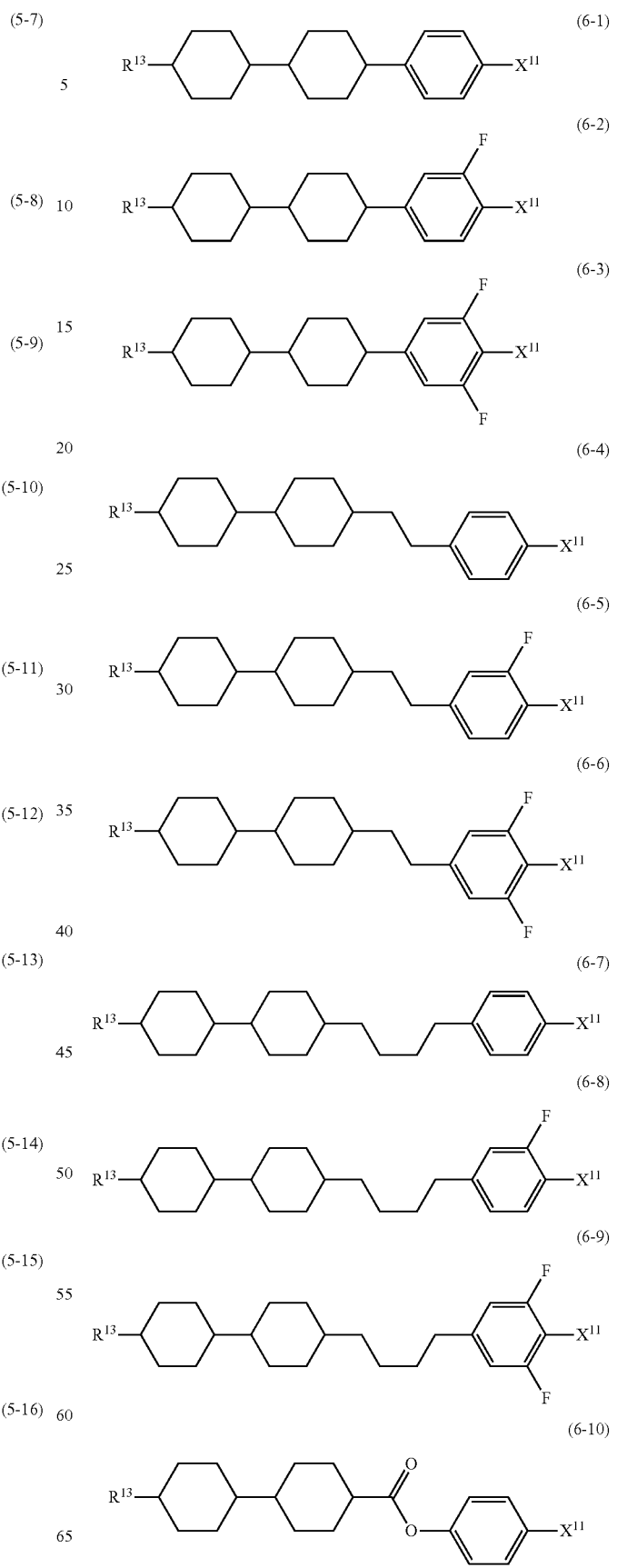

(6-11)
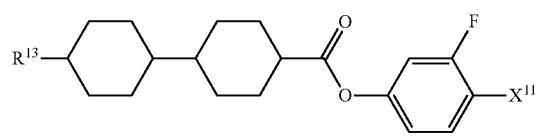
(6-12)
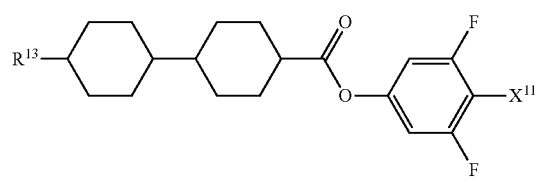
(6-13)
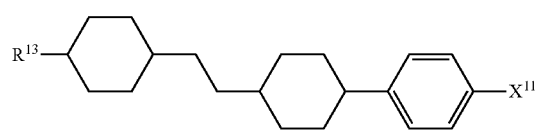
(6-14)
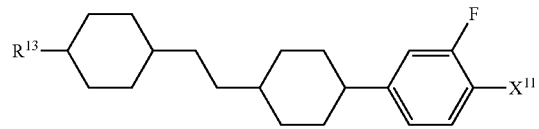
(6-15)
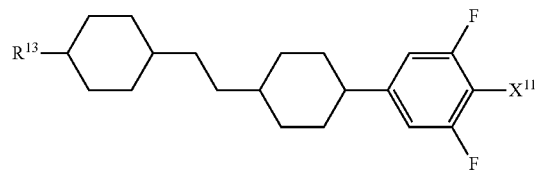
(6-16)
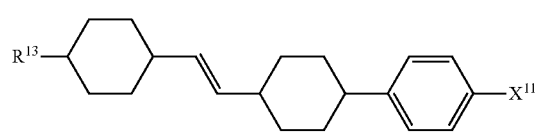
(6-17)
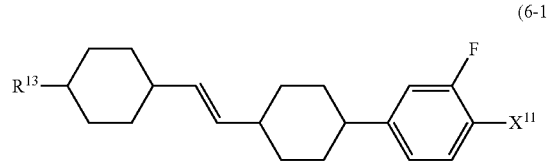
(6-18)
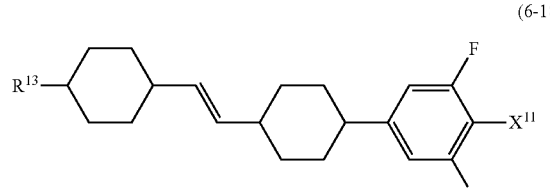
(6-19)
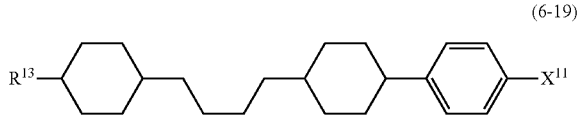
(6-20)
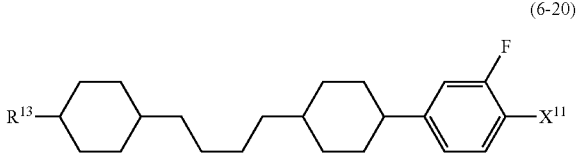
(6-21)
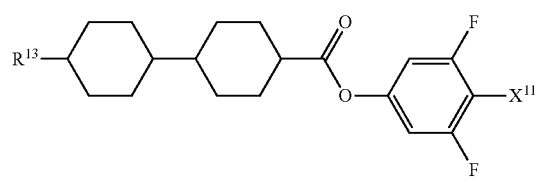
(6-22)
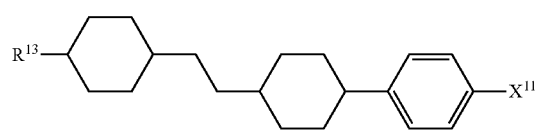
(6-23)
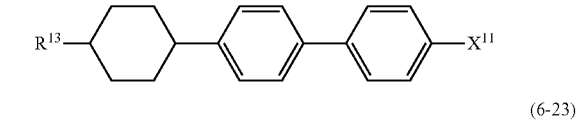
(6-24)
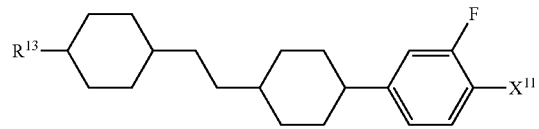
(6-25)
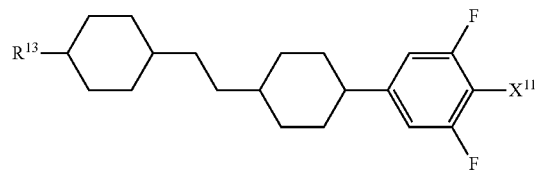
(6-26)
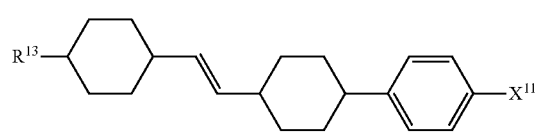
(6-27)
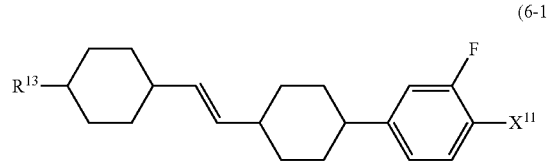
(6-28)
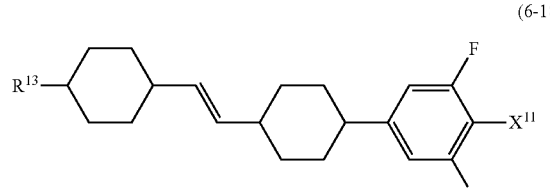

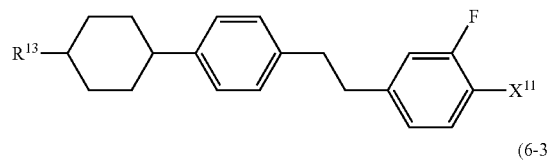
(6-29)
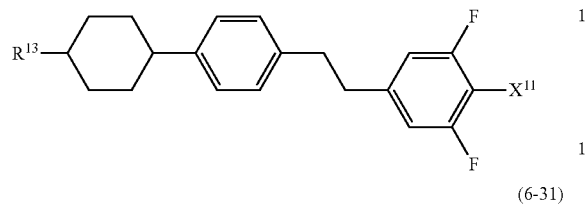
(6-30)
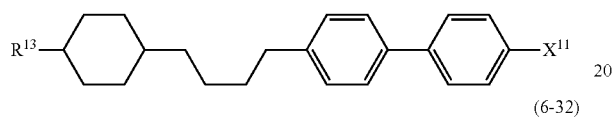
(6-31)
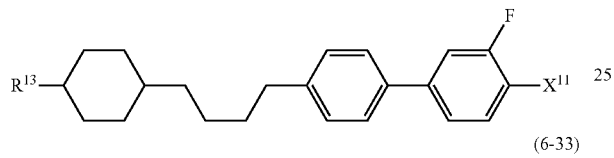
(6-32)
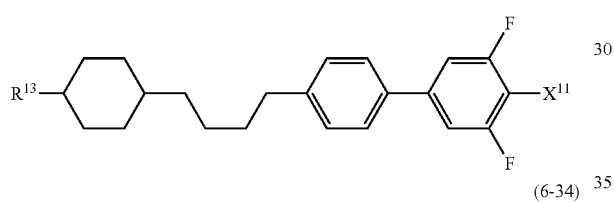
(6-33)
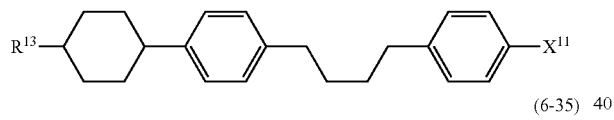
(6-34)
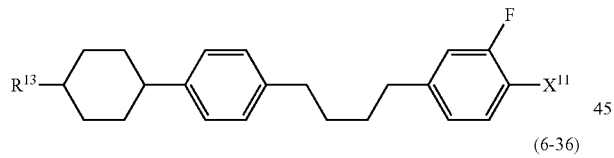
(6-35)
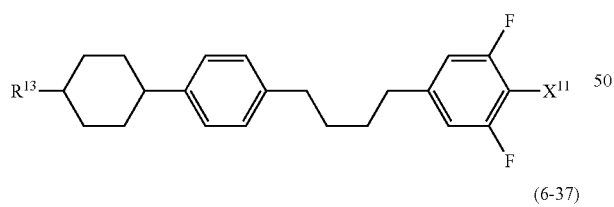
(6-36)
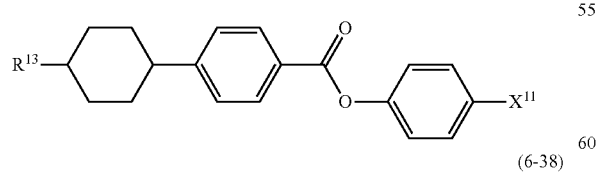
(6-37)
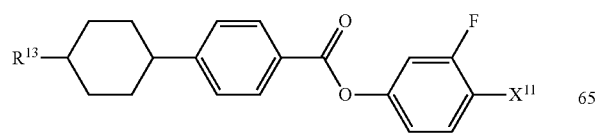
(6-38)
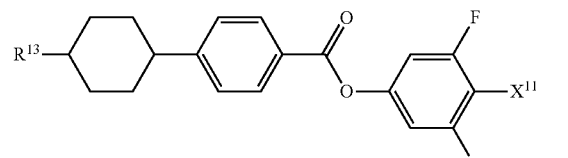
(6-39)
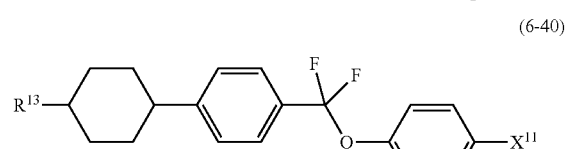
(6-40)
(6-41)
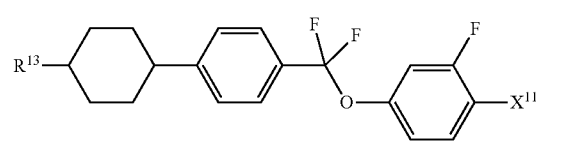
(6-42)
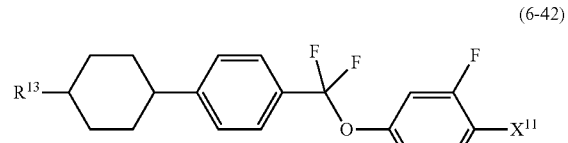
(6-43)
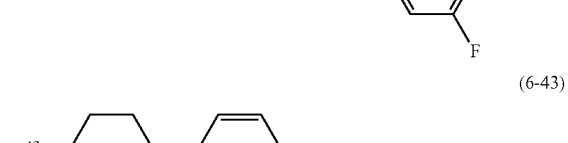
(6-44)
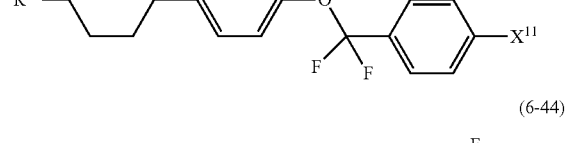
(6-45)
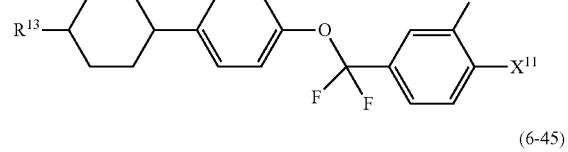
(6-46)
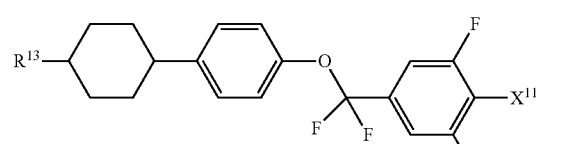
(6-47)
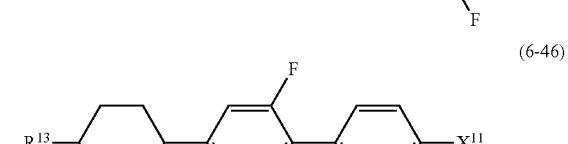
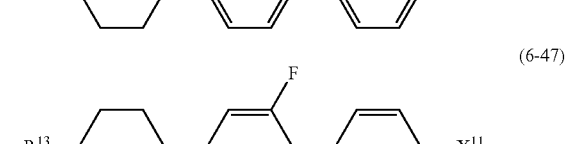
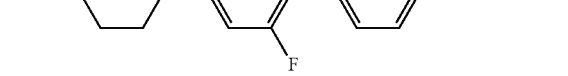

(6-48)
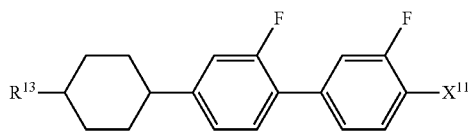
(6-49)
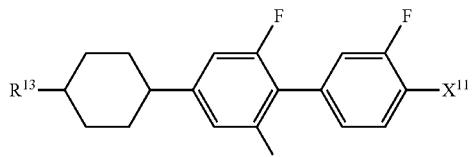
(6-50)
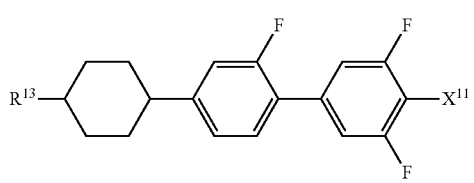
(6-51)
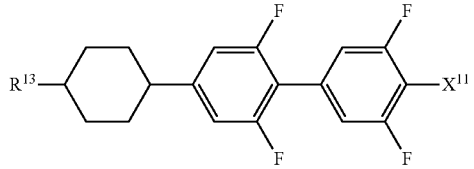
(6-52)
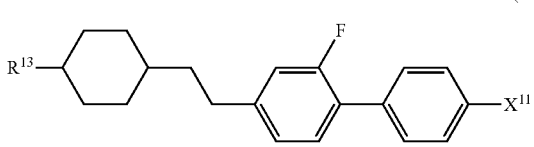
(6-53)
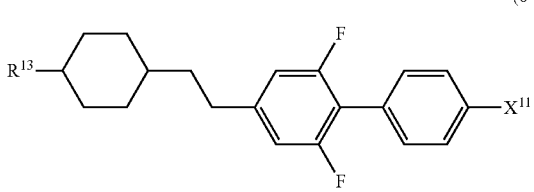
(6-54)
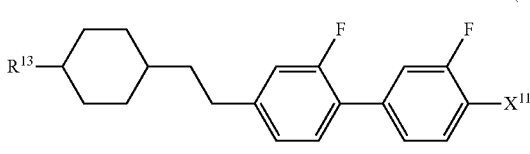
(6-55)
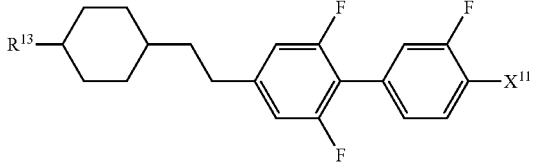
(6-56)
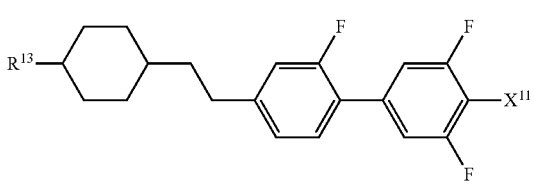
(6-57)
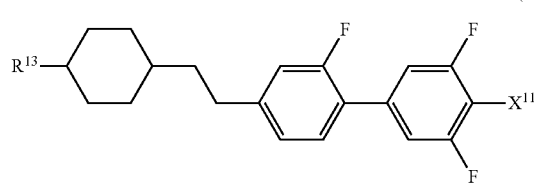
(6-58)
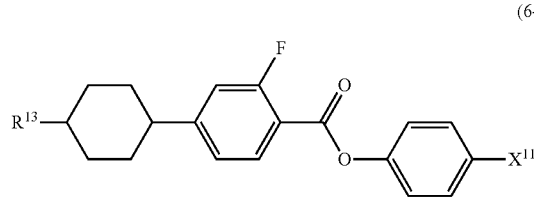
(6-59)
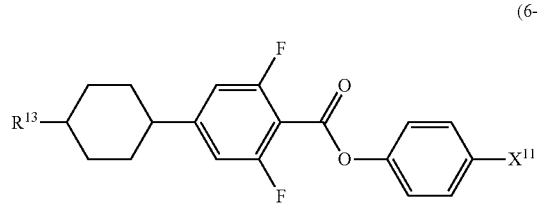
(6-60)
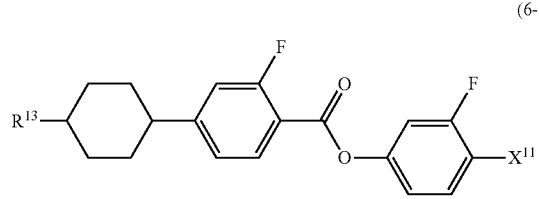
(6-61)
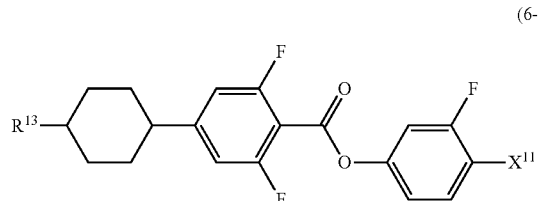
(6-62)
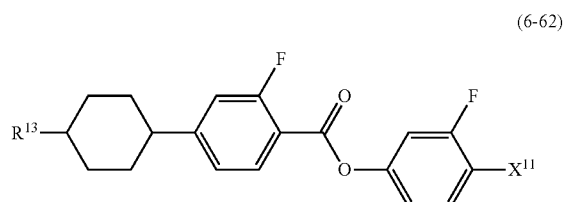
(6-63)
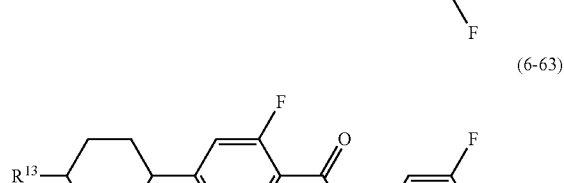
(6-64)
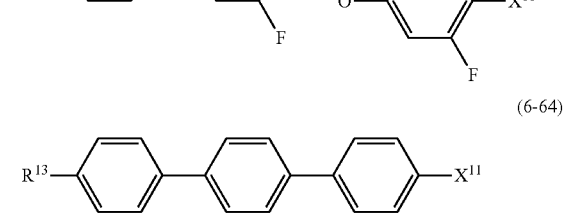

(6-65) 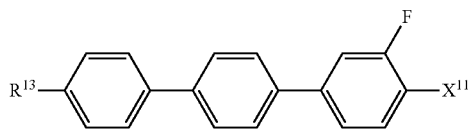
(6-66) 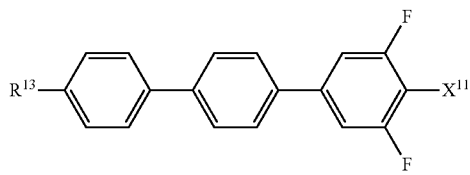
(6-67) 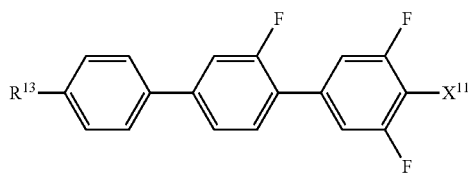
(6-68) 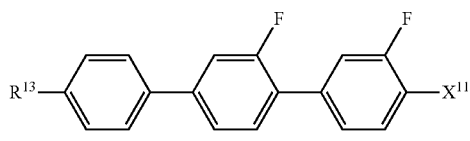
(6-69) 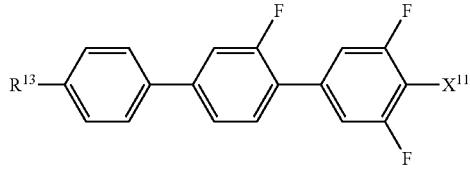
(6-70) 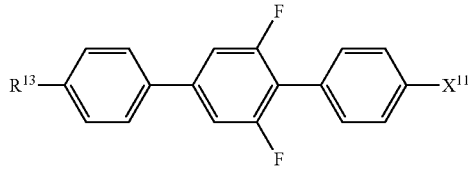
(6-71) 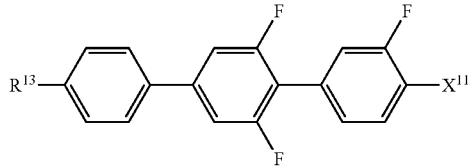
(6-72) 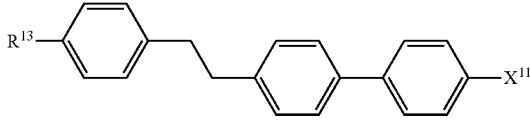
(6-73) 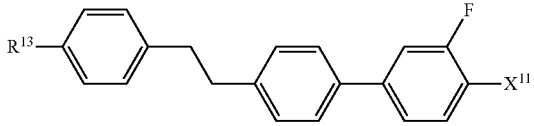
(6-74) 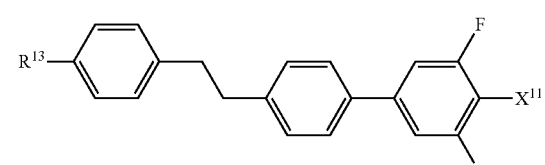
(6-75) 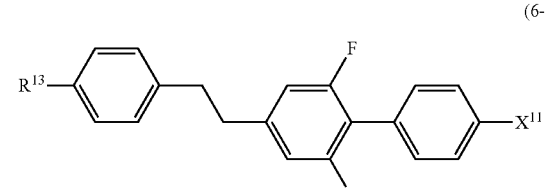
(6-76) 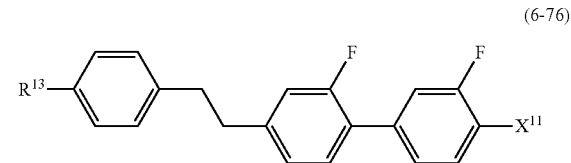
(6-77) 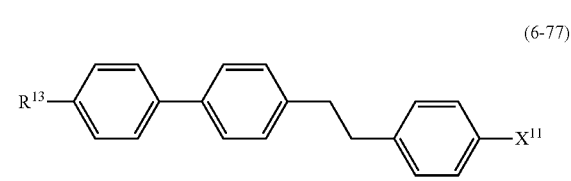
(6-78) 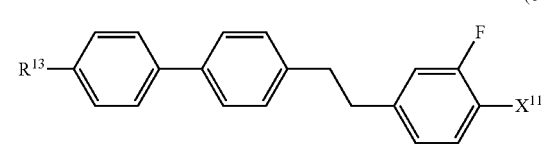
(6-79) 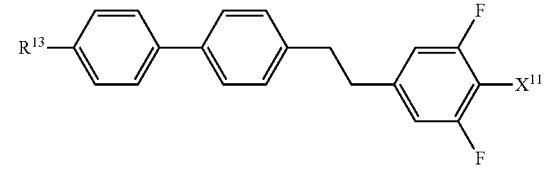
(6-80) 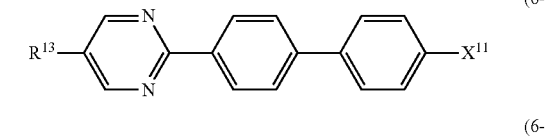
(6-81) 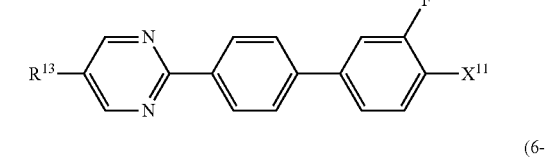
(6-82) 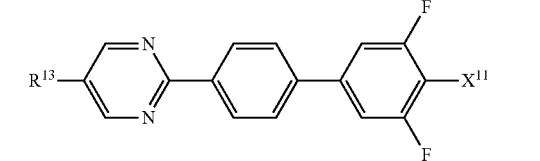

(6-83) 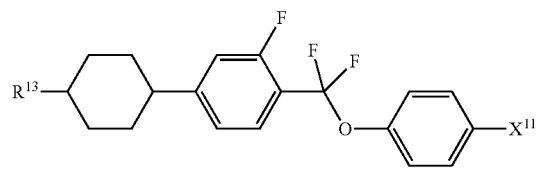
(6-84) 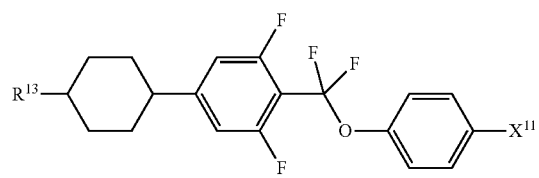
(6-85) 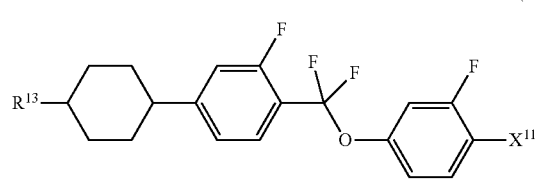
(6-86) 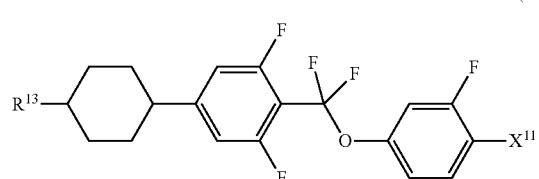
(6-87) 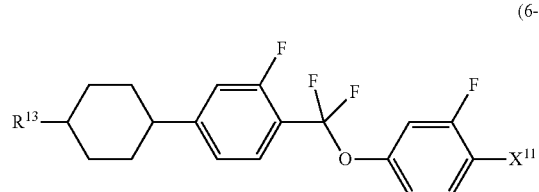
(6-88) 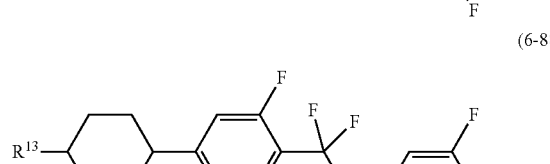
(6-89) 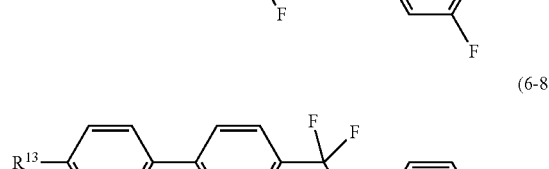
(6-90) 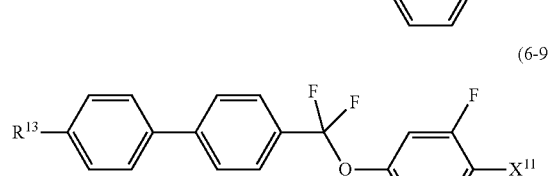
(6-91) 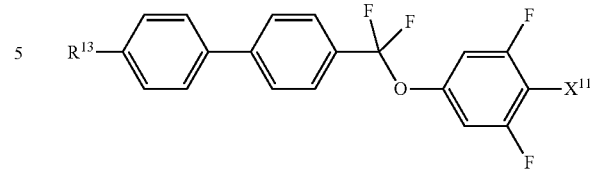
(6-92) 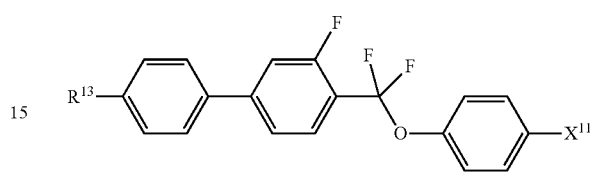
(6-93) 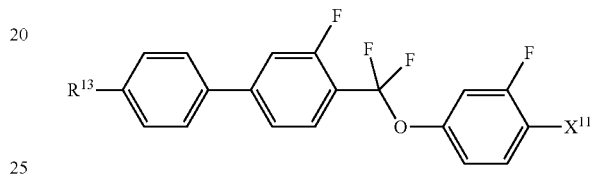
(6-94) 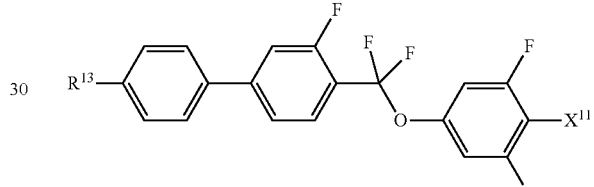
(6-95) 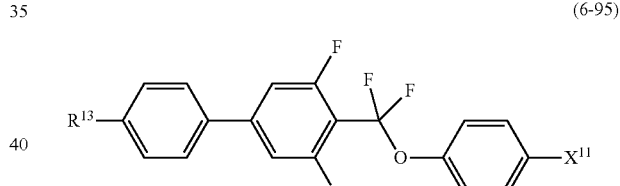
(6-96) 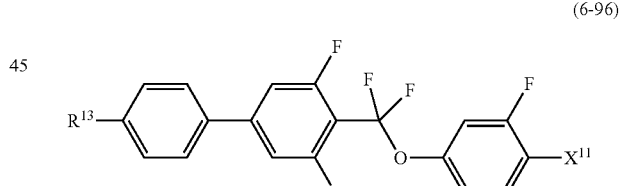
(6-97) 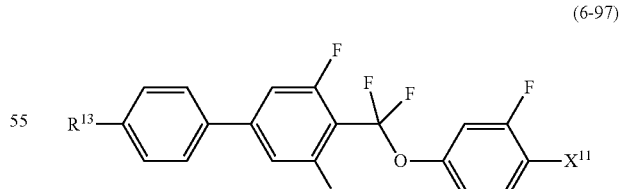
(6-98) 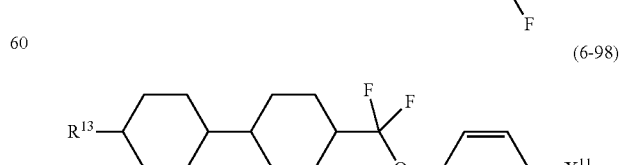

(6-99) 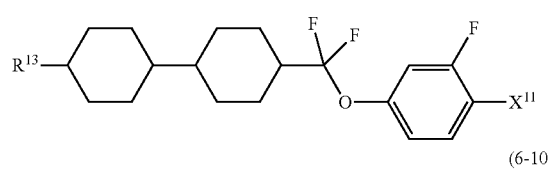
(6-100) 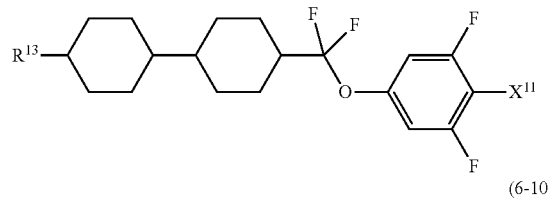
(6-101) 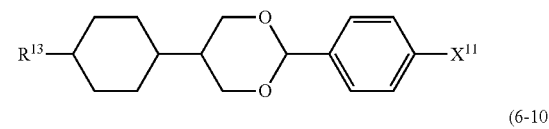
(6-102) 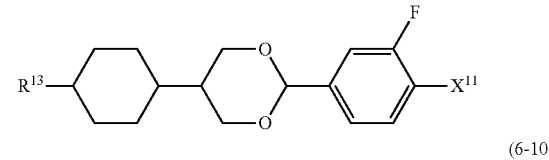
(6-103) 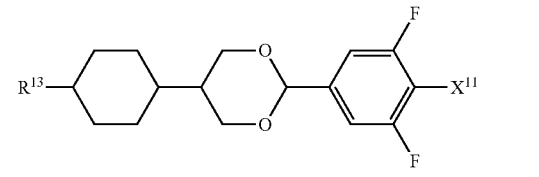
(6-104) 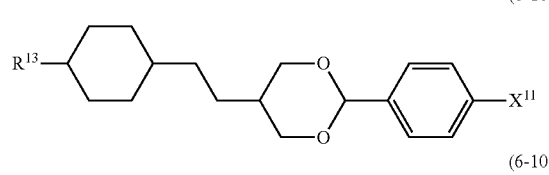
(6-105) 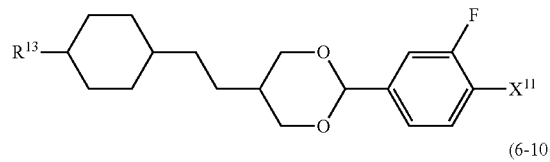
(6-106) 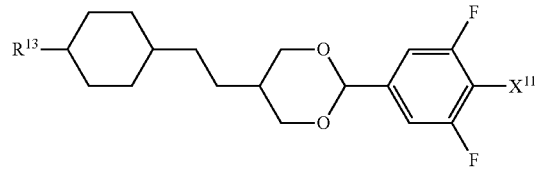
(6-107) 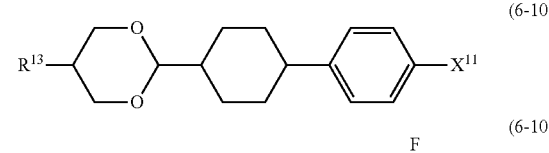
(6-108) 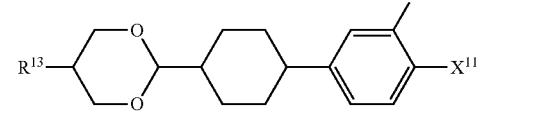
(6-109) 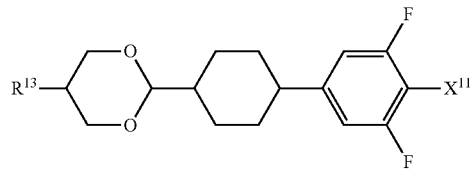
(6-110) 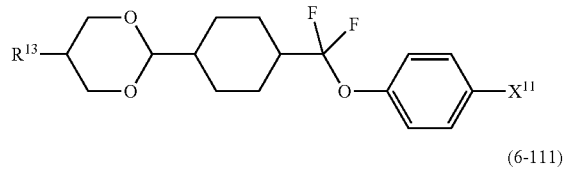
(6-111) 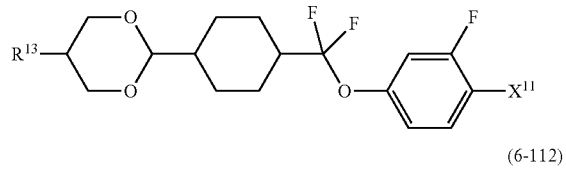
(6-112) 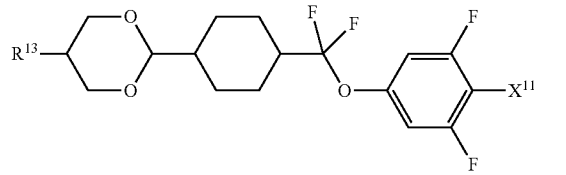
(6-113) 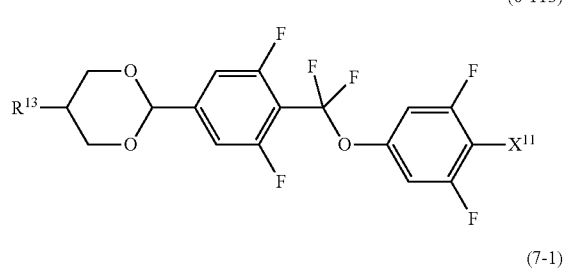
(7-1) 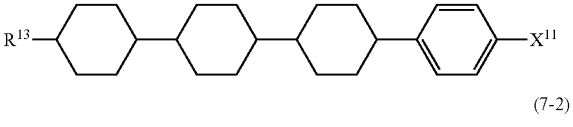
(7-2) 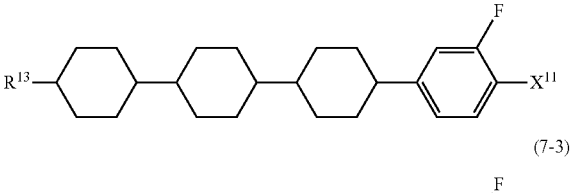
(7-3) 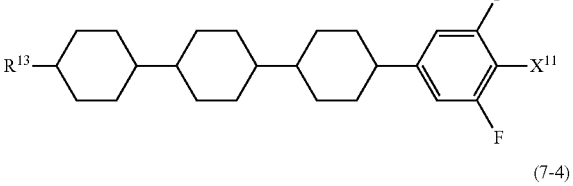
(7-4) 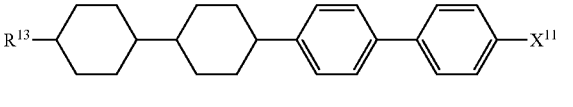

(7-5) 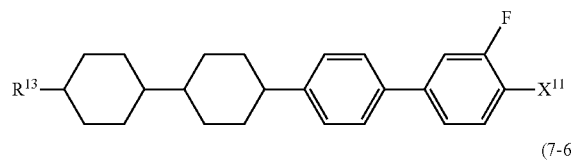
(7-6) 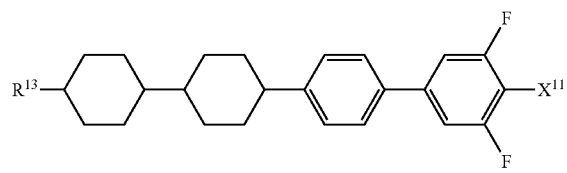
(7-7) 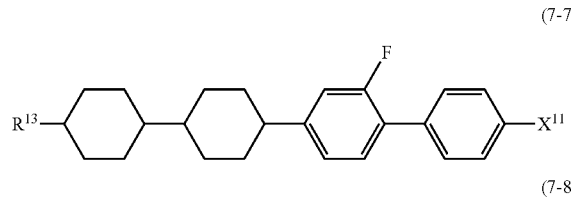
(7-8) 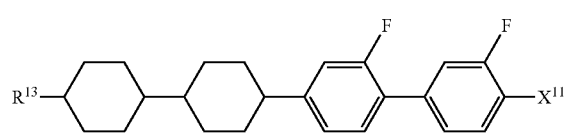
(7-9) 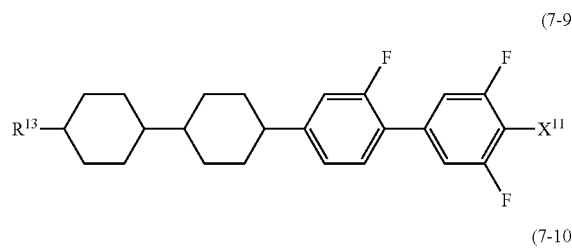
(7-10) 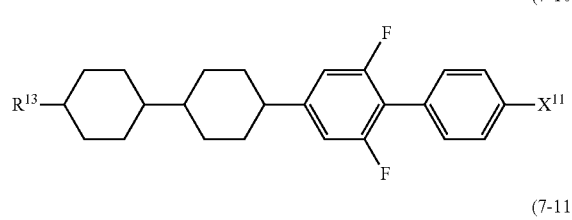
(7-11) 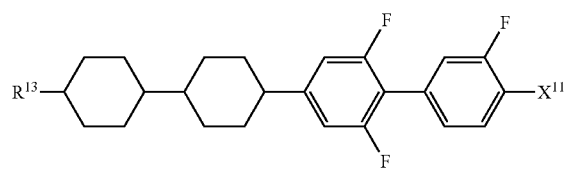
(7-12) 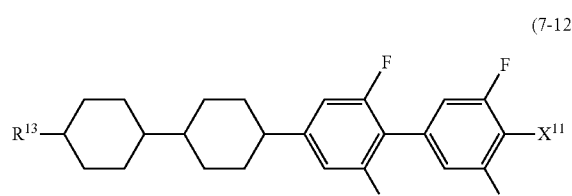
(7-13) 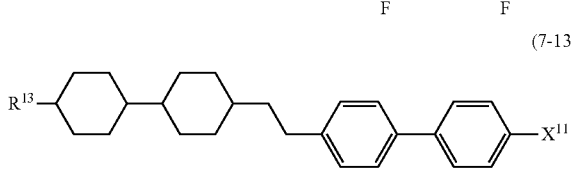
(7-14) 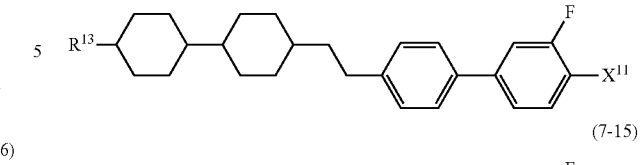
(7-15) 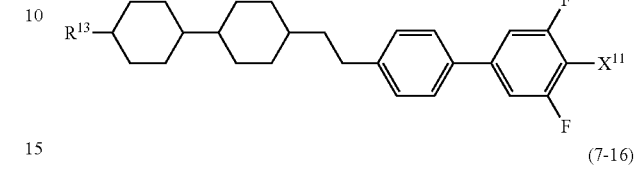
(7-16) 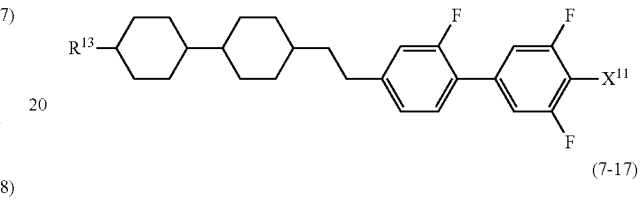
(7-17) 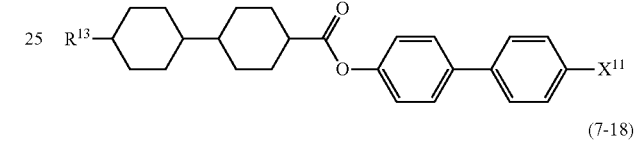
(7-18) 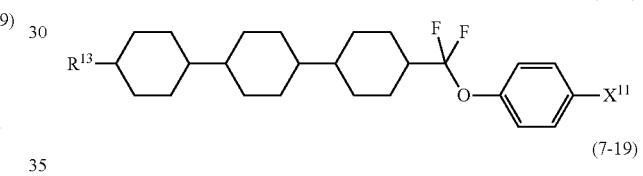
(7-19) 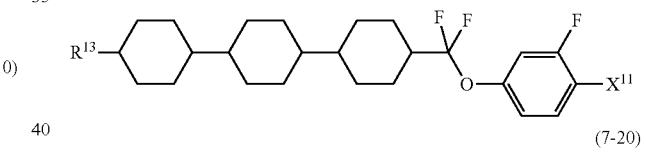
(7-20) 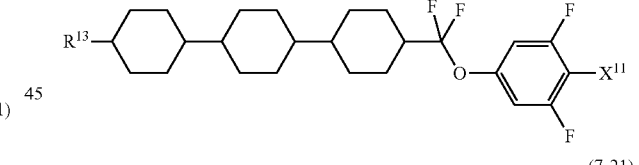
(7-21) 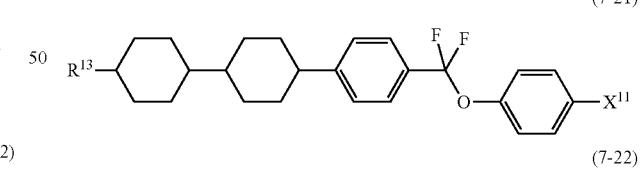
(7-22) 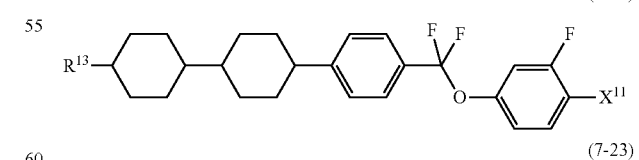
(7-23) 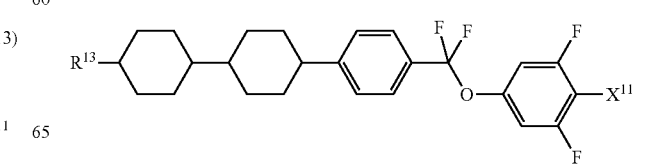

-continued
(7-24)
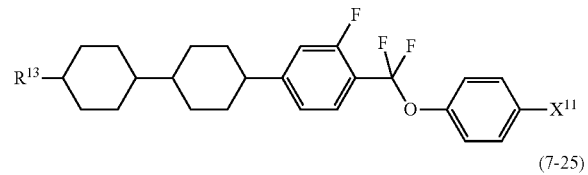
(7-25)
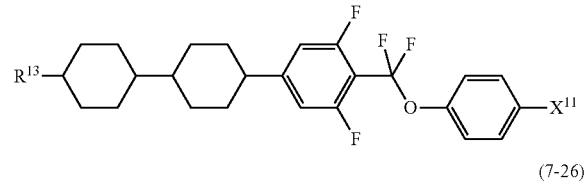
(7-26)
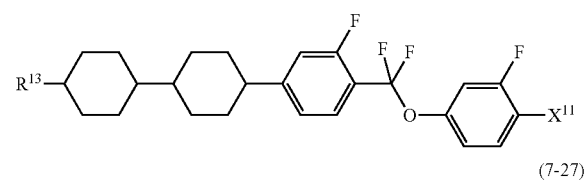
(7-27)
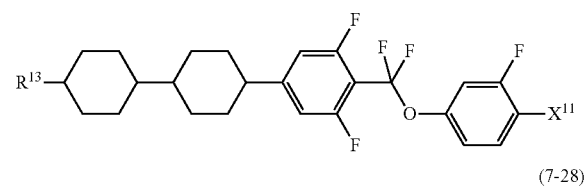
(7-28)
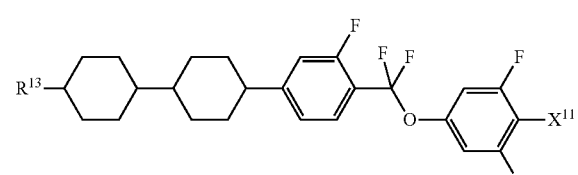
(7-29)
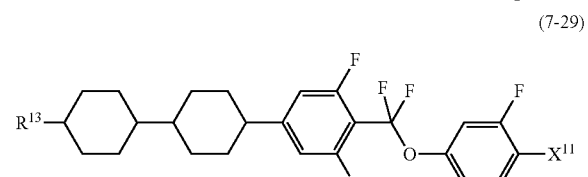
(7-30)
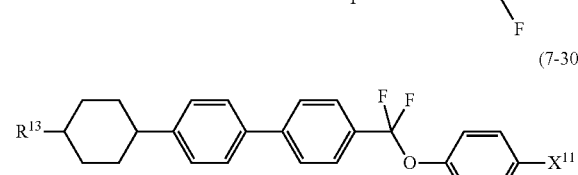
(7-31)
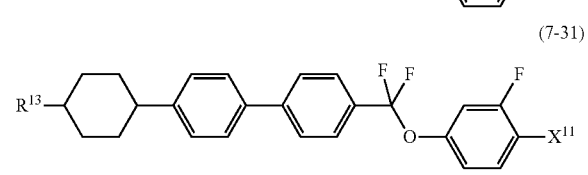
(7-32)
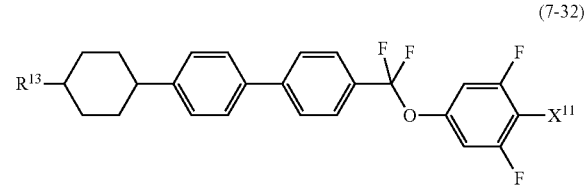
(7-33)
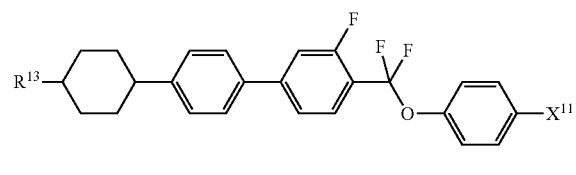
(7-34)
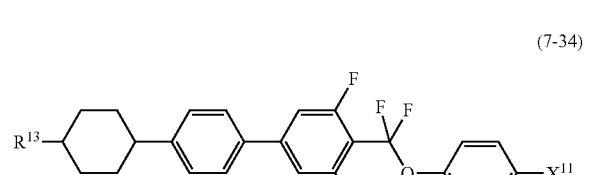
(7-35)
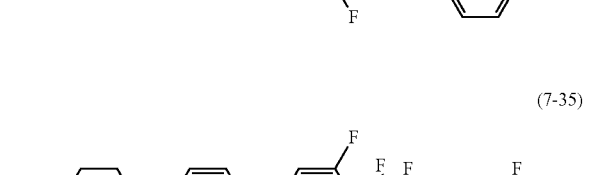
(7-36)
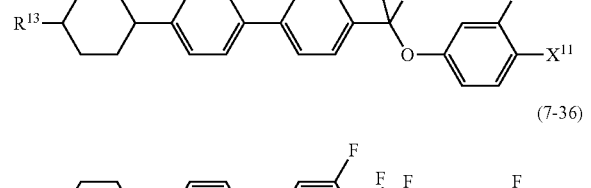
(7-37)
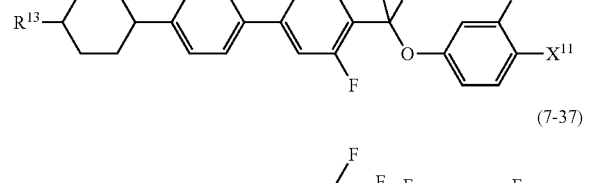
(7-38)
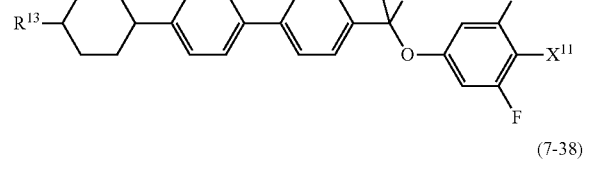
(7-39)
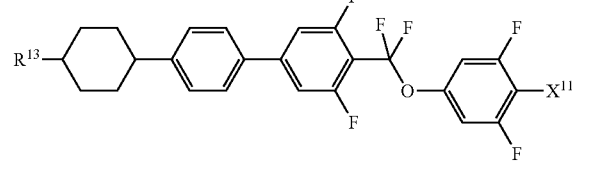
(7-40)
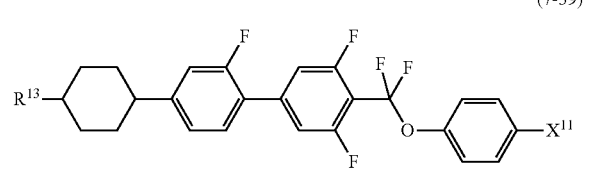

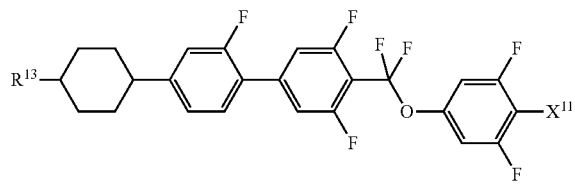
(7-41)
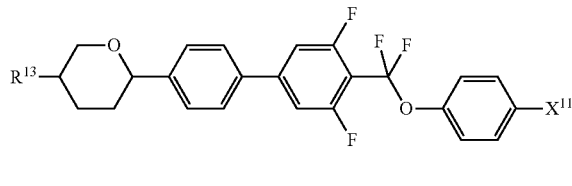
(7-49)
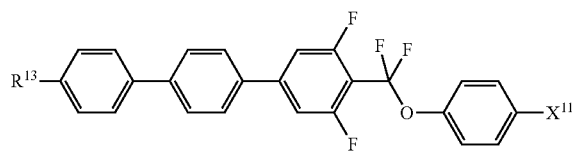
(7-42)
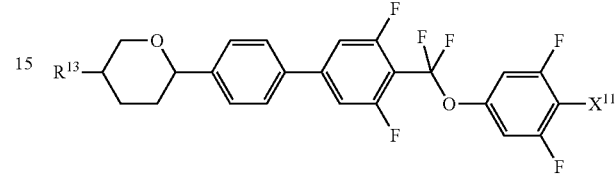
(7-50)
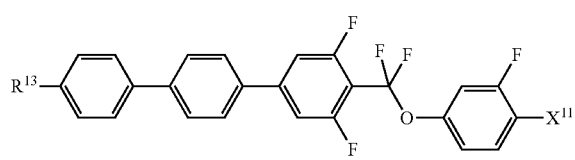
(7-43)
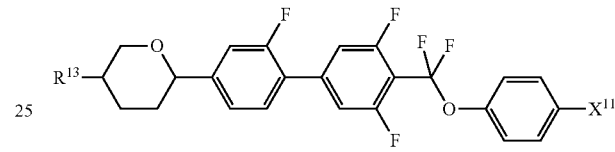
(7-51)
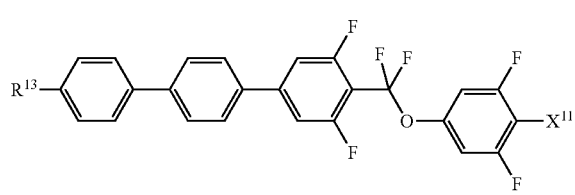
(7-44)
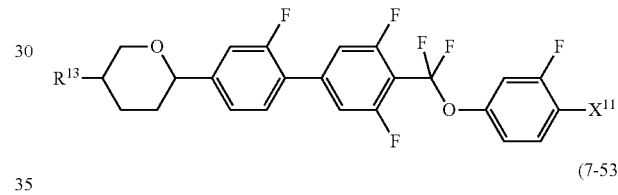
(7-52)
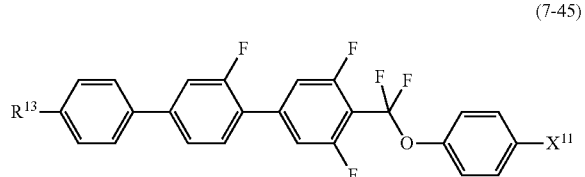
(7-45)
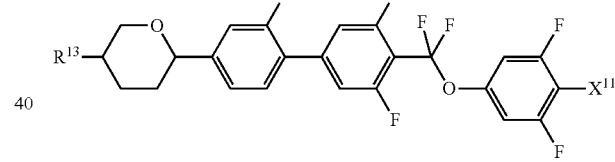
(7-53)
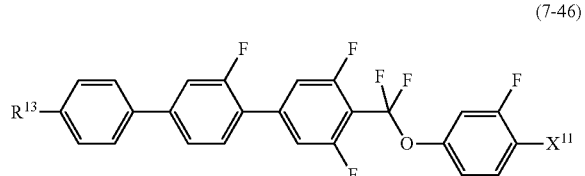
(7-46)
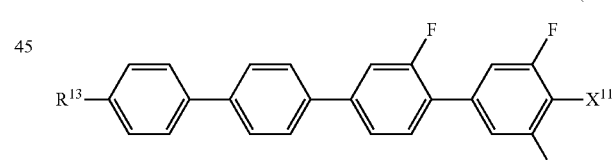
(7-54)
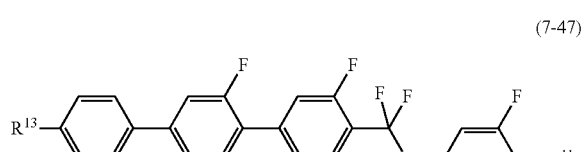
(7-47)
(7-48)
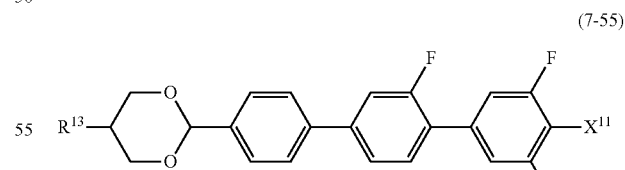
(7-55)
(7-56)

(7-57)
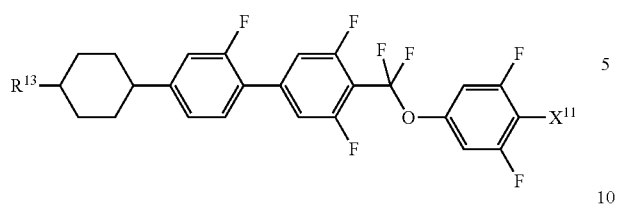

Component C has a positive dielectric anisotropy and a superb stability to heat or light, and therefore is used for preparing a composition for the modes such as IPS, FFS and OCB. A content of component C is suitably in the range of approximately 1% by weight to approximately 99% by weight based on the weight of the liquid crystal composition, preferably in the range of approximately 10% by weight to approximately 97% by weight, further preferably in the range of approximately 40% by weight to approximately 95% by weight. When component C is added to a composition having a negative dielectric anisotropy, the content of component C is preferably approximately 30% by weight or less. By adding component C, an elastic constant of the composition can be adjusted and a voltage-transmittance curve of a device can be adjusted.

Component D is compound (8) in which a right terminal group is —C≡N or —C≡C—C≡N. Preferred examples of component D include compounds (8-1) to (8-64). In the compounds, $R^{14}$ is alkyl having 1 to 10 carbons or alkenyl having 2 to 10 carbons, and in the alkyl and the alkenyl, at least one piece of —CH$_2$— may be replaced by —O—, and at least one piece of hydrogen may be replaced by fluorine; and $X^{12}$ is —C≡N or —C≡C—C≡N.

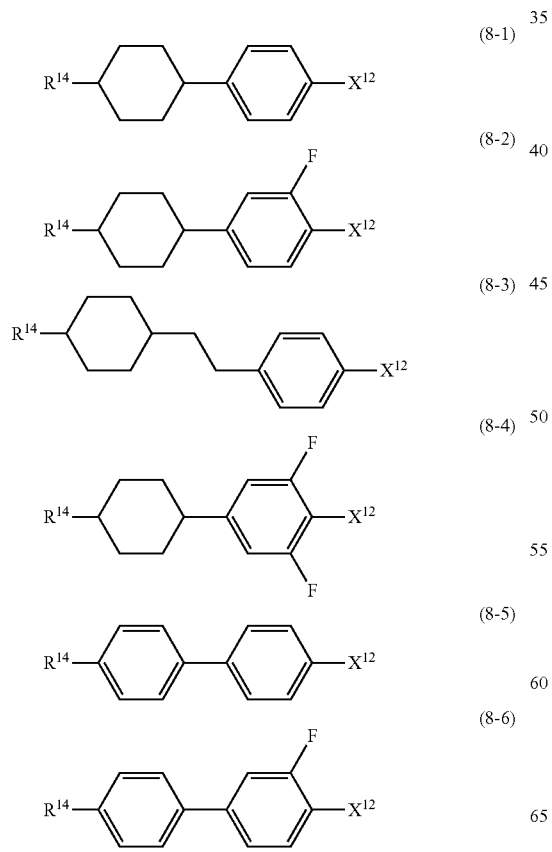

(8-1)
(8-2)
(8-3)
(8-4)
(8-5)
(8-6)

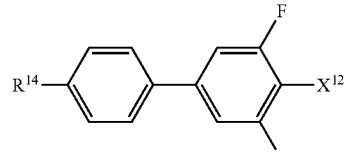
(8-7)

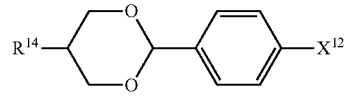
(8-8)

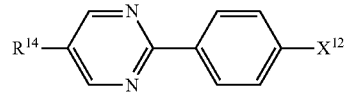
(8-9)

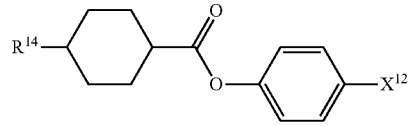
(8-10)

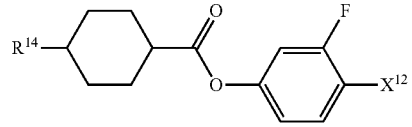
(8-11)

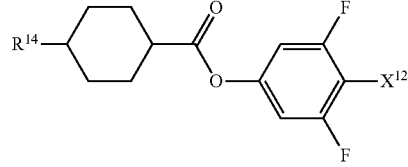
(8-12)

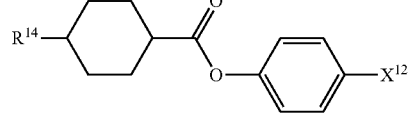
(8-13)

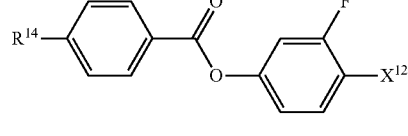
(8-14)

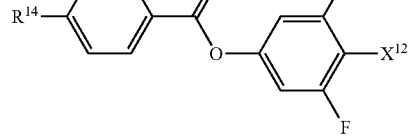
(8-15)

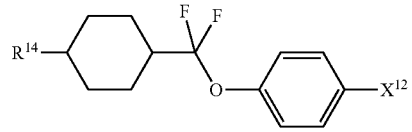
(8-16)

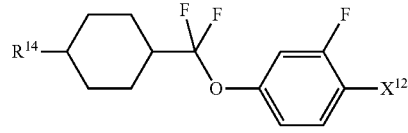
(8-17)

(8-18) 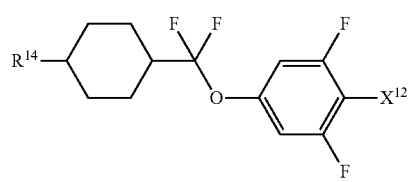
(8-19) 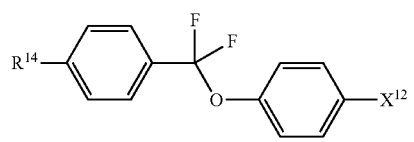
(8-20) 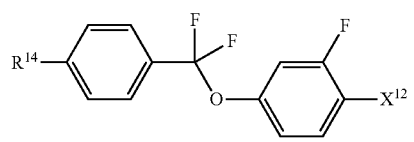
(8-21) 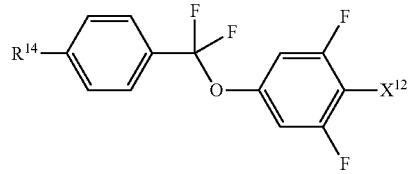
(8-22) 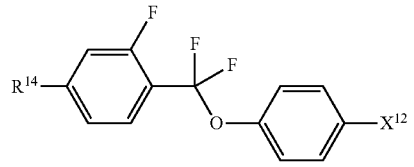
(8-23) 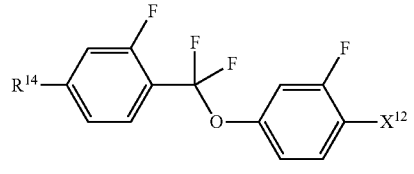
(8-24) 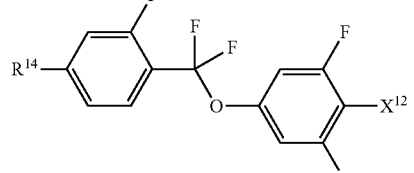
(8-25) 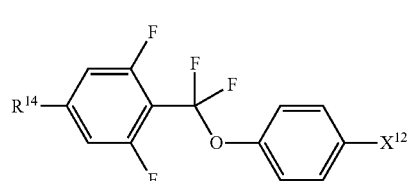
(8-26) 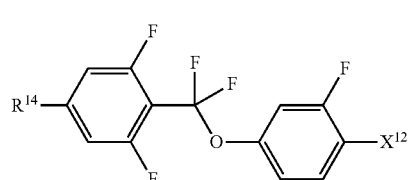
(8-27) 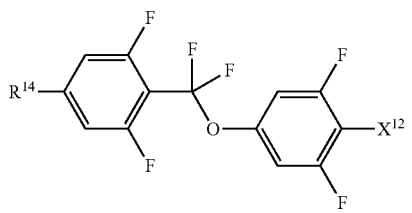
(8-28) 
(8-29) 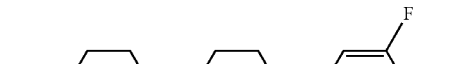
(8-30) 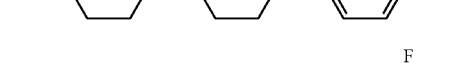
(8-31) 
(8-32) 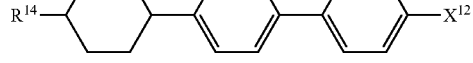
(8-33) 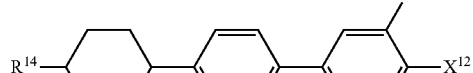
(8-34) 
(8-35) 
(8-36) 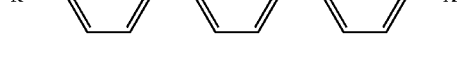
(8-37) 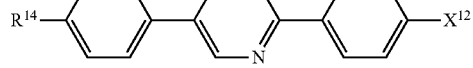

(8-38)
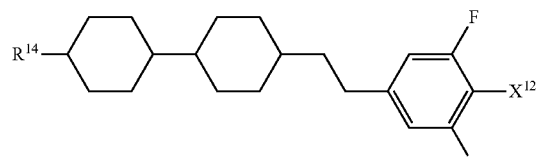
(8-39)
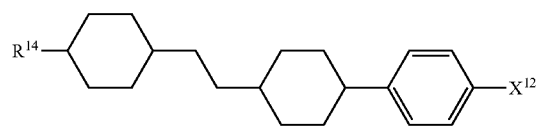
(8-40)
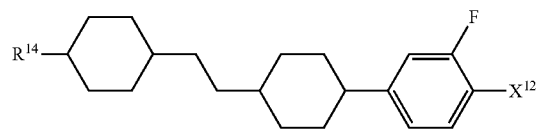
(8-41)
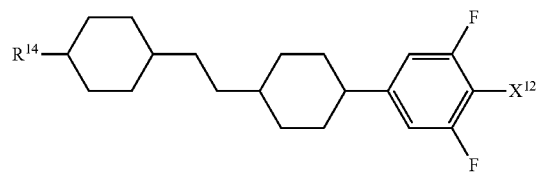
(8-42)
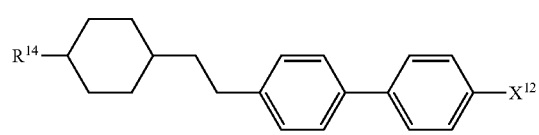
(8-43)
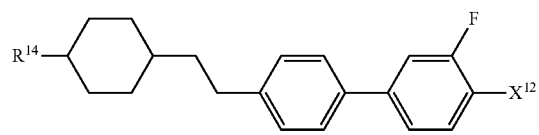
(8-44)
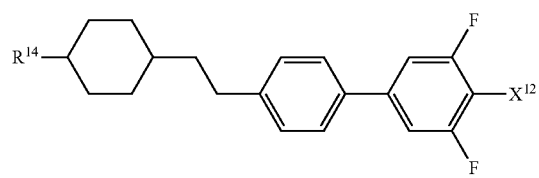
(8-45)
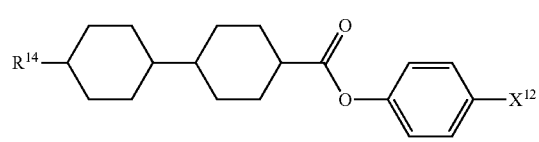
(8-46)
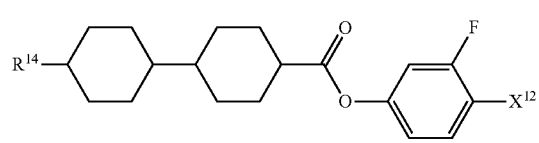
(8-47)
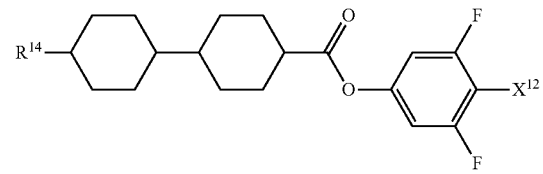
(8-48)
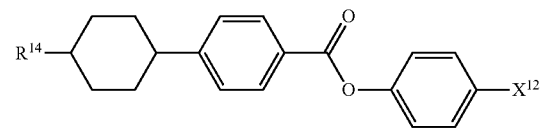
(8-49)
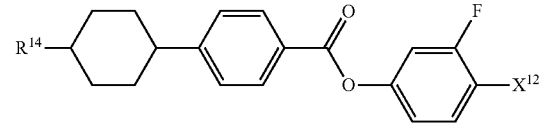
(8-50)
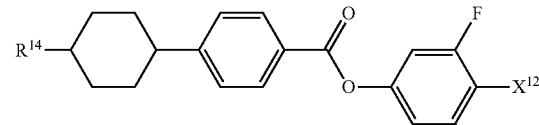
(8-51)
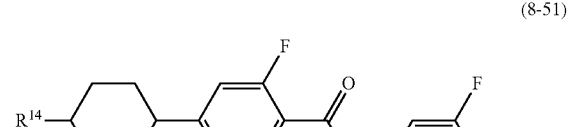
(8-52)
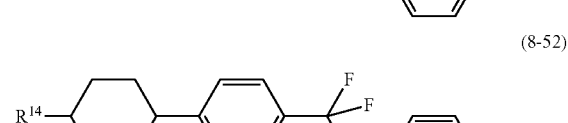
(8-53)
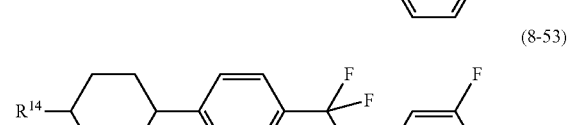
(8-54)
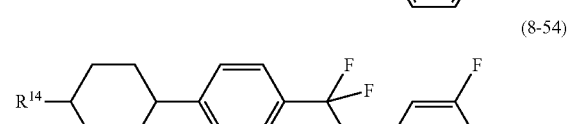
(8-55)
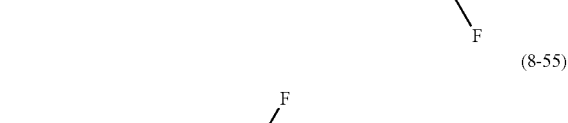
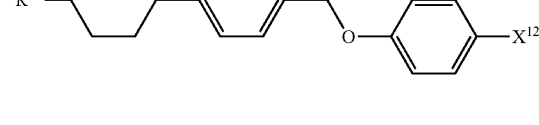

-continued (8-56)
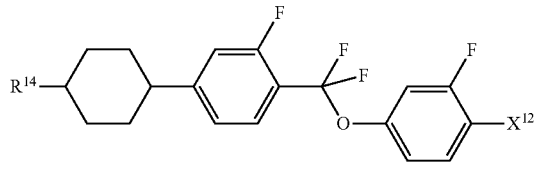

(8-57)
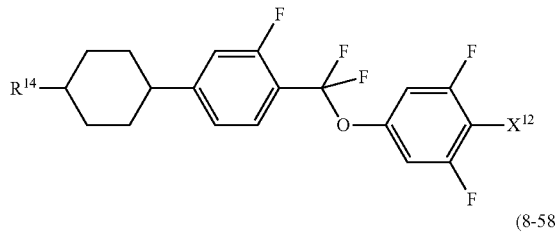

(8-58)

(8-59)
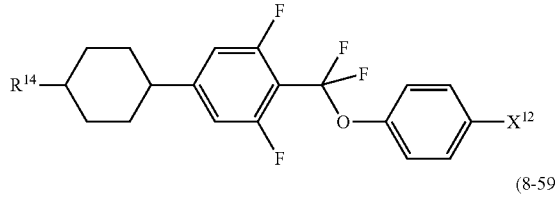

(8-60)
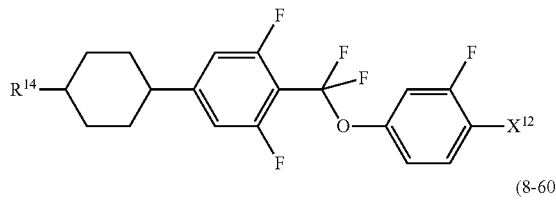

(8-61)
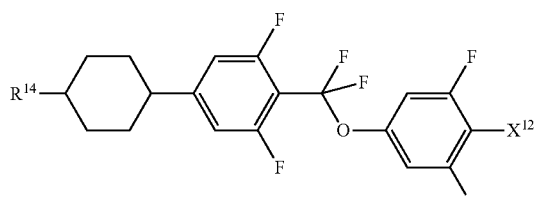

(8-62)
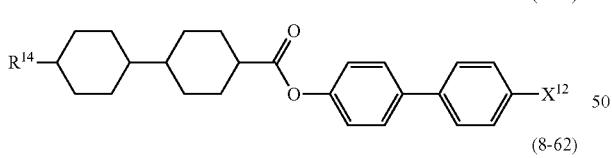

(8-63)
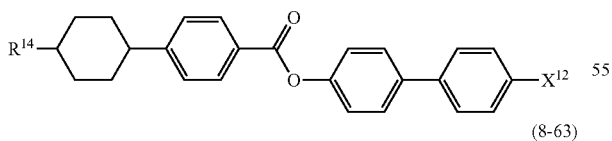

(8-64)
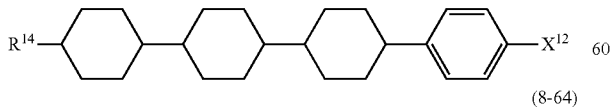

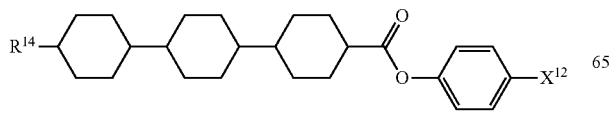

Component D has a large value of positive dielectric anisotropy, and therefore is used for preparing a composition for the TN mode or the like. The dielectric anisotropy of the composition can be increased by adding the component D thereto. Component D is effective in extending the temperature range of the liquid crystal phase, adjusting the viscosity or adjusting the optical anisotropy. Component D is also useful for adjusting the voltage-transmittance curve of the device.

When a composition for the TN mode in which dielectric anisotropy is positive is prepared, the content of component D is suitably in the range of approximately 1% by weight to approximately 99% by weight, preferably in the range of approximately 10% by weight to approximately 97% by weight, and further preferably, in the range of approximately 40% by weight to approximately 95% by weight, based on the weight of the liquid crystal composition. When component D is added to a composition having a negative dielectric anisotropy, the content of component D is preferably approximately 30% or less. When component D is added, an elastic constant of the composition can be adjusted and the voltage-transmittance curve of the device can be adjusted.

Component E includes compounds (9) to (15). The compounds have phenylene in which lateral positions are substituted by two halogens, such as 2,3-difluoro-1,4-phenylene. Preferred examples of component E include compounds (9-1) to (9-8), compounds (10-1) to (10-17), compound (11-1), compounds (12-1) to (12-3), compounds (13-1) to (13-11), compounds (14-1) to (14-3) and compounds (15-1) to (15-3). In the compounds, $R^{15}$ and $R^{16}$ are each independently alkyl having 1 to 10 carbons or alkenyl having 2 to 10 carbons, and in the alkyl and the alkenyl, at least one piece of —CH$_2$— may be replaced by —O— and at least one piece of hydrogen may be replaced by fluorine; $R^{17}$ is hydrogen, fluorine, alkyl having 1 to 10, carbons or alkenyl having 2 to 10 carbons, and in the alkyl and the alkenyl, at least one piece of —CH$_2$— may be replaced by —O—, and at least one piece of hydrogen may be replaced by fluorine.

(9-1)
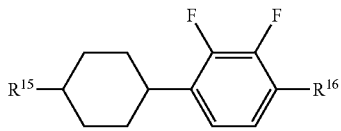

(9-2)
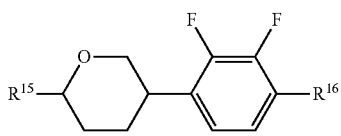

(9-3)
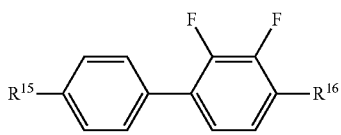

(9-4)
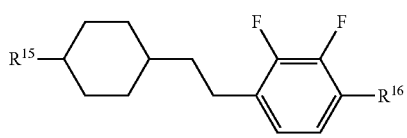

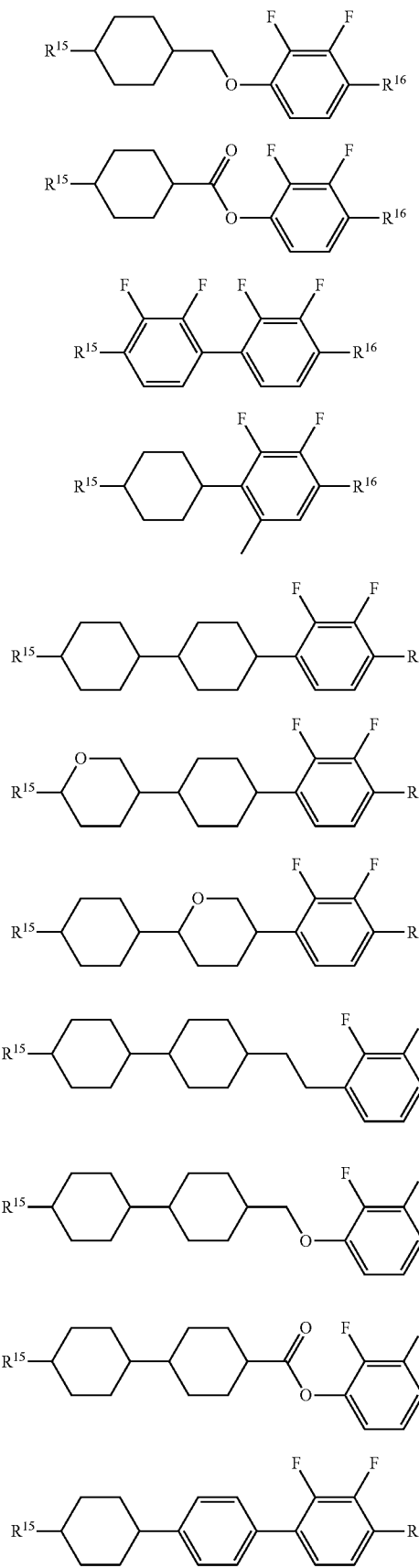
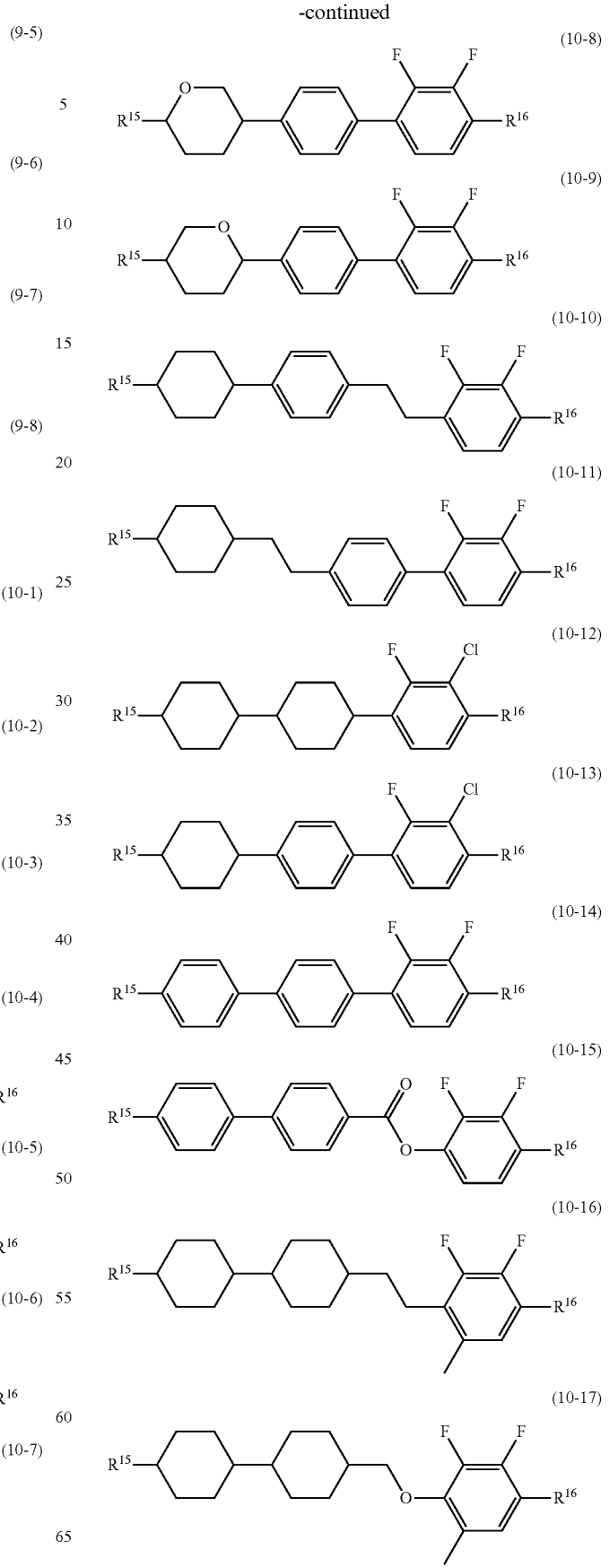

(11-1) 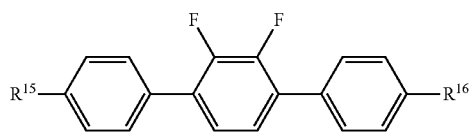
(12-1) 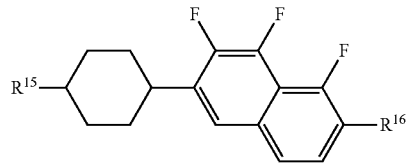
(12-2) 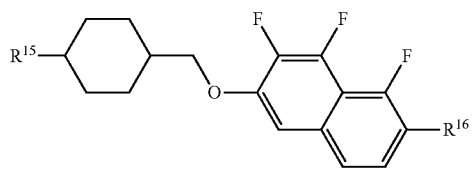
(12-3) 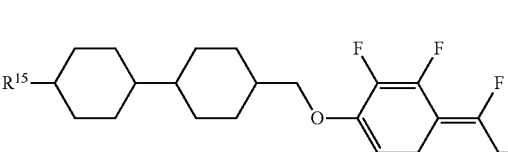
(13-1) 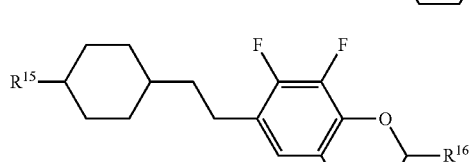
(13-2) 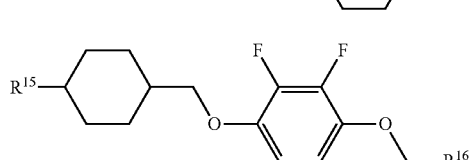
(13-3) 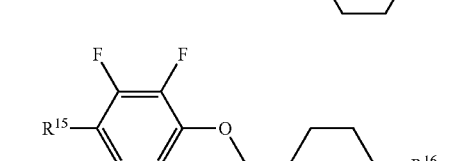
(13-4) 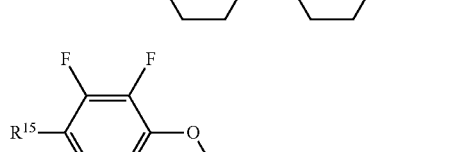
(13-5) 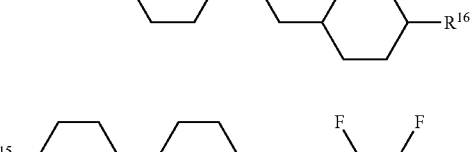
(13-6) 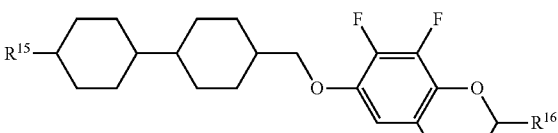
(13-7) 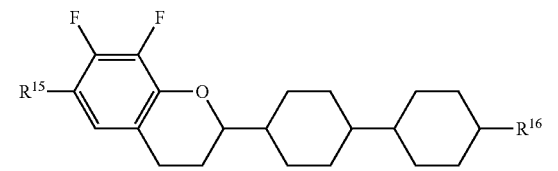
(13-8) 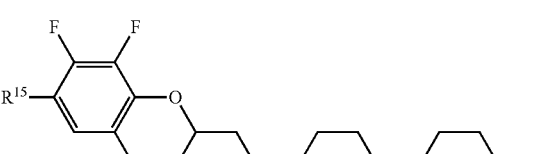
(13-9) 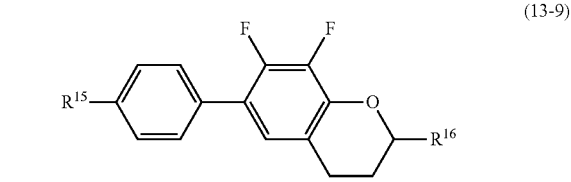
(13-10) 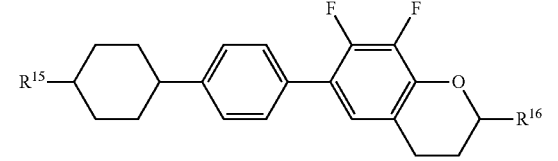
(13-11) 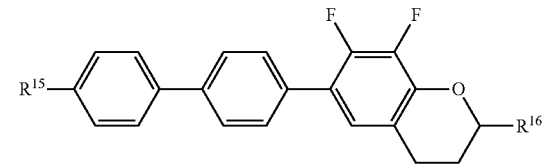
(14-1) 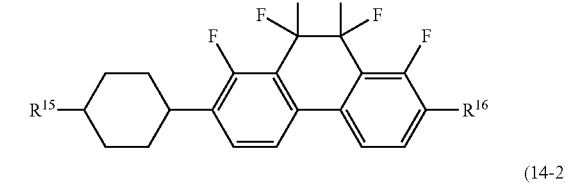
(14-2) 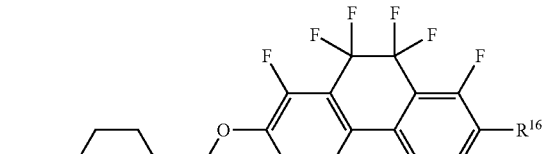

-continued

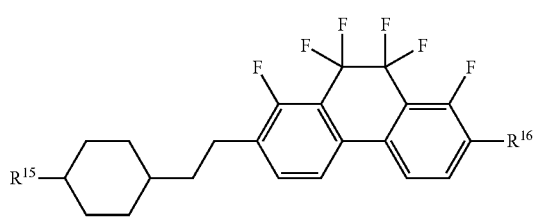
(14-3)

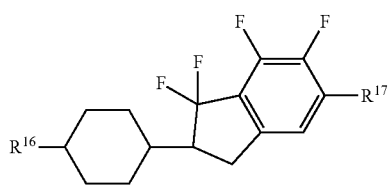
(15-1)

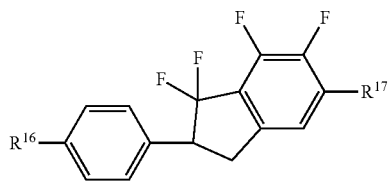
(15-2)

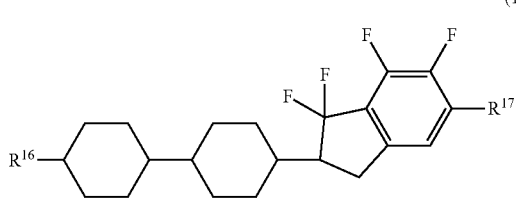
(15-3)

Component E has a large negative dielectric anisotropy. Component E is used for preparing a composition for the IPS mode, the VA mode, the PSA mode or the like. When the content of component E is increased, the dielectric anisotropy becomes negatively larger, but viscosity becomes also larger. Thus, as long as a desired value of threshold voltage of the device is satisfied, the content is preferably as small as possible. Considering that the dielectric anisotropy is approximately −5, the content is preferably approximately 40% by weight or more for allowing full voltage drive.

Among types of component E, compound (9) is a bicyclic compound, and therefore is effective in decreasing the viscosity, adjusting the optical anisotropy or increasing the dielectric anisotropy. Compounds (10) and (11) are a tricyclic compound, and therefore effective in increasing the maximum temperature, the optical anisotropy or the dielectric anisotropy. Compounds (12) to (15) are effective in increasing the dielectric anisotropy.

When a composition for a mode in which dielectric anisotropy is negative is prepared, such as the IPS mode, the VA mode or the PSA mode, the content of component E is preferably approximately 40% by weight or more, and further preferably, in the range of approximately 50% by weight to approximately 95% by weight, based on the weight of the liquid crystal composition. When component E is added to a composition having a positive dielectric anisotropy, the content of component E is preferably approximately 30% or less. When component E is added, an elastic constant of the composition can be adjusted and the voltage-transmittance curve of the device can be adjusted.

The liquid crystal composition satisfying at least one of the physical properties such as a high stability to heat and light, a high maximum temperature, a low minimum temperature, a small viscosity, a suitable optical anisotropy, a large dielectric anisotropy, a large specific resistance and a suitable elastic constant can be prepared by suitably combining components B, C, D and E described above. A liquid crystal compound different from component B, C and D and E may be added, when necessary.

3-2. Additive

The liquid crystal composition is prepared by a publicly known method. For example, the component compounds are mixed and dissolved in each other by heating. According to an application, an additive may be added to the composition. Examples of the additive include a polymerizable compound, a polymerization initiator, a polymerization inhibitor, an optically active compound, an antioxidant, an ultraviolet light absorber, a light stabilizer, a heat stabilizer, a dye and a defoaming agent. Such additives are well known to those skilled in the art, and are described in literatures.

In a liquid crystal display device having the polymer sustained alignment (PSA) mode, the composition contains a polymer. A polymerizable compound is added for the purpose of forming the polymer in the composition. The polymer is formed in the composition by irradiating the composition with ultraviolet light to polymerize the polymerizable compound while voltage is being applied between electrodes. By the method, suitable pretilt is attained, and therefore a device is produced in which a response time is shortened and image persistence is improved.

Preferred examples of the polymerizable compound include an acrylate, a methacrylate, a vinyl compound, a vinyloxy compound, a propenyl ether, an epoxy compound (oxirane, oxetane) and a vinyl ketone. Further preferred examples include a compound that has at least one acryloyloxy and a compound that has at least one methacryloyloxy. Still further preferred examples include a compound that has both acryloyloxy and methacryloyloxy.

Still further preferred examples include compounds (M-1) to (M-17). In the compounds, $R^{25}$ to $R^{31}$ are each independently hydrogen or methyl; s, v and x are each independently 0 or 1; and t and u are each independently integers of 1 to 10. $L^{21}$ to $L^{26}$ are each independently hydrogen or fluorine; and $L^{27}$ and $L^{28}$ are each independently hydrogen, fluorine or methyl.

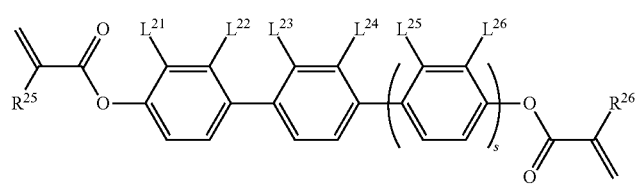
(M-1)

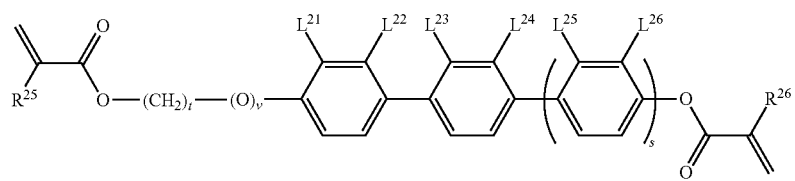
(M-2)
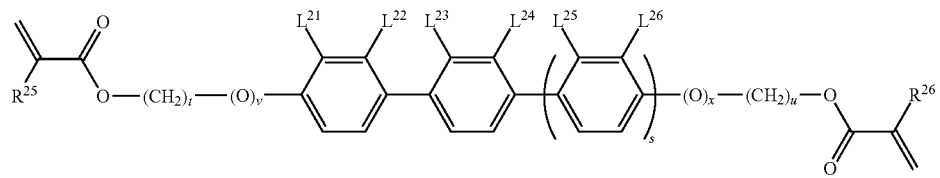
(M-3)
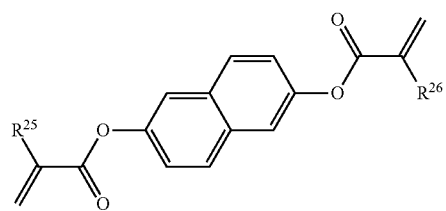
(M-4)
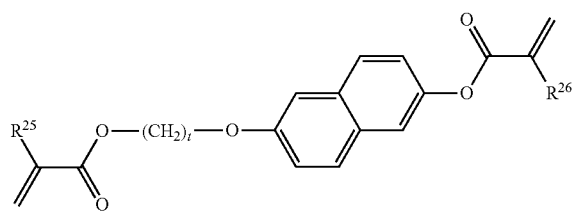
(M-5)
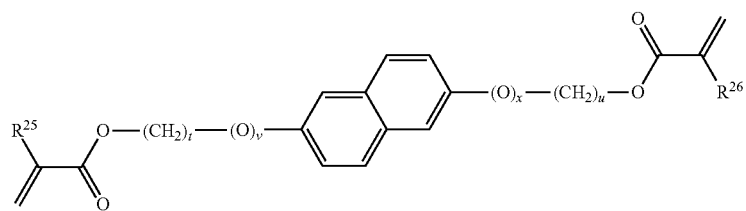
(M-6)
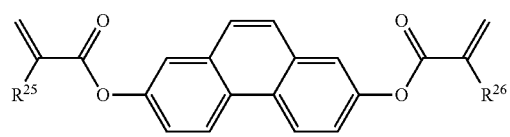
(M-7)
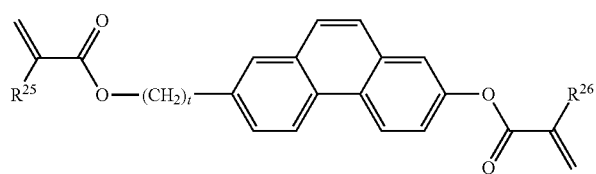
(M-8)
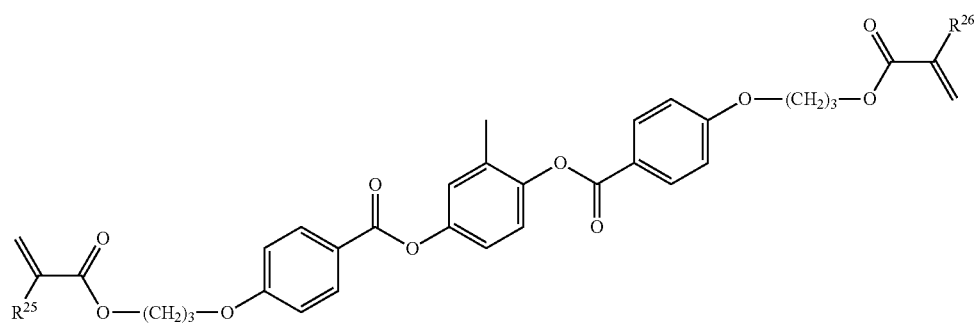
(M-9)

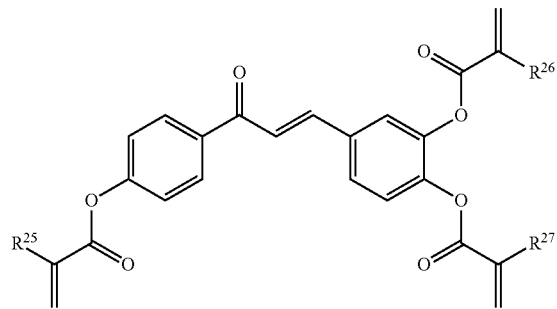
(M-10)
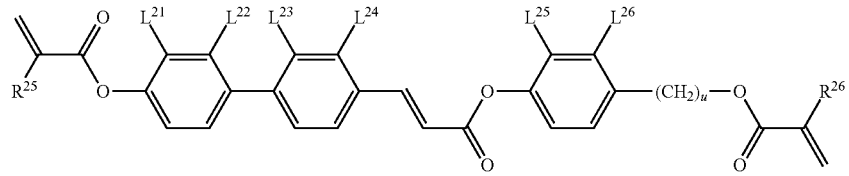
(M-11)
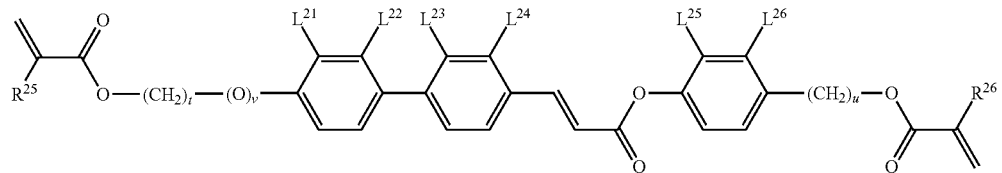
(M-12)
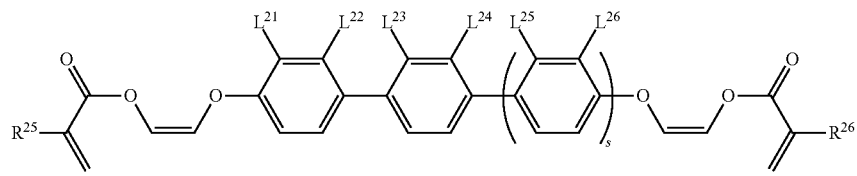
(M-13)
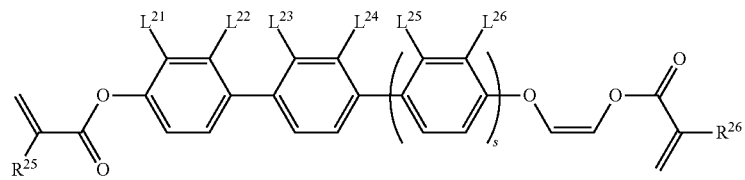
(M-14)
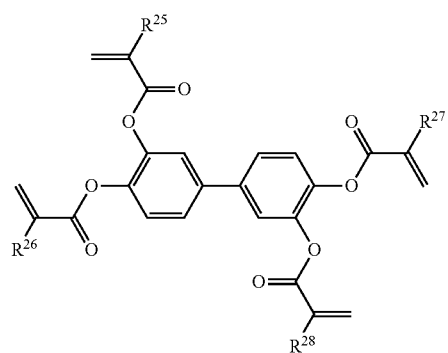
(M-15)
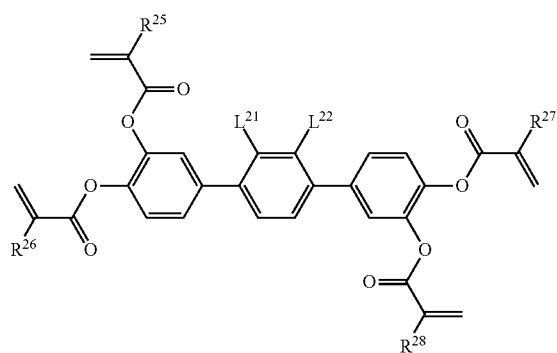
(M-16)

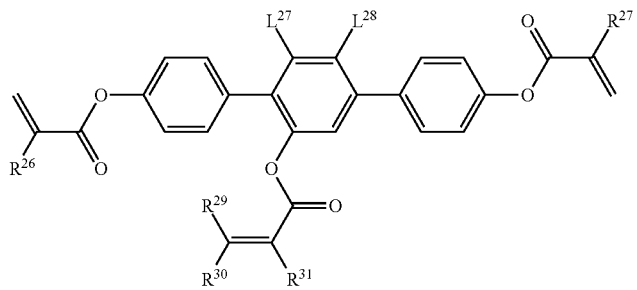

(M-17)

The polymerizable compound can be rapidly polymerized by adding a polymerization initiator. An amount of remaining polymerizable compound can be decreased by optimizing a reaction temperature. Examples of an optical radical polymerization initiator include TPO 1173 and 4265 from the Darocur series of BASF SE, and 184, 369, 500, 651, 784, 819, 907, 1300, 1700, 1800, 1850 and 2959 from the Irgacure series.

Additional examples of the optical radical polymerization initiator include 4-methoxyphenyl-2,4-bis(trichloromethyl) triazine, 2-(4-butoxystyryl)-5-trichloromethyl-1,3,4-oxadiazole, 9-phenylacridine, 9,10-benzophenazine, a benzophenone/Michler's ketone mixture, hexaarylbiimidazole/mercaptobenzimidazole mixture, 1-(4-isopropylphenyl)-2-hydroxy-2-methylpropane-1-on, benzyldimethylketal, 2-methyl-1-[4-(methylthio)phenyl]-2-morpholinopropane-1-on, a 2,4-diethylxanthone/p-dimethylaminobenzoic acid methyl mixture, and a benzophenone/methyltriethanolamine mixture.

Polymerization can be performed by adding the optical radical polymerization initiator to the liquid crystal composition, and then irradiating the composition with ultraviolet light under application of an electric field. However, an unreacted polymerization initiator or a decomposition product of the polymerization initiator may cause poor display such as image persistence in the device. In order to prevent such a phenomenon, photopolymerization may be performed without adding the polymerization initiator. A preferred wavelength range of the light for irradiation is approximately 150 to approximately 500 nm. Further preferred wavelength range is approximately 250 to approximately 450 nm, and most preferred wavelength range is approximately 300 to approximately 400 nm.

When the polymerizable compound is stored, the polymerization inhibitor may be added in order to prevent polymerization. The polymerizable compound is added to a composition usually without removing the polymerization inhibitor. Examples of the polymerization inhibitor include a hydroquinone derivative such as hydroquinone and methylhydroquinone, 4-t-butylcatechol, 4-methoxyphenol and phenothiazine.

The optically active is effective in inducing a helical structure in liquid crystal molecules to give a necessary twist angle, thereby preventing a reverse twist. Spiral pitch can be adjusted by adding the optically active compound. Two or more optically active compounds may be added for the purpose of adjusting temperature dependence of the helical pitch. Preferred examples of the optically active compound include compounds (Op-1) to (Op-18) described below. In compound (Op-18), ring J is 1,4-cyclohexylene or 1,4-phenylene, and $R^{28}$ is alkyl having 1 to 10 carbons.

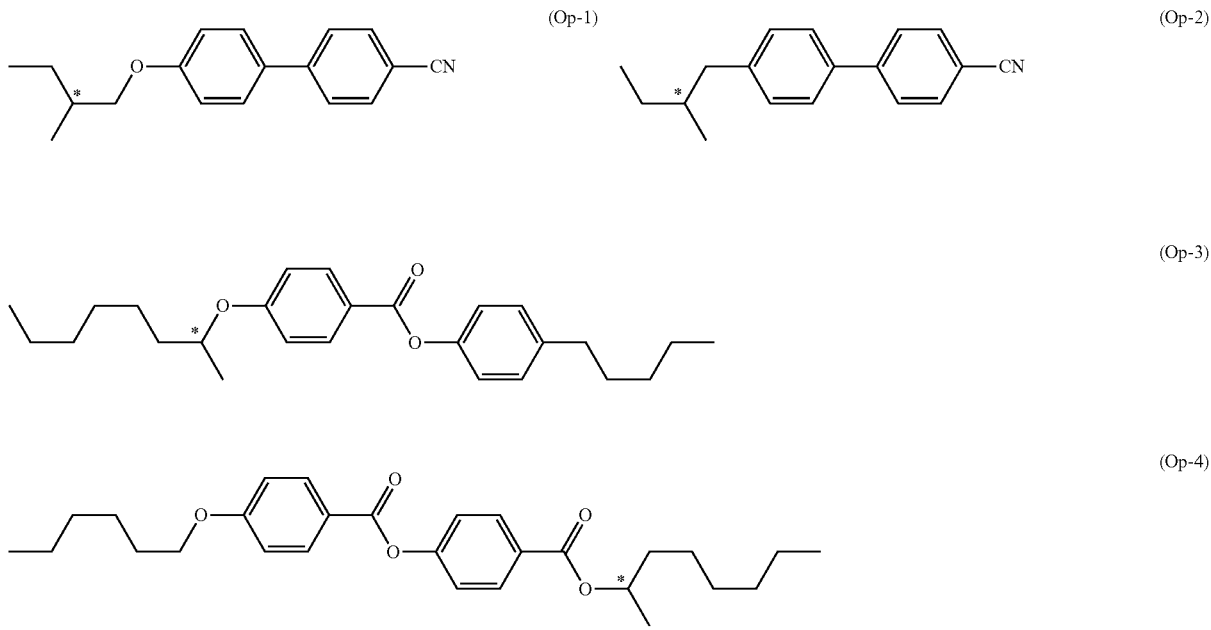

-continued
(Op-5)
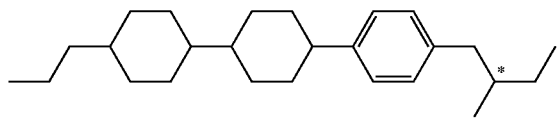
(Op-6)
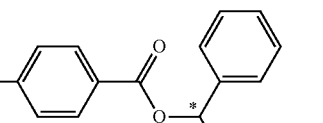
(Op-7)
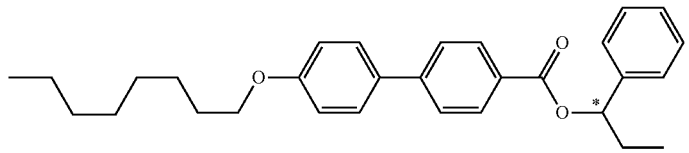
(Op-8)
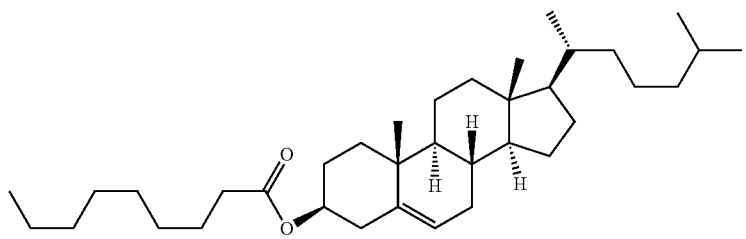
(Op-9)
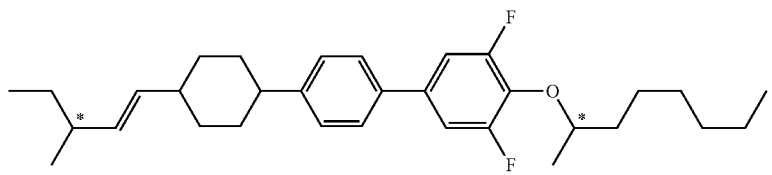
(Op-10)
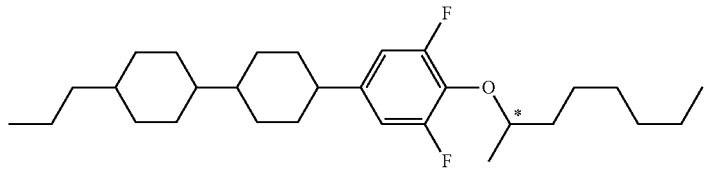
(Op-11)
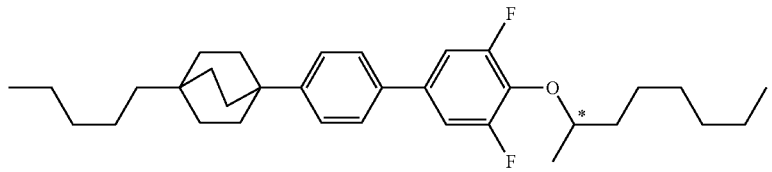
(Op-12)
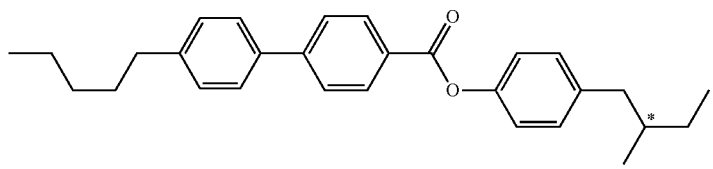
(Op-13)
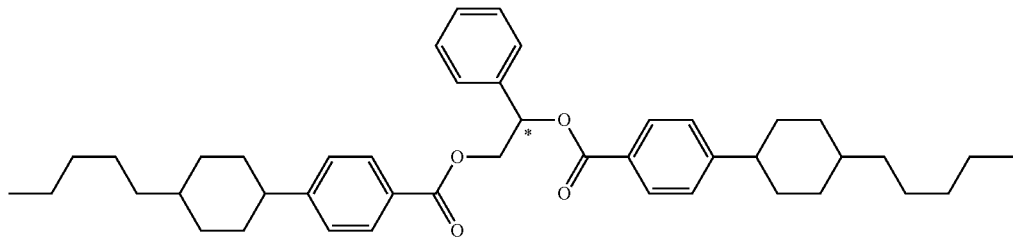

-continued (Op-14)
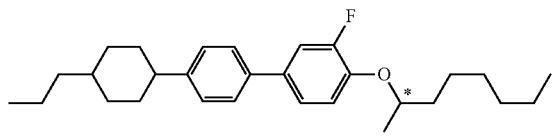

(Op-15)
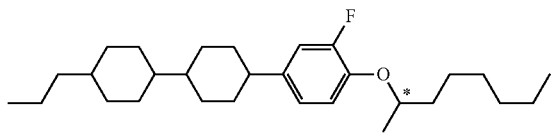

(Op-16)
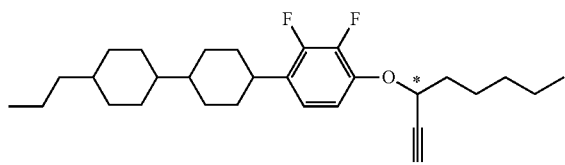

(Op-17)
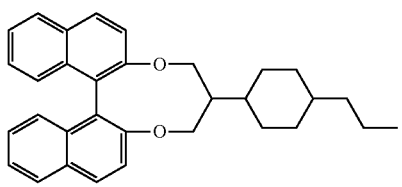

(Op-18)
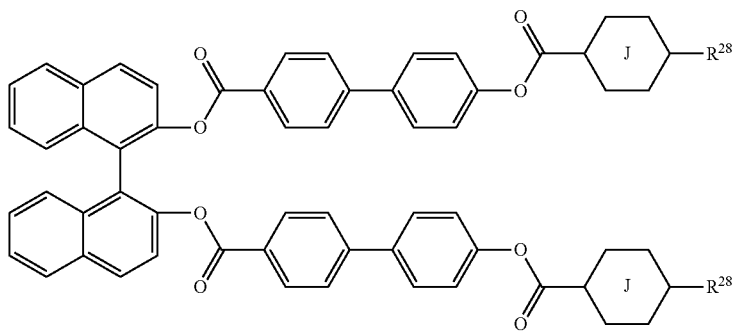

The antioxidant is effective in maintaining a large voltage holding ratio. Preferred examples of the antioxidant include compounds (AO-1) and (AO-2) described below; IRGANOX 415, IRGANOX 565, IRGANOX 1010, IRGANOX 1035, IRGANOX 3114 and IRGANOX 1098 (trade name; BASF SE). The ultraviolet light absorber is effective for preventing a decrease of the maximum temperature. Preferred examples of the ultraviolet light absorber include a benzophenone derivative, a benzoate derivative and a triazole derivative, and specific examples thereof include compounds (AO-3) and (AO-4); TINUVIN329, TINUVIN P, TINUVIN 326, TINUVIN 234, TINUVIN 213, TINUVIN 400, TINUVIN 328 and TINUVIN 99-2 (trade name; BASF SE); and 1,4-diazabicyclo [2.2.2]octane (DABCO).

A light stabilizer such as amine having steric hindrance is preferred for maintaining a large voltage holding ratio. Preferred examples of the light stabilizer include compounds (AO-5) and (AO-6) below; TINUVIN 144, TINUVIN 765 and TINUVIN 770DF (trade names: BASF). The heat stabilizer is also effective for maintaining a large voltage holding ratio, and preferred examples include IRGAFOS 168 (trade name: BASF). A dichroic dye such as an azo dye or an anthraquinone dye is added to the composition to be adapted for a device having a guest host (GH) mode. The defoaming agent is effective for preventing foam formation. Preferred examples of the defoaming agent include dimethyl silicone oil and methylphenyl silicone oil.

(AO-1)
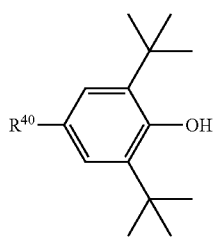

(AO-2)
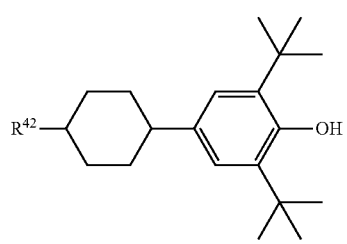

(AO-3)
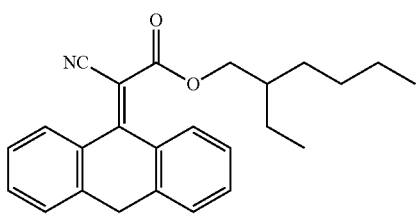

(AO-4)

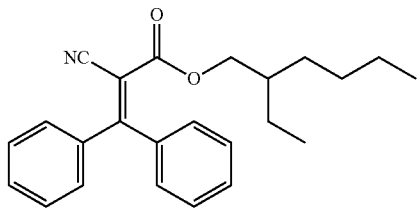

(AO-5)

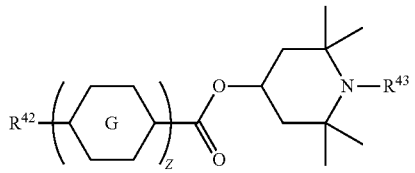

(AO-6)

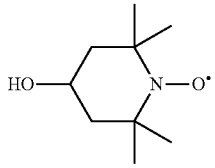

In compound (AO-1), $R^{40}$ is alkyl having 1 to 20 carbons, alkoxy having 1 to 20 carbons, $-COOR^{41}$ or $-CH_2CH_2COOR^{41}$, in which $R^{41}$ is alkyl having 1 to 20 carbons. In compounds (AO-2) and (AO-5), $R^{42}$ is alkyl having 1 to 20 carbons. In compound (AO-5), $R^{43}$ is hydrogen, methyl, or O. (oxygen radical); ring G is 1,4-cyclohexylene or 1,4-phenylene; and z is 1, 2 or 3.

4. Liquid Crystal Display Device

The liquid crystal composition has an operating mode such as PC, TN, STN, OCB or PSA, and can be used for a liquid crystal display device driven by an active matrix. The composition has the operating mode such as PC, TN, STN, OCB, VA or IPS, and can be used also for a liquid crystal display device driven by a passive-matrix method. The devices can be applied to any of a reflection type, a transmissive type and a transflective type.

The composition is also suitable for a NCAP (nematic curvilinear aligned phase) device, wherein the composition is microencapsulated. The composition can be used also for a polymer distributed liquid crystal display device (PDLCD) and a polymer network liquid crystal display device (PN-LCD). A large amount of polymerizable compound is added in such a composition. On the other hand, when the amount of addition of the polymerizable compound is approximately 10% by weight or less based on the weight of the liquid crystal composition, a liquid crystal display device of the PSA mode is produced. A preferred ratio is in the range of approximately 0.1% by weight to approximately 2% by weight. A further preferred ratio is in the range of approximately 0.2% by weight to approximately 1.0% by weight. The device of the PSA mode can be driven with a drive mode such as an active matrix and a passive matrix. Such a device can be applied to any of a reflection type, a transmissive type and transflective type.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

The invention will be described in greater detail by way of Examples (including Synthesis Examples and Use Examples). The invention is not restricted by the Examples. The invention includes a mixture of a composition of Use Example 1 and a composition of Use Example 2. The invention also includes a composition prepared by mixing at least two of the compositions of Use Examples.

1. Example of Compound (1)

Compound (1) was prepared by procedures as described below. A prepared compound was identified by a method such as NMR analysis. Physical properties of a compound or composition and characteristics of a device were measured by the following method.

NMR analysis: For measurement, DRX-500 made by Bruker BioSpin Corporation was used. In $^1$H-NMR measurement, a sample was dissolved in a deuterated solvent such as $CDCl_3$, and measurement was carried out under conditions of room temperature, 500 MHz and 16 times of accumulation. Tetramethylsilane was used as an internal standard. In $^{19}$F-NMR measurement, measurement was carried out under conditions of 24 times of accumulation using $CFCl_3$ as an internal standard. In the explanation of nuclear magnetic resonance spectra, s, d, t, q, quin, sex, m stand for a singlet, a doublet, a triplet, a quartet, a quintet, a sextet and a multiplet, respectively, and br means broad.

Gas chromatographic analysis: GC-2010 Gas Chromatograph made by Shimadzu Corporation was used for measurement. As a column, capillary column DB-1 (length 60 m, bore 0.25 mm, film thickness 0.25 μm) made by Agilent Technologies, Inc. was used. Helium (1 mL per minute) was used as a carrier gas. Temperature in a sample vaporizing chamber was set at 300° C. and temperature of a detector (FID) part was set at 300° C. A sample was dissolved in acetone and prepared to be a solution of 1% by weight, and 1 microliter of the solution obtained was injected into the sample vaporizing chamber. A Shimadzu GCSolution System and so forth were used for a recorder.

HPLC analysis: For measurement, Prominence (LC-20 AD; SPD-20A) made by Shimadzu Corporation was used. As a column, YMC-Pack ODS-A (length 150 mm, bore 4.6 mm, particle diameter 5 μm) made by YMC Co., Ltd. was used. An eluate prepared by suitably mixing acetonitrile and water was used. As a detector, a UV detector, an RI detector, a CORONA detector or the like was appropriately used. When the DV detector was used, a detection wavelength was adjusted at 254 nanometers. A sample was dissolved in acetonitrile and prepared to be a solution of 0.1% by weight, and 1 microliter of the solution was introduced into a sample chamber. As a recorder, C-R7Aplus made by Shimadzu Corporation was used.

UV-Visible spectrophotometry: For measurement, PharmaSpec UV-1700 made by Shimadzu Corporation was used. A detection wavelength was adjusted in the range from 190 nanometers to 700 nanometers. A sample was dissolved in acetonitrile and prepared to be a solution of 0.01 millimole per liter, and measurement was carried out by putting the solution in a quartz cell (optical path length 1 cm).

Sample for measurement: In measuring a phase structure and a transition temperature (a clearing point, a melting point, a polymerization starting temperature, and so forth), a compound per se was used as a sample. In measuring physical properties such as a maximum temperature of a nematic phase, viscosity, optical anisotropy and dielectric anisotropy, a mixture of a compound and a base liquid crystal was used as a sample.

In the case where a mixture of the compound with the base liquid crystal was used as the sample, an extrapolated value was calculated using the following formula, and the value was described.

<Extrapolated value>=(100x<measured value of a sample>−<wt % of base liquid crystal>x<measured value of base liquid crystal>)/<wt % of a compound>.

Base liquid crystal (A): When the dielectric anisotropy of a compound was zero or positive, the following base liquid crystal (A) was used. A proportion of each component was expressed in terms of weight %.

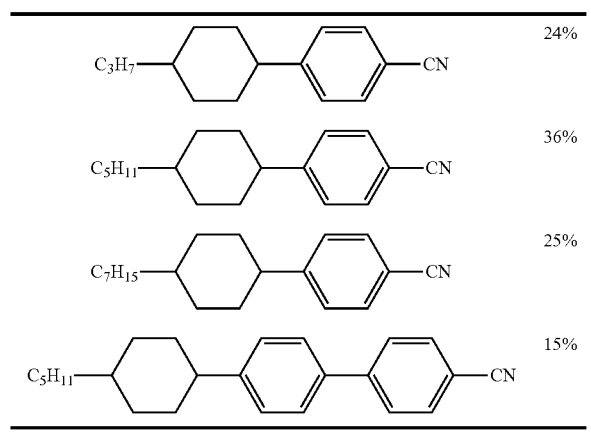

A ratio of the compound to the base liquid crystal (A) was adjusted to 15% by weight:85% by weight. When a crystal (or a smectic phase) deposits at 25° C. at the ratio, the ratio of the compound to the base liquid crystal (A) was changed in the order of 10% by weight:90% by weight, 5% by weight:95% by weight, and 1% by weight:99% by weight, and the sample was measured at a ratio where the crystal (or the smectic phase) does not deposit anymore at 25° C. In addition, unless otherwise noted, the ratio of the compound to the base liquid crystal (A) was 15% by weight:85% by weight.

Measuring method: Physical properties of a compound were measured according to the methods described below. Most of the measurement methods are described in the JEITA Standard (JEITA ED-2521B) discussed and established by Japan Electronics and Information Technology Industries Association (JEITA). Methods obtained by modifying the Standard were also used. No thin-film transistor (TFT) was attached to a TN device used for measurement.

(1) Phase structure: A sample was placed on a hot plate of a melting point apparatus (FP-52 Hot Stage made by Mettler Toledo International Inc.) equipped with a polarizing microscope. A phase state and the change thereof were observed with the polarizing microscope while heating the sample at a rate of 3° C. per minute, and types of phases were specified.

(2) Transition temperature (° C.): For measurement, a scanning calorimeter, Diamond DSC System, made by PerkinElmer, Inc., or a high sensitivity differential scanning calorimeter, X-DSC7000, made by SII Nanotechnology, Inc., were used. A sample was heated or cooled at a rate of 3° C. per minute, a starting point of an endothermic peak or exothermic peak caused by a change in phase of the sample was determined according to extrapolation, and thus a transition temperature was finally determined. A melting point and polymerization starting temperature of a compound were also measured using the instrument. Temperature at which a compound undergoes transition from a solid to a liquid crystal phase such as a smectic phase and a nematic phase may be occasionally abbreviated as "minimum temperature of the liquid crystal phase." Temperature at which a compound undergoes transition from a liquid crystal phase to a liquid may be occasionally abbreviated as "clearing point."

Crystals were expressed as C. When kinds of the crystals were distinguishable, each of the crystals was expressed as $C_1$ or $C_2$. A smectic phase or a nematic phase was expressed as S or N. When smectic A phase, smectic B phase, smectic C phase or smectic F phase was distinguishable among the smectic phases, the phases were expressed as $S_A$, $S_B$, $S_C$ or $S_F$, respectively. A liquid (isotropic) was expressed as I. A transition temperature was expressed as "C, 50.0; N, 100.0; I," for example. The expression indicates that a transition temperature from a crystal to a nematic phase is 50.0° C., and a transition temperature from the nematic phase to a liquid is 100.0° C.

(3) Compatibility at a low temperature: Samples in which the base liquid crystal and a compound were mixed for the compound to be 20% by weight, 15% by weight, 10% by weight, 5% by weight, 3% by weight and 1% by weight were prepared, and put in glass vials. After the glass vials were kept in freezers at −10° C. or −20° C. for a predetermined period of time, whether or not crystals or a smectic phase precipitated was observed.

(4) Maximum temperature of nematic phase ($T_{NI}$ or NI; ° C.): A sample was placed on a hot plate of a melting point apparatus equipped with a polarizing microscope and was heated at a rate of 1° C. per minute. Temperature was measured when part of the sample began to change from a nematic phase to an isotropic liquid. When the sample was a mixture of compound (1) and the base liquid crystal, the maximum temperature was expressed as a symbol $T_{NI}$. When the sample was a mixture of compound (1) and a compound like component B, C, D or the like, the maximum temperature was expressed as a symbol NI. A higher limit of a temperature range of the nematic phase may be occasionally abbreviated as "maximum temperature."

(5) Minimum temperature of nematic phase ($T_C$; ° C.): A sample having a nematic phase was put in glass vials and kept in freezers at temperatures of 0° C., −10° C., −20° C., −30° C. and −40° C. for 10 days, and then liquid crystal phases were observed. For example, when the sample maintained the nematic phase at −20° C. and changed to crystals or a smectic phase at −30° C., $T_c$ was expressed as $T_c$<−20° C. A lower limit of the temperature range of the nematic phase may be occasionally abbreviated as "minimum temperature."

(6) Viscosity (bulk viscosity; η; measured at 20° C.; mPa·s): A cone plate (E type) rotational viscometer made by Tokyo Keiki Inc. was used for measurement.

(7) Viscosity (rotational viscosity; γ1; measured at 25° C.; mPa·s): Measurement was carried out according to the method described in M. Imai et al., Molecular Crystals and Liquid Crystals, Vol. 259, p. 37 (1995). A sample was put in a TN device in which a twist angle was 0 degrees and a distance (cell gap) between two glass substrates was 5 micrometers. A voltage was applied stepwise to the device in the range of 16 V to 19.5 V at an increment of 0.5 V. After a period of 0.2 second with no voltage, a voltage was applied repeatedly under the conditions of only one rectangular wave (rectangular pulse; 0.2 second) and no voltage (2 seconds). A peak current and a peak time of a transient current generated by the applied voltage were measured. A value of the rotational viscosity was obtained from the measured values and a calculation equation (8) on page 40 of the paper presented by M. Imai et al. A dielectric anisotropy value required for the calculation was obtained by the method described below using the device used for measuring the rotation viscosity.

(8) Optical anisotropy (refractive index anisotropy; measured at 25° C.; $\Delta n$): Measurement was carried out by means of an Abbe refractometer with a polarizing plate mounted on an ocular by using light at a wavelength of 589 nanometers. A surface of a main prism was rubbed in one direction, and then a sample was added dropwise onto the main prism. A refractive index ($n\|$) was measured when the direction of polarized light was parallel to the direction of rubbing. A refractive index ($n\perp$) was measured when the direction of polarized light was perpendicular to the direction of rubbing. A value of optical anisotropy ($\Delta n$) was calculated from the equation: $\Delta n = n\| - n\perp$.

(9) Dielectric anisotropy ($\Delta \in$; measured at 25° C.): A sample was put in a TN device in which a distance (cell gap) between two glass substrates was 9 micrometers and a twist angle was 80 degrees. Sine waves (10 V, 1 kHz) were applied to the device, and after 2 seconds, a dielectric constant ($\in\|$) in the major axis direction of liquid crystal molecules was measured. Sine waves (0.5 V, 1 kHz) were applied to the device, and after 2 seconds, a dielectric constant ($\in\perp$) in the minor axis direction of the liquid crystal molecules was measured. A value of dielectric anisotropy was calculated from an equation: $\Delta\in = \in\| - \in\perp$.

(10) Elastic constant (K; measured at 25° C.; pN): HP4284A LCR Meter made by YOKOGAWA-Hewlett Packard Co. was used for measurement. A sample was put in a horizontal alignment device in which a distance (cell gap) between two glass substrates was 20 micrometers. An electric charge of 0 V to 20 V was applied to the device, and electrostatic capacity and applied voltage were measured. Values of electrostatic capacity (C) and applied voltage (V) measured were fitted to equation (2.98) and equation (2.101) on page 75 of "Liquid Crystal Device Handbook (Ekisho Debaisu Handobukku, in Japanese)" (The Nikkan Kogyo Shimbun, Ltd.), and values of $K_{11}$ and $K_{33}$ were obtained from equation (2.99). Next, $K_{22}$ was calculated assigning the value of $K_{11}$ and $K_{33}$ already obtained to formula (3.18) on page 171. Elastic constant K was represented by an average of $K_{11}$, $K_{22}$ and $K_{33}$ thus obtained.

(11) Threshold voltage (Vth; measured at 25° C.; V): An LCD-5100 luminance meter made by Otsuka Electronics Co., Ltd. was used for measurement. A light source was a halogen lamp. A sample was put in a normally white mode TN device in which a distance (cell gap) between two glass substrates was $0.45/\Delta n$ (μm) and a twist angle was 80 degrees. A voltage (32 Hz, rectangular waves) applied to the device was increased stepwise from 0 V to 10 V at an increment of 0.02 V. On the above occasion, the device was irradiated with light from a perpendicular direction, and an amount of light transmitted through the device was measured. A voltage-transmittance curve was prepared in which the maximum value of the amount of light corresponded to 100% transmittance and the minimum value of the amount of light corresponded to 0% transmittance. A threshold voltage was expressed as a voltage at 90% transmittance.

(12) Voltage holding ratio (VHR-1; measured at 25° C.; %): A TN device used for measurement had a polyimide alignment film and a distance (cell gap) between two glass substrates was 5 micrometers. A sample was put in the device, and then the device was sealed with an ultraviolet-curable adhesive. The device was charged by applying pulse voltage (60 microseconds at 5 V) at 25° C. A decaying voltage was measured for 16.7 milliseconds with a high-speed voltmeter, and area A between a voltage curve and a horizontal axis in a unit cycle was obtained. Area B was an area without decay. A voltage holding ratio was expressed as a percentage of area A to area B.

(13) Voltage holding ratio (VHR-2; measured at 80° C.; %): A voltage holding ratio was measured by the method described above except that measurement was performed at 80° C. instead of 25° C. The result obtained was expressed with a symbol VHR-2.

(14) Specific resistance (p; measured at 25° C.; $\Omega$cm): Into a vessel equipped with electrodes, 1.0 milliliter of a sample was injected. A DC voltage (10 V) was applied to the vessel, and a DC current after 10 seconds was measured. A specific resistance was calculated from the following equation: (specific resistance)={(voltage)×(electric capacity of a vessel)}/{(direct current)×(dielectric constant of vacuum)}.

(15) Response Time ($\tau$; measured at 25° C.; ms): An LCD-5100 luminance meter made by Otsuka Electronics Co., Ltd. was used for measurement. A light source was a halogen lamp. A low-pass filter was set at 5 kHz. A sample was put in a normally white mode TN device in which a distance (cell gap) between two glass substrates was 5.0 micrometers and a twist angle was 80 degrees. Rectangular waves (60 Hz, 5 V, 0.5 second) were applied to the device. On the occasion, the device was irradiated with light from a perpendicular direction, and an amount of light transmitted through the device was measured. The maximum amount of light was regarded as 100% transmittance, and the minimum amount of light as 0% transmittance. Rise time ($\tau$r: rise time; ms) was the time taken for transmittance to change from 90% to 10%. Fall time ($\tau$f: fall time; ms) was the time taken for transmittance to change from 10% to 90%. Response time was represented by a sum of the rise time and fall time thus determined.

Raw material: Solmix (registered trade name) A-11 is a mixture of ethanol (85.50), methanol (13.4%) and isopropanol (1.10), and was purchased from Japan Alcohol Trading Company Ltd. Tetrahydrofuran may be occasionally abbreviated to THF. Tetrabutylammonium bromide may be occasionally abbreviated to TBAB. N,N-dimethylformamide may be occasionally abbreviated to DMF. Then, 2-propanol may be occasionally abbreviated to IPA. Furthermore, 1,2-dimethoxyethane may be occasionally abbreviated to DME.

Synthesis Example 1

Synthesis of Compound (No. 221)

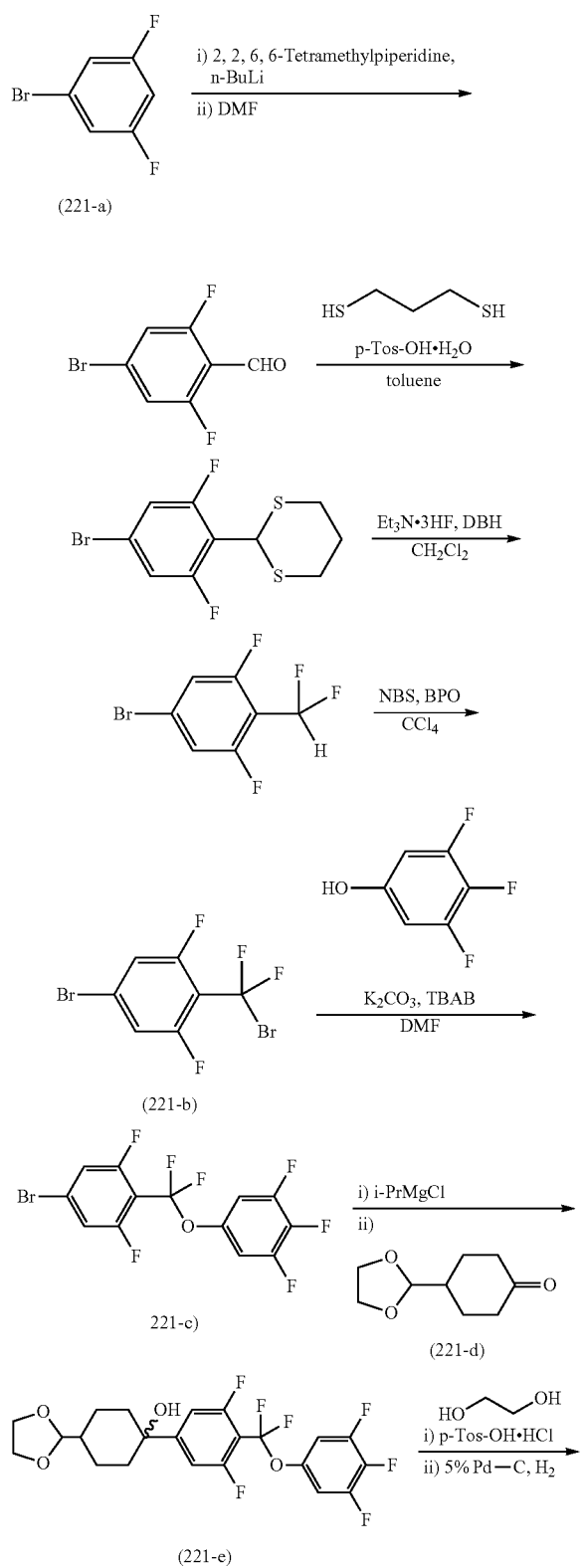

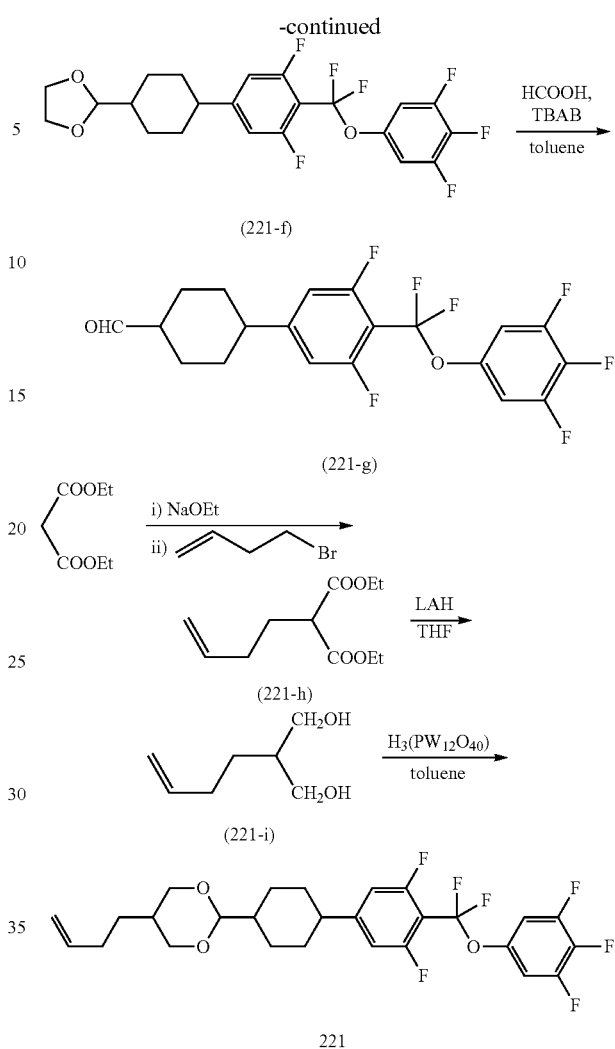

First Step:

Compound (221-b) was prepared from compound (221-a) with reference to JP 2013-155155 A. Then, 3,4,5-trifluorophenol (15.8 g, 0.107 mol), potassium carbonate (31.012 g, 0.224 mol) and tetrabutylammonium bromide (TBAB) (1.651 g, 5.16 mmol) were added to DMF (100 mL), and the resulting mixture was stirred at 60° C. for 1 hour. Compound (221-b) (33.6 g) was added to the solution, and the resulting mixture was stirred at 110° C. for 1 hour. The reaction mixture was returned to room temperature, poured into water (100 mL), and subjected to extraction with toluene (50 mL×3). The extract was washed with water (20 mL×2), dried over anhydrous magnesium sulfate, and concentrated under reduced pressure. The resulting residue was purified by silica gel chromatography (heptane) to obtain compound (221-c) (14.809 g; 36%) as a colorless crystal.

Second Step:

To isopropylmagnesium chloride (2.0 mol/mol THF solution; 20 mL, 0.040 mol), a THF (15 mL) solution of compound (221-c) (14.809 g, 0.0381 mol) was added dropwise at 0° C. or lower. After 1 hour, a THF (10 mL) solution of compound (221-d) (6.485 g, 0.0381 mol) was added dropwise thereto at 0° C. or lower. Compound (221-d) was prepared with reference to WO 2008-094574 A. After 30 minutes, the reaction mixture was returned to room temperature, and further stirred overnight. The resulting reaction mixture was poured into water (30 mL) and subjected to extraction with ethyl acetate (30 mL×3). The extract was washed with saturated brine (20 mL×2), dried over anhydrous magnesium sulfate, and concentrated under reduced pressure. The residue was purified by silica gel chromatography (heptane:ethyl acetate=4:1) to obtain compound (221-e) (16.472 g, 90%) as a colorless oily matter.

Third Step:

To a toluene (150 mL) solution of compound (221-e) (16.472 g, 0.0343 mol), p-toluenesulfonic acid monohydrate (0.494 g, 0.03 wt %) and ethylene glycol (2.36 g, 0.0343 mol) were added, and the resulting mixture was stirred at 85° C. for 3 hours. The reaction mixture was washed with saturated sodium bicarbonate water (30 mL×3), dried over anhydrous magnesium sulfate, and concentrated under reduced pressure. The resulting residue was purified by silica gel chromatography (heptane:ethyl acetate=9:1), and recrystallized from IPA to obtain compound (221-f) (4.777 g; 30%) as a colorless crystal.

Fourth Step:

To a toluene (50 mL) solution of compound (221-f) (4.777 g, 0.0102 mol), TBAB (0.1 g, 0.3 mol) and formic acid (HCCOH) (23.885 mL) were added, and the resulting mixture was stirred at 80° C. for 6 hours. The reaction mixture was returned to room temperature, washed with saturated sodium bicarbonate water (10 mL×2), dried over anhydrous magnesium sulfate, and concentrated under reduced pressure. The residue was purified by silica gel chromatography (heptane:ethyl acetate=6:1) to obtain compound (221-g) (4.324 g) as a colorless oily matter.

Fifth Step:

To ethanol (200 mL), sodium ethylate (20% ethanol solution; 166.342 g, 0.489 mol) was added, and then diethyl malonate (78.303 g, 0.489 mol) was added dropwise thereto at room temperature. The resulting mixture was stirred at 50° C. for 30 minutes, returned to room temperature, 4-bromo-1-butene (60 g, 0.444 mol) was added thereto, and the resulting solution was stirred at room temperature overnight. The reaction mixture was concentrated under reduced pressure and, water (60 mL) was added thereto, and then subjected to extraction with diethyl ether (120 mL×3). The extract was washed with saturated brine (30 mL×2), dried over anhydrous magnesium sulfate, and concentrated under reduced pressure. The residue was distilled under reduced pressure to obtain compound (221-h) (56.6 g, 57%) as a colorless oily matter. Then, bp.: 70 to 78° C./0.5 kPa.

Sixth Step:

To a THF (200 mL) suspension of lithium aluminum hydride (LAH; 14.037 g, 0.370 mol), a THF (100 mL) solution of compound (221-h) was added dropwise at 0° C. The reaction mixture was stirred for 1 hour at room temperature, and then stirred at 45 to 50° C. overnight. The reaction mixture was quenched with water, and stirred for 30 minutes while the mixture was neutralized with 1 N hydrochloric acid. The reaction mixture turned cloudy, and was subjected to filtration with Cerite and washing with acetone and methylene chloride. Combined filtrate was concentrated under reduced pressure, and subjected to extraction with ethyl acetate (100 mL×3). The extract was dried over anhydrous magnesium sulfate and concentrated under reduced pressure. The residue was purified by silica gel chromatography (heptane:ethyl acetate=3:2, and then heptane:ethyl acetate=4:1) to obtain compound (221-i) (19.9 g, 58%) as a colorless oily matter.

Seventh Step:

To a toluene (50 mL) solution of compound (221-g) (2.4 g, 5.710 mmol), compound (221-i) (0.818 g, 6.280 mmol) and 12 tungsto(VI) phosphoric acid n-hydrate (0.822 g, 5.710 mmol) were added, and the resulting mixture was stirred at 90° C. After 5 hours, the reaction mixture was returned to room temperature, washed with saturated sodium bicarbonate water (10 mL×2), water (10 mL×2) and saturated brine (10 mL×2), dried over anhydrous magnesium sulfate, and concentrated under reduced pressure. The resulting residue was purified by silica gel chromatography (heptane:ethyl acetate=9:1), and recrystallized from heptane-ethanol to obtain compound (221) (0.65 g; 21%) as a colorless crystal.

$^1$H-NMR (δ ppm; CDCl$_3$): 6.95 (dd, J=7.6, 6.1 Hz, 2H), 6.82 (d, J=10.8 Hz, 2H), 5.77 (ddt, J=17.1, 10.2, 6.5 Hz), 5.02 (dd, J=17.1, 1.7 Hz, 1H), 4.98 (dd, J=10.2, 1.7 Hz, 1H), 4.22 (d, J=5.1 Hz, 1H), 4.10 (dd, J=11.5, 4.6 Hz, 2H), 3.31 (dd, J=11.5, 11.3 Hz, 2H), 2.48 (tt, J=12.0, 3.2 Hz, 1H) 2.06-1.92 (m, 6H), 1.62-1.49 (m, 1H), 1.37 (dq, J=12.7, 2.9 Hz, 2H), 1.25 (dq, J=12.6, 2.7 Hz, 2H), 1.14 (dt, J=8.0, 7.3 Hz, 2H).

$^{19}$F-NMR (δ ppm; CDCl$_3$): −62.18 (t, J=26.1 Hz, 2F), −112.00 (dt, J=26.1, 10.8 Hz, 2F), −133.14 (dd, J=20.3, 7.6 Hz, 2F), −163.89 (tt, J=20.3, 6.1 Hz, 1F).

Transition temperature: C 74.6 C 85.3N 124.9 I. Maximum temperature (T$_{NI}$)=79.7° C.; dielectric anisotropy (Δ∈)=39.2; optical anisotropy (Δn)=0.097; viscosity (η)=77.9 mPa·s.

Synthesis Example 2

Synthesis of Compound (No. 236)

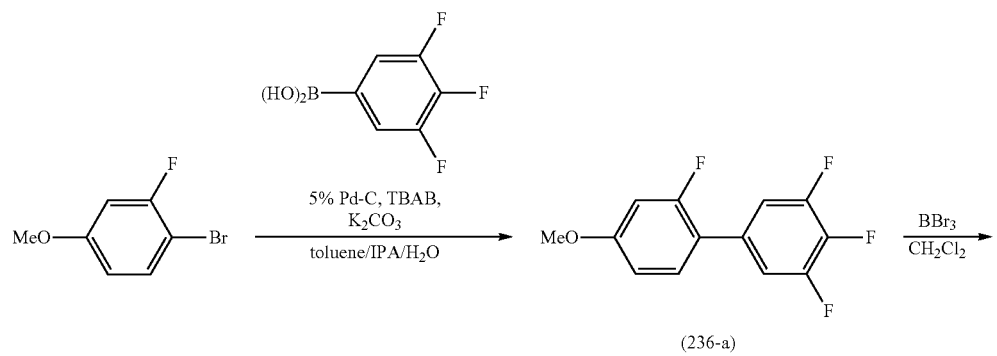

(236-a)

-continued
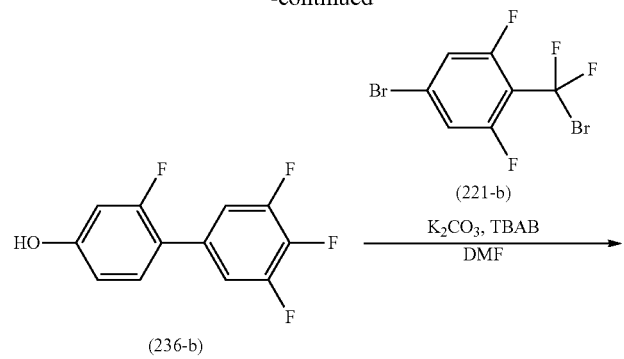
(236-b) + (221-b) →[K₂CO₃, TBAB / DMF]
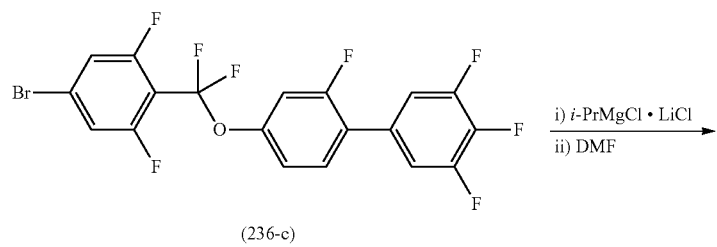
(236-c) →[i) i-PrMgCl · LiCl; ii) DMF]
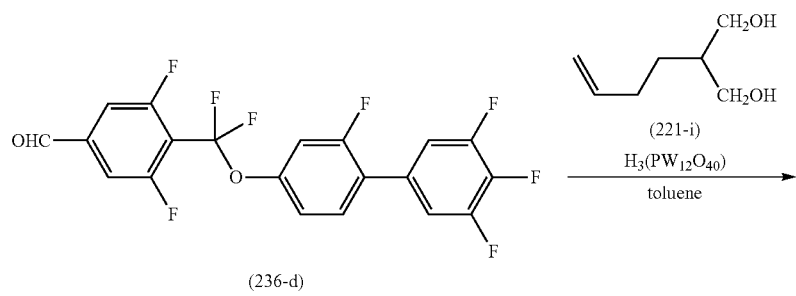
(236-d) + (221-i) →[H₃(PW₁₂O₄₀) / toluene]
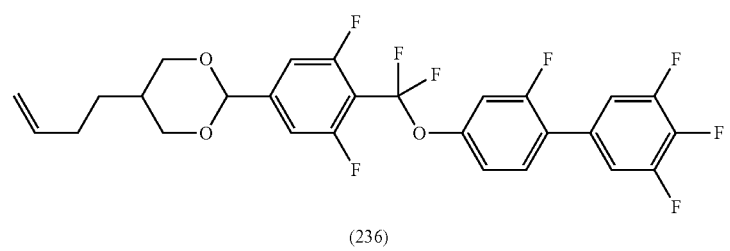
(236)

First Step:

A mixture of 3,4,5-trifluorophenylboronic acid (47.187 g, 0.268 mol), 1-bromo-2-fluoro-4-methoxybenzene (50 g, 0.244 mol), TBAB (19.654 g, 0.0610 mol), potassium carbonate (67.410 g, 0.488 mol), 2-propanol (210 mL), toluene (210 mL) and water (60 mL) was heated and refluxed for 6 hours. The reaction mixture was poured into water (300 mL), and subjected to extraction with toluene (200 mL×3). The extract was washed with saturated brine (50 mL×2), dried over anhydrous magnesium sulfate, and concentrated under reduced pressure. The resulting residue was purified by silica gel chromatography (heptane) to obtain compound (236-a) (50 g; 80%) as a colorless crystal.

Second Step:

To a methylene chloride (300 mL) solution of compound (236-a) (50 g, 0.195 mol), boron tribromide (27.680 mL, 0.293 mol) was added dropwise at −20° C. or lower. After 30 minutes, the reaction mixture was returned to room temperature and further stirred overnight. The reaction mixture was poured into ice water (300 mL) and subjected to extraction with ethyl acetate (200 mL×3). The extract was washed with saturated brine (100 mL×2), dried over anhydrous magnesium sulfate, and concentrated under reduced pressure. The resulting residue was purified by silica gel chromatography (heptane:ethyl acetate=4:1) to obtain compound (236-b) (42.54 g, 90%) as a colorless crystal.

Third Step:

Compound (236-b) (40 g, 0.165 mol), potassium carbonate (47.939 g, 0.347 mol) and tetrabutylammoniumbromide (TBAB) (2.662 g, 8.26 mmol) were added to DMF (300 mL), and the resulting mixture was stirred at 60° C. for 1 hour. Compound (221-b) (53.168 g, 0.165 mol) was added to the solution, and the resulting mixture was stirred at 110° C. for 1 hour. Compound (221-b) was prepared from compound (221-a) with reference to JP 2013-155155 A. The reaction mixture was returned to room temperature, poured into water (300 mL), and subjected to extraction with toluene (200 mL×3). The extract was washed with water (50 mL×2), dried over anhydrous magnesium sulfate, and concentrated under reduced pressure. The resulting residue was purified by silica gel chromatography (heptane) to obtain compound (236-c) (31.920 g, 40%) as a colorless crystal.

Fourth Step:

To isopropylmagnesium chloride•lithium chloride (1.3 mol/mol THF solution; 55.870 mL, 0.0726 mol), a THF (60 mL) solution of compound (236-c) (31.920 g, 0.0660 mol) was added dropwise at 0° C. or lower. After 1 hour, a THF (20 mL) solution of DMF (9.652 g, 0.132 mol) was added dropwise at 0° C. or lower. After 30 minutes, the reaction mixture was returned to room temperature and further stirred overnight. The reaction mixture was poured into water (200 mL), and subjected to extraction with ethyl acetate (150 mL×3). The extract was washed with saturated brine (50 mL×2), dried over anhydrous magnesium sulfate, and concentrated under reduced pressure. The resulting residue was purified by silica gel chromatography (heptane:ethyl acetate=4:1) to obtain compound (236-e) (24.260 g, 85%) as a colorless crystal.

Fifth Step:

To a toluene (50 mL) solution of compound (236-e) (5.0 g, 0.0116 mol), compound (221-i) (1.58 g, 0.0122 mmol) and 12 tungsto(VI) phosphoric acid n-hydrate (0.25 g, 0.090 mmol) were added, and the resulting mixture was stirred at 90° C. for 5 hours. The reaction mixture was returned to room temperature, washed with saturated sodium bicarbonate water (10 mL×2), water (10 mL×2) and saturated brine (10 mL×2), dried over anhydrous magnesium sulfate, and concentrated under reduced pressure. The resulting residue was purified by silica gel chromatography (heptane:ethyl acetate=9:1), and recrystallized from heptane-ethanol to obtain compound (221) (2.37 g, 38%) as a colorless crystal.

$^1$H-NMR (δ ppm; CDCl$_3$): 7.34 (dd, J=8.6, 8.5 Hz, 1H), 7.16-7.10 (m, 6H), 5.78 (ddt, J=17.1, 10.2, 6.5 Hz, 1H), 5.37 (s, 1H), 5.05 (dd, J=17.1, 1.4 Hz, 1H), 5.01 (dd, J=10.2, 1.1 Hz, 1H), 4.25 (dd, J=11.6, 4.6 Hz, 2H), 3.54 (dd, J=11.6, 11.5 Hz, 2H), 2.18-2.06 (m, 3H), 1.22 (dt, J=8.0, 7.2 Hz, 2H).

$^{19}$F-NMR (δ ppm; CDCl$_3$): −61.44 (t, J=26.3 Hz, 2F), −110.53 (dt, J=26.3, 10.6 Hz, 2F), −114.89 (dd, J=9.8, 8.6 Hz, 1F) −134.76 (dd, 20.2, 7.9 Hz, 2F), −161.77 (tt, J=20.2, 6.9 Hz, 1F).

Transition temperature: C 30.0 N 68.2 I. Maximum temperature ($T_{NI}$)=57.0° C.; dielectric anisotropy (Δ∈)=42.57; optical anisotropy (Δn) 0.137; viscosity (η)=62.8 mPa·s.

Comparative Example 1

Compound (s-1) described below was selected as an object of comparison. The reason is that the above compound is different from the compounds of the invention in that a left-terminal group of the compound is alkyl. The compound was prepared according to Synthetic Example described above.

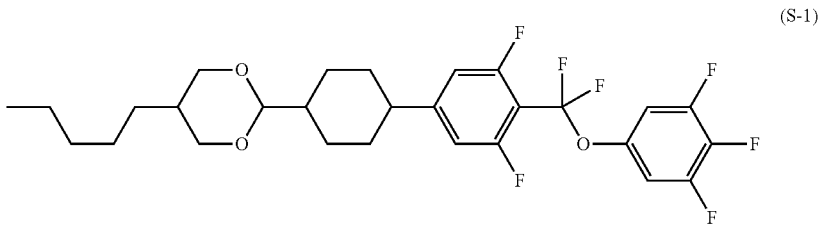 [SMILES: CCCCCC1COC(C2CCC(c3cc(F)c(C(F)(F)Oc4cc(F)c(F)c(F)c4)c(F)c3)CC2)OC1]

(S-1)

$^1$H-NMR (δ ppm; CDCl$_3$): 6.95 (dd, J=7.6, 6.1 Hz, 2H), 6.82 (d, J=10.8 Hz, 2H) 4.22 (d, J=5.1 Hz, 1H), 4.10 (dd, J=11.5, 4.6 Hz, 2H), 3.30 (dd, J=11.5, 11.3 Hz, 2H), 2.48 (tt, J=12.0, 3.2 Hz, 1H) 1.98-1.92 (m, 4H), 1.62-1.45 (m, 2H), 1.41-1.20 (m, 10H), 1.05-0.98 (m, 2H), 0.88 (t, J=6.8 Hz, 3H).

$^{19}$F-NMR (δ ppm; CDCl$_3$): −62.18 (t, J=26.1 Hz, 2F), −112.00 (dt, J=26.1, 10.8 Hz, 2F), −133.14 (dd, J=20.3, 7.6 Hz, 2F), −163.89 (tt, J=20.3, 6.1 Hz, 1F).

Transition temperature: C$_1$ 67.7 C$_2$ 74.5 S$_C$ 77.7 N 136.9 I. Maximum temperature ($T_{NI}$)=97.0° C.; dielectric anisotropy (Δ∈)=36.2; optical anisotropy (Δn)=0.1037; viscosity (η)=83.9 mPa·s.

TABLE 1

Physical properties of compound (No. 221) and comparative compound (s-1)

| | Compound (No. 221) | Comparative compound (s-1) |
|---|---|---|
| Structure | (structure shown) | (structure shown) |
| Maximum temperature ($T_{NI}$) | 79.7° C. | 97.0° C. |
| Dielectric anisotropy ($\Delta\epsilon$) | 39.2 | 36.2 |
| Optical anisotropy ($\Delta n$) | 0.097 | 0.104 |
| Viscosity ($\eta$) | 77.9 mPa·s | 83.9 mPa·s |

Physical properties of compound (No. 221) obtained in Synthesis Example 1 and comparative compound (s-1) are summarized in Table 1. Table 1 shows that compound (No. 221) is superior in view of larger dielectric anisotropy and smaller viscosity.

Comparative Example 2

Compound (s-2) described below was selected as an object of comparison. The reason is that the above compound is different from the compound of the invention in that a left terminal group of the compound is alkyl. The compound was prepared according to Synthetic Example described above.

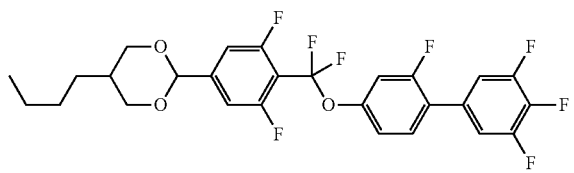 [SMILES: CCCCC1COC(c2cc(F)c(C(F)(F)Oc3ccc(-c4cc(F)c(F)c(F)c4)c(F)c3)c(F)c2)OC1]

(S-2)

$^1$H-NMR (δ ppm; CDCl$_3$): 7.34 (dd, J=8.6, 8.5 Hz, 1H), 7.16-7.10 (m, 6H), 5.36 (s, 1H) 4.24 (dd, J=11.6, 4.5 Hz, 2H), 3.52 (dd, J=11.5, 11.4 Hz, 2H), 2.12-2.08 (m, 1H), 1.30-1.24 (m, 4H), 1.13-1.09 (m, 2H), 0.91 (t, J=6.9 Hz, 3H).

$^{19}$F-NMR (δ ppm; CDCl$_3$): −61.44 (t, J=26.3 Hz, 2F), −110.53 (dt, J=26.3, 10.6 Hz, 2F), −114.89 (dd, J=9.8, 8.6 Hz, 1F) −134.76 (dd, 20.2, 7.9 Hz, 2F), −161.77 (tt, J=20.2, 6.9 Hz, 1F).

Transition temperature: C 48.4 N 74.7 I. Maximum temperature ($T_{NI}$)=61.0° C.; dielectric anisotropy ($\Delta\epsilon$)=40.47; optical anisotropy ($\Delta n$)=0.124; viscosity ($\eta$)=70.8 mPa·s.

TABLE 2

Physical properties of compound (No. 236) and comparison compound (s-2)

| | Compound (No. 236) | Comparative compound (s-2) |
|---|---|---|
| Structure | (structure shown) | (structure shown) |
| Maximum temperature ($T_{NI}$) | 57.0° C. | 61.0° C. |
| Dielectric anisotropy ($\Delta\epsilon$) | 42.57 | 40.47 |

TABLE 2-continued

| | | |
|---|---|---|
| Optical anisotropy (Δn) | 0.137 | 0.137 |
| Viscosity (η) | 62.8 mPa·s | 70.8 mPa·s |

Physical properties of compound (No. 236) obtained in Synthetic Example 2 and comparative compound (S-2) are summarized in Table 2. Table 2 shows that compound (No. 236) is superior in view of higher dielectric anisotropy and lower viscosity.

According to the synthesis method of compound (No. 1) described above and synthesis procedures described in Synthetic Examples 1 and 2, compounds (No. 1) to (No. 220) and compounds (No. 222) to (No. 238) are prepared.

No.

1

2

3

4

5

| No. | |
|---|---|
| 6 | 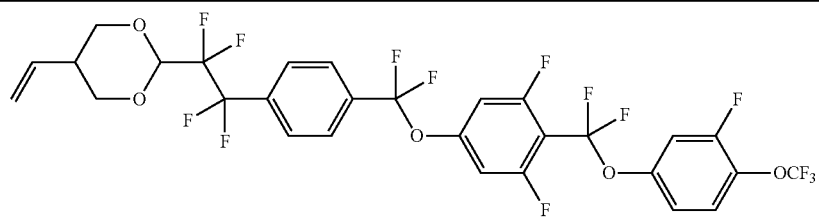 |
| 7 | 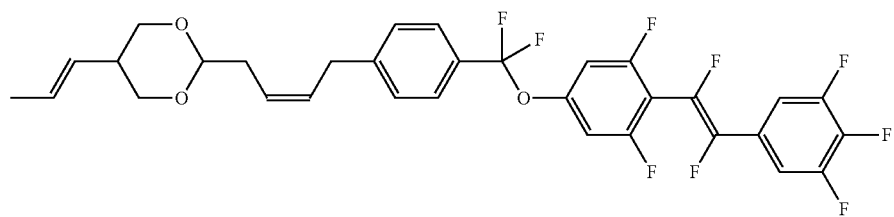 [SMILES: C/C=C/C1COC(C/C=C\Cc2ccc(C(F)(F)Oc3cc(F)c(/C(F)=C(\F)c4cc(F)c(F)c(F)c4)c(F)c3)cc2)OC1] |
| 8 | 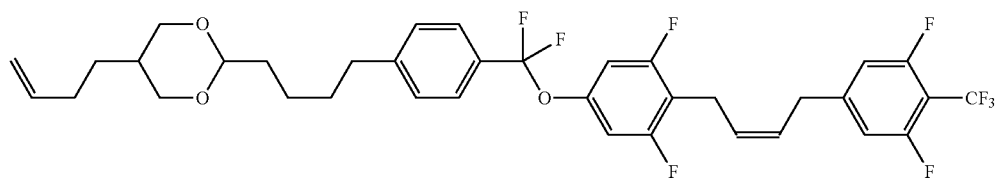 [SMILES: C=CCCC1COC(CCCCc2ccc(C(F)(F)Oc3cc(F)c(C/C=C\Cc4cc(F)c(C(F)(F)F)c(F)c4)c(F)c3)cc2)OC1] |
| 9 | 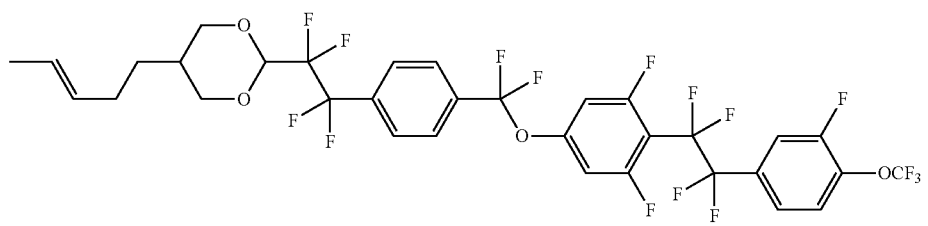 [SMILES: C/C=C/CCC1COC(C(F)(F)C(F)(F)c2ccc(C(F)(F)Oc3cc(F)c(C(F)(F)C(F)(F)c4ccc(OC(F)(F)F)c(F)c4)c(F)c3)cc2)OC1] |
| 10 | 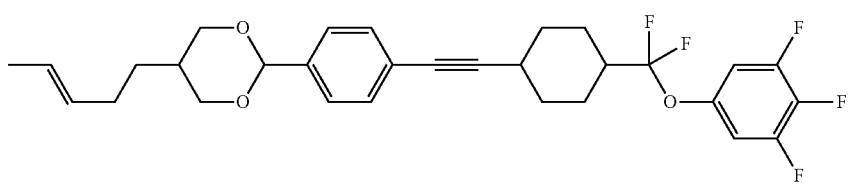 [SMILES: C/C=C/CCC1COC(c2ccc(C#CC3CCC(C(F)(F)Oc4cc(F)c(F)c(F)c4)CC3)cc2)OC1] |
| 11 | 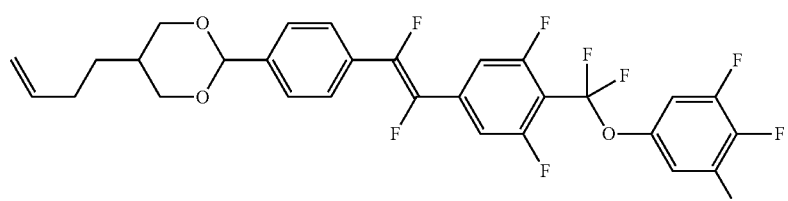 |
| 12 | 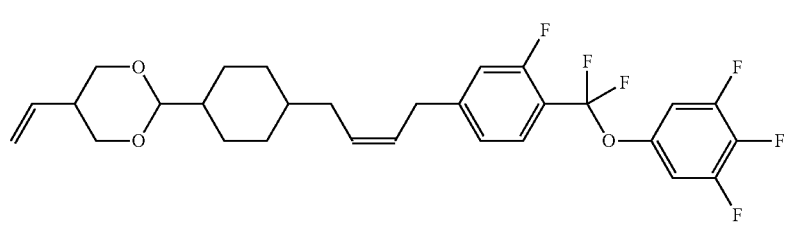 |

| No. | |
|---|---|
| 13 | 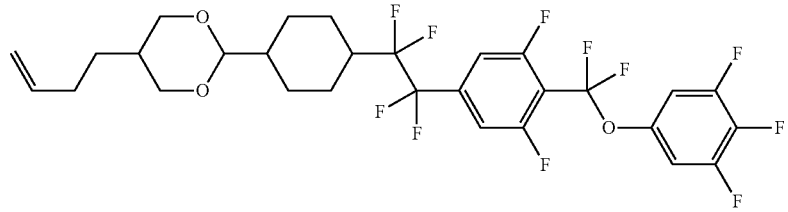 [SMILES: C=CCCC1COC(C2CCC(C(F)(F)C(F)(F)c3cc(F)c(C(F)(F)Oc4cc(F)c(F)c(F)c4)c(F)c3)CC2)OC1] |
| 14 | 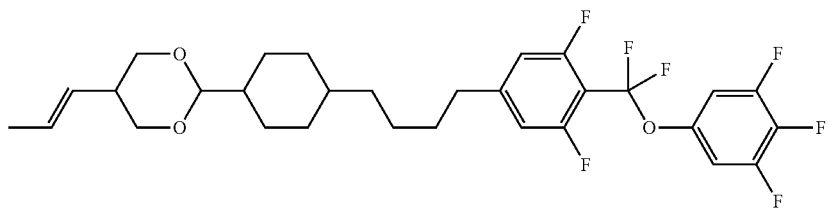 |
| 15 | 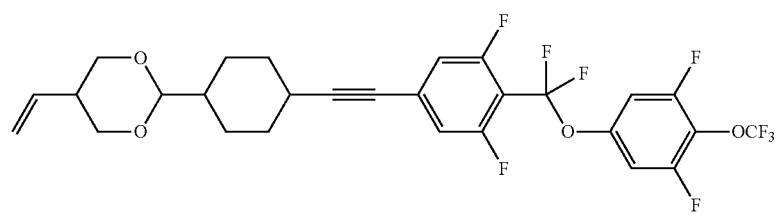 |
| 16 | 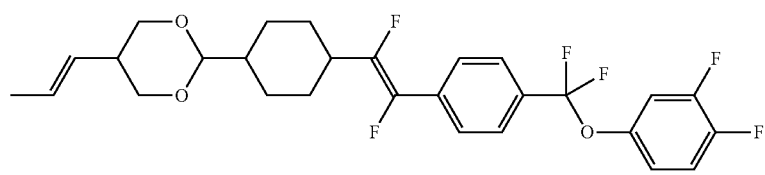 [SMILES: C/C=C/C1COC(C2CCC(/C(F)=C(\F)c3ccc(C(F)(F)Oc4ccc(F)c(F)c4)cc3)CC2)OC1] |
| 17 | 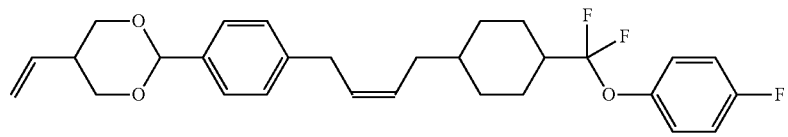 [SMILES: C=CC1COC(c2ccc(C/C=C\CC3CCC(C(F)(F)Oc4ccc(F)cc4)CC3)cc2)OC1] |
| 18 | 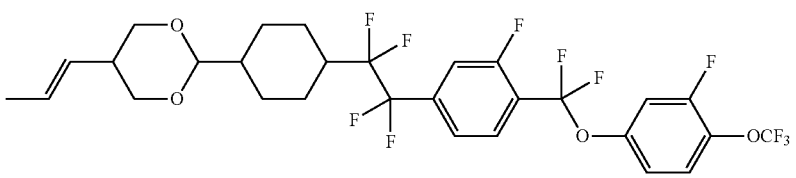 [SMILES: C/C=C/C1COC(C2CCC(C(F)(F)C(F)(F)c3ccc(C(F)(F)Oc4ccc(OC(F)(F)F)c(F)c4)c(F)c3)CC2)OC1] |
| 19 | 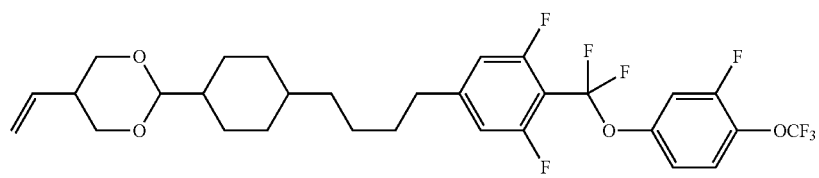 [SMILES: C=CC1COC(C2CCC(CCCCc3cc(F)c(C(F)(F)Oc4ccc(OC(F)(F)F)c(F)c4)c(F)c3)CC2)OC1] |
| 20 | 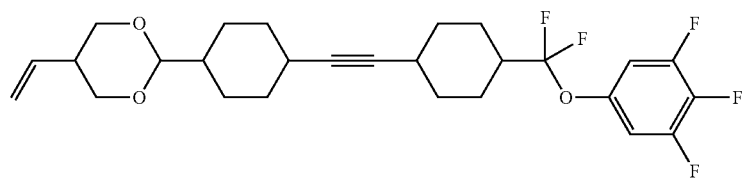 [SMILES: C=CC1COC(C2CCC(C#CC3CCC(C(F)(F)Oc4cc(F)c(F)c(F)c4)CC3)CC2)OC1] |

| No. | |
|---|---|
| 21 | 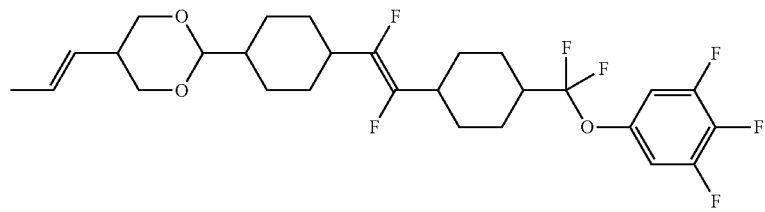 [SMILES: C/C=C/C1COC(C2CCC(/C(F)=C(\F)C3CCC(C(F)(F)Oc4cc(F)c(F)c(F)c4)CC3)CC2)OC1] |
| 22 | 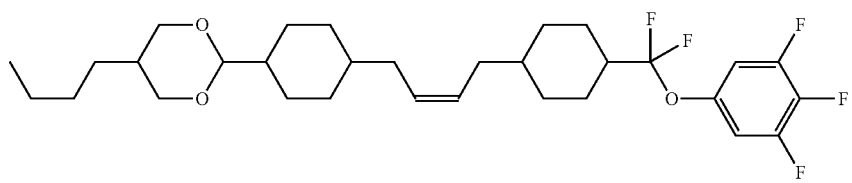 [SMILES: CCCCC1COC(C2CCC(C/C=C\CC3CCC(C(F)(F)Oc4cc(F)c(F)c(F)c4)CC3)CC2)OC1] |
| 23 | 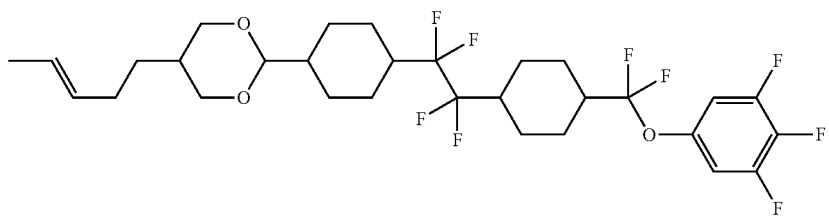 [SMILES: C/C=C/CCC1COC(C2CCC(C(F)(F)C(F)(F)C3CCC(C(F)(F)Oc4cc(F)c(F)c(F)c4)CC3)CC2)OC1] |
| 24 | 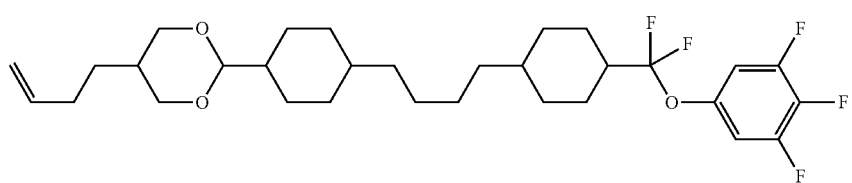 [SMILES: C=CCCC1COC(C2CCC(CCCCC3CCC(C(F)(F)Oc4cc(F)c(F)c(F)c4)CC3)CC2)OC1] |
| 25 | 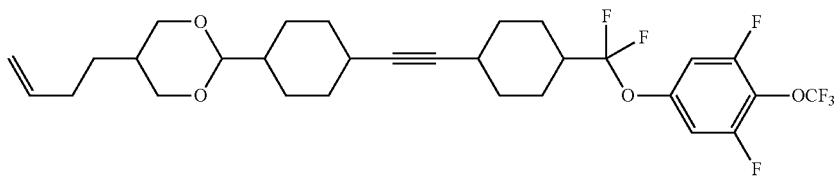 [SMILES: C=CCCC1COC(C2CCC(C#CC3CCC(C(F)(F)Oc4cc(F)c(OC(F)(F)F)c(F)c4)CC3)CC2)OC1] |
| 26 | 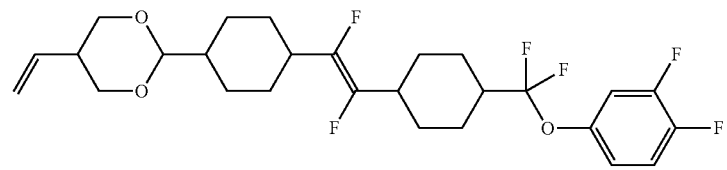 [SMILES: C=CC1COC(C2CCC(/C(F)=C(\F)C3CCC(C(F)(F)Oc4ccc(F)c(F)c4)CC3)CC2)OC1] |
| 27 | 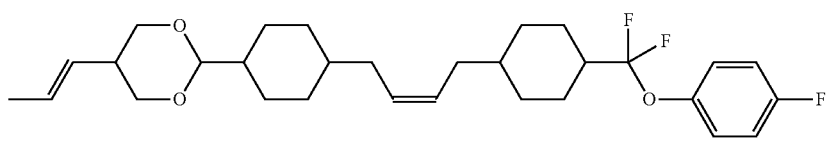 [SMILES: C/C=C/C1COC(C2CCC(C/C=C\CC3CCC(C(F)(F)Oc4ccc(F)cc4)CC3)CC2)OC1] |
| 28 | 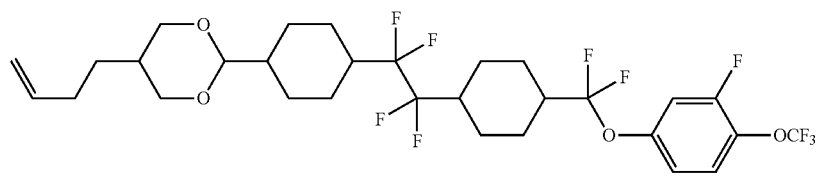 [SMILES: C=CCCC1COC(C2CCC(C(F)(F)C(F)(F)C3CCC(C(F)(F)Oc4ccc(OC(F)(F)F)c(F)c4)CC3)CC2)OC1] |

| No. | |
|---|---|
| 29 | 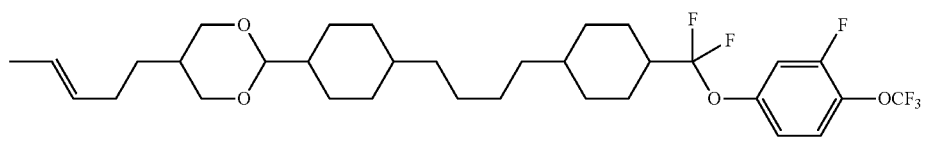 [SMILES: C/C=C/CCC1COC(C2CCC(CCCCC3CCC(C(F)(F)Oc4ccc(OC(F)(F)F)c(F)c4)CC3)CC2)OC1] |
| 30 | 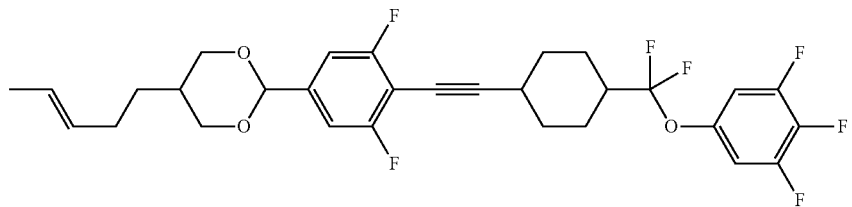 [SMILES: C/C=C/CCC1COC(c2cc(F)c(C#CC3CCC(C(F)(F)Oc4cc(F)c(F)c(F)c4)CC3)c(F)c2)OC1] |
| 31 | 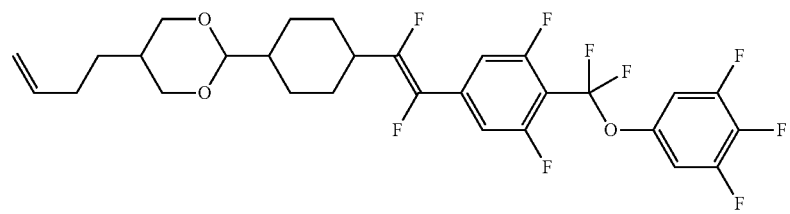 [SMILES: C=CCCC1COC(C2CCC(/C(F)=C(\F)c3cc(F)c(C(F)(F)Oc4cc(F)c(F)c(F)c4)c(F)c3)CC2)OC1] |
| 32 | 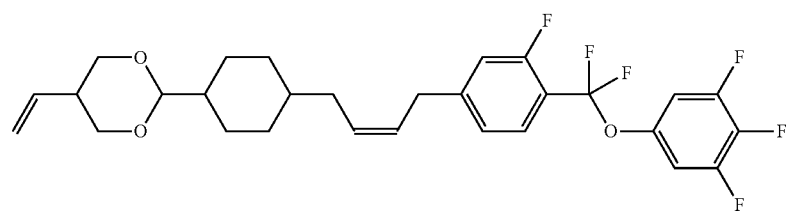 [SMILES: C=CC1COC(C2CCC(C/C=C\Cc3ccc(C(F)(F)Oc4cc(F)c(F)c(F)c4)c(F)c3)CC2)OC1] |
| 33 | 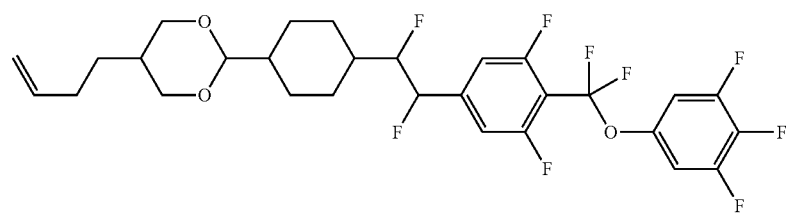 |
| 34 | 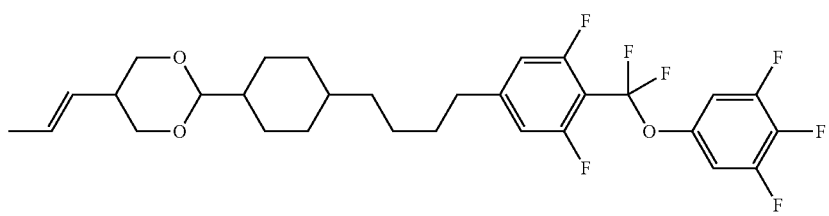 |
| 35 | 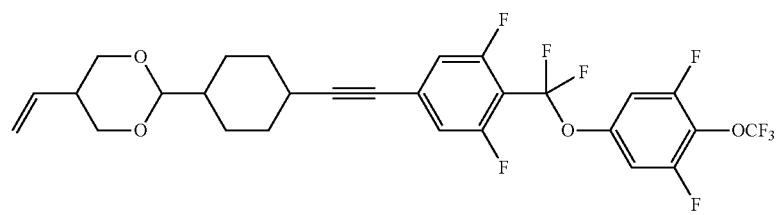 [SMILES: C=CC1COC(C2CCC(C#Cc3cc(F)c(C(F)(F)Oc4cc(F)c(OC(F)(F)F)c(F)c4)c(F)c3)CC2)OC1] |

| No. | |
|---|---|
| 36 | 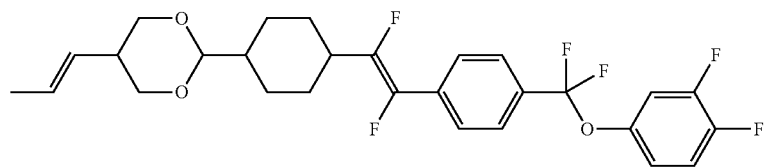 [SMILES: C/C=C/C1COC(C2CCC(/C(F)=C(\F)c3ccc(C(F)(F)Oc4ccc(F)c(F)c4)cc3)CC2)OC1] |
| 37 | 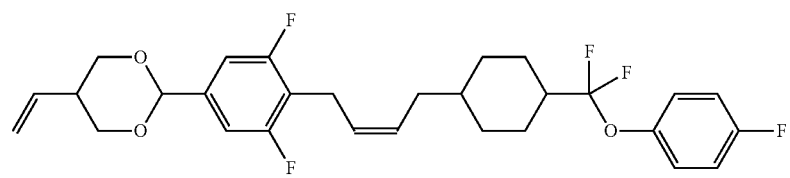 [SMILES: C=CC1COC(c2cc(F)c(C/C=C\CC3CCC(C(F)(F)Oc4ccc(F)cc4)CC3)c(F)c2)OC1] |
| 38 | 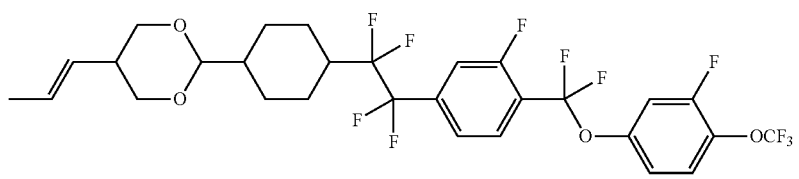 [SMILES: C/C=C/C1COC(C2CCC(C(F)(F)C(F)(F)c3ccc(C(F)(F)Oc4ccc(OC(F)(F)F)c(F)c4)c(F)c3)CC2)OC1] |
| 39 | 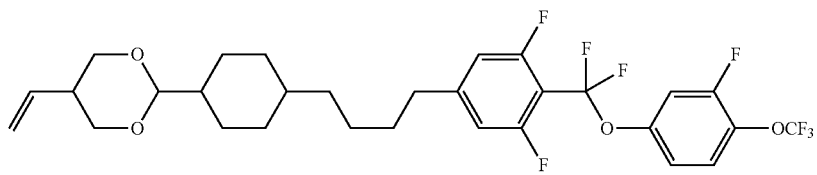 [SMILES: C=CC1COC(C2CCC(CCCCc3cc(F)c(C(F)(F)Oc4ccc(OC(F)(F)F)c(F)c4)c(F)c3)CC2)OC1] |
| 40 | 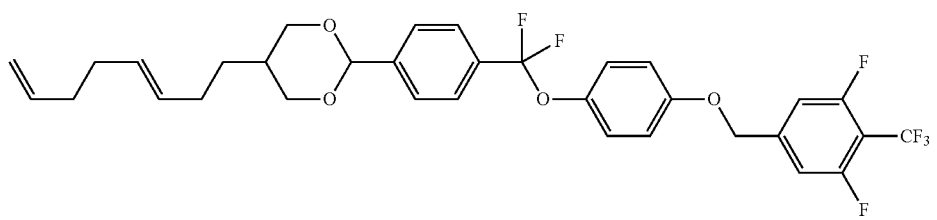 [SMILES: C=CCC/C=C/CCC1COC(c2ccc(C(F)(F)Oc3ccc(OCc4cc(F)c(C(F)(F)F)c(F)c4)cc3)cc2)OC1] |
| 41 | 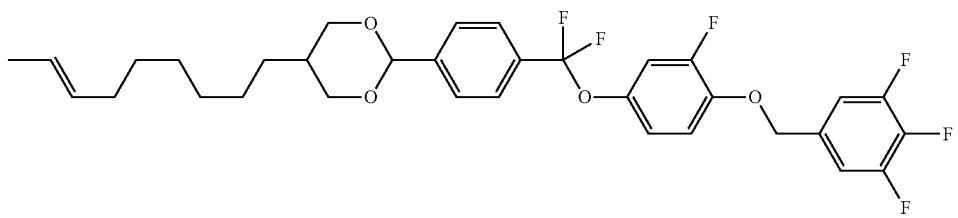 [SMILES: C/C=C/CCCCCCC1COC(c2ccc(C(F)(F)Oc3ccc(OCc4cc(F)c(F)c(F)c4)c(F)c3)cc2)OC1] |
| 42 | 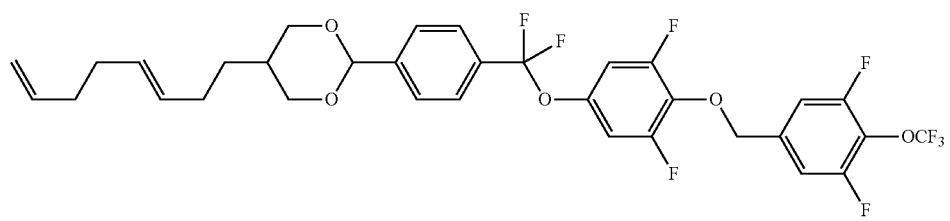 [SMILES: C=CCC/C=C/CCC1COC(c2ccc(C(F)(F)Oc3cc(F)c(OCc4cc(F)c(OC(F)(F)F)c(F)c4)c(F)c3)cc2)OC1] |

| No. | |
|---|---|
| 43 | 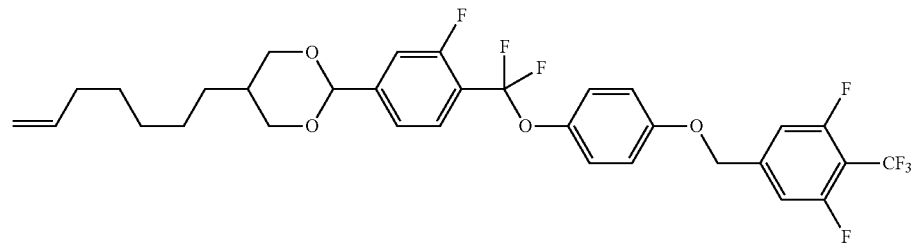 [SMILES: C=CCCCCCC1COC(c2ccc(C(F)(F)Oc3ccc(OCc4cc(F)c(C(F)(F)F)c(F)c4)cc3)c(F)c2)OC1] |
| 44 | 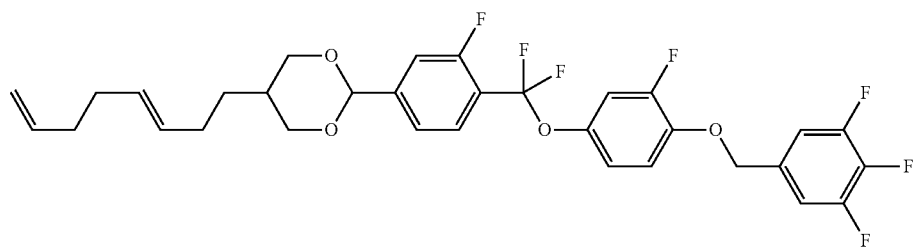 [SMILES: C=CCC/C=C/CCC1COC(c2ccc(C(F)(F)Oc3ccc(OCc4cc(F)c(F)c(F)c4)c(F)c3)c(F)c2)OC1] |
| 45 | 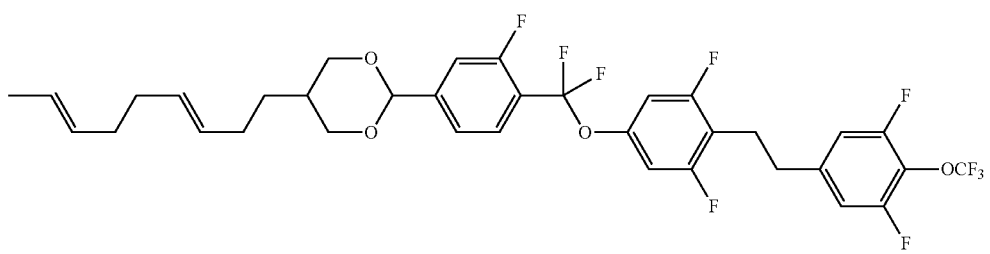 [SMILES: C/C=C/CC/C=C/CCC1COC(c2ccc(C(F)(F)Oc3cc(F)c(CCc4cc(F)c(OC(F)(F)F)c(F)c4)c(F)c3)c(F)c2)OC1] |
| 45 | 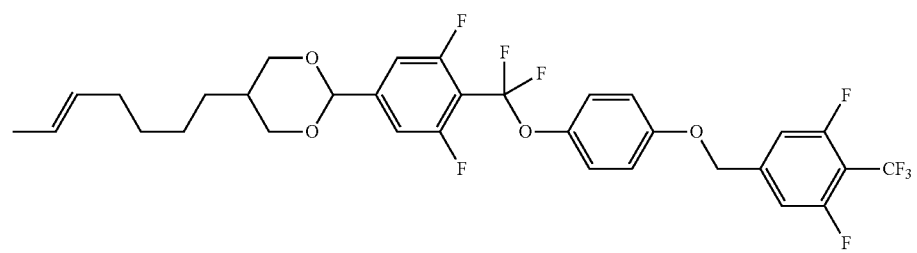 [SMILES: C/C=C/CCCCC1COC(c2cc(F)c(C(F)(F)Oc3ccc(OCc4cc(F)c(C(F)(F)F)c(F)c4)cc3)c(F)c2)OC1] |
| 46 | 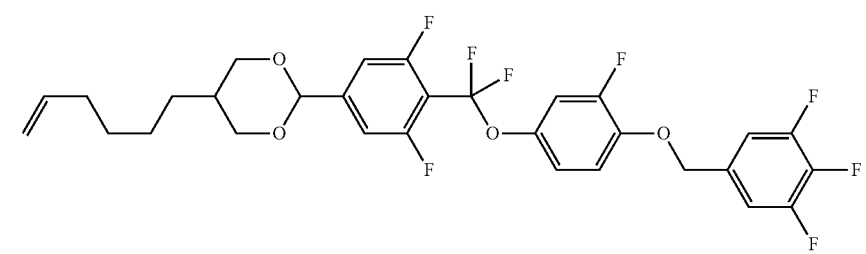 [SMILES: C=CCCCCC1COC(c2cc(F)c(C(F)(F)Oc3ccc(OCc4cc(F)c(F)c(F)c4)c(F)c3)c(F)c2)OC1] |
| 47 | 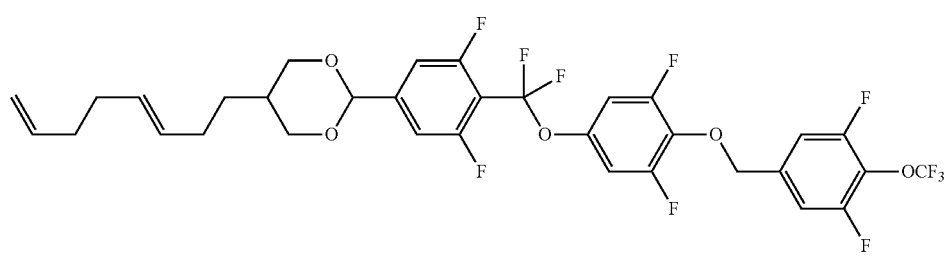 [SMILES: C=CCC/C=C/CCC1COC(c2cc(F)c(C(F)(F)Oc3cc(F)c(OCc4cc(F)c(OC(F)(F)F)c(F)c4)c(F)c3)c(F)c2)OC1] |

-continued
| No. | |
|---|---|
| 48 | 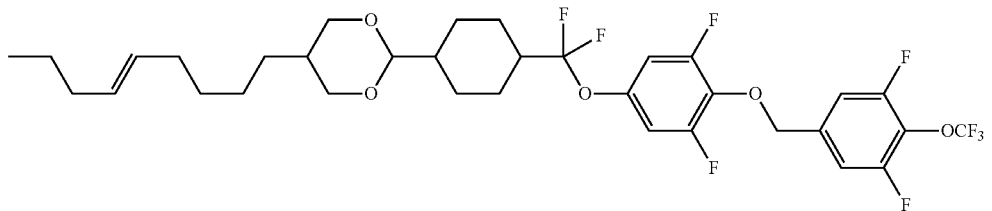 [SMILES: CCC/C=C/CCCCC1COC(C2CCC(C(F)(F)Oc3cc(F)c(OCc4cc(F)c(OC(F)(F)F)c(F)c4)c(F)c3)CC2)OC1] |
| 49 | 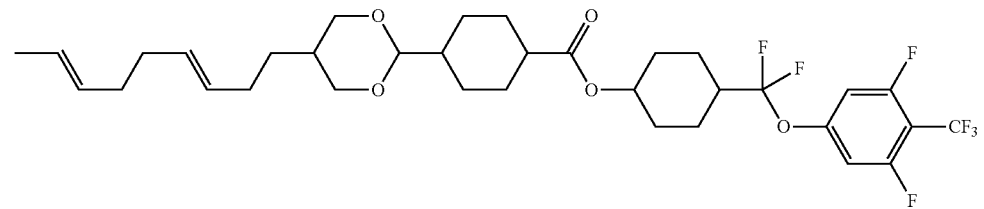 [SMILES: C/C=C/CC/C=C/CCC1COC(C2CCC(C(=O)OC3CCC(C(F)(F)Oc4cc(F)c(C(F)(F)F)c(F)c4)CC3)CC2)OC1] |
| 50 | 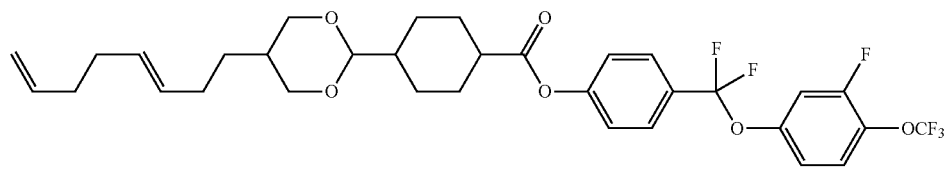 [SMILES: C=CCC/C=C/CCC1COC(C2CCC(C(=O)Oc3ccc(C(F)(F)Oc4ccc(OC(F)(F)F)c(F)c4)cc3)CC2)OC1] |
| 51 | 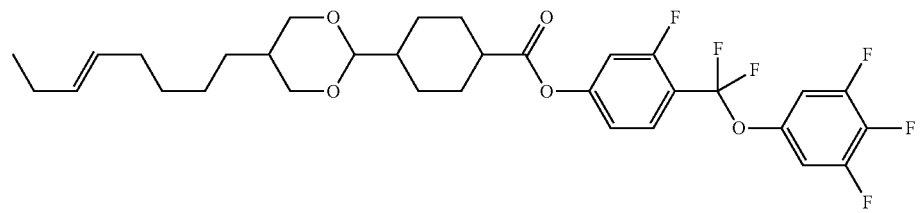 [SMILES: CC/C=C/CCCCC1COC(C2CCC(C(=O)Oc3ccc(C(F)(F)Oc4cc(F)c(F)c(F)c4)c(F)c3)CC2)OC1] |
| 52 | 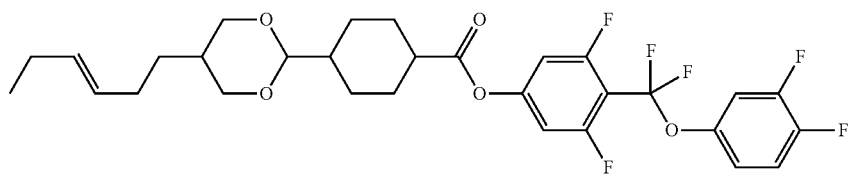 [SMILES: CC/C=C/CCC1COC(C2CCC(C(=O)Oc3cc(F)c(C(F)(F)Oc4ccc(F)c(F)c4)c(F)c3)CC2)OC1] |
| 53 | 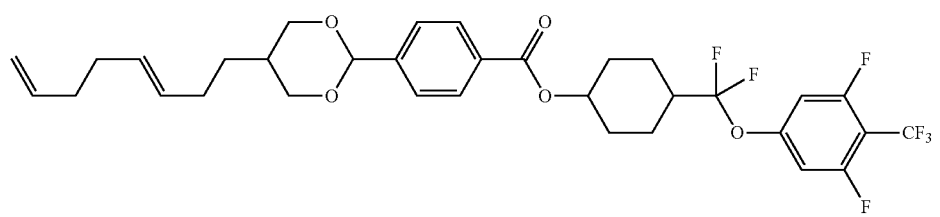 [SMILES: C=CCC/C=C/CCC1COC(c2ccc(C(=O)OC3CCC(C(F)(F)Oc4cc(F)c(C(F)(F)F)c(F)c4)CC3)cc2)OC1] |
| 54 | 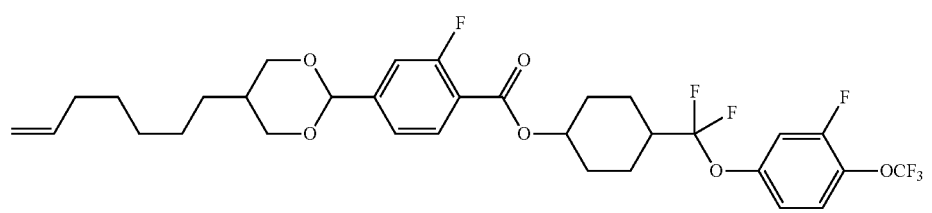 [SMILES: C=CCCCCCC1COC(c2ccc(C(=O)OC3CCC(C(F)(F)Oc4ccc(OC(F)(F)F)c(F)c4)CC3)c(F)c2)OC1] |

| No. | |
|---|---|
| 55 | 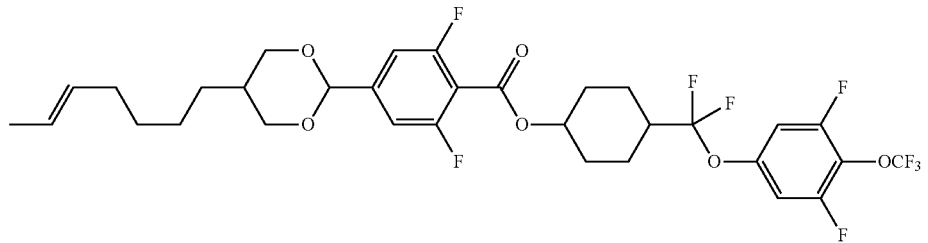 [SMILES: C/C=C/CCCCC1COC(c2cc(F)c(C(=O)OC3CCC(C(F)(F)Oc4cc(F)c(OC(F)(F)F)c(F)c4)CC3)c(F)c2)OC1] |
| 56 | 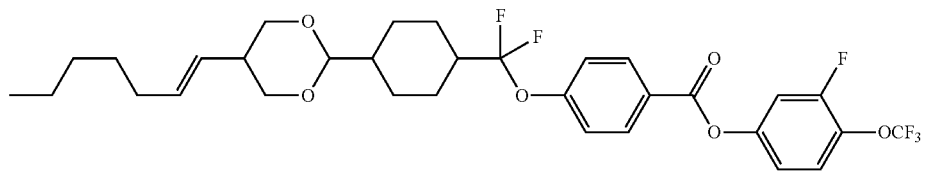 [SMILES: CCCCC/C=C/C1COC(C2CCC(C(F)(F)Oc3ccc(C(=O)Oc4ccc(OC(F)(F)F)c(F)c4)cc3)CC2)OC1] |
| 57 | 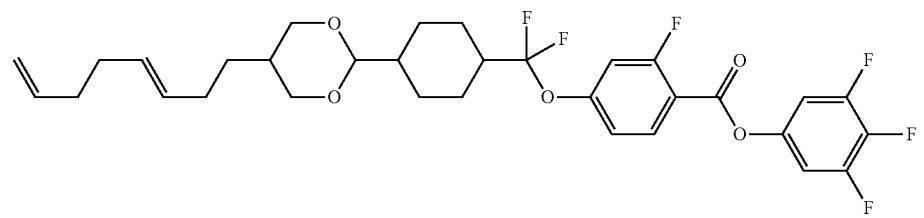 [SMILES: C=CCC/C=C/CCC1COC(C2CCC(C(F)(F)Oc3ccc(C(=O)Oc4cc(F)c(F)c(F)c4)c(F)c3)CC2)OC1] |
| 58 | 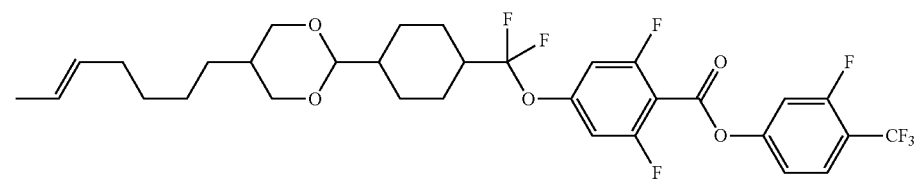 [SMILES: C/C=C/CCCCC1COC(C2CCC(C(F)(F)Oc3cc(F)c(C(=O)Oc4ccc(C(F)(F)F)c(F)c4)c(F)c3)CC2)OC1] |
| 59 | 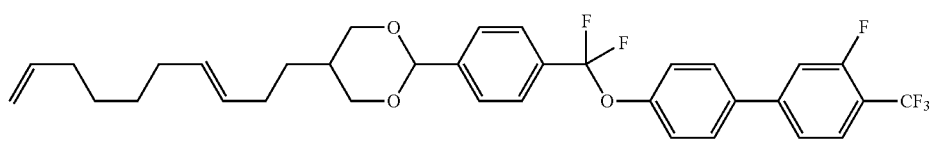 [SMILES: C=CCCCC/C=C/CCC1COC(c2ccc(C(F)(F)Oc3ccc(-c4ccc(C(F)(F)F)c(F)c4)cc3)cc2)OC1] |
| 60 | 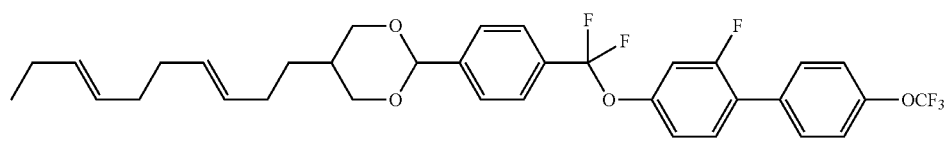 [SMILES: CC/C=C/CC/C=C/CCC1COC(c2ccc(C(F)(F)Oc3ccc(-c4ccc(OC(F)(F)F)cc4)c(F)c3)cc2)OC1] |
| 61 | 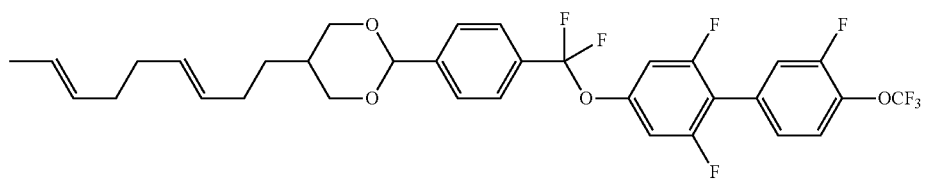 [SMILES: C/C=C/CC/C=C/CCC1COC(c2ccc(C(F)(F)Oc3cc(F)c(-c4ccc(OC(F)(F)F)c(F)c4)c(F)c3)cc2)OC1] |
| 62 | 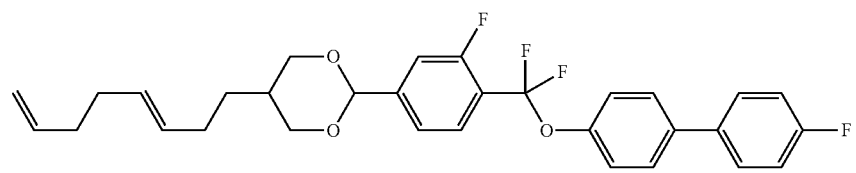 [SMILES: C=CCC/C=C/CCC1COC(c2ccc(C(F)(F)Oc3ccc(-c4ccc(F)cc4)cc3)c(F)c2)OC1] |

-continued
| No. | |
|---|---|
| 63 | 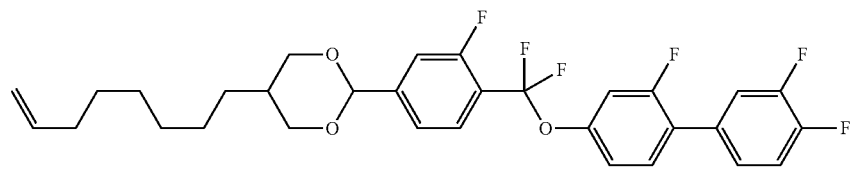 [SMILES: C=CCCCCCCC1COC(c2ccc(C(F)(F)Oc3ccc(-c4ccc(F)c(F)c4)c(F)c3)c(F)c2)OC1] |
| 64 | 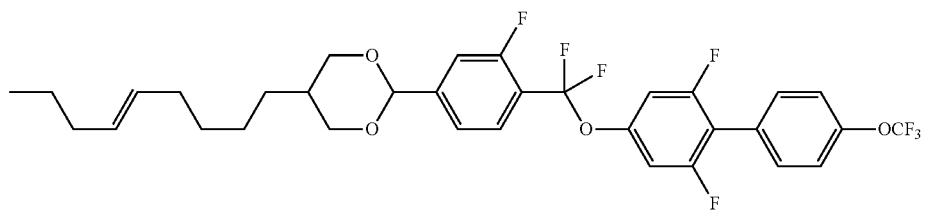 |
| 65 | 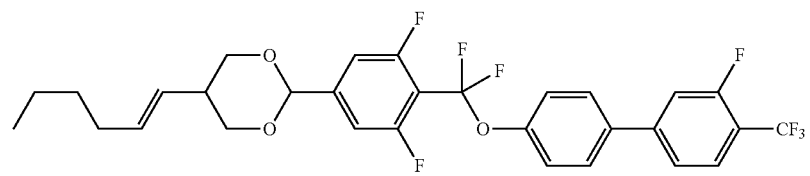 [SMILES: CCCC/C=C/C1COC(c2cc(F)c(C(F)(F)Oc3ccc(-c4ccc(C(F)(F)F)c(F)c4)cc3)c(F)c2)OC1] |
| 66 | 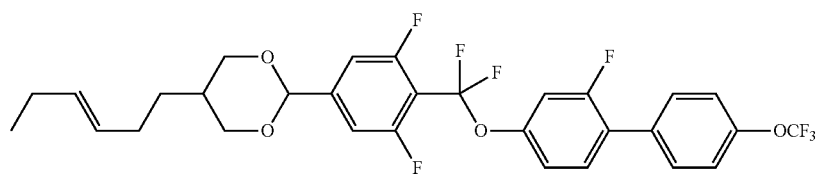 [SMILES: CC/C=C/CCC1COC(c2cc(F)c(C(F)(F)Oc3ccc(-c4ccc(OC(F)(F)F)cc4)c(F)c3)c(F)c2)OC1] |
| 67 | 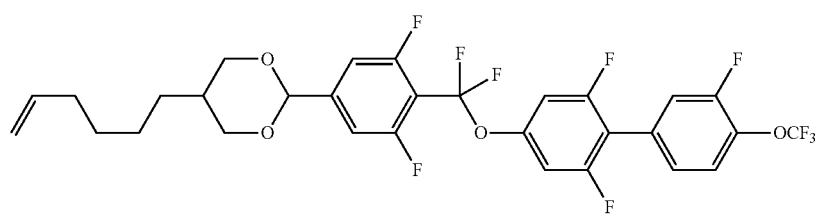 [SMILES: C=CCCCCC1COC(c2cc(F)c(C(F)(F)Oc3cc(F)c(-c4ccc(OC(F)(F)F)c(F)c4)c(F)c3)c(F)c2)OC1] |
| 68 | 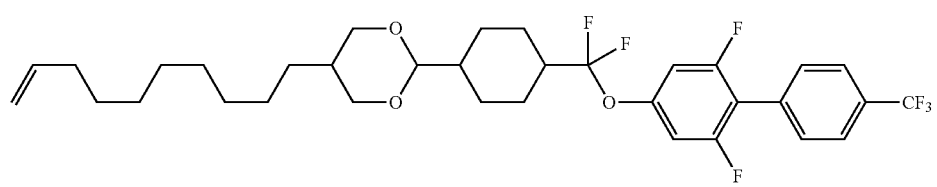 [SMILES: C=CCCCCCCCCC1COC(C2CCC(C(F)(F)Oc3cc(F)c(-c4ccc(C(F)(F)F)cc4)c(F)c3)CC2)OC1] |
| 69 | 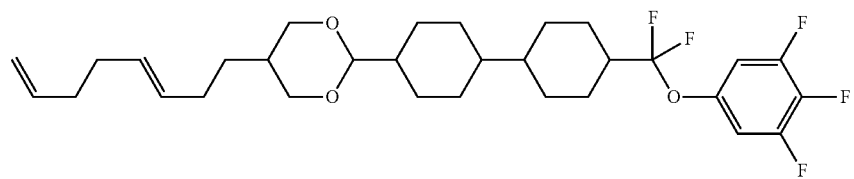 [SMILES: C=CCC/C=C/CCC1COC(C2CCC(C3CCC(C(F)(F)Oc4cc(F)c(F)c(F)c4)CC3)CC2)OC1] |
| 70 | 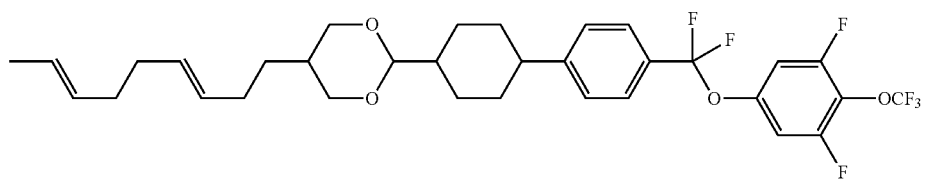 [SMILES: C/C=C/CC/C=C/CCC1COC(C2CCC(c3ccc(C(F)(F)Oc4cc(F)c(OC(F)(F)F)c(F)c4)cc3)CC2)OC1] |

| No. | |
|---|---|
| 71 | 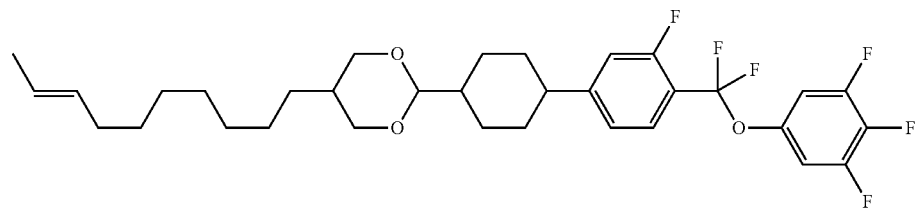 |
| 72 | 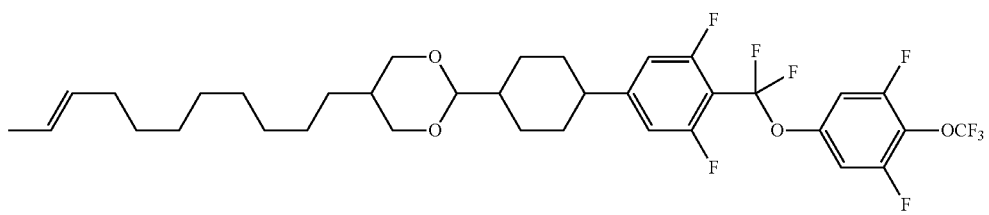 [SMILES: C/C=C/CCCCCCCCC1COC(C2CCC(c3cc(F)c(C(F)(F)Oc4cc(F)c(OC(F)(F)F)c(F)c4)c(F)c3)CC2)OC1] |
| 73 | 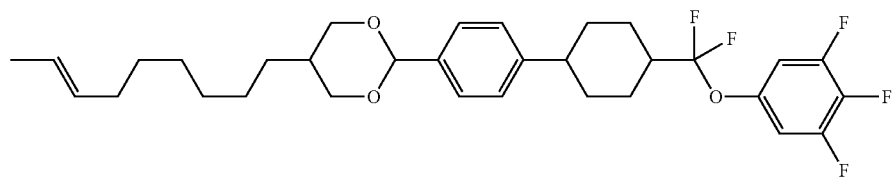 [SMILES: C/C=C/CCCCCCC1COC(c2ccc(C3CCC(C(F)(F)Oc4cc(F)c(F)c(F)c4)CC3)cc2)OC1] |
| 74 | 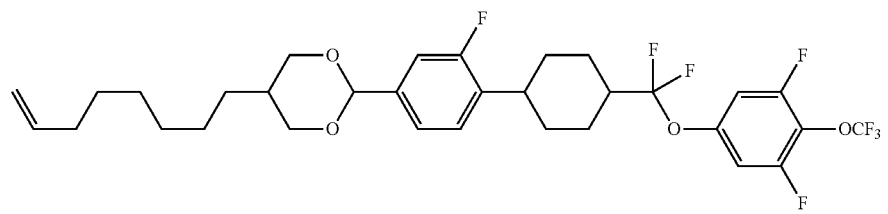 [SMILES: C=CCCCCCCC1COC(c2ccc(C3CCC(C(F)(F)Oc4cc(F)c(OC(F)(F)F)c(F)c4)CC3)c(F)c2)OC1] |
| 75 | 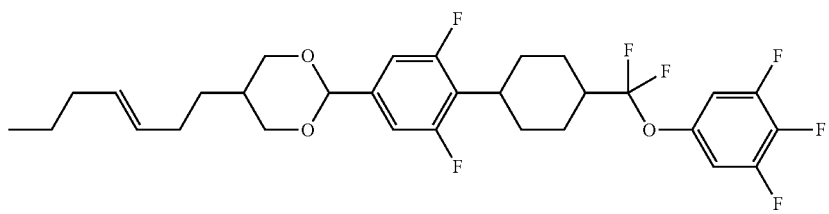 [SMILES: CCC/C=C/CCC1COC(c2cc(F)c(C3CCC(C(F)(F)Oc4cc(F)c(F)c(F)c4)CC3)c(F)c2)OC1] |
| 76 | 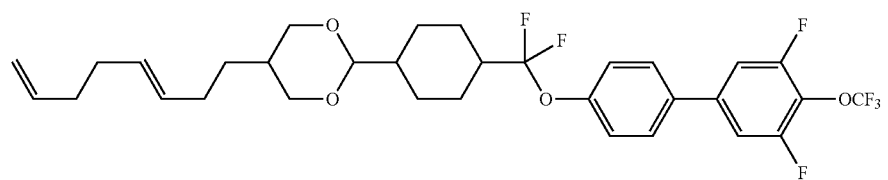 [SMILES: C=CCC/C=C/CCC1COC(C2CCC(C(F)(F)Oc3ccc(-c4cc(F)c(OC(F)(F)F)c(F)c4)cc3)CC2)OC1] |
| 77 | 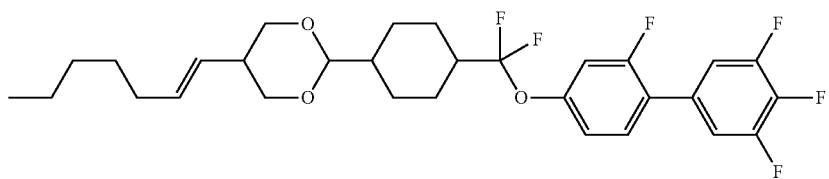 [SMILES: CCCCC/C=C/C1COC(C2CCC(C(F)(F)Oc3ccc(-c4cc(F)c(F)c(F)c4)c(F)c3)CC2)OC1] |

-continued
| No. | |
|---|---|
| 78 | 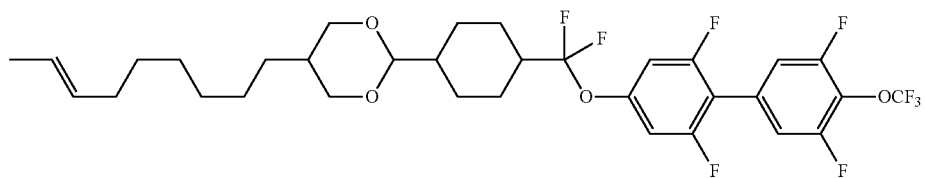 [SMILES: C/C=C/CCCCCCC1COC(C2CCC(C(F)(F)Oc3cc(F)c(-c4cc(F)c(OC(F)(F)F)c(F)c4)c(F)c3)CC2)OC1] |
| 79 | 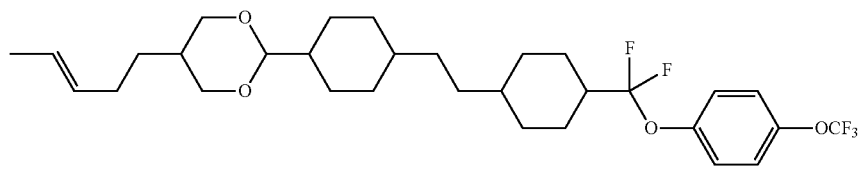 [SMILES: C/C=C/CCC1COC(C2CCC(CCC3CCC(C(F)(F)Oc4ccc(OC(F)(F)F)cc4)CC3)CC2)OC1] |
| 80 | 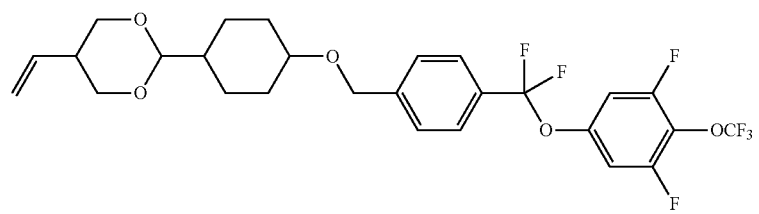 [SMILES: C=CC1COC(C2CCC(OCc3ccc(C(F)(F)Oc4cc(F)c(OC(F)(F)F)c(F)c4)cc3)CC2)OC1] |
| 81 | 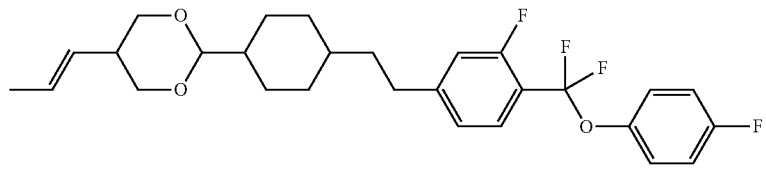 [SMILES: C/C=C/C1COC(C2CCC(CCc3ccc(C(F)(F)Oc4ccc(F)cc4)c(F)c3)CC2)OC1] |
| 82 | 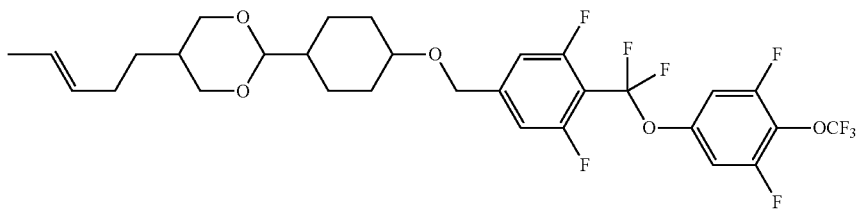 [SMILES: C/C=C/CCC1COC(C2CCC(OCc3cc(F)c(C(F)(F)Oc4cc(F)c(OC(F)(F)F)c(F)c4)c(F)c3)CC2)OC1] |
| 83 | 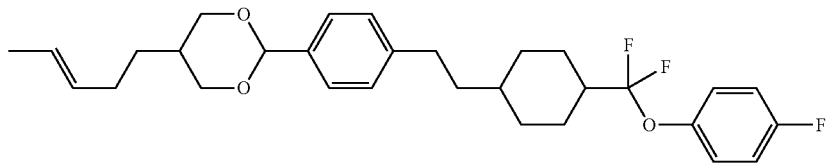 [SMILES: C/C=C/CCC1COC(c2ccc(CCC3CCC(C(F)(F)Oc4ccc(F)cc4)CC3)cc2)OC1] |
| 84 | 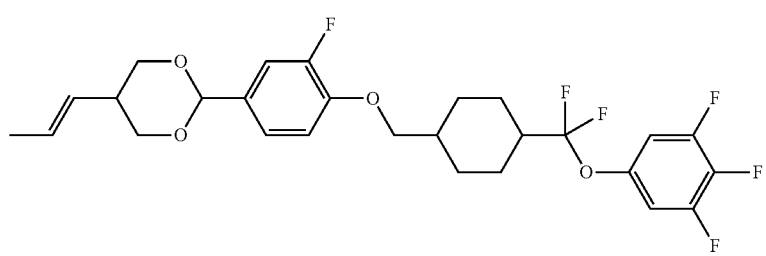 [SMILES: C/C=C/C1COC(c2ccc(OCC3CCC(C(F)(F)Oc4cc(F)c(F)c(F)c4)CC3)c(F)c2)OC1] |

| No. | |
|---|---|
| 85 | 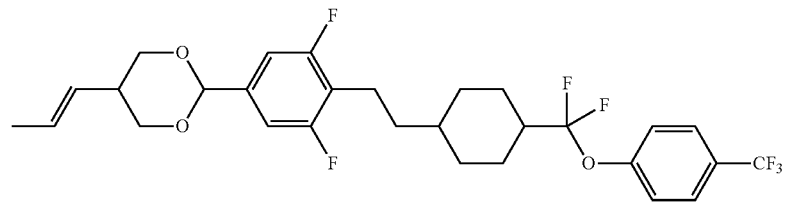 [SMILES: C/C=C/C1COC(c2cc(F)c(CCC3CCC(C(F)(F)Oc4ccc(C(F)(F)F)cc4)CC3)c(F)c2)OC1] |
| 86 | 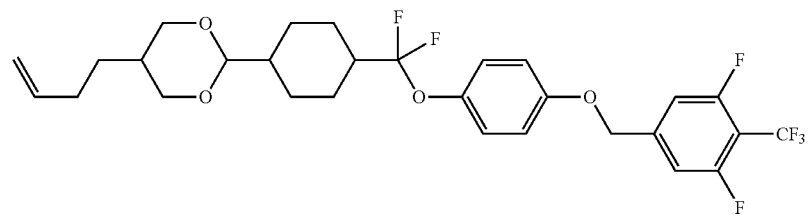 [SMILES: C=CCCC1COC(C2CCC(C(F)(F)Oc3ccc(OCc4cc(F)c(C(F)(F)F)c(F)c4)cc3)CC2)OC1] |
| 87 | 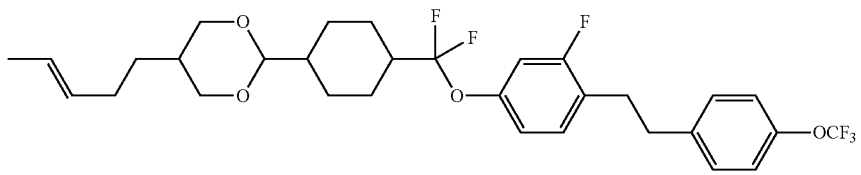 |
| 88 | 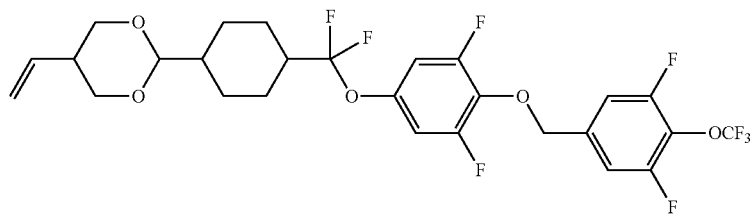 |
| 89 | 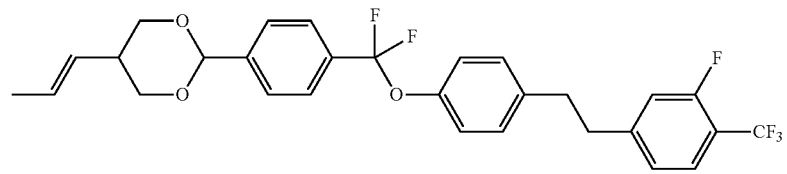 [SMILES: C/C=C/C1COC(c2ccc(C(F)(F)Oc3ccc(CCc4ccc(C(F)(F)F)c(F)c4)cc3)cc2)OC1] |
| 90 | 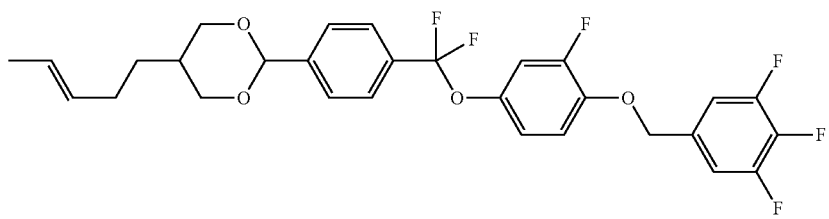 |
| 91 | 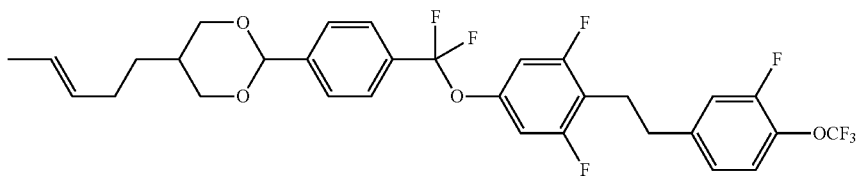 |

-continued
| No. | |
|---|---|
| 92 | 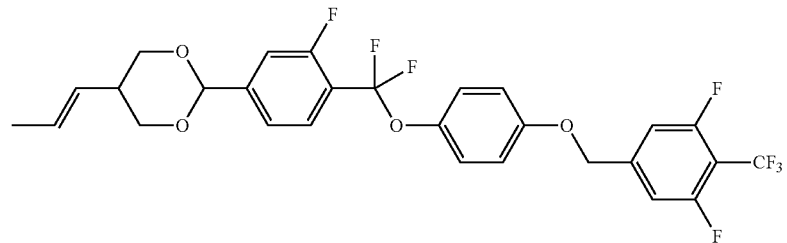 [SMILES: C/C=C/C1COC(c2ccc(C(F)(F)Oc3ccc(OCc4cc(F)c(C(F)(F)F)c(F)c4)cc3)c(F)c2)OC1] |
| 93 | 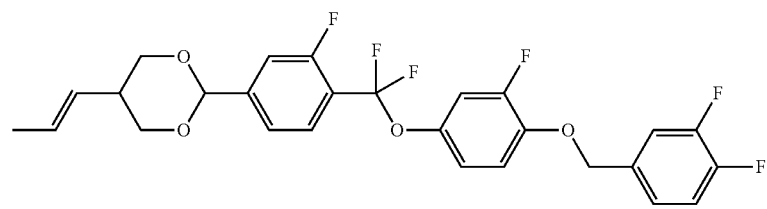 [SMILES: C/C=C/C1COC(c2ccc(C(F)(F)Oc3ccc(OCc4ccc(F)c(F)c4)c(F)c3)c(F)c2)OC1] |
| 94 | 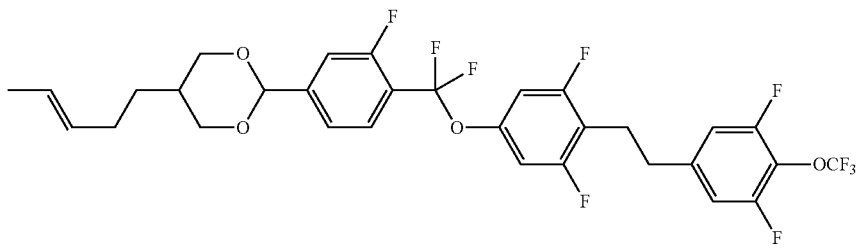 [SMILES: C/C=C/CCC1COC(c2ccc(C(F)(F)Oc3cc(F)c(CCc4cc(F)c(OC(F)(F)F)c(F)c4)c(F)c3)c(F)c2)OC1] |
| 95 | 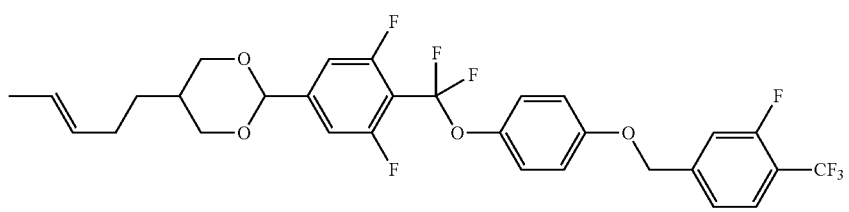 [SMILES: C/C=C/CCC1COC(c2cc(F)c(C(F)(F)Oc3ccc(OCc4ccc(C(F)(F)F)c(F)c4)cc3)c(F)c2)OC1] |
| 96 | 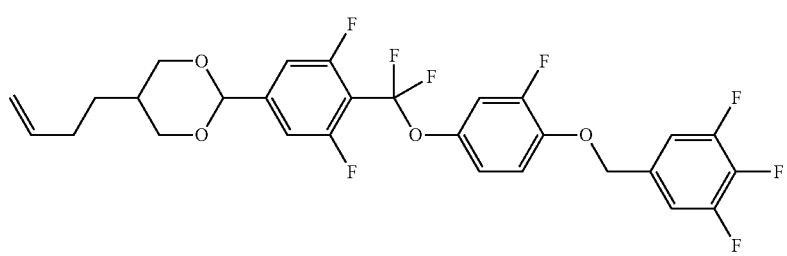 [SMILES: C=CCCC1COC(c2cc(F)c(C(F)(F)Oc3ccc(OCc4cc(F)c(F)c(F)c4)c(F)c3)c(F)c2)OC1] |
| 97 | 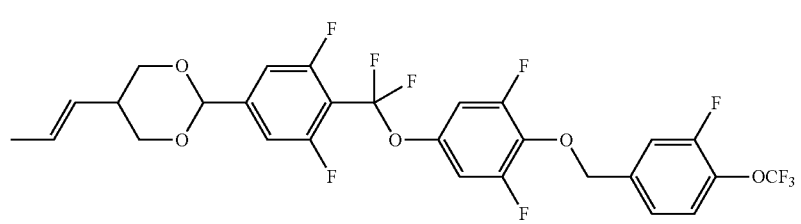 [SMILES: C/C=C/C1COC(c2cc(F)c(C(F)(F)Oc3cc(F)c(OCc4ccc(OC(F)(F)F)c(F)c4)c(F)c3)c(F)c2)OC1] |

-continued
| No. | |
|---|---|
| 98 | 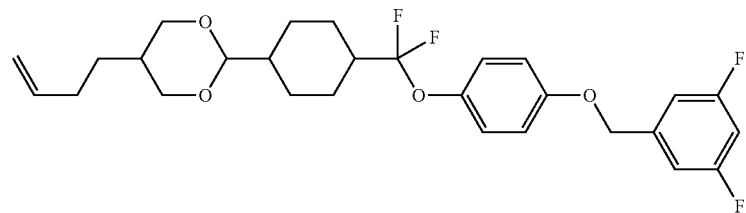 [SMILES: C=CCCC1COC(C2CCC(C(F)(F)Oc3ccc(OCc4cc(F)cc(F)c4)cc3)CC2)OC1] |
| 99 | 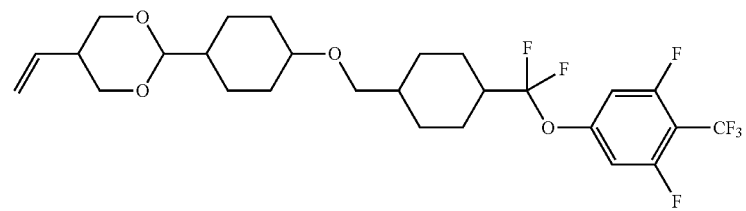 [SMILES: C=CC1COC(C2CCC(OCC3CCC(C(F)(F)Oc4cc(F)c(C(F)(F)F)c(F)c4)CC3)CC2)OC1] |
| 100 | 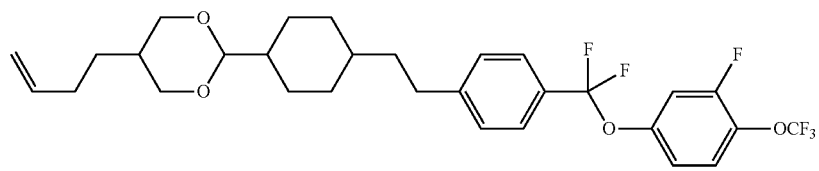 [SMILES: C=CCCC1COC(C2CCC(CCc3ccc(C(F)(F)Oc4ccc(OC(F)(F)F)c(F)c4)cc3)CC2)OC1] |
| 101 | 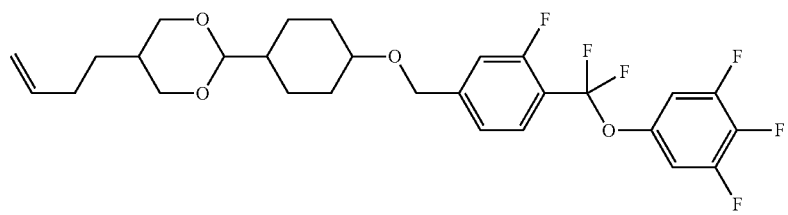 |
| 102 | 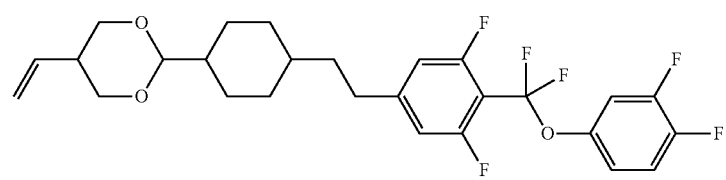 [SMILES: C=CC1COC(C2CCC(CCc3cc(F)c(C(F)(F)Oc4ccc(F)c(F)c4)c(F)c3)CC2)OC1] |
| 103 | 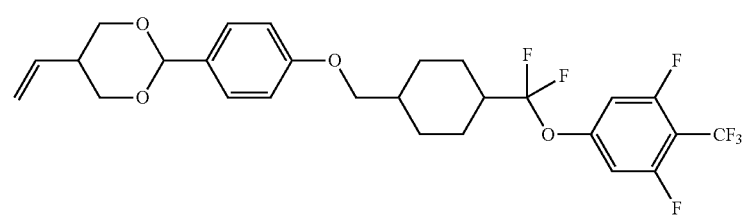 |
| 104 | 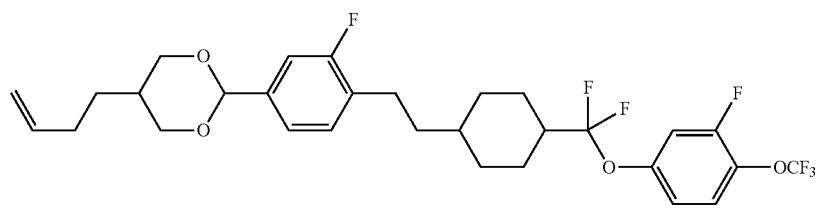 [SMILES: C=CCCC1COC(c2ccc(CCC3CCC(C(F)(F)Oc4ccc(OC(F)(F)F)c(F)c4)CC3)c(F)c2)OC1] |

| No. |  |
|---|---|
| 105 | 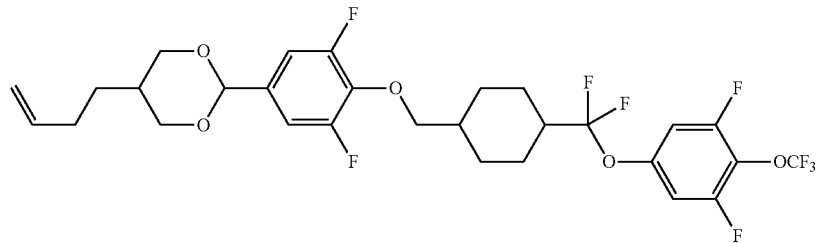 [SMILES: C=CCCC1COC(c2cc(F)c(OCC3CCC(C(F)(F)Oc4cc(F)c(OC(F)(F)F)c(F)c4)CC3)c(F)c2)OC1] |
| 106 | 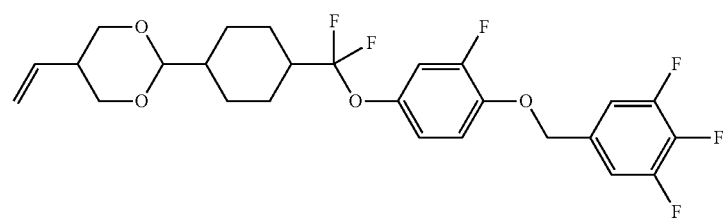 [SMILES: C=CC1COC(C2CCC(C(F)(F)Oc3ccc(OCc4cc(F)c(F)c(F)c4)c(F)c3)CC2)OC1] |
| 107 | 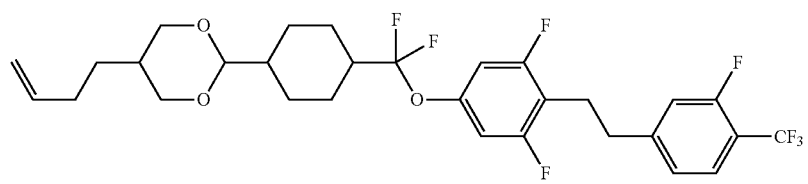 |
| 108 | 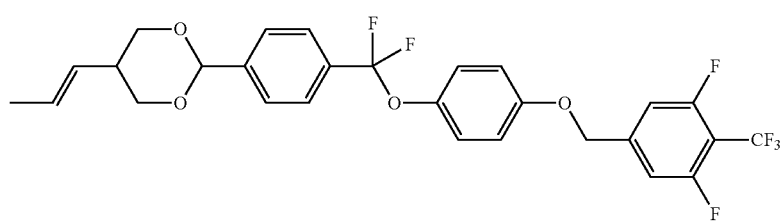 |
| 109 | 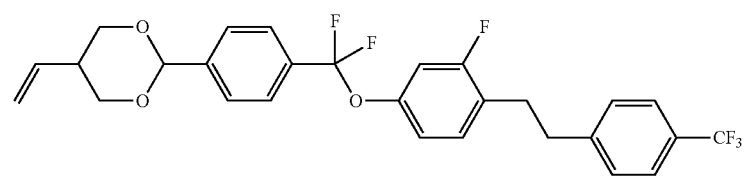 [SMILES: C=CC1COC(c2ccc(C(F)(F)Oc3ccc(CCc4ccc(C(F)(F)F)cc4)c(F)c3)cc2)OC1] |
| 110 | 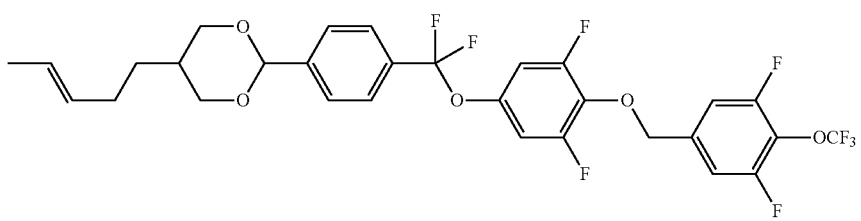 [SMILES: C/C=C/CCC1COC(c2ccc(C(F)(F)Oc3cc(F)c(OCc4cc(F)c(OC(F)(F)F)c(F)c4)c(F)c3)cc2)OC1] |
| 111 | |

-continued
| No. | |
|---|---|
| 112 | 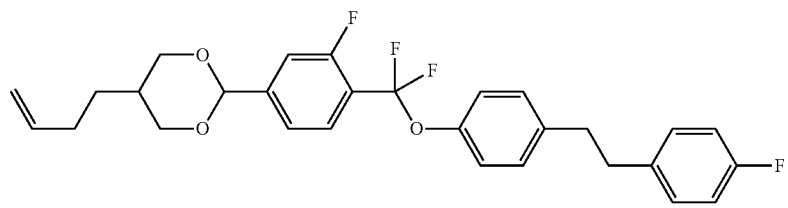 [SMILES: C=CCCC1COC(c2ccc(C(F)(F)Oc3ccc(CCc4ccc(F)cc4)cc3)c(F)c2)OC1] |
| 113 | 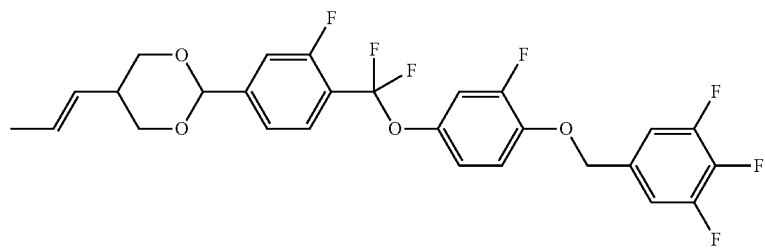 [SMILES: C/C=C/C1COC(c2ccc(C(F)(F)Oc3ccc(OCc4cc(F)c(F)c(F)c4)c(F)c3)c(F)c2)OC1] |
| 114 | 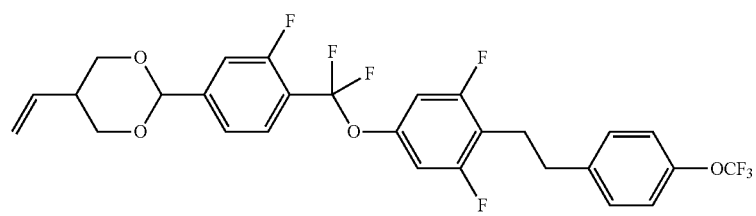 [SMILES: C=CC1COC(c2ccc(C(F)(F)Oc3cc(F)c(CCc4ccc(OC(F)(F)F)cc4)c(F)c3)c(F)c2)OC1] |
| 115 | 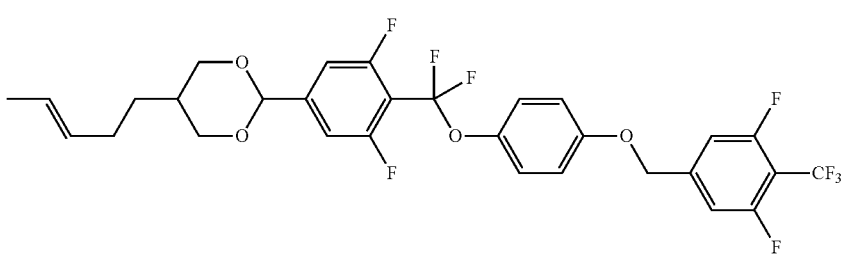 [SMILES: C/C=C/CCC1COC(c2cc(F)c(C(F)(F)Oc3ccc(OCc4cc(F)c(C(F)(F)F)c(F)c4)cc3)c(F)c2)OC1] |
| 116 | 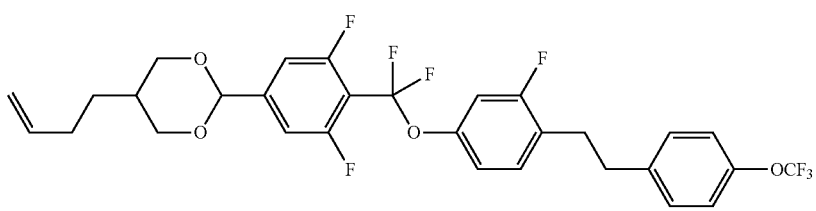 [SMILES: C=CCCC1COC(c2cc(F)c(C(F)(F)Oc3ccc(CCc4ccc(OC(F)(F)F)cc4)c(F)c3)c(F)c2)OC1] |
| 117 | 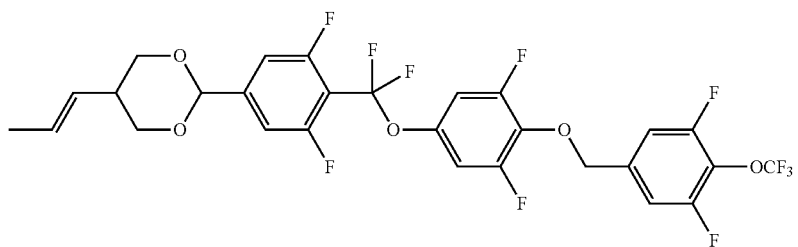 [SMILES: C/C=C/C1COC(c2cc(F)c(C(F)(F)Oc3cc(F)c(OCc4cc(F)c(OC(F)(F)F)c(F)c4)c(F)c3)c(F)c2)OC1] |
| 118 | 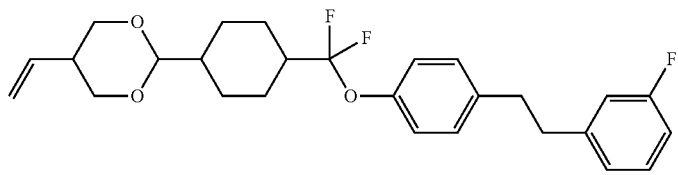 [SMILES: C=CC1COC(C2CCC(C(F)(F)Oc3ccc(CCc4cccc(F)c4)cc3)CC2)OC1] |

-continued
| No. | |
|---|---|
| 119 | 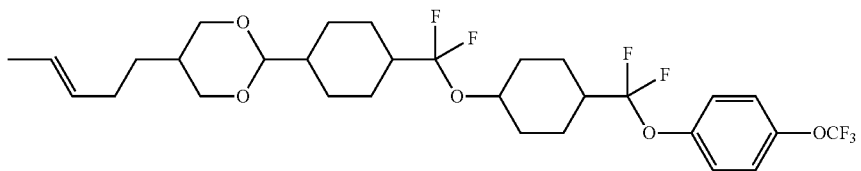 [SMILES: C/C=C/CCC1COC(C2CCC(C(F)(F)OC3CCC(C(F)(F)Oc4ccc(OC(F)(F)F)cc4)CC3)CC2)OC1] |
| 120 | 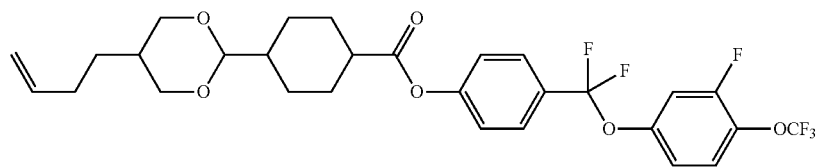 [SMILES: C=CCCC1COC(C2CCC(C(=O)Oc3ccc(C(F)(F)Oc4ccc(OC(F)(F)F)c(F)c4)cc3)CC2)OC1] |
| 121 | 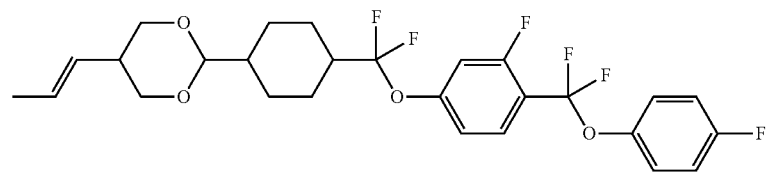 [SMILES: C/C=C/C1COC(C2CCC(C(F)(F)Oc3ccc(C(F)(F)Oc4ccc(F)cc4)c(F)c3)CC2)OC1] |
| 122 | 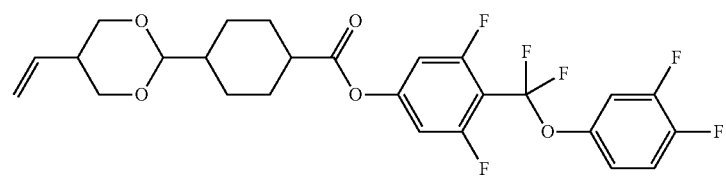 [SMILES: C=CC1COC(C2CCC(C(=O)Oc3cc(F)c(C(F)(F)Oc4ccc(F)c(F)c4)c(F)c3)CC2)OC1] |
| 123 | 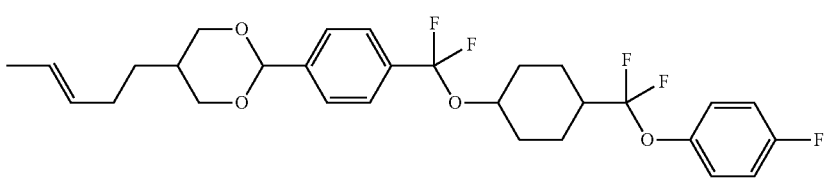 [SMILES: C/C=C/CCC1COC(c2ccc(C(F)(F)OC3CCC(C(F)(F)Oc4ccc(F)cc4)CC3)cc2)OC1] |
| 124 | 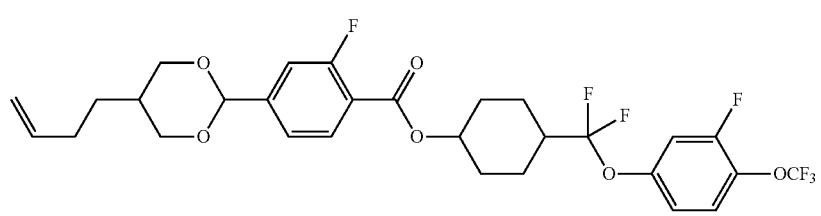 [SMILES: C=CCCC1COC(c2ccc(C(=O)OC3CCC(C(F)(F)Oc4ccc(OC(F)(F)F)c(F)c4)CC3)c(F)c2)OC1] |
| 125 | 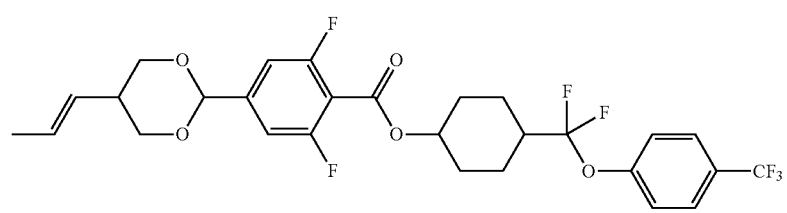 [SMILES: C/C=C/C1COC(c2cc(F)c(C(=O)OC3CCC(C(F)(F)Oc4ccc(C(F)(F)F)cc4)CC3)c(F)c2)OC1] |
| 126 | 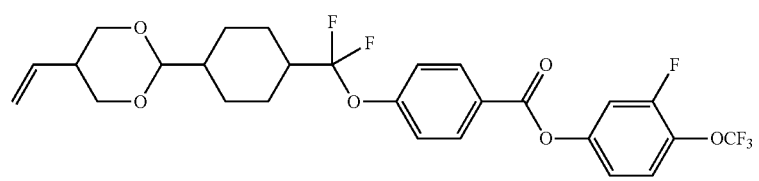 [SMILES: C=CC1COC(C2CCC(C(F)(F)Oc3ccc(C(=O)Oc4ccc(OC(F)(F)F)c(F)c4)cc3)CC2)OC1] |

| No. | |
|---|---|
| 127 | 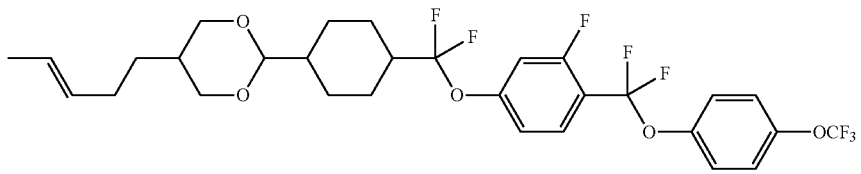 [SMILES: C/C=C/CCC1COC(C2CCC(C(F)(F)Oc3ccc(C(F)(F)Oc4ccc(OC(F)(F)F)cc4)c(F)c3)CC2)OC1] |
| 128 | 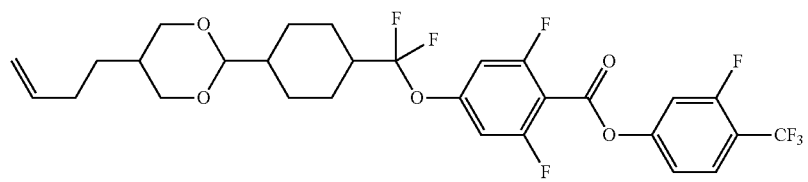 |
| 129 | 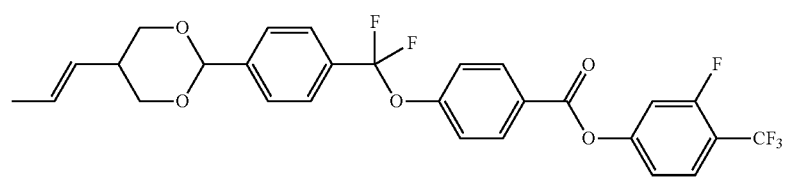 |
| 130 | 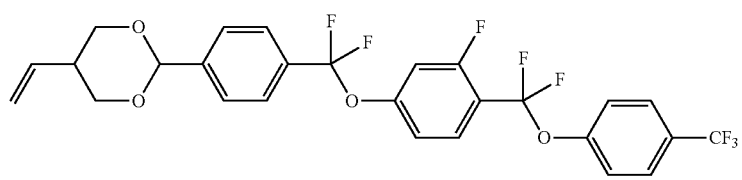 [SMILES: C=CC1COC(c2ccc(C(F)(F)Oc3ccc(C(F)(F)Oc4ccc(C(F)(F)F)cc4)c(F)c3)cc2)OC1] |
| 131 | 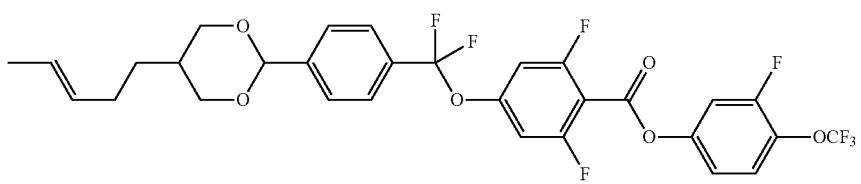 [SMILES: C/C=C/CCC1COC(c2ccc(C(F)(F)Oc3cc(F)c(C(=O)Oc4ccc(OC(F)(F)F)c(F)c4)c(F)c3)cc2)OC1] |
| 132 | 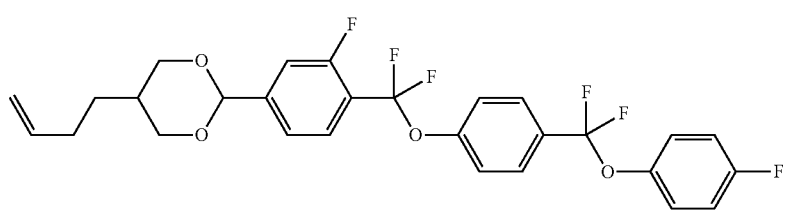 [SMILES: C=CCCC1COC(c2ccc(C(F)(F)Oc3ccc(C(F)(F)Oc4ccc(F)cc4)cc3)c(F)c2)OC1] |
| 133 | 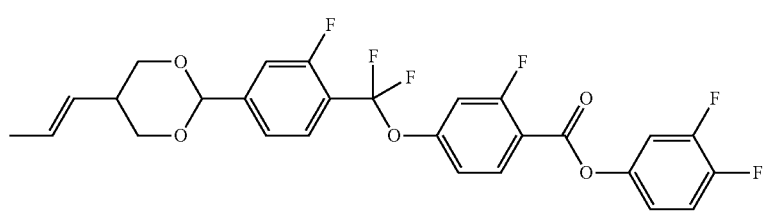 [SMILES: C/C=C/C1COC(c2ccc(C(F)(F)Oc3ccc(C(=O)Oc4ccc(F)c(F)c4)c(F)c3)c(F)c2)OC1] |
| 134 | 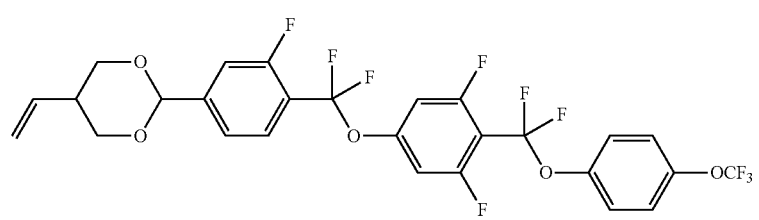 [SMILES: C=CC1COC(c2ccc(C(F)(F)Oc3cc(F)c(C(F)(F)Oc4ccc(OC(F)(F)F)cc4)c(F)c3)c(F)c2)OC1] |

-continued
| No. | |
|---|---|
| 135 | 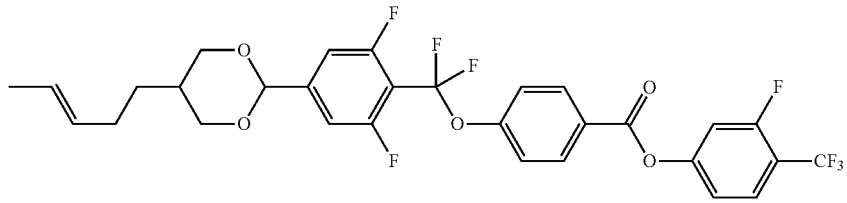 [SMILES: C/C=C/CCC1COC(c2cc(F)c(C(F)(F)Oc3ccc(C(=O)Oc4ccc(C(F)(F)F)c(F)c4)cc3)c(F)c2)OC1] |
| 136 | 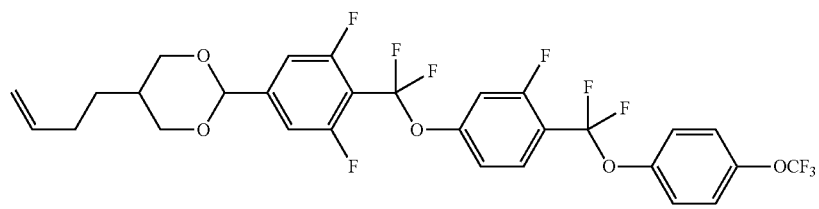 |
| 137 | 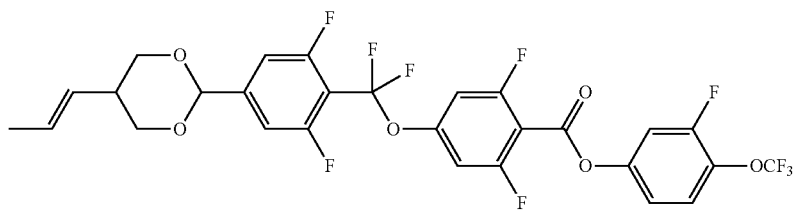 [SMILES: C/C=C/C1COC(c2cc(F)c(C(F)(F)Oc3cc(F)c(C(=O)Oc4ccc(OC(F)(F)F)c(F)c4)c(F)c3)c(F)c2)OC1] |
| 138 | 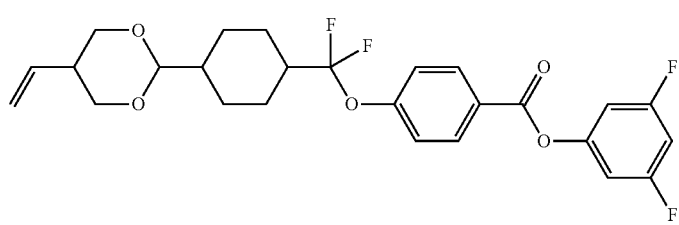 [SMILES: C=CC1COC(C2CCC(C(F)(F)Oc3ccc(C(=O)Oc4cc(F)cc(F)c4)cc3)CC2)OC1] |
| 139 | 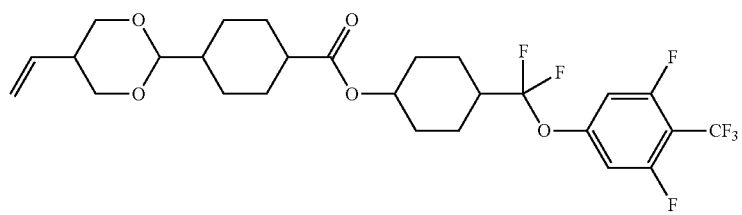 [SMILES: C=CC1COC(C2CCC(C(=O)OC3CCC(C(F)(F)Oc4cc(F)c(C(F)(F)F)c(F)c4)CC3)CC2)OC1] |
| 140 | 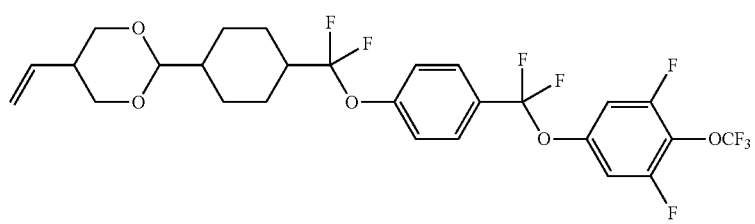 [SMILES: C=CC1COC(C2CCC(C(F)(F)Oc3ccc(C(F)(F)Oc4cc(F)c(OC(F)(F)F)c(F)c4)cc3)CC2)OC1] |
| 141 | 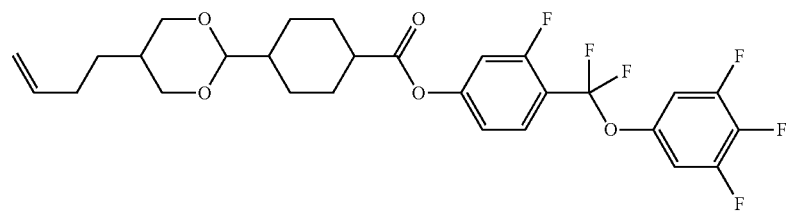 [SMILES: C=CCCC1COC(C2CCC(C(=O)Oc3ccc(C(F)(F)Oc4cc(F)c(F)c(F)c4)c(F)c3)CC2)OC1] |

-continued
| No. | |
|---|---|
| 142 | 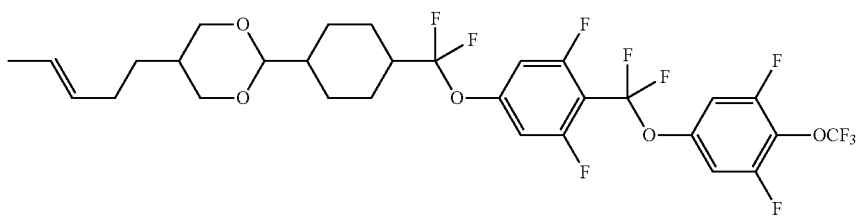 [SMILES: C/C=C/CCC1COC(C2CCC(C(F)(F)Oc3cc(F)c(C(F)(F)Oc4cc(F)c(OC(F)(F)F)c(F)c4)c(F)c3)CC2)OC1] |
| 143 | 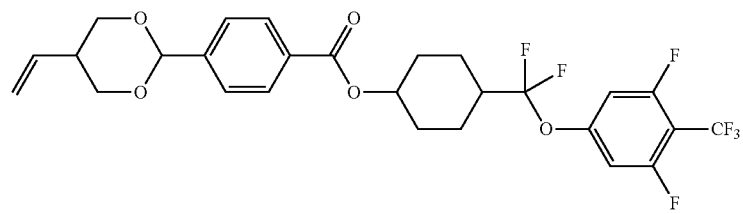 [SMILES: C=CC1COC(c2ccc(C(=O)OC3CCC(C(F)(F)Oc4cc(F)c(C(F)(F)F)c(F)c4)CC3)cc2)OC1] |
| 144 | 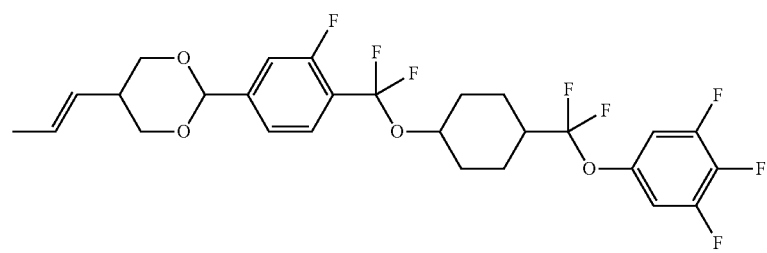 [SMILES: C/C=C/C1COC(c2ccc(C(F)(F)OC3CCC(C(F)(F)Oc4cc(F)c(F)c(F)c4)CC3)c(F)c2)OC1] |
| 145 | 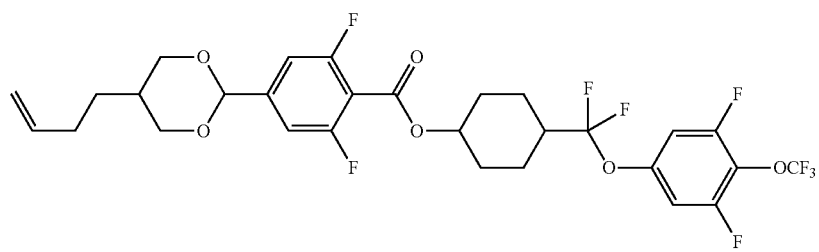 [SMILES: C=CCCC1COC(c2cc(F)c(C(=O)OC3CCC(C(F)(F)Oc4cc(F)c(OC(F)(F)F)c(F)c4)CC3)c(F)c2)OC1] |
| 146 | 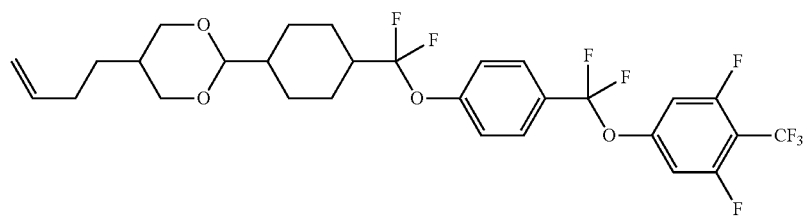 [SMILES: C=CCCC1COC(C2CCC(C(F)(F)Oc3ccc(C(F)(F)Oc4cc(F)c(C(F)(F)F)c(F)c4)cc3)CC2)OC1] |
| 147 | 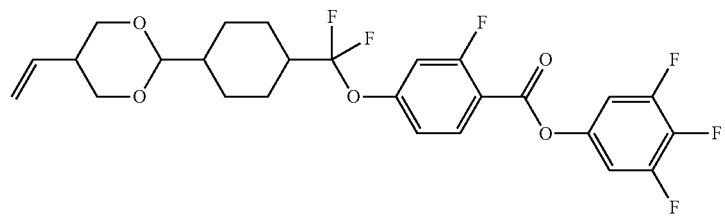 |
| 148 | 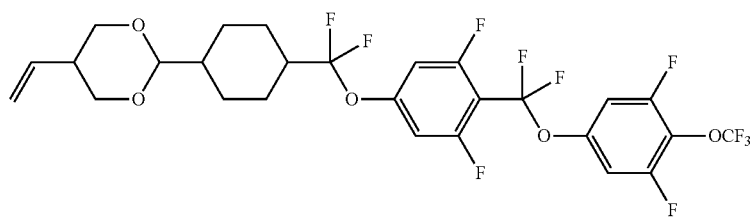 [SMILES: C=CC1COC(C2CCC(C(F)(F)Oc3cc(F)c(C(F)(F)Oc4cc(F)c(OC(F)(F)F)c(F)c4)c(F)c3)CC2)OC1] |

| No. | |
|---|---|
| 149 | 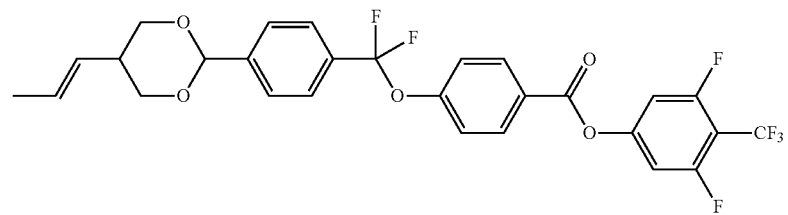 [SMILES: C/C=C/C1COC(c2ccc(C(F)(F)Oc3ccc(C(=O)Oc4cc(F)c(C(F)(F)F)c(F)c4)cc3)cc2)OC1] |
| 150 | 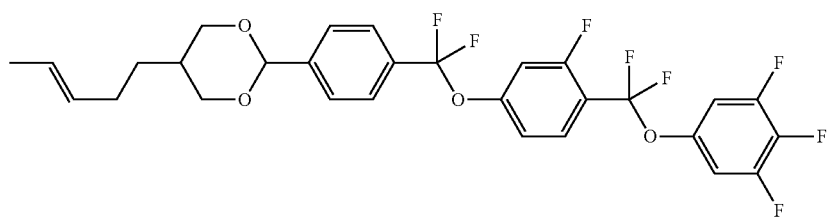 [SMILES: C/C=C/CCC1COC(c2ccc(C(F)(F)Oc3ccc(C(F)(F)Oc4cc(F)c(F)c(F)c4)c(F)c3)cc2)OC1] |
| 151 | 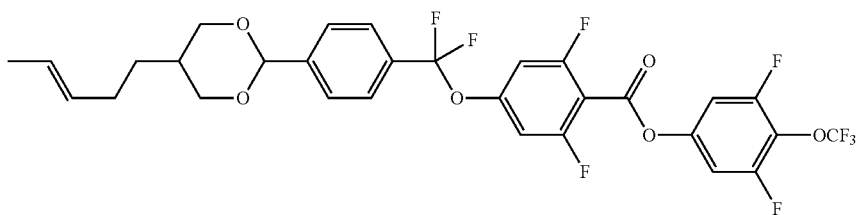 [SMILES: C/C=C/CCC1COC(c2ccc(C(F)(F)Oc3cc(F)c(C(=O)Oc4cc(F)c(OC(F)(F)F)c(F)c4)c(F)c3)cc2)OC1] |
| 152 | 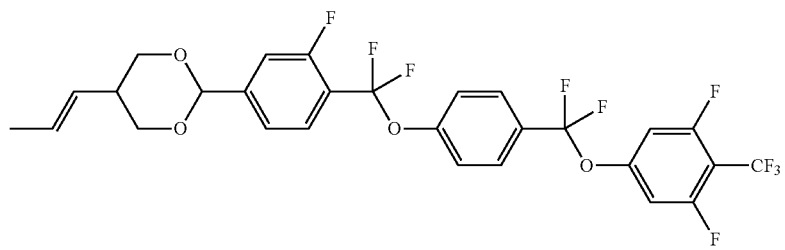 |
| 153 | 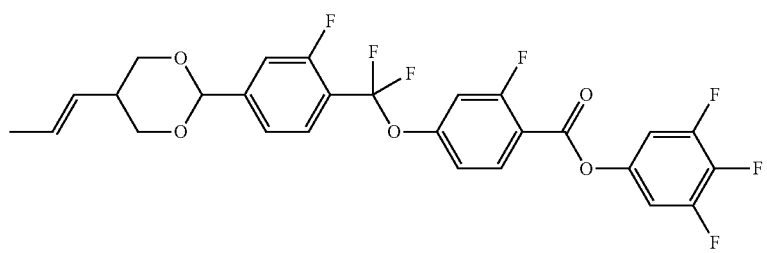 [SMILES: C/C=C/C1COC(c2ccc(C(F)(F)Oc3ccc(C(=O)Oc4cc(F)c(F)c(F)c4)c(F)c3)c(F)c2)OC1] |
| 154 | 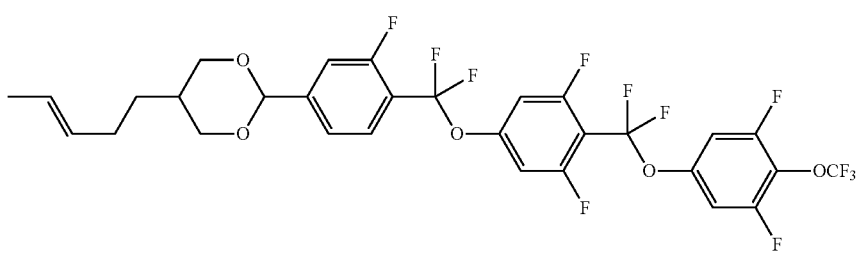 [SMILES: C/C=C/CCC1COC(c2ccc(C(F)(F)Oc3cc(F)c(C(F)(F)Oc4cc(F)c(OC(F)(F)F)c(F)c4)c(F)c3)c(F)c2)OC1] |

| No. | |
|---|---|
| 155 | 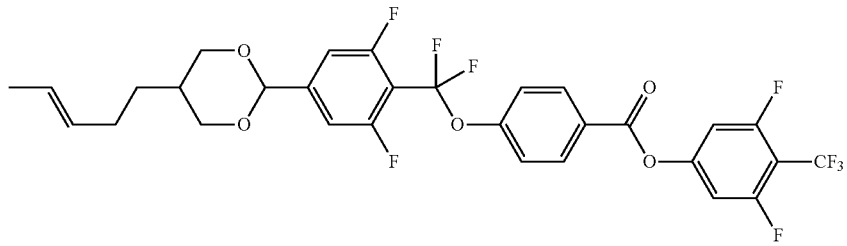 [SMILES: C/C=C/CCC1COC(c2cc(F)c(C(F)(F)Oc3ccc(C(=O)Oc4cc(F)c(C(F)(F)F)c(F)c4)cc3)c(F)c2)OC1] |
| 156 | 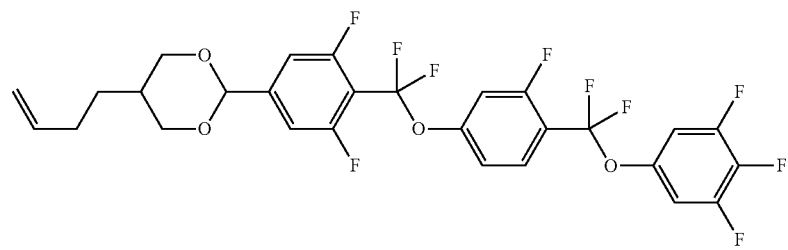 [SMILES: C=CCCC1COC(c2cc(F)c(C(F)(F)Oc3ccc(C(F)(F)Oc4cc(F)c(F)c(F)c4)c(F)c3)c(F)c2)OC1] |
| 157 | 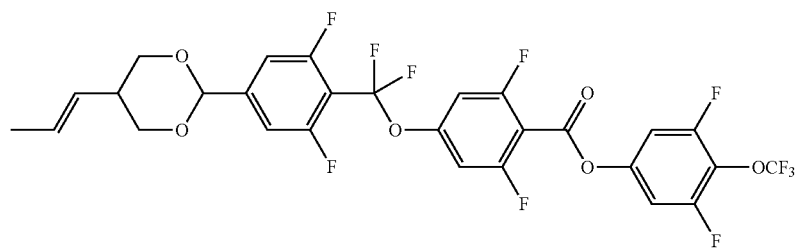 [SMILES: C/C=C/C1COC(c2cc(F)c(C(F)(F)Oc3cc(F)c(C(=O)Oc4cc(F)c(OC(F)(F)F)c(F)c4)c(F)c3)c(F)c2)OC1] |
| 158 | 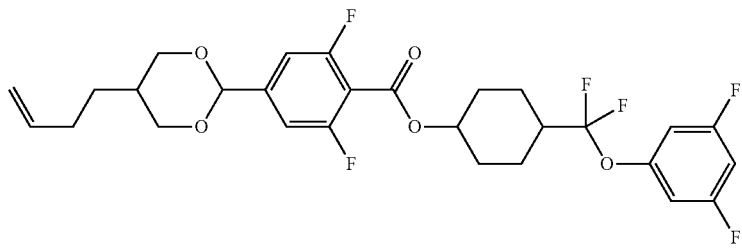 [SMILES: C=CCCC1COC(c2cc(F)c(C(=O)OC3CCC(C(F)(F)Oc4cc(F)cc(F)c4)CC3)c(F)c2)OC1] |
| 159 | 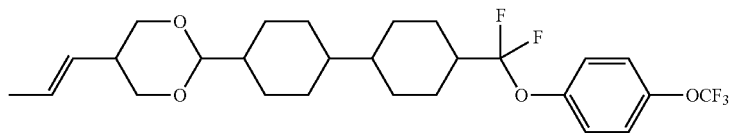 [SMILES: C/C=C/C1COC(C2CCC(C3CCC(C(F)(F)Oc4ccc(OC(F)(F)F)cc4)CC3)CC2)OC1] |
| 160 | 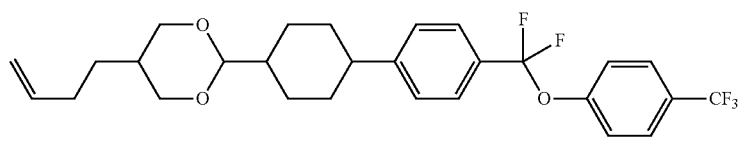 [SMILES: C=CCCC1COC(C2CCC(c3ccc(C(F)(F)Oc4ccc(C(F)(F)F)cc4)cc3)CC2)OC1] |
| 161 | 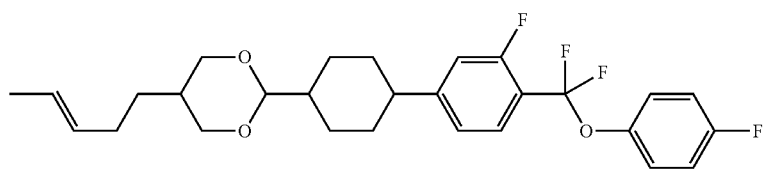 [SMILES: C/C=C/CCC1COC(C2CCC(c3ccc(C(F)(F)Oc4ccc(F)cc4)c(F)c3)CC2)OC1] |

-continued
| No. | |
|---|---|
| 162 | 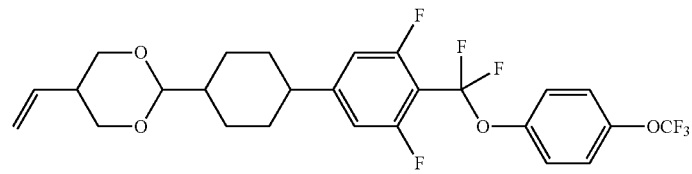 [SMILES: C=CC1COC(C2CCC(c3cc(F)c(C(F)(F)Oc4ccc(OC(F)(F)F)cc4)c(F)c3)CC2)OC1] |
| 163 | 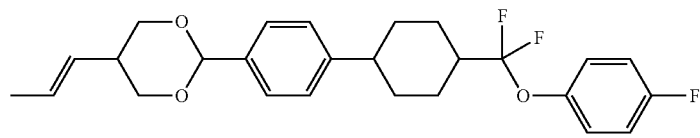 [SMILES: C/C=C/C1COC(c2ccc(C3CCC(C(F)(F)Oc4ccc(F)cc4)CC3)cc2)OC1] |
| 164 | 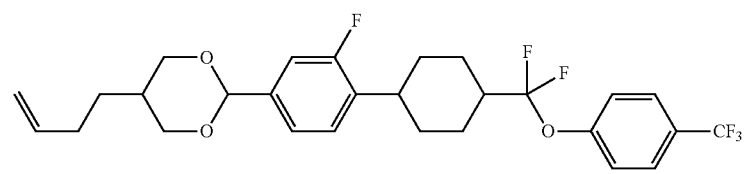 [SMILES: C=CCCC1COC(c2ccc(C3CCC(C(F)(F)Oc4ccc(C(F)(F)F)cc4)CC3)c(F)c2)OC1] |
| 165 | 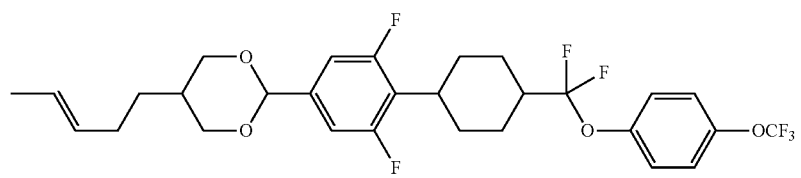 [SMILES: C/C=C/CCC1COC(c2cc(F)c(C3CCC(C(F)(F)Oc4ccc(OC(F)(F)F)cc4)CC3)c(F)c2)OC1] |
| 166 | 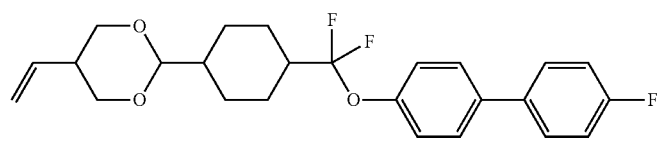 [SMILES: C=CC1COC(C2CCC(C(F)(F)Oc3ccc(-c4ccc(F)cc4)cc3)CC2)OC1] |
| 167 | 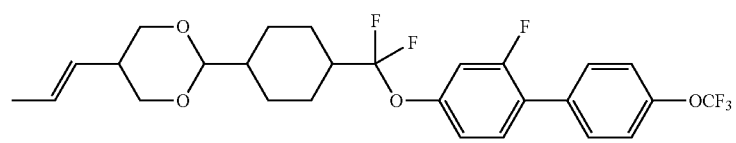 |
| 168 | 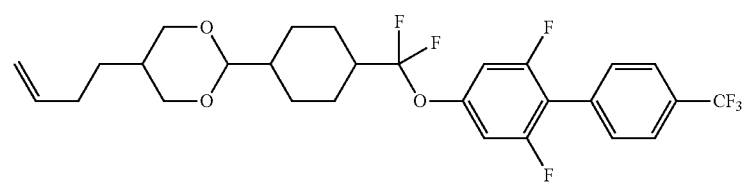 [SMILES: C=CCCC1COC(C2CCC(C(F)(F)Oc3cc(F)c(-c4ccc(C(F)(F)F)cc4)c(F)c3)CC2)OC1] |
| 169 | 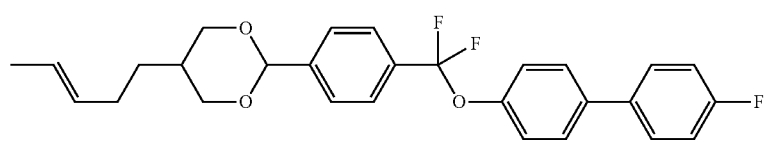 [SMILES: C/C=C/CCC1COC(c2ccc(C(F)(F)Oc3ccc(-c4ccc(F)cc4)cc3)cc2)OC1] |
| 170 | 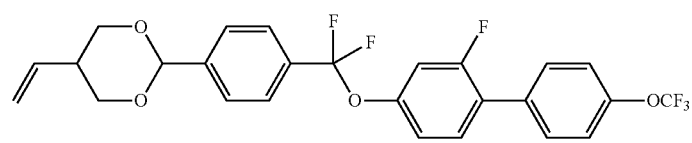 [SMILES: C=CC1COC(c2ccc(C(F)(F)Oc3ccc(-c4ccc(OC(F)(F)F)cc4)c(F)c3)cc2)OC1] |

| No. | |
|---|---|
| 171 | 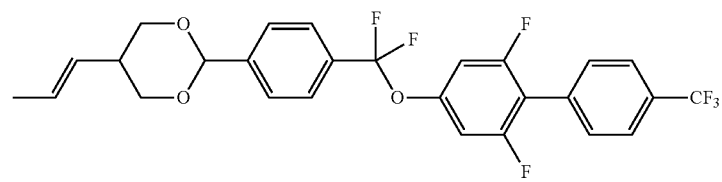 [SMILES: C/C=C/C1COC(c2ccc(C(F)(F)Oc3cc(F)c(-c4ccc(C(F)(F)F)cc4)c(F)c3)cc2)OC1] |
| 172 | 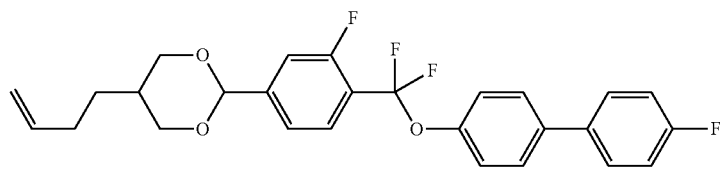 [SMILES: C=CCCC1COC(c2ccc(C(F)(F)Oc3ccc(-c4ccc(F)cc4)cc3)c(F)c2)OC1] |
| 173 | 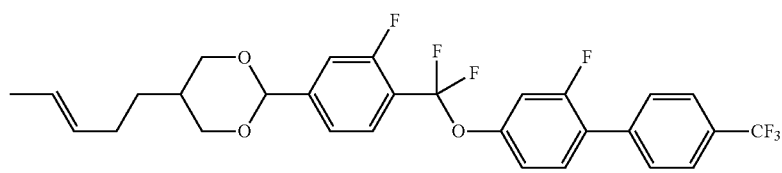 [SMILES: C/C=C/CCC1COC(c2ccc(C(F)(F)Oc3ccc(-c4ccc(C(F)(F)F)cc4)c(F)c3)c(F)c2)OC1] |
| 174 | 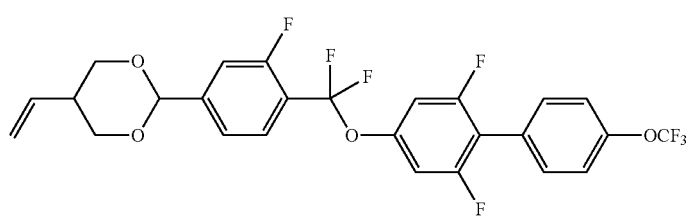 [SMILES: C=CC1COC(c2ccc(C(F)(F)Oc3cc(F)c(-c4ccc(OC(F)(F)F)cc4)c(F)c3)c(F)c2)OC1] |
| 175 | 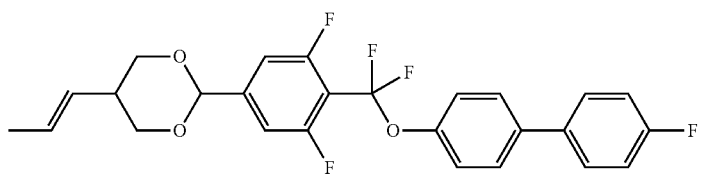 [SMILES: C/C=C/C1COC(c2cc(F)c(C(F)(F)Oc3ccc(-c4ccc(F)cc4)cc3)c(F)c2)OC1] |
| 176 | 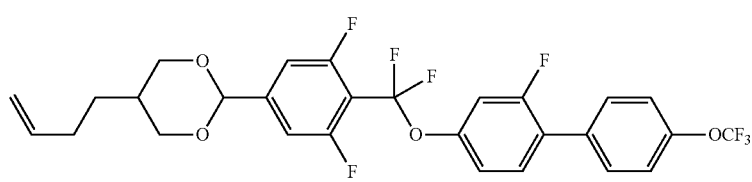 [SMILES: C=CCCC1COC(c2cc(F)c(C(F)(F)Oc3ccc(-c4ccc(OC(F)(F)F)cc4)c(F)c3)c(F)c2)OC1] |
| 177 | 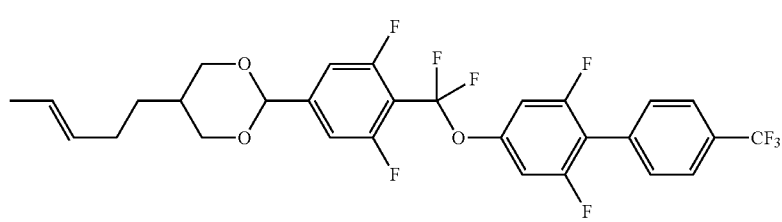 [SMILES: C/C=C/CCC1COC(c2cc(F)c(C(F)(F)Oc3cc(F)c(-c4ccc(C(F)(F)F)cc4)c(F)c3)c(F)c2)OC1] |
| 178 | 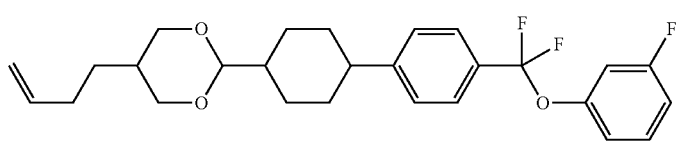 [SMILES: C=CCCC1COC(C2CCC(c3ccc(C(F)(F)Oc4cccc(F)c4)cc3)CC2)OC1] |

-continued
| No. | |
|---|---|
| 179 | 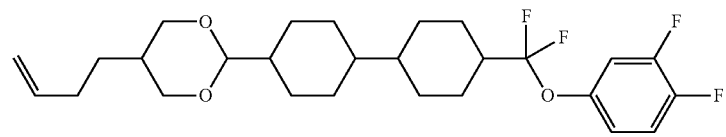 [SMILES: C=CCCC1COC(C2CCC(C3CCC(C(F)(F)Oc4ccc(F)c(F)c4)CC3)CC2)OC1] |
| 180 | 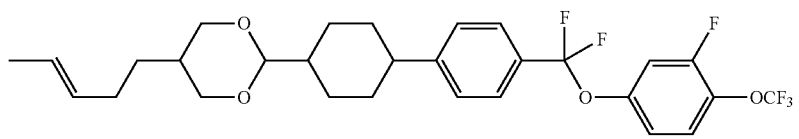 [SMILES: C/C=C/CCC1COC(C2CCC(c3ccc(C(F)(F)Oc4ccc(OC(F)(F)F)c(F)c4)cc3)CC2)OC1] |
| 181 | 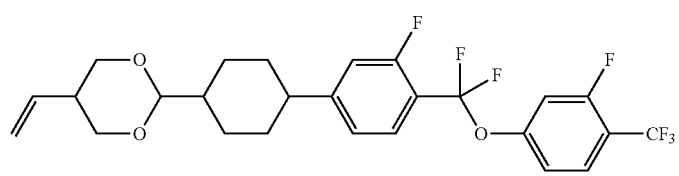 [SMILES: C=CC1COC(C2CCC(c3ccc(C(F)(F)Oc4ccc(C(F)(F)F)c(F)c4)c(F)c3)CC2)OC1] |
| 182 | 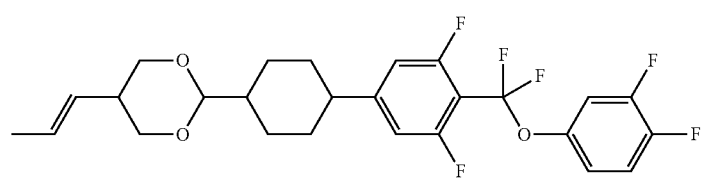 [SMILES: C/C=C/C1COC(C2CCC(c3cc(F)c(C(F)(F)Oc4ccc(F)c(F)c4)c(F)c3)CC2)OC1] |
| 183 | 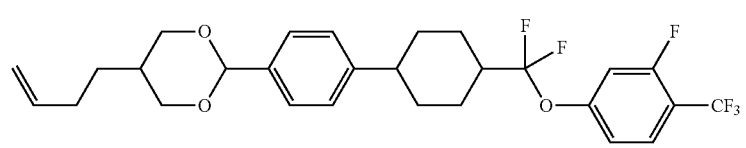 |
| 184 | 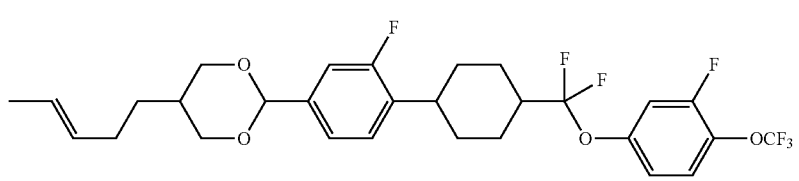 [SMILES: C/C=C/CCC1COC(c2ccc(C3CCC(C(F)(F)Oc4ccc(OC(F)(F)F)c(F)c4)CC3)c(F)c2)OC1] |
| 185 | 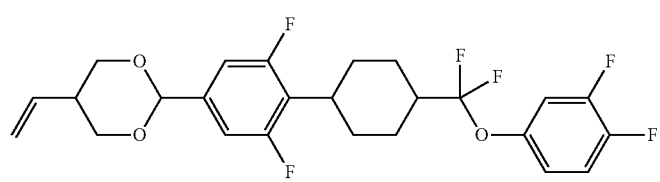 [SMILES: C=CC1COC(c2cc(F)c(C3CCC(C(F)(F)Oc4ccc(F)c(F)c4)CC3)c(F)c2)OC1] |
| 186 | 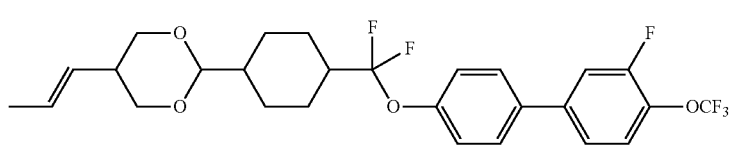 [SMILES: C/C=C/C1COC(C2CCC(C(F)(F)Oc3ccc(-c4ccc(OC(F)(F)F)c(F)c4)cc3)CC2)OC1] |
| 187 | 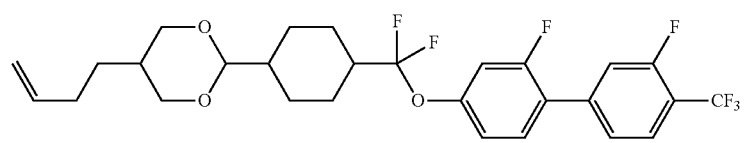 [SMILES: C=CCCC1COC(C2CCC(C(F)(F)Oc3ccc(-c4ccc(C(F)(F)F)c(F)c4)c(F)c3)CC2)OC1] |

| No. | |
|---|---|
| 188 | 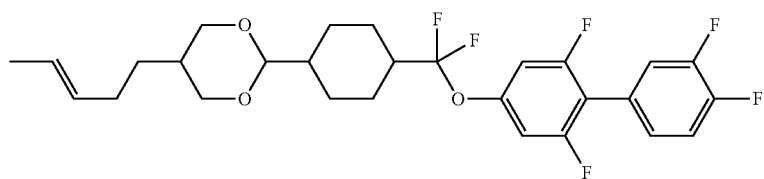 [SMILES: C/C=C/CCC1COC(C2CCC(C(F)(F)Oc3cc(F)c(-c4ccc(F)c(F)c4)c(F)c3)CC2)OC1] |
| 189 | 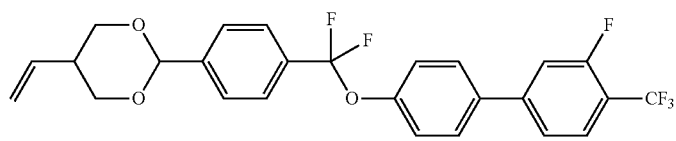 [SMILES: C=CC1COC(c2ccc(C(F)(F)Oc3ccc(-c4ccc(C(F)(F)F)c(F)c4)cc3)cc2)OC1] |
| 190 | 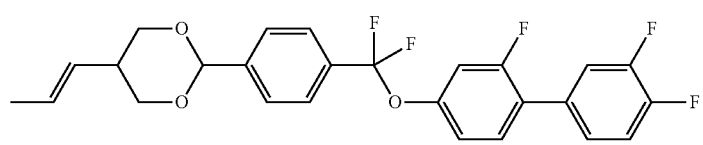 |
| 191 | 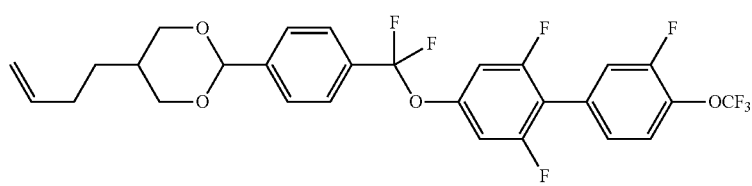 [SMILES: C=CCCC1COC(c2ccc(C(F)(F)Oc3cc(F)c(-c4ccc(OC(F)(F)F)c(F)c4)c(F)c3)cc2)OC1] |
| 192 | 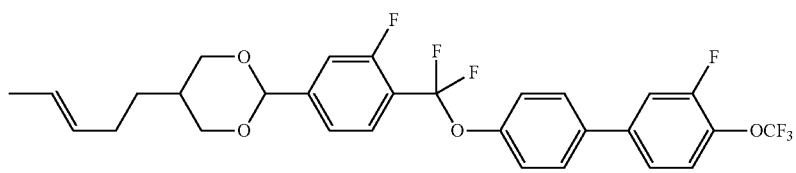 [SMILES: C/C=C/CCC1COC(c2ccc(C(F)(F)Oc3ccc(-c4ccc(OC(F)(F)F)c(F)c4)cc3)c(F)c2)OC1] |
| 193 | 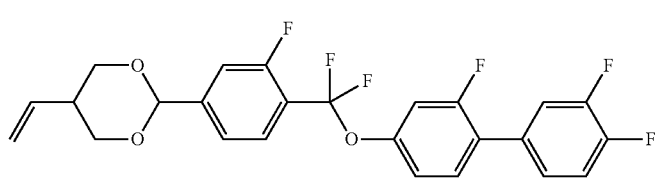 [SMILES: C=CC1COC(c2ccc(C(F)(F)Oc3ccc(-c4ccc(F)c(F)c4)c(F)c3)c(F)c2)OC1] |
| 194 | 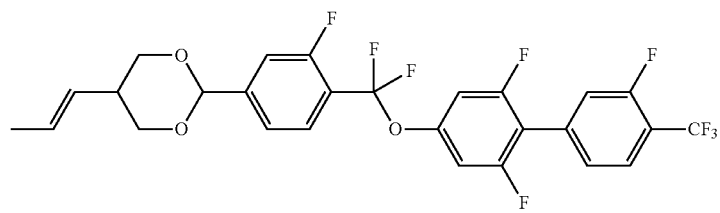 [SMILES: C/C=C/C1COC(c2ccc(C(F)(F)Oc3cc(F)c(-c4ccc(C(F)(F)F)c(F)c4)c(F)c3)c(F)c2)OC1] |
| 195 | 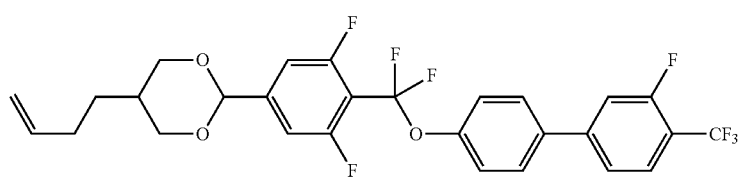 [SMILES: C=CCCC1COC(c2cc(F)c(C(F)(F)Oc3ccc(-c4ccc(C(F)(F)F)c(F)c4)cc3)c(F)c2)OC1] |
| 196 | 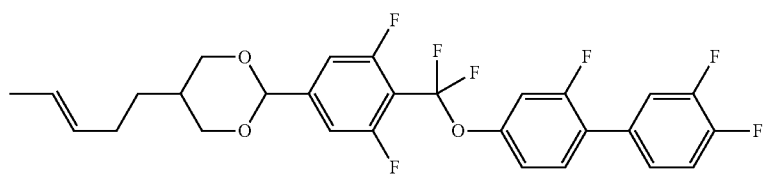 [SMILES: C/C=C/CCC1COC(c2cc(F)c(C(F)(F)Oc3ccc(-c4ccc(F)c(F)c4)c(F)c3)c(F)c2)OC1] |

| No. | |
|---|---|
| 197 | 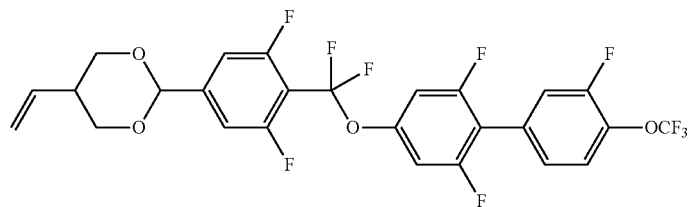 [SMILES: C=CC1COC(c2cc(F)c(C(F)(F)Oc3cc(F)c(-c4ccc(OC(F)(F)F)c(F)c4)c(F)c3)c(F)c2)OC1] |
| 198 | 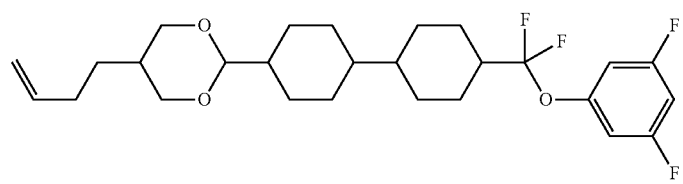 [SMILES: C=CCCC1COC(C2CCC(C3CCC(C(F)(F)Oc4cc(F)cc(F)c4)CC3)CC2)OC1] |
| 199 | 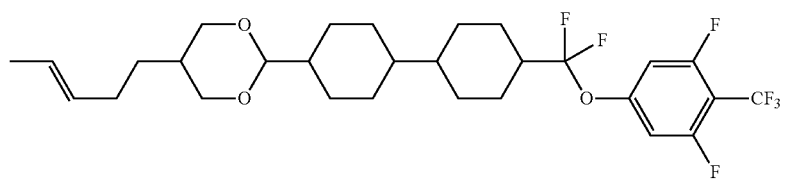 [SMILES: C/C=C/CCC1COC(C2CCC(C3CCC(C(F)(F)Oc4cc(F)c(C(F)(F)F)c(F)c4)CC3)CC2)OC1] |
| 200 | 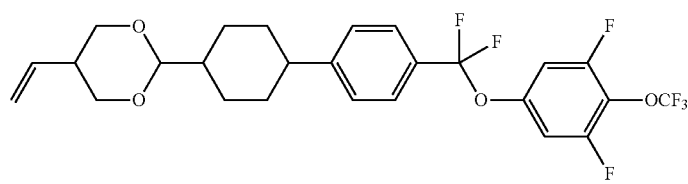 [SMILES: C=CC1COC(C2CCC(c3ccc(C(F)(F)Oc4cc(F)c(OC(F)(F)F)c(F)c4)cc3)CC2)OC1] |
| 201 | 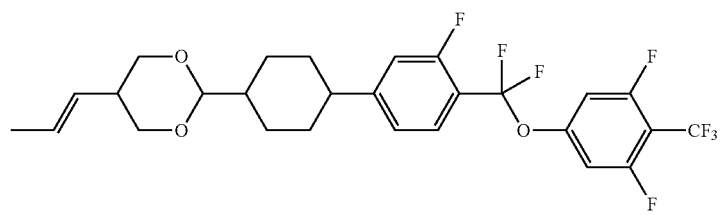 |
| 202 | 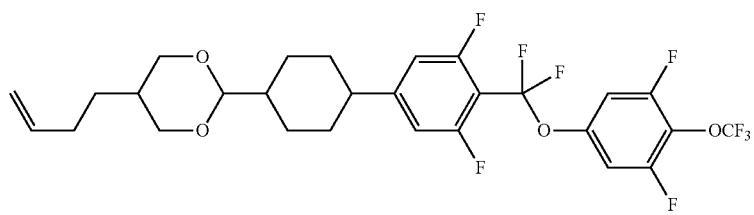 [SMILES: C=CCCC1COC(C2CCC(c3cc(F)c(C(F)(F)Oc4cc(F)c(OC(F)(F)F)c(F)c4)c(F)c3)CC2)OC1] |
| 203 | 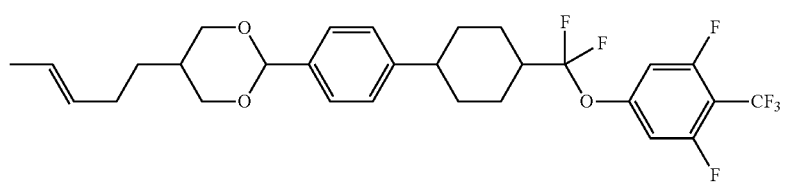 [SMILES: C/C=C/CCC1COC(c2ccc(C3CCC(C(F)(F)Oc4cc(F)c(C(F)(F)F)c(F)c4)CC3)cc2)OC1] |

| No. | |
|---|---|
| 204 | 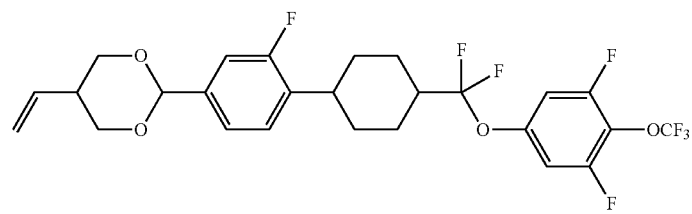 |
| 205 | 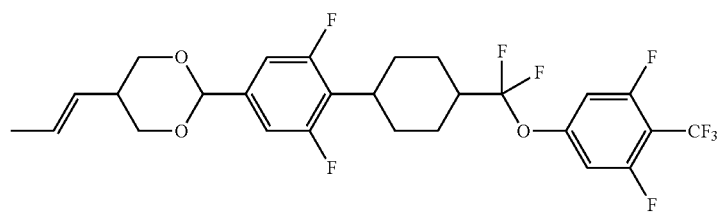 [SMILES: C/C=C/C1COC(c2cc(F)c(C3CCC(C(F)(F)Oc4cc(F)c(C(F)(F)F)c(F)c4)CC3)c(F)c2)OC1] |
| 206 | 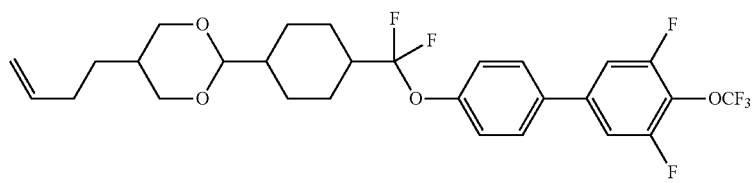 [SMILES: C=CCCC1COC(C2CCC(C(F)(F)Oc3ccc(-c4cc(F)c(OC(F)(F)F)c(F)c4)cc3)CC2)OC1] |
| 207 | 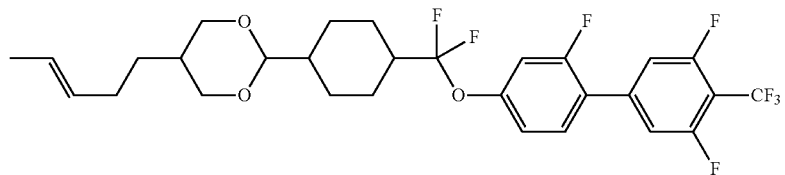 [SMILES: C/C=C/CCC1COC(C2CCC(C(F)(F)Oc3ccc(-c4cc(F)c(C(F)(F)F)c(F)c4)c(F)c3)CC2)OC1] |
| 208 | 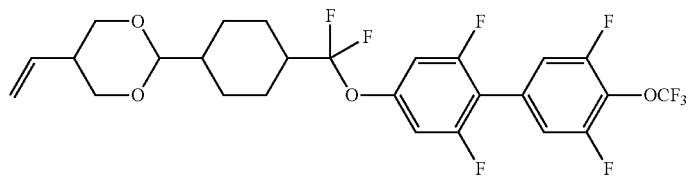 [SMILES: C=CC1COC(C2CCC(C(F)(F)Oc3cc(F)c(-c4cc(F)c(OC(F)(F)F)c(F)c4)c(F)c3)CC2)OC1] |
| 209 | 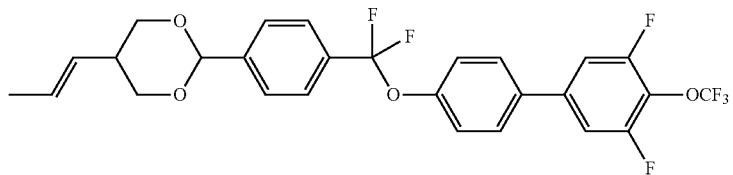 [SMILES: C/C=C/C1COC(c2ccc(C(F)(F)Oc3ccc(-c4cc(F)c(OC(F)(F)F)c(F)c4)cc3)cc2)OC1] |
| 210 | 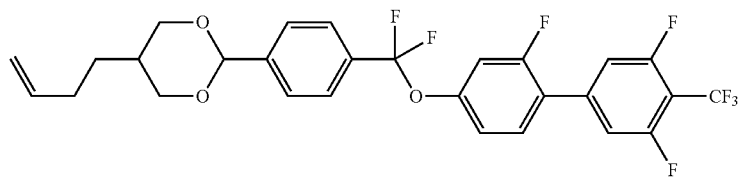 [SMILES: C=CCCC1COC(c2ccc(C(F)(F)Oc3ccc(-c4cc(F)c(C(F)(F)F)c(F)c4)c(F)c3)cc2)OC1] |
| 211 | 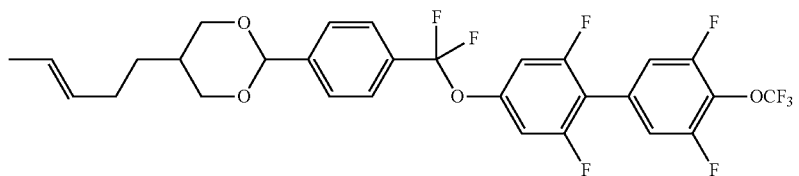 [SMILES: C/C=C/CCC1COC(c2ccc(C(F)(F)Oc3cc(F)c(-c4cc(F)c(OC(F)(F)F)c(F)c4)c(F)c3)cc2)OC1] |

| No. | |
|---|---|
| 212 | 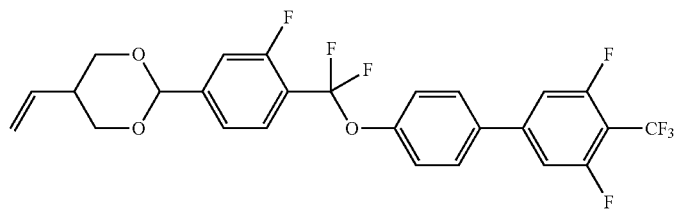 [SMILES: C=CC1COC(c2ccc(C(F)(F)Oc3ccc(-c4cc(F)c(C(F)(F)F)c(F)c4)cc3)c(F)c2)OC1] |
| 213 | 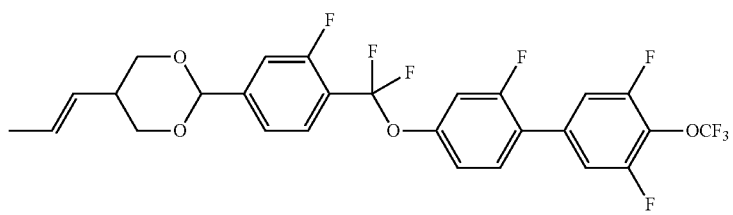 [SMILES: C/C=C/C1COC(c2ccc(C(F)(F)Oc3ccc(-c4cc(F)c(OC(F)(F)F)c(F)c4)c(F)c3)c(F)c2)OC1] |
| 214 | 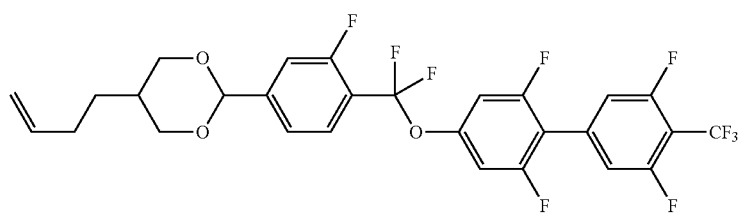 [SMILES: C=CCCC1COC(c2ccc(C(F)(F)Oc3cc(F)c(-c4cc(F)c(C(F)(F)F)c(F)c4)c(F)c3)c(F)c2)OC1] |
| 215 | 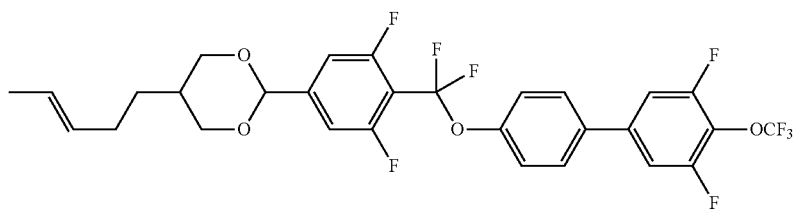 [SMILES: C/C=C/CCC1COC(c2cc(F)c(C(F)(F)Oc3ccc(-c4cc(F)c(OC(F)(F)F)c(F)c4)cc3)c(F)c2)OC1] |
| 216 | 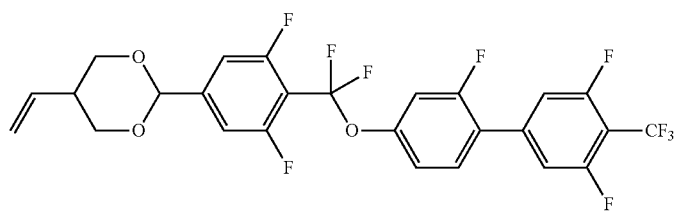 |
| 217 | 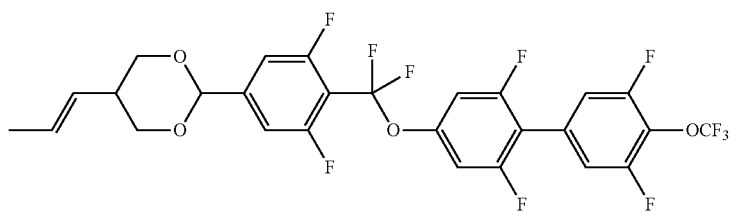 [SMILES: C/C=C/C1COC(c2cc(F)c(C(F)(F)Oc3cc(F)c(-c4cc(F)c(OC(F)(F)F)c(F)c4)c(F)c3)c(F)c2)OC1] |
| 218 | 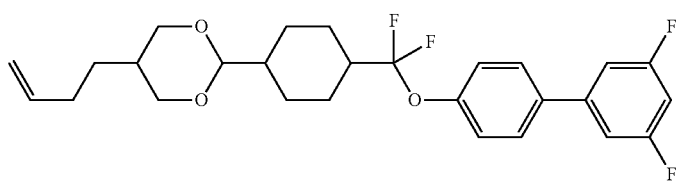 [SMILES: C=CCCC1COC(C2CCC(C(F)(F)Oc3ccc(-c4cc(F)cc(F)c4)cc3)CC2)OC1] |

| No. | |
|---|---|
| 219 | 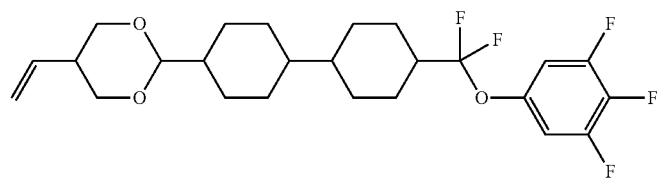 [SMILES: C=CC1COC(C2CCC(C3CCC(C(F)(F)Oc4cc(F)c(F)c(F)c4)CC3)CC2)OC1] |
| 220 | 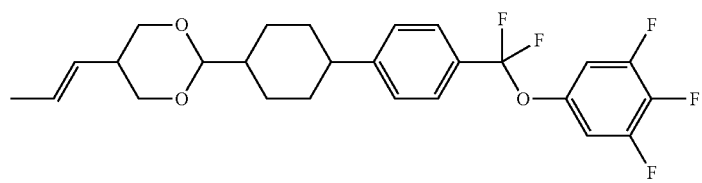 [SMILES: C/C=C/C1COC(C2CCC(c3ccc(C(F)(F)Oc4cc(F)c(F)c(F)c4)cc3)CC2)OC1] |
| 221 | 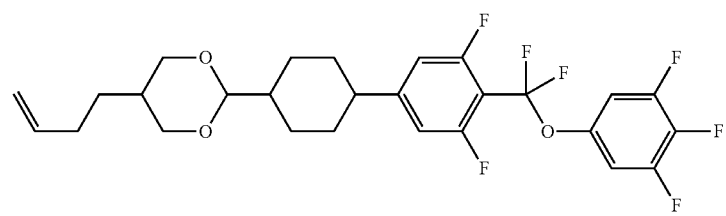 [SMILES: C=CCCC1COC(C2CCC(c3cc(F)c(C(F)(F)Oc4cc(F)c(F)c(F)c4)c(F)c3)CC2)OC1] |
| 222 | 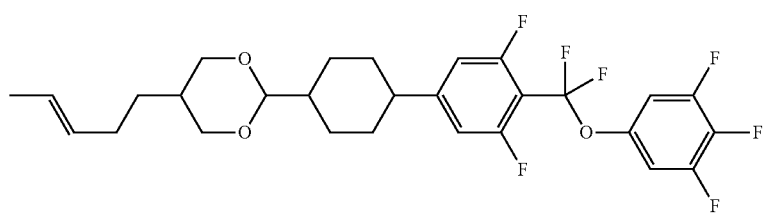 [SMILES: C/C=C/CCC1COC(C2CCC(c3cc(F)c(C(F)(F)Oc4cc(F)c(F)c(F)c4)c(F)c3)CC2)OC1] |
| 223 | 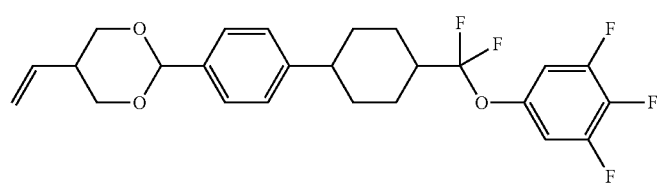 [SMILES: C=CC1COC(c2ccc(C3CCC(C(F)(F)Oc4cc(F)c(F)c(F)c4)CC3)cc2)OC1] |
| 224 | 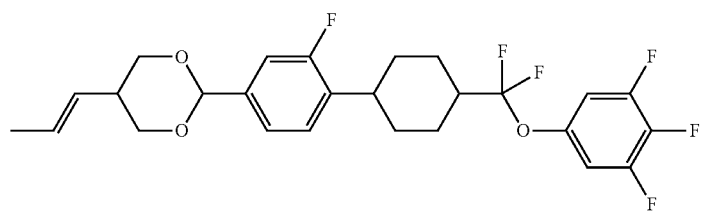 [SMILES: C/C=C/C1COC(c2ccc(C3CCC(C(F)(F)Oc4cc(F)c(F)c(F)c4)CC3)c(F)c2)OC1] |
| 225 | 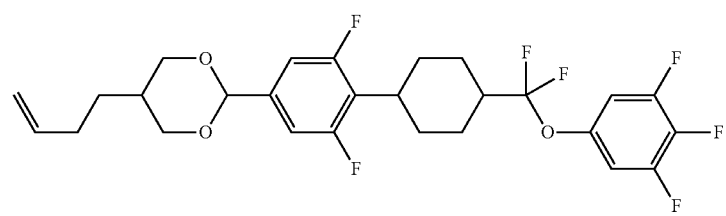 [SMILES: C=CCCC1COC(c2cc(F)c(C3CCC(C(F)(F)Oc4cc(F)c(F)c(F)c4)CC3)c(F)c2)OC1] |
| 226 | 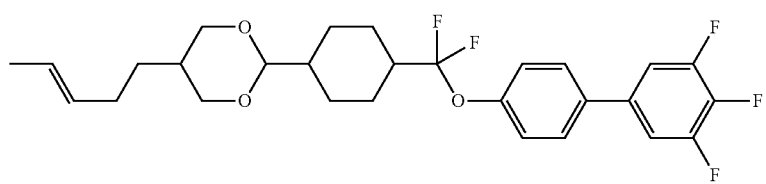 [SMILES: C/C=C/CCC1COC(C2CCC(C(F)(F)Oc3ccc(-c4cc(F)c(F)c(F)c4)cc3)CC2)OC1] |

US 9,657,230 B2
147                                                                 148
-continued
| No. | |
|---|---|
| 227 | 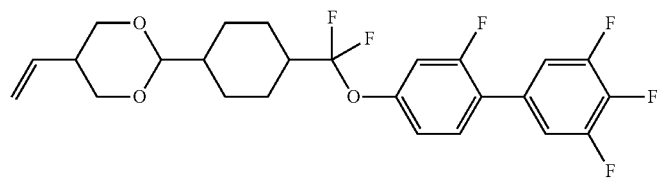 [SMILES: C=CC1COC(C2CCC(C(F)(F)Oc3ccc(-c4cc(F)c(F)c(F)c4)c(F)c3)CC2)OC1] |
| 228 | 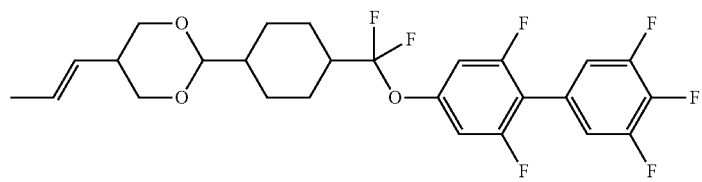 [SMILES: C/C=C/C1COC(C2CCC(C(F)(F)Oc3cc(F)c(-c4cc(F)c(F)c(F)c4)c(F)c3)CC2)OC1] |
| 229 | 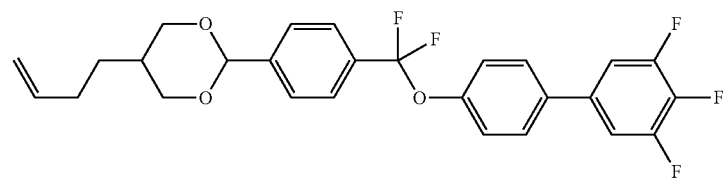 [SMILES: C=CCCC1COC(c2ccc(C(F)(F)Oc3ccc(-c4cc(F)c(F)c(F)c4)cc3)cc2)OC1] |
| 230 | 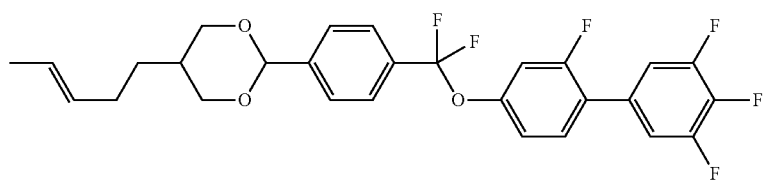 [SMILES: C/C=C/CCC1COC(c2ccc(C(F)(F)Oc3ccc(-c4cc(F)c(F)c(F)c4)c(F)c3)cc2)OC1] |
| 231 | 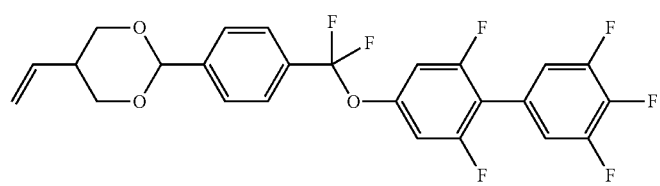 [SMILES: C=CC1COC(c2ccc(C(F)(F)Oc3cc(F)c(-c4cc(F)c(F)c(F)c4)c(F)c3)cc2)OC1] |
| 232 | 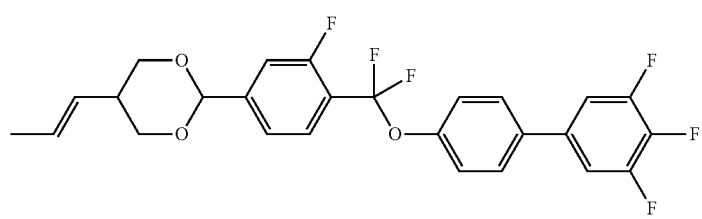 |
| 233 | 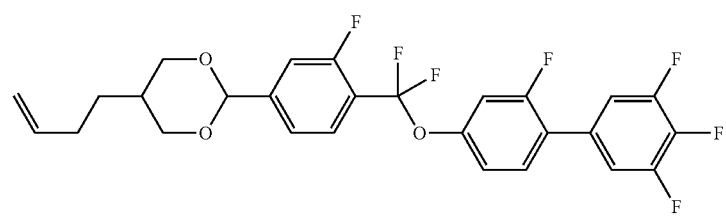 [SMILES: C=CCCC1COC(c2ccc(C(F)(F)Oc3ccc(-c4cc(F)c(F)c(F)c4)c(F)c3)c(F)c2)OC1] |
| 234 | 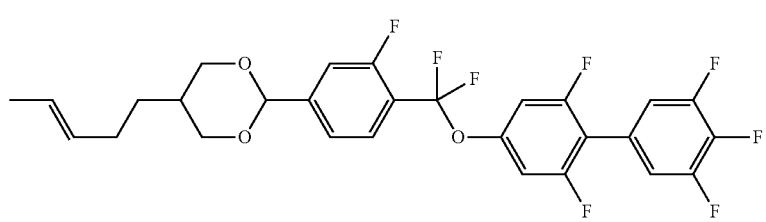 |

| No. | |
|---|---|
| 235 | 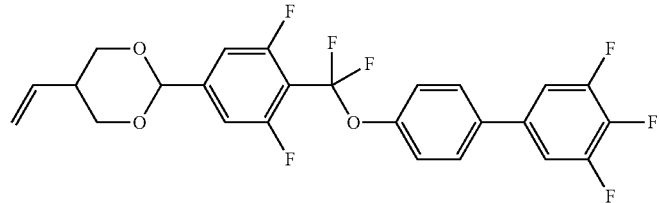 [SMILES: C=CC1COC(c2cc(F)c(C(F)(F)Oc3ccc(-c4cc(F)c(F)c(F)c4)cc3)c(F)c2)OC1] |
| 236 | 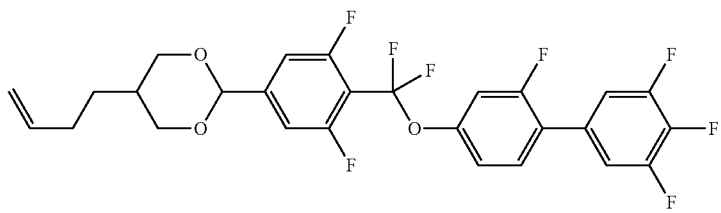 |
| 237 | 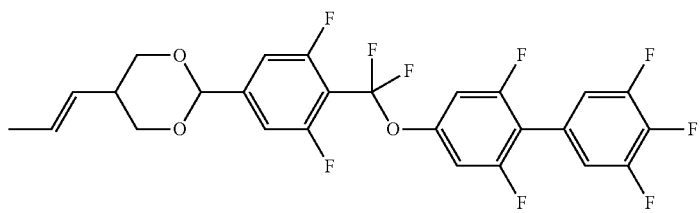 [SMILES: C/C=C/C1COC(c2cc(F)c(C(F)(F)Oc3cc(F)c(-c4cc(F)c(F)c(F)c4)c(F)c3)c(F)c2)OC1] |
| 238 | 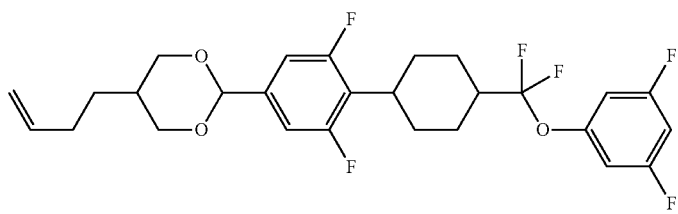 [SMILES: C=CCCC1COC(c2cc(F)c(C3CCC(C(F)(F)Oc4cc(F)cc(F)c4)CC3)c(F)c2)OC1] |

2. Example of Composition

Compositions of the invention will be described in detail by way of Examples. The invention includes a mixture of the composition of Use Example 1 and the composition of Use Example 2. The invention also includes a mixture in which at least two compositions in Use Examples are mixed. Compounds in Use Examples were expressed using symbols according to definitions of Table 3 described below. In Table 3, a configuration of 1,4-cyclohexylene is trans. A parenthesized number next to a symbolized compound in Use Examples corresponds to the chemical formula of the compound. A symbol (-) means any other liquid crystal compound. A proportion (percentage) of a liquid crystal compound is expressed in terms of weight percentage (% by weight) based on the weight of the liquid crystal composition. Values of physical properties of the composition were summarized in a last part. Physical properties were measured according to the methods described above, and measured values were directly described without extrapolation.

TABLE 3

Method for Description of Compounds using Symbols
R—(A$_1$)—Z$_1$— . . . —Z$_n$—(A$_n$)—R'

| 1) Left-terminal Group R— | Symbol |
|---|---|
| $C_nH_{2n+1}$— | n- |
| $C_nH_{2n+1}O$— | nO— |
| $C_mH_{2m+1}OC_nH_{2n}$— | mOn— |
| $CH_2$=CH— | V— |
| $C_nH_{2n+1}$—CH=CH— | nV— |
| $CH_2$=CH—$C_nH_{2n}$— | Vn— |
| $C_mH_{2m+1}$—CH=CH—$C_nH_{2n}$— | mVn— |
| $CF_2$=CH— | VFF— |
| $CF_2$=CH—$C_nH_{2n}$— | VFFn— |

| 2) Right-terminal Group —R' | Symbol |
|---|---|
| —$C_nH_{2n+1}$ | -n |
| —$OC_nH_{2n+1}$ | —On |
| —COOCH$_3$ | —EMe |
| —CH=CH$_2$ | —V |
| —CH=CH—$C_nH_{2n+1}$ | —Vn |

TABLE 3-continued

Method for Description of Compounds using Symbols
R—(A₁)—Z₁— ... —Zₙ—(Aₙ)—R'

| | |
|---|---|
| —CₙH₂ₙ—CH=CH₂ | —nV |
| —CₘH₂ₘ—CH=CH—CₙH₂ₙ₊₁ | —mVn |
| —CH=CF₂ | —VFF |
| —F | —F |
| —Cl | —CL |
| —OCF₃ | —OCF3 |
| —OCF₂H | —OCF2H |
| —CF₃ | —CF3 |
| —OCH=CH—CF₃ | —OVCF3 |
| —C≡N | —C |

| 3) Bonding Group —Zₙ— | Symbol |
|---|---|
| —CₙH₂ₙ— | n |
| —COO— | E |
| —CH=CH— | V |
| —CH₂O— | 1O |
| —OCH₂— | O1 |
| —CF₂O— | X |
| —C≡C— | T |

| 4) Ring Structure —Aₙ— | Symbol |
|---|---|
|  | H |
|  | B |
| 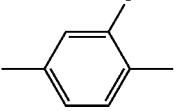 | B(F) |
| 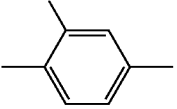 | B(2F) |
| 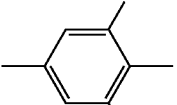 | B(F,F) |
| 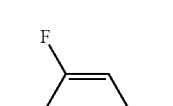 | B(2F,5F) |
| 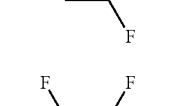 | B(2F,3F) |
| 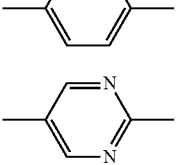 | Py |
|  | G |
| 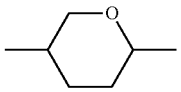 | dh |
| 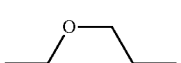 | Dh |
| 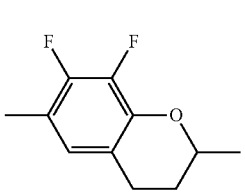 | Cro |
| 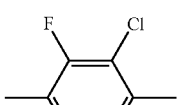 | B(2F,3CL) |

Examples of Description

Example 1  3-HH—V

Example 2  4O-BHHXB(F,F)—F

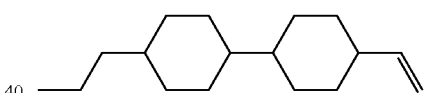

Use Example 1

| | | |
|---|---|---|
| V2-GB(F,F)XB(F)B(F,F)-F | (No. 236) | 5% |
| 3-HB-O2 | (2-5) | 10% |
| 5-HB-CL | (5-2) | 13% |
| 3-HBB(F,F)-F | (6-24) | 7% |
| 3-PyB(F)-F | (5-15) | 10% |
| 5-PyB(F)-F | (5-15) | 10% |
| 3-PyBB-F | (6-80) | 10% |
| 4-PyBB-F | (6-80) | 8% |
| 5-PyBB-F | (6-80) | 10% |
| 5-HBB(F)B-2 | (4-5) | 8% |
| 5-HBB(F)B-3 | (4-5) | 9% |

NI = 92.4° C.; η = 40.1 mPa·s; Δn = 0.185; Δε = 9.7.

Use Example 2

| | | |
|---|---|---|
| V2-GHB(F,F)XB(F,F)-F | (No. 221) | 5% |
| 2-HB-C | (8-1) | 5% |
| 3-HB-C | (8-1) | 12% |
| 3-HB-O2 | (2-5) | 12% |
| 2-BTB-1 | (2-10) | 3% |
| 3-HHB-F | (6-1) | 3% |
| 3-HHB-1 | (3-1) | 8% |
| 3-HHB-O1 | (3-1) | 4% |
| 3-HHB-3 | (3-1) | 14% |
| 3-HHEB-F | (6-10) | 4% |
| 5-HHEB-F | (6-10) | 4% |
| 2-HHB(F)-F | (6-2) | 7% |
| 3-HHB(F)-F | (6-2) | 7% |
| 5-HHB(F)-F | (6-2) | 7% |
| 3-HHB(F,F)-F | (6-3) | 5% |

NI = 100.6° C.; η = 21.5 mPa · s; Δn = 0.100; Δε = 6.4.

Use Example 3

| | | |
|---|---|---|
| V2-GB(F,F)XB(F)B(F,F)-F | (No. 236) | 3% |
| 7-HB(F,F)-F | (5-4) | 3% |
| 3-HB-O2 | (2-5) | 7% |
| 2-HHB(F)-F | (6-2) | 10% |
| 3-HHB(F)-F | (6-2) | 10% |
| 5-HHB(F)-F | (6-2) | 10% |
| 2-HBB(F)-F | (6-23) | 9% |
| 3-HBB(F)-F | (6-23) | 9% |
| 5-HBB(F)-F | (6-23) | 16% |
| 2-HBB-F | (6-22) | 4% |
| 3-HBB-F | (6-22) | 4% |
| 5-HBB-F | (6-22) | 3% |
| 3-HBB(F,F)-F | (6-24) | 5% |
| 5-HBB(F,F)-F | (6-24) | 7% |

NI = 85.3° C.; η = 25.6 mPa · s; Δn = 0.116; Δε = 6.7.

Use Example 4

| | | |
|---|---|---|
| V2-GHB(F,F)XB(F,F)-F | (No. 221) | 3% |
| 5-HB-CL | (5-2) | 16% |
| 3-HH-4 | (2-1) | 12% |
| 3-HH-5 | (2-1) | 4% |
| 3-HHB-F | (6-1) | 4% |
| 3-HHB-CL | (6-1) | 4% |
| 4-HHB-CL | (6-1) | 4% |
| 3-HHB(F)-F | (6-2) | 8% |
| 4-HHB(F)-F | (6-2) | 8% |
| 5-HHB(F)-F | (6-2) | 9% |
| 7-HHB(F)-F | (6-2) | 8% |
| 5-HBB(F)-F | (6-23) | 3% |
| 1O1-HBBH-5 | (4-1) | 3% |
| 3-HHBB(F,F)-F | (7-6) | 2% |
| 4-HHBB(F,F)-F | (7-6) | 3% |
| 5-HHBB(F,F)-F | (7-6) | 3% |
| 3-HH2BB(F,F)-F | (7-15) | 3% |
| 4-HH2BB(F,F)-F | (7-15) | 3% |

NI = 114.0° C.; η = 20.4 mPa · s; Δn = 0.091; Δε = 4.7.

Use Example 5

| | | |
|---|---|---|
| V2-GB(F,F)XB(F)B(F,F)-F | (No. 236) | 5% |
| 3-HHB(F,F)-F | (6-3) | 9% |
| 3-H2HB(F,F)-F | (6-15) | 8% |
| 4-H2HB(F,F)-F | (6-15) | 8% |
| 5-H2HB(F,F)-F | (6-15) | 8% |
| 3-HBB(F,F)-F | (6-24) | 21% |
| 5-HBB(F,F)-F | (6-24) | 17% |
| 3-H2BB(F,F)-F | (6-27) | 10% |
| 5-HHBB(F,F)-F | (7-6) | 3% |
| 5-HHEBB-F | (7-17) | 2% |
| 3-HH2BB(F,F)-F | (7-15) | 3% |
| 1O1-HBBH-4 | (4-1) | 3% |
| 1O1-HBBH-5 | (4-1) | 3% |

NI = 94.0° C.; η = 35.7 mPa · s; Δn = 0.116; Δε = 10.7.

A pitch was 64.9 micrometers when compound (Op-5) was added to the composition described above at a proportion of 0.25% by weight.

Use Example 6

| | | |
|---|---|---|
| V2-GHB(F,F)XB(F,F)-F | (No. 221) | 5% |
| 5-HB-F | (5-2) | 12% |
| 6-HB-F | (5-2) | 9% |
| 7-HB-F | (5-2) | 7% |
| 2-HHB-OCF3 | (6-1) | 7% |
| 3-HHB-OCF3 | (6-1) | 7% |
| 4-HHB-OCF3 | (6-1) | 7% |
| 5-HHB-OCF3 | (6-1) | 4% |
| 3-HH2B-OCF3 | (6-4) | 4% |
| 5-HH2B-OCF3 | (6-4) | 3% |
| 3-HHB(F,F)-OCF2H | (6-3) | 3% |
| 3-HHB(F,F)-OCF3 | (6-3) | 3% |
| 3-HH2B(F)-F | (6-5) | 3% |
| 3-HBB(F)-F | (6-23) | 10% |
| 5-HBB(F)-F | (6-23) | 10% |
| 5-HBBH-3 | (4-1) | 3% |
| 3-HB(F)BH-3 | (4-2) | 3% |

NI = 85.7° C.; η = 17.2 mPa · s; Δn = 0.093; Δε = 6.0.

Use Example 7

| | | |
|---|---|---|
| V2-GB(F,F)XB(F)B(F,F)-F | (No. 236) | 5% |
| 5-HB-CL | (5-2) | 11% |
| 3-HH-4 | (2-1) | 8% |
| 3-HHB-1 | (3-1) | 5% |
| 3-HHB(F,F)-F | (6-3) | 8% |
| 3-HBB(F,F)-F | (6-24) | 20% |
| 5-HBB(F,F)-F | (6-24) | 15% |
| 3-HHEB(F,F)-F | (6-12) | 8% |
| 4-HHEB(F,F)-F | (6-12) | 3% |
| 5-HHEB(F,F)-F | (6-12) | 3% |
| 2-HBEB(F,F)-F | (6-39) | 3% |
| 3-HBEB(F,F)-F | (6-39) | 4% |
| 5-HBEB(F,F)-F | (6-39) | 3% |
| 3-HHBB(F,F)-F | (7-6) | 4% |

NI = 76.5° C.; η = 22.7 mPa · s; Δn = 0.104; Δε = 10.1.

Use Example 8

| | | |
|---|---|---|
| V2-GHB(F,F)XB(F,F)-F | (No. 221) | 4% |
| 3-HB-CL | (5-2) | 6% |
| 5-HB-CL | (5-2) | 4% |
| 3-HHB-OCF3 | (6-1) | 5% |
| 3-H2HB-OCF3 | (6-13) | 5% |
| 5-H4HB-OCF3 | (6-19) | 11% |
| V-HHB(F)-F | (6-2) | 5% |
| 3-HHB(F)-F | (6-2) | 5% |
| 5-HHB(F)-F | (6-2) | 5% |

-continued

| | | |
|---|---|---|
| 3-H4HB(F,F)-CF3 | (6-20) | 8% |
| 5-H4HB(F,F)-CF3 | (6-20) | 10% |
| 5-H2HB(F,F)-F | (6-15) | 5% |
| 5-H4HB(F,F)-F | (6-15) | 7% |
| 2-H2BB(F)-F | (6-27) | 5% |
| 3-H2BB(F)-F | (6-27) | 10% |
| 3-HBEB(F,F)-F | (6-39) | 5% |

NI = 69.8° C.; η = 25.3 mPa · s; Δn = 0.097; Δε = 8.3.

Use Example 9

| | | |
|---|---|---|
| V2-GB(F,F)XB(F)B(F,F)-F | (No. 236) | 4% |
| 5-HB-CL | (5-2) | 17% |
| 7-HB(F,F)-F | (5-4) | 3% |
| 3-HH-4 | (2-1) | 10% |
| 3-HH-5 | (2-1) | 5% |
| 3-HB-O2 | (2-5) | 15% |
| 3-HHB-1 | (3-1) | 8% |
| 3-HHB-O1 | (3-1) | 5% |
| 2-HHB(F)-F | (6-2) | 6% |
| 3-HHB(F)-F | (6-2) | 7% |
| 5-HHB(F)-F | (6-2) | 6% |
| 3-HHB(F,F)-F | (6-3) | 6% |
| 3-H2HB(F,F)-F | (6-15) | 4% |
| 4-H2HB(F,F)-F | (6-15) | 4% |

NI = 70.1° C.; η = 14.8 mPa · s; Δn = 0.077; Δε = 4.2.

Use Example 10

| | | |
|---|---|---|
| V2-GHB(F,F)XB(F,F)-F | (No. 221) | 5% |
| 5-HB-CL | (5-2) | 3% |
| 7-HB(F)-F | (5-3) | 7% |
| 3-HH-4 | (2-1) | 9% |
| 3-HH-EMe | (2-1) | 23% |
| 3-HHEB-F | (6-10) | 8% |
| 5-HHEB-F | (6-10) | 8% |
| 3-HHEB(F,F)-F | (6-12) | 8% |
| 4-HHEB(F,F)-F | (6-12) | 5% |
| 4-HGB(F,F)-F | (6-103) | 5% |
| 5-HGB(F,F)-F | (6-103) | 5% |
| 2-H2GB(F,F)-F | (6-106) | 4% |
| 3-H2GB(F,F)-F | (6-106) | 5% |
| 5-GHB(F,F)-F | (6-109) | 5% |

NI = 80.0° C.; η = 21.1 mPa · s; Δn = 0.065; Δε = 6.9.

Use Example 11

| | | |
|---|---|---|
| V2-GB(F,F)XB(F)B(F,F)-F | (No. 236) | 5% |
| 3-HB-O1 | (2-5) | 15% |
| 3-HH-4 | (2-2) | 5% |
| 3-HB(2F,3F)-O2 | (9-1) | 12% |
| 5-HB(2F,3F)-O2 | (9-1) | 12% |
| 2-HHB(2F,3F)-1 | (10-1) | 11% |
| 3-HHB(2F,3F)-1 | (10-1) | 12% |
| 3-HHB(2F,3F)-O2 | (10-1) | 11% |
| 5-HHB(2F,3F)-O2 | (10-1) | 11% |
| 3-HHB-1 | (3-1) | 6% |

NI = 82.0° C.; η = 36.4 mPa · s; Δn = 0.091; Δε = −3.1.

Use Example 12

| | | |
|---|---|---|
| V2-GHB(F,F)XB(F,F)-F | (No. 221) | 5% |
| 2-HH-5 | (2-1) | 3% |
| 3-HH-4 | (2-1) | 15% |
| 3-HH-5 | (2-1) | 3% |
| 3-HB-O2 | (2-5) | 12% |
| 3-H2B(2F,3F)-O2 | (9-4) | 14% |
| 5-H2B(2F,3F)-O2 | (9-4) | 15% |
| 3-HHB(2F,3CL)-O2 | (10-12) | 3% |
| 2-HBB(2F,3F)-O2 | (10-7) | 3% |
| 3-HBB(2F,3F)-O2 | (10-7) | 9% |
| 5-HBB(2F,3F)-O2 | (10-7) | 9% |
| 3-HHB-1 | (3-1) | 3% |
| 3-HHB-3 | (3-1) | 3% |
| 3-HHB-O1 | (3-1) | 3% |

NI = 74.5° C.; η = 21.4 mPa · s; Δn = 0.093; Δε = −3.9.

Use Example 13

| | | |
|---|---|---|
| V2-GB(F,F)XB(F)B(F,F)-F | (No. 236) | 5% |
| 2-HH-3 | (2-1) | 21% |
| 3-HH-4 | (2-1) | 9% |
| 1-BB-3 | (2-8) | 9% |
| 3-HB-O2 | (2-5) | 2% |
| 3-BB(2F,3F)-O2 | (9-3) | 8% |
| 5-BB(2F,3F)-O2 | (9-3) | 6% |
| 2-HH1OB(2F,3F)-O2 | (10-5) | 11% |
| 3-HH1OB(2F,3F)-O2 | (10-5) | 20% |
| 3-HHB-1 | (3-1) | 4% |
| 3-HHB-O1 | (2-1) | 3% |
| 5-B(F)BB-2 | (3-8) | 2% |

NI = 71.8° C.; η = 16.4 mPa · s; Δn = 0.098; Δε = −2.9.

Use Example 14

| | | |
|---|---|---|
| V2-GHB(F,F)XB(F,F)-F | (No. 221) | 4% |
| 2-HH-3 | (2-1) | 15% |
| 7-HB-1 | (2-5) | 9% |
| 5-HB-O2 | (2-5) | 7% |
| 3-HB(2F,3F)-O2 | (9-1) | 17% |
| 5-HB(2F,3F)-O2 | (9-1) | 15% |
| 3-HHB(2F,3CL)-O2 | (10-12) | 3% |
| 4-HHB(2F,3CL)-O2 | (10-12) | 3% |
| 5-HHB(2F,3CL)-O2 | (10-12) | 2% |
| 3-HH1OCro(7F,8F)-5 | (13-6) | 5% |
| 5-HBB(F)B-2 | (4-5) | 10% |
| 5-HBB(F)B-3 | (4-5) | 10% |

NI = 78.5° C.; η = 25.8 mPa · s; Δn = 0.106; Δε = −2.4.

Use Example 15

| | | |
|---|---|---|
| V2-GB(F,F)XB(F)B(F,F)-F | (No. 236) | 5% |
| 1-BB-3 | (2-8) | 10% |
| 3-HH-V | (2-1) | 28% |
| 3-BB(2F,3F)-O2 | (9-3) | 13% |
| 2-HH1OB(2F,3F)-O2 | (10-5) | 16% |
| 3-HH1OB(2F,3F)-O2 | (10-5) | 14% |
| 3-HHB-1 | (3-1) | 8% |
| 5-B(F)BB-2 | (3-8) | 6% |

NI = 72.2° C.; η = 15.7 mPa · s; Δn = 0.109; Δε = −2.7.

Use Example 16

| | | |
|---|---|---|
| V2-GHB(F,F)XB(F,F)-F | (No. 221) | 3% |
| 2-HH-3 | (2-1) | 6% |
| 3-HH-V1 | (2-1) | 10% |
| 1V2-HH-1 | (2-1) | 7% |
| 1V2-HH-3 | (2-1) | 7% |
| 3-BB(2F,3F)-O2 | (9-3) | 7% |
| 5-BB(2F,3F)-O2 | (9-3) | 4% |
| 3-H1OB(2F,3F)-O2 | (9-5) | 7% |
| 2-HH1OB(2F,3F)-O2 | (10-5) | 7% |
| 3-HH1OB(2F,3F)-O2 | (10-5) | 19% |
| 3-HDhB(2F,3F)-O2 | (10-3) | 7% |
| 3-HHB-1 | (3-1) | 3% |
| 3-HHB-3 | (3-1) | 2% |
| 2-BB(2F,3F)B-3 | (11-1) | 11% |

NI = 86.1° C.; η = 22.9 mPa · s; Δn = 0.108; Δε = −4.3.

Use Example 17

| | | |
|---|---|---|
| V2-GB(F,F)XB(F)B(F,F)-F | (No. 236) | 4% |
| 1V2-BEB(F,F)-C | (8-15) | 6% |
| 3-HB-C | (8-1) | 16% |
| 2-BTB-1 | (2-10) | 10% |
| 5-HH-VFF | (2-1) | 28% |
| 3-HHB-1 | (3-1) | 4% |
| VFF-HHB-1 | (3-1) | 8% |
| VFF2-HHB-1 | (3-1) | 11% |
| 3-H2BTB-2 | (3-17) | 5% |
| 3-H2BTB-3 | (3-17) | 4% |
| 3-H2BTB-4 | (3-17) | 4% |

NI = 81.8° C.; η = 14.1 mPa · s; Δn = 0.132; Δε = 7.9.

Use Example 18

| | | |
|---|---|---|
| V2-GHB(F,F)XB(F,F)-F | (No. 221) | 5% |
| 5-HB(F)B(F,F)XB(F,F)-F | (7-41) | 4% |
| 3-BB(F)B(F,F)XB(F,F)-F | (7-47) | 3% |
| 4-BB(F)B(F,F)XB(F,F)-F | (7-47) | 5% |
| 5-BB(F)B(F,F)XB(F,F)-F | (7-47) | 3% |
| 3-HH-V | (2-1) | 41% |
| 3-HH-V1 | (2-1) | 5% |
| 3-HHEH-5 | (3-13) | 3% |
| 3-HHB-1 | (3-1) | 4% |
| V-HHB-1 | (3-1) | 5% |
| V2-BB(F)B-1 | (3-6) | 5% |
| 1V2-BB-F | (5-1) | 3% |
| 3-BB(F,F)XB(F,F)-F | (6-97) | 11% |
| 3-HHBB(F,F)-F | (7-6) | 3% |

NI = 81.5° C.; η = 14.1 mPa · s; Δn = 0.103; Δε = 7.3.

Use Example 19

| | | |
|---|---|---|
| V2-GB(F,F)XB(F)B(F,F)-F | (No. 236) | 3% |
| V2-GHB(F,F)XB(F,F)-F | (No. 221) | 3% |
| 3-GB(F)B(F,F)XB(F,F)-F | (7-57) | 4% |
| 3-BB(F)B(F,F)XB(F,F)-F | (7-47) | 3% |
| 4-BB(F)B(F,F)XB(F,F)-F | (7-47) | 7% |
| 5-BB(F)B(F,F)XB(F,F)-F | (7-47) | 3% |
| 3-HH-V | (2-1) | 40% |
| 3-HH-V1 | (2-1) | 5% |
| 3-HHEH-5 | (3-13) | 3% |
| 3-HHB-1 | (3-1) | 4% |
| V-HHB-1 | (3-1) | 4% |
| V2-BB(F)B-1 | (3-6) | 5% |
| 1V2-BB-F | (5-1) | 3% |
| 3-BB(F,F)XB(F,F)-F | (6-97) | 5% |
| 3-GB(F,F)XB(F,F)-F | (6-113) | 5% |
| 3-HHBB(F,F)-F | (7-6) | 3% |

NI = 80.9° C.; η = 16.2 mPa · s; Δn = 0.105; Δε = 9.1.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

INDUSTRIAL APPLICABILITY

The liquid crystal compound of the invention has excellent physical properties. A liquid crystal composition containing the compound can be widely utilized for a liquid crystal display device used for a personal computer, television and so forth.

What is claimed is:

1. A compound represented by formula (1):

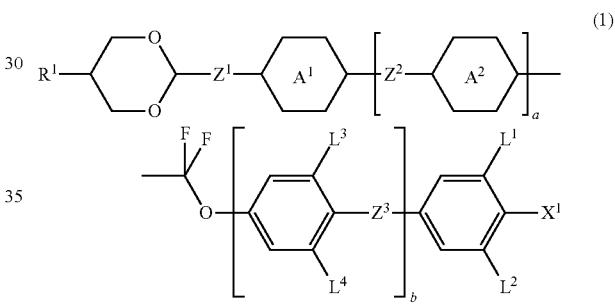

wherein, in formula (1), $R^1$ is alkenyl having 2 to 10 carbons, and in the alkenyl, at least one hydrogen may be replaced by fluorine; ring $A^1$ and ring $A^2$ are each independently 1,4-cyclohexylene, 1,4-phenylene, or 1,4-phenylene in which at least one hydrogen is replaced by fluorine; $Z^1$, $Z^2$ and $Z^3$ are each independently a single bond, —COO—, —OCH$_2$—, —CF$_2$O—, —CH$_2$CH$_2$—, —CF$_2$CF$_2$—, —CF═CF—, —C≡C—, —(CH$_2$)$_4$— or —CH$_2$CH═CHCH$_2$—; $X^1$ is hydrogen, fluorine, —CF$_3$ or —OCF$_3$; $L^1$, $L^2$, $L^3$ and $L^4$ are each independently hydrogen or fluorine; and a and b are each independently 0 or 1, a sum of a and b is 1, and when a is 1, at least one of ring $A^1$ and ring $A^2$ is 1,4-cyclohexylene.

2. The compound according to claim 1, represented by any one of formula (1-1), formula (1-2) and formula (1-3):

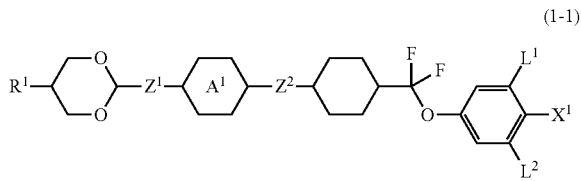

(1-1)

(1-2)
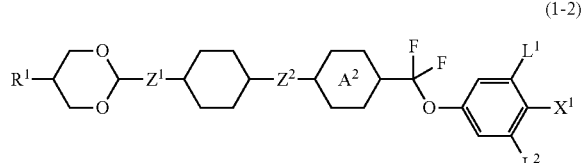

(1-3)
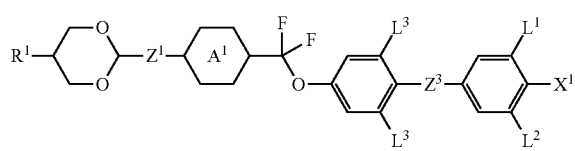

wherein, in formula (1-1) to formula (1-3), $R^1$ is alkenyl having 2 to 10 carbons; ring $A^1$ and ring $A^2$ are each independently 1,4-cyclohexylene, 1,4-phenylene, or 1,4-phenylene in which arbitrary hydrogen is replaced by fluorine; $Z^1$, $Z^2$ and $Z^3$ are each independently a single bond, —COO—, —CF$_2$O—, —OCH$_2$— or —CH$_2$CH$_2$; $X^1$ is hydrogen, fluorine, —CF$_3$ or —OCF$_3$; and $L^1$, $L^2$, $L^3$ and $L^4$ are each independently hydrogen or fluorine.

3. The compound according to claim 2, wherein, in formula (1-1), formula (1-2) or formula (1-3), $R^1$ is alkenyl having 2 to 5 carbons; ring $A^1$ and ring $A^2$ are each independently 1,4-cyclohexylene, 1,4-phenylene, or 1,4-phenylene in which arbitrary hydrogen is replaced by fluorine; $Z^1$, $Z^2$ and $Z^3$ are each independently a single bond, —COO— or —CF$_2$O—; $X^1$ is hydrogen, fluorine, —CF$_3$ or —OCF$_3$; and $L^1$, $L^2$, $L^3$ and $L^4$ are each independently hydrogen or fluorine.

4. The compound according to claim 1, represented by any one of formula (1-a) to formula (1-s):

(1-a)
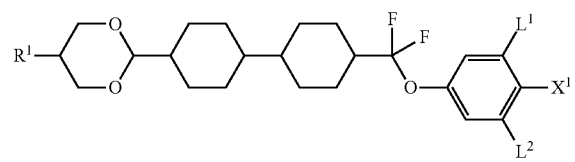

(1-b)
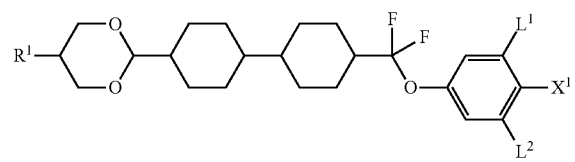

(1-c)
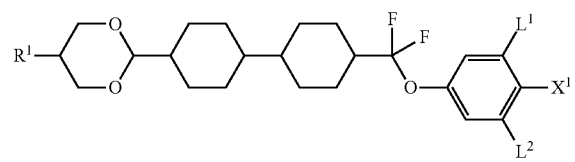

(1-d)
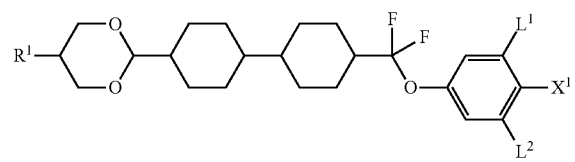

(1-e)
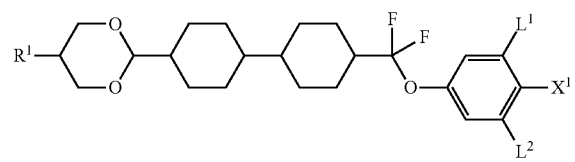

(1-f)
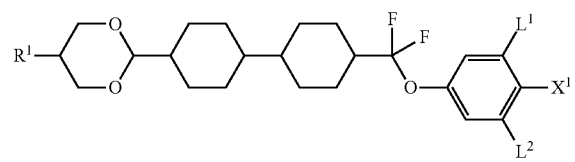

(1-g)
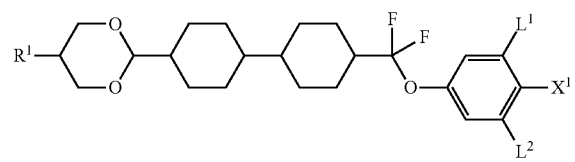

(1-h)
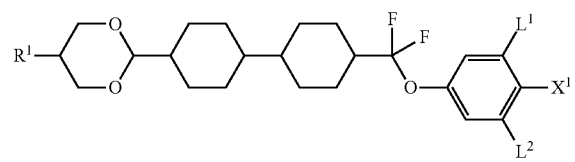

(1-i)
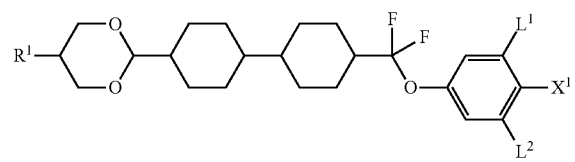

(1-j)
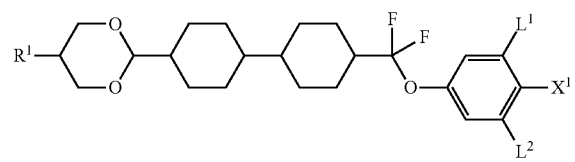

(1-k)
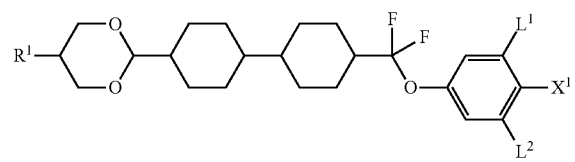

wherein, in formula (1-a) to formula (1-s), $R^1$ is alkenyl having 2 to 5 carbons; $X^1$ is hydrogen, fluorine, —$CF_3$ or —$OCF_3$; and $L^1$ and $L^2$ are each independently hydrogen or fluorine.

5. The compound according to claim 4, wherein, in formula (1-a) to formula (1-s), $R^1$ is vinyl, 1-propenyl, 3-butenyl or 3-pentenyl.

6. The compound according to claim 4, wherein, in formula (1-a) to formula (1-s), $R^1$ is vinyl, 1-propenyl, 3-butenyl or 3-pentenyl; $X^1$ is fluorine; and $L^1$ and $L^2$ are hydrogen or fluorine.

7. The compound according to claim 4, wherein, in formula (1-a) to formula (1-s), $R^1$ is vinyl, 1-propenyl, 3-butenyl, or 3-pentenyl; $X^1$ is —$OCF_3$; and $L^1$ and $L^2$ are each independently hydrogen or fluorine.

8. A liquid crystal composition, containing at least one compound according to claim 1.

9. The liquid crystal composition according to claim 8, further containing at least one compound selected from the group of compounds represented by formula (2) to formula (4):

wherein, in formula (2) to formula (4),
- $R^{11}$ and $R^{12}$ are each independently alkyl having 1 to 10 carbons or alkenyl having 2 to 10 carbons, and in the alkyl and the alkenyl, at least one —$CH_2$— may be replaced by —O—, and at least one hydrogen may be replaced by fluorine;
- ring $B^1$, ring $B^2$, ring $B^3$ and ring $B^4$ are each independently 1,4-cyclohexylene, 1,4-phenylene, 2-fluoro-1,4-phenylene, 2,5-difluoro-1,4-phenylene or pyrimidine-2,5-diyl; and
- $Z^{11}$, $Z^{12}$ and $Z^{13}$ are each independently a single bond, —$CH_2CH_2$—, —CH=CH—, —C≡C— or —COO—.

10. The liquid crystal composition according to claim 8, further containing at least one compound selected from the group of compounds represented by formula (5) to formula (7):

-continued (6)
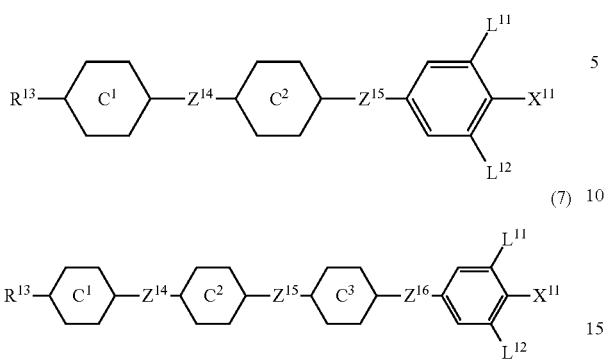

(7)
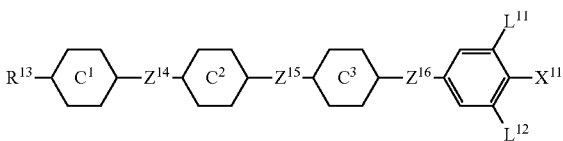

wherein, in formula (5) to formula (7),
 $R^{13}$ is alkyl having 1 to 10 carbons or alkenyl having 2 to 10 carbons, and in the alkyl and the alkenyl, at least one —$CH_2$— may be replaced by —O— and at least one hydrogen may be replaced by fluorine;
 $X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;
 ring $C^1$, ring $C^2$ and ring $C^3$ are each independently 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;
 $Z^{14}$, $Z^{15}$ and $Z^{16}$ are each independently a single bond, —$CH_2CH_2$—, —CH=CH—, —C≡C—, —COO—, —$CF_2O$—, —$OCF_2$—, —$CH_2O$— or —$(CH_2)_4$—; and $L^{11}$ and $L^{12}$ are each independently hydrogen or fluorine.

11. The liquid crystal composition according to claim 8, further containing at least one compound represented by formula (8):

(8)
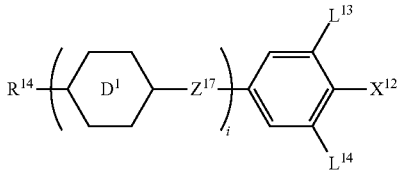

wherein, in formula (8),
 $R^{14}$ is alkyl having 1 to 10 carbons or alkenyl having 2 to 10 carbons, and in the alkyl and the alkenyl, at least one —$CH_2$— may be replaced by —O— and at least one hydrogen may be replaced by fluorine;
 $X^{12}$ is —C≡N or —C≡C—C≡N;
 ring $D^1$ is each independently 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;
 $Z^{17}$ is each independently a single bond, —$CH_2CH_2$—, —C≡C—, —COO—, —$CF_2O$—, —$OCF_2$—, or —$CH_2O$—;
 $L^{13}$ and $L^{14}$ are each independently hydrogen or fluorine; and
 i is 1, 2, 3 or 4.

12. The liquid crystal composition according to claim 8, further containing at least one compound selected from the group of compounds represented by formula (9) to formula (15):

(9)
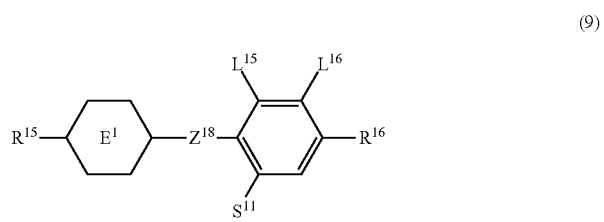

(10)
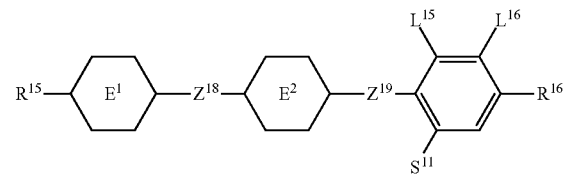

(11)
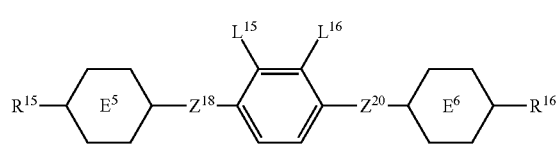

(12)
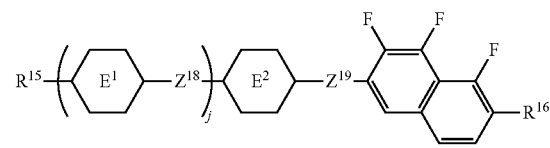

(13)
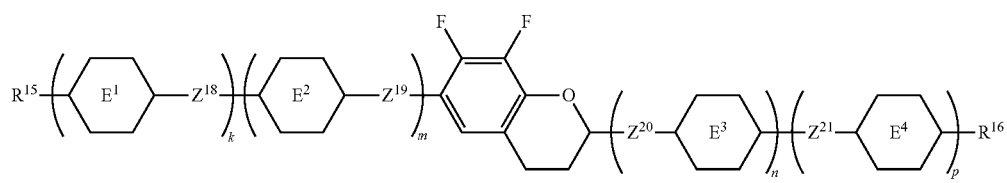

(14)
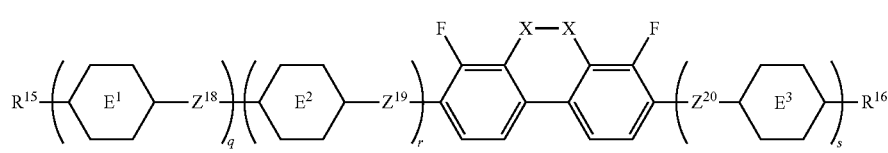

-continued

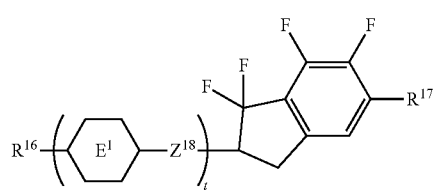
(15)

wherein, in formula (9) to formula (15),
$R^{15}$ and $R^{16}$ are each independently alkyl having 1 to 10 carbons or alkenyl having 2 to 10 carbons, and in the alkyl and the alkenyl, at least one —$CH_2$— may be replaced by —O—, and at least one hydrogen may be replaced by fluorine;
$R^{17}$ is hydrogen, fluorine, alkyl having 1 to 10 carbons or alkenyl having 2 to 10 carbons, and in the alkyl and the alkenyl, at least one —$CH_2$— may be replaced by —O—, and at least one hydrogen may be replaced by fluorine;
ring $E^1$, ring $E^2$, ring $E^3$ and ring $E^4$ are each independently 1,4-cyclohexylene, 1,4-cyclohexenylene, 1,4-phenylene in which at least one hydrogen may be replaced by fluorine, tetrahydropyran-2,5-diyl or decahydronaphthalene-2,6-diyl;
ring $E^5$ and ring $E^6$ are each independently 1,4-cyclohexylene, 1,4-cyclohexenylene, 1,4-phenylene, tetrahydropyran-2,5-diyl or decahydronaphthalene-2,6-diyl;
$Z^{18}$, $Z^{19}$, $Z^{20}$ and $Z^{21}$ are each independently a single bond, —$CH_2CH_2$—, —COO—, —$CH_2O$—, —$OCF_2$— or —$OCF_2CH_2CH_2$;
$L^{15}$ and $L^{16}$ are each independently fluorine or chlorine;
$S^{11}$ is hydrogen or methyl;
X is —CHF— or —$CF_2$—; and
j, k, m, n, p, q, r and s are each independently 0 or 1, a sum of k, m, n and p is 1 or 2, a sum of q, r and s is 0, 1, 2 or 3, and t is 1, 2 or 3.

13. A liquid crystal display device, containing the liquid crystal composition according to claim 8.

* * * * *